United States Patent
Ziesche

(10) Patent No.: US 10,508,307 B2
(45) Date of Patent: *Dec. 17, 2019

(54) METHODS OF DIAGNOSING CHRONIC OBSTRUCTIVE PULMONARY DISEASE (COPD) USING NOVEL MOLECULAR BIOMARKERS

(71) Applicant: Transgenion—International Institute for Regenerative Translational Medicine GmbH, Vienna (AT)

(72) Inventor: Rolf Ziesche, Neusiedl am See (AT)

(73) Assignee: Transgenion—International Institute for Regenerative Translational Medicine GmbH, Vienna (AT)

(*) Notice: Subject to any disclaimer, the term of this patent is extended or adjusted under 35 U.S.C. 154(b) by 0 days.

This patent is subject to a terminal disclaimer.

(21) Appl. No.: 15/316,105

(22) PCT Filed: Jun. 3, 2015

(86) PCT No.: PCT/EP2015/062431
§ 371 (c)(1),
(2) Date: Dec. 2, 2016

(87) PCT Pub. No.: WO2015/185656
PCT Pub. Date: Dec. 10, 2015

(65) Prior Publication Data
US 2017/0107574 A1    Apr. 20, 2017

(30) Foreign Application Priority Data
Jun. 5, 2014 (EP) .................................. 14171388

(51) Int. Cl.
*C12Q 1/6883* (2018.01)
*G01N 33/68* (2006.01)
*A61K 31/44* (2006.01)

(52) U.S. Cl.
CPC ............ *C12Q 1/6883* (2013.01); *A61K 31/44* (2013.01); *G01N 33/6893* (2013.01); *C12Q 2600/112* (2013.01); *C12Q 2600/118* (2013.01); *C12Q 2600/158* (2013.01); *G01N 2333/47* (2013.01); *G01N 2800/122* (2013.01); *G01N 2800/50* (2013.01)

(58) Field of Classification Search
None
See application file for complete search history.

(56) References Cited

U.S. PATENT DOCUMENTS

| | | | |
|---|---|---|---|
| 2005/0208496 A1 | 9/2005 | Ohtani et al. | |
| 2013/0165343 A1 | 6/2013 | Robinson et al. | |
| 2013/0324428 A1 | 12/2013 | Ryu et al. | |
| 2017/0335393 A1 | 11/2017 | Ziesche | |
| 2017/0349947 A1 | 12/2017 | Ziesche | |

FOREIGN PATENT DOCUMENTS

| | | |
|---|---|---|
| WO | WO 2008/003701 | 1/2008 |
| WO | WO 2010/064702 | 6/2010 |
| WO | WO 2013/104990 | 7/2013 |
| WO | WO 2013/177060 | 11/2013 |
| WO | WO 2013/190092 | 12/2013 |

OTHER PUBLICATIONS

Renner et al. Gastroenterology. 2007. 133:1499-1509. (Year: 2007).*
Hoshikawa et al. Physical Genomics. 2003. 12: 209-219. (Year: 2003).*
Kendrick et al. A gene's mRNA level does not usually predict its protein level. Sep. 25, 2014. (Year: 2014).*
Maier et al. FEBS Letters. 2009. 583:3966-3973. (Year: 2009).*
Pascal et al. BMC Genomics. 2008. 9:246. (Year: 2008).*
Chan et al. G&P magazine. 2006. 6(3): 20-26. (Year: 2006).*
Saito-Hisaminato et al. DNA Research. 2002. 9:35-45. (Year: 2002).*
Whitehead et al. Genome Biology. 2005. 6:R13. (Year: 2005).*
Llinas et al. Pulmonary Pharmacology & Therapeutics. 2011. 24:32-41. (Year: 2011).*
Steiling et al. Ann Am Thorac. 2013. vol. 10, Supplement. pp. 5190-5196. (Year: 2013).*

(Continued)

*Primary Examiner* — Joseph G. Dauner
(74) *Attorney, Agent, or Firm* — Parker Highlander PLLC

(57) ABSTRACT

The present invention relates to in vitro methods for the diagnosis of chronic obstructive pulmonary disease (COPD), wherein the expression of the marker gene DMBT1 is determined. In particular, the invention relates to an in vitro diagnostic method of assessing the susceptibility of a subject to develop progressive COPD involving the appearance of irreversible lung damage, wherein the expression of the marker gene DMBT1 and optionally one or more further marker genes selected from KIAA1199, TMSB15A, DPP6, SLC51B, NUDT11, ELF5, AZGP1, PRRX1, AQP3, SFN, GPR110, GDF15, RASGRF2, RND1, PLA1A, FGG, CEACAM5, HYAL2, AHRR, CXCL3, CYP1A1, CYP1B1, CYP1A2, CST6, NTRK2, COMP, ITGA10, CTHRC1, TAL1, FIBIN, BEX5, BEX1, ESM1 and GHRL is determined. The invention also relates to an in vitro method of diagnosing stable COPD or assessing the susceptibility of a subject to develop stable COPD, wherein the expression of DMBT1 and optionally one or more further marker genes selected from KIAA1199, TMSB15A, DPP6, SLC51B, NUDT11, ELF5, AZGP1, PRRX1, AQP3, SFN, GPR110, GDF15, RASGRF2, RND1, PLA1A, FGG, CEACAM5, HYAL2, AHRR, CXCL3, CYP1A1, CYP1B1, CYP1A2, CST6, NTRK2, COMP, ITGA10, CTHRC1, TAL1, FIBIN, BEX5, BEX1, ESM1 and GHRL is determined. Furthermore, the invention relates to the use of primers for transcripts of the aforementioned marker genes, the use of nucleic acid probes to transcripts of these marker genes, the use of microarrays comprising nucleic acid probes to transcripts of these marker genes, and the use of antibodies against the proteins expressed from these marker genes in corresponding in vitro methods. In vitro methods of monitoring the progression of COPD are also provided, In which the expression of marker genes according to the invention is determined.

Figure 1:
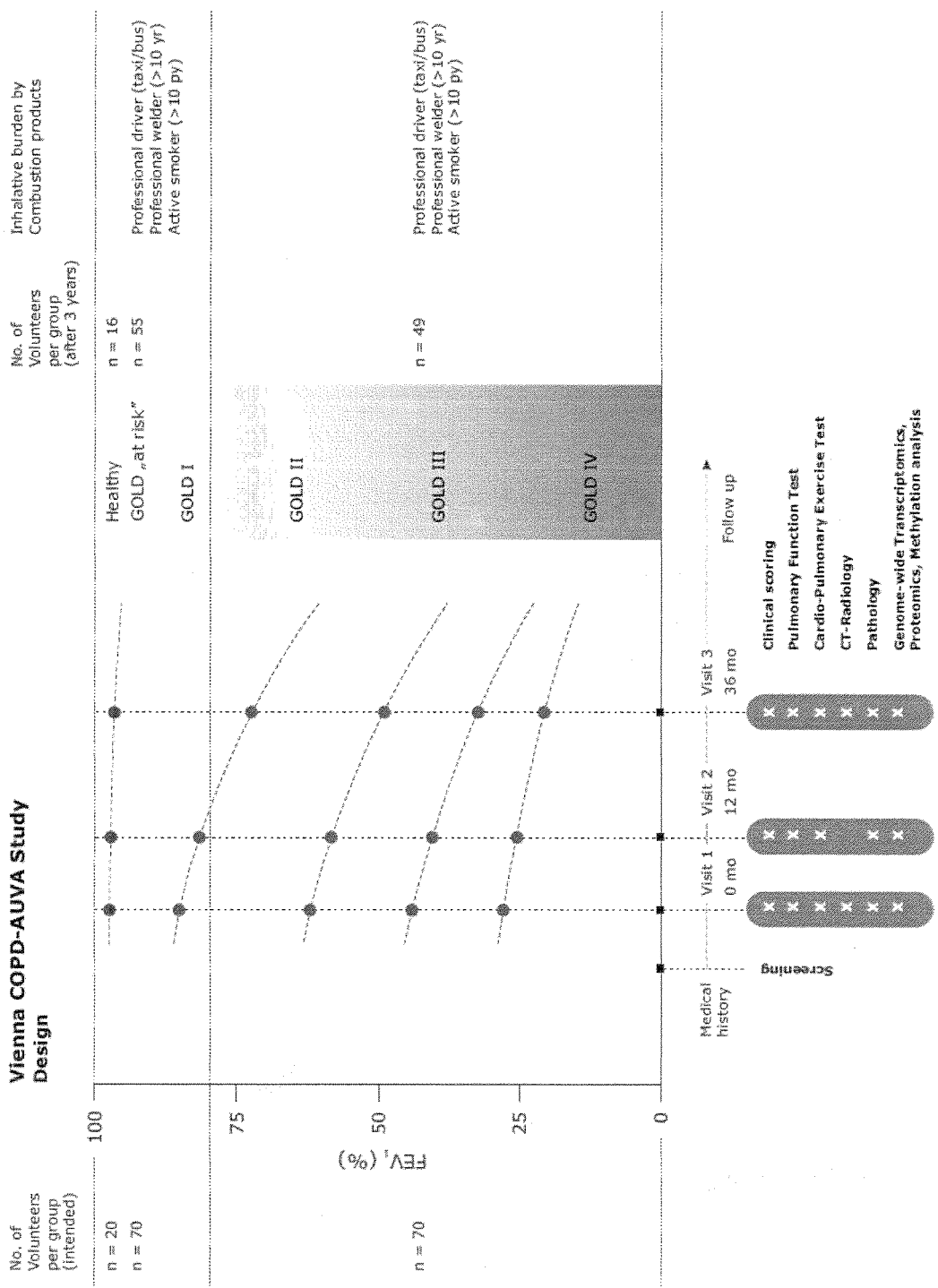

6 Claims, 28 Drawing Sheets
Specification includes a Sequence Listing.

(56) References Cited

OTHER PUBLICATIONS van den Berge et al. Thorax. 2014. 68:14-23. (Year: 2014).*
Bahr et al. American Journal of Respiratory Cell and Molecular Biology. 2013. 49:316-323. (Year: 2013).*
Calverley et al. Am J Respir Crit Care Med. 2007. 176:154-161. (Year: 2000).*
Baye et al. P T. 2012. 37(3):149-150, 157-161. (Year: 2012).*
Calverley et al. Lancet. 2009. 374:685-394. (Year: 2009).*
Rabe et al. Lancet. 2005. 366:563-57. (Year: 2005).*
Spira et al. Am J Respir Cell Mol Biol. 2004. 31:601-610. (Year: 2004).*
Bhattacharya et al., "Molecular biomarkers for quantitative and discrete COPD phenotypes," *American Journal of Respiratory and Cell and Molecular Biology*, 40(3):359-367, 2009.
Gosselink et al., "Differential expression of tissue repair genes in the pathogenesis of chronic obstructive pulmonary disease," *American Journal of Respiratory and Critical Care Medicine*, 181(12):1329-1335, 2010.
PCT International Preliminary Report on Patentability issued in International Application No. PCT/EP2015/062431, dated Dec. 15, 2016.
PCT International Search Report and Written Opinion issued in International Application No. PCT/EP2015/062431, dated Sep. 14, 2015.
Richens et al., "Systems biology coupled with label-free high-throughput detection as a novel approach for diagnosis of chronic obstructive pulmonary disease," *Respiratory Research*, 10(1):29, 2009.
Savarimuthu Francis et al., "Genes and gene ontologies common to airflow obstruction and emphysema in the lungs of patients with COPD," *PLOS ONE*, 6(3):e17442, 2011.

Steiling et al., "A dynamic bronchial airway gene expression signature of chronic and lung function impairment," *American Journal of Respiratory and Critical Care Medicine*, 187(9):933-942, 2013.
Affymetrix Inc. Human Genome U95 Set. GeneChip® Human Genome U95 Set, available via URL: < tools.thermofisher.com/content/sfs/brochures/hgu95_datasheet.pdf>, 2001-2003, printed on Jan. 8, 2019, pp. 1-2.
Affymetrix NetAffx. Expression Probeset Details for Human Genome U95 Sets for the KIA 1199, TMSB15A, and DMBT1 genes, available via URL: <affymetrix.com/analysis/netaffx/xmlquery.affx?netaffx=netaffx4_annot>, printed on Jan. 8, 2019, 14 pages.
Banyard et al., "Differential regulation of human thymosin beta 15 isoforms by transforming growth factor beta 1", *Genes Chromosomes Cancer*, 48(6):502-509, 2009.
Chen et al., "Discordant protein and mRNA expression in lung adenocarcinomas", *Mol. Cell. Proteomics*, 1:304-313, 2002.
Coleman, "Of mouse and man—what is the value of the mouse in predicting gene expression in humans?", *Drug Discov. Today*, 8(6):233-235, 2003.
Haynes et al., "Proteome analysis: biological assay or data archive?" *Electrophoresis*, 19:1862-1871, 1998.
Liu et al., "Comparison of differentially expressed genes in T lymphocytes between human autoimmune disease and murine models of autoimmune disease", *Clin. Immunol.*, 112:225-230, 2004.
Min et al., "Variability of gene expression profiles in human blood and lymphoblastoid cell lines", *BMC Genomics*, 11:96, 2010.
Palmer, "Cell-type specific gene expression profiles of leukocytes in human peripheral blood", *BMC Genomics*, 7:115, 2006.
Vogel et al., "Insights into the regulation of protein abundance from proteomic and transcriptomic analyses", *Nat. Rev. Genet.*, 13(4):227-232, 2012.

* cited by examiner

Fig. 3

A)

Healthy participants

| Initials | Gender | ID | Clinical strata / Healthy controls | Age | GOLD V1 | GOLD V2 | GOLD V3 | Bronchitis & Phlegm V1 | Bronchitis & Phlegm V2 | Bronchitis & Phlegm V3 | Pack Years Total | Smoking habits V1 | Smoking habits V2 | Smoking habits V3 |
|---|---|---|---|---|---|---|---|---|---|---|---|---|---|---|
| AC | F | 145 | Healthy | 40.2 | 0 | 0 | 0 | n.a. | n.a. | n.a. | n.a. | -1 | -1 | -1 |
| BR | M | 24 | Healthy | 48.3 | 0 | 0 | 0 | n.a. | n.a. | n.a. | n.a. | -1 | -1 | -1 |
| GI | F | 159 | Healthy | 24.2 | 0 | 0 | 0 | n.a. | n.a. | n.a. | n.a. | -1 | -1 | -1 |
| HD | F | 44 | Healthy | 33.0 | 0 | 0 | 0 | n.a. | n.a. | n.a. | n.a. | -1 | -1 | -1 |
| KH | M | 35 | Healthy | 62.7 | 0 | 0 | 0 | n.a. | n.a. | n.a. | n.a. | -1 | -1 | -1 |
| LH | F | 161 | Healthy | 33.3 | 0 | 0 | 0 | n.a. | n.a. | n.a. | n.a. | -1 | -1 | -1 |
| MA | F | 158 | Healthy | 24.2 | 0 | 0 | 0 | n.a. | n.a. | n.a. | n.a. | -1 | -1 | -1 |
| MO | F | 31 | Healthy | 41.5 | 0 | 0 | 0 | n.a. | n.a. | n.a. | n.a. | -1 | -1 | -1 |
| SE | M | 57 | Healthy | 35.6 | 0 | 0 | 0 | n.a. | n.a. | n.a. | n.a. | -1 | -1 | -1 |
| SH | M | 23 | Healthy | 45.2 | 0 | 0 | 0 | n.a. | n.a. | n.a. | n.a. | -1 | -1 | -1 |
| SS | M | 34 | Healthy | 27.2 | 0 | 0 | 0 | n.a. | n.a. | n.a. | n.a. | -1 | -1 | -1 |
| TK | F | 163 | Healthy | 24.6 | 0 | 0 | 0 | n.a. | n.a. | n.a. | n.a. | -1 | -1 | -1 |
| TT | M | 50 | Healthy | 58.9 | 0 | 0 | 0 | n.a. | n.a. | n.a. | n.a. | -1 | -1 | -1 |
| WH | M | 123 | Healthy | 27.0 | 0 | 0 | 0 | n.a. | n.a. | n.a. | n.a. | -1 | -1 | -1 |
| WW | M | 155 | Healthy | 28.2 | 0 | 0 | 0 | n.a. | n.a. | n.a. | n.a. | -1 | -1 | -1 |
| ZB | M | 128 | Healthy | 28.0 | 0 | 0 | 0 | n.a. | n.a. | n.a. | n.a. | -1 | -1 | -1 |
|  | n 16 |  | Age (yrs, mean) 36.4 |  |  |  |  |  |  |  |  |  |  |  |

Fig. 3 (cont.)

B)

COPD „at risk" at Visit 1 (GOLD 0)

| Initials | Gender | ID | Clinical strata COPD "at risk" | Age | GOLD V1 | GOLD V2 | GOLD V3 | Intensity of Bronchitis V1 | Intensity of Bronchitis V2 | Intensity of Bronchitis V3 | Pack Years Total | Smoking habits V1 | Smoking habits V2 | Smoking habits V3 |
|---|---|---|---|---|---|---|---|---|---|---|---|---|---|---|
| AA | M | 1 | Car/Bus driver COPD "0 | 42.0 | 0 | 0 | 0 | 2 | 2 | 2 | 30 | 4 | 4 | 4 |
| BH | M | 140 | Welder COPD "0 | 31.2 | 0 | 0 | 0 | 1 | 2 | 3 | 16 | 5 | 5 | 5 |
| BM | M | 106 | Welder COPD "0 | 40.2 | 0 | 0 | 0 | 3 | 0 | 0 | 10 | 3 | 0 | 0 |
| BR | M | 166 | Welder COPD "0 | 37.7 | 0 | 0 | 0 | 3 | 1 | 1 | 15 | 3 | 3 | 2 |
| DA | M | 84 | Welder COPD "0 | 46.4 | 0 | 2 | 0 | 0 | 0 | 0 | 13 | 2 | 2 | 1 |
| DM | F | 88 | Car/Bus driver COPD "0 | 50.2 | 0 | 1 | 1 | 0 | 0 | 1 | 70 | 3 | 2 | 2 |
| DE | M | 103 | Welder COPD "0 | 33.0 | 0 | 0 | n.d. | 3 | 1 | n.d. | 6 | 1 | 2 | n.d. |
| ER | M | 165 | Welder COPD "0 | 40.7 | 0 | 0 | n.d. | 0 | -1 | n.d | 30 | 2 | 2 | n.d |
| EF | M | 25 | Car/Bus driver COPD "0 | 53.0 | 0 | 0 | 0 | 1 | 1 | 0 | 25 | 0 | 0 | 0 |
| ES | M | 39 | Car/Bus driver COPD "0 | 67.7 | 0 | 0 | 0 | 0 | 2 | 2 | 150 | 5 | 5 | 5 |
| FE | F | 131 | Car/Bus driver COPD "0 | 64.7 | 0 | 0 | 0 | 1 | 1 | 0 | 8 | 0 | 0 | 0 |
| GT | M | 134 | Car/Bus driver COPD "0 | 47.5 | 0 | 2 | 1 | 2 | 2 | 0 | 45 | 4 | 4 | 4 |
| HJ | M | 20 | Car/Bus driver COPD "0 | 50.4 | 0 | 0 | 0 | 3 | 3 | 3 | 15 | 2 | 2 | 2 |
| HA | F | 72 | Car/Bus driver COPD "0 | 49.2 | 0 | 0 | 0 | 0 | 0 | 0 | 14 | 2 | 2 | 2 |
| HK | M | 97 | Car/Bus driver COPD "0 | 52.1 | 0 | 0 | 0 | 3 | 3 | 2 | 40 | 2 | n.d | n.d |
| JW | M | 40 | Car/Bus driver COPD "0 | 68.8 | 0 | 0 | 0 | 1 | 1 | 1 | 20 | 5 | 5 | 5 |
| JS | F | 32 | Car/Bus driver COPD "0 | 46.5 | 0 | 0 | 0 | 0 | 0 | 1 | 10 | 1 | 1 | 1 |
| KR | M | 86 | Car/Bus driver COPD "0 | 49.5 | 0 | 0 | 0 | 0 | 0 | 0 | 30 | 3 | 3 | 3 |
| KE | M | 176 | Welder COPD "0 | 50.7 | 0 | 2 | n.d. | 2 | 2 | n.d | 55 | 3 | 3 | n.d. |
| KJ | M | 168 | Welder COPD "0 | 32.1 | 0 | 0 | 0 | 2 | 2 | 1 | 10 | 3 | 0 | 1 |
| KG | M | 16 | Car/Bus driver COPD "0 | 43.8 | 0 | 0 | 0 | 0 | 0 | 0 | 20 | 3 | 3 | 3 |
| KEM | F | 101 | Car/Bus driver COPD "0 | 65.2 | 0 | 0 | 0 | 2 | 2 | 3 | 40 | 3 | 4 | 4 |
| KJ | M | 13 | Car/Bus driver COPD "0 | 54.2 | 0 | 0 | 0 | 0 | 0 | -1 | 35 | 3 | 0 | 0 |
| KH | M | 47 | Car/Bus driver COPD "0 | 65.5 | 0 | 0 | 0 | 0 | -1 | -1 | 50 | 3 | 5 | 3 |
| LJ | M | 4 | Car/Bus driver COPD "0 | 56.3 | 0 | 1 | n.d. | 0 | 0 | n.d | 40 | 0 | 0 | n.d |
| MT | M | 154 | Welder COPD "0 | 37.6 | 0 | 0 | 2 | 2 | 3 | 1 | 20 | 3 | 2 | 2 |
| MW | M | 58 | Car/Bus driver COPD "0 | 58.4 | 0 | 0 | 0 | 1 | 1 | 1 | 30 | 0 | 0 | 0 |
| MP | M | 79 | Welder COPD "0 | 53.2 | 0 | 0 | 0 | 0 | 0 | 1 | 32 | 3 | 4 | 3 |
| MS | M | 10 | Car/Bus driver COPD "0 | 36.3 | 0 | 0 | 0 | 1 | 1 | 0 | 18 | 3 | 3 | 3 |
| OI | M | 167 | Welder COPD "0 | 52.7 | 0 | 0 | n.d. | 1 | 0 | n.d | 10 | 0 | 0 | n.d. |
| PC | M | 139 | Car/Bus driver COPD "0 | 61.8 | 0 | 2 | n.d. | 1 | 1 | n.d | 30 | 0 | 0 | n.d. |
| PEM | M | 90 | Welder COPD "0 | 46.1 | 0 | 0 | 0 | 2 | 2 | 3 | 17 | 1 | 1 | 0 |
| PEM | M | 74 | Welder COPD "0 | 47.0 | 0 | 0 | 0 | -1 | -1 | 1 | 0 | -1 | -1 | -1 |
| PRM | M | 5 | Car/Bus driver COPD "0 | 57.2 | 0 | 0 | 0 | 1 | 1 | 1 | 60 | 6 | 6 | 5 |
| RM | M | 115 | Welder COPD "0 | 45.8 | 0 | 2 | 2 | 2 | 2 | 1 | 35 | 0 | 3 | 1 |
| RR | M | 36 | Car/Bus driver COPD "0 | 55.2 | 0 | 0 | 0 | 1 | 1 | 1 | 38 | 0 | 0 | 0 |
| RH | M | 91 | Welder COPD "0 | 61.1 | 0 | 0 | 0 | 1 | 1 | 0 | 85 | 5 | 3 | 3 |
| SB | F | 67 | Car/Bus driver COPD "0 | 49.3 | 0 | 0 | 0 | 0 | 0 | 0 | 15 | 2 | 2 | 2 |
| SW | M | 117 | Car/Bus driver COPD "0 | 52.2 | 0 | 0 | 0 | 0 | 0 | 1 | 40 | 0 | 2 | 2 |
| SIW | M | 118 | Welder COPD "0 | 49.7 | 0 | 0 | 0 | 0 | 0 | 2 | 27 | 3 | 3 | 2 |
| SR | M | 152 | Car/Bus driver COPD "0 | 38.6 | 0 | 0 | 0 | 0 | 0 | -1 | 10 | 0 | 0 | 0 |
| STJ | M | 21 | Car/Bus driver COPD "0 | 60.8 | 0 | 0 | 0 | 1 | 1 | 0 | 50 | 4 | 3 | 0 |
| STB | F | 56 | Car/Bus driver COPD "0 | 61.3 | 0 | 0 | n.d. | 0 | 0 | 0 | 25 | 0 | 0 | 0 |
| STS | M | 83 | Welder COPD "0 | 48.2 | 0 | 0 | 0 | 2 | 2 | 3 | 60 | 5 | 5 | 5 |
| STP | M | 156 | Welder COPD "0 | 47.0 | 0 | 0 | 0 | 0 | 0 | 0 | 15 | 0 | 0 | 0 |
| STA | M | 17 | Car/Bus driver COPD "0 | 45.4 | 0 | 0 | 0 | 0 | 0 | 2 | 20 | 4 | 4 | 4 |
| TJ | M | 19 | Car/Bus driver COPD "0 | 53.9 | 0 | 0 | 0 | 1 | 1 | 1 | 40 | 4 | 4 | 2 |
| TA | F | 46 | Car/Bus driver COPD "0 | 58.1 | 0 | 2 | 2 | 0 | 1 | -1 | 100 | 4 | 4 | 4 |
| WC | M | 172 | Welder COPD "0 | 42.9 | 0 | 0 | 0 | 0 | 2 | 0 | 36 | 4 | 4 | 3 |
| WW | M | 124 | Welder COPD "0 | 44.0 | 0 | 2 | 2 | 1 | 1 | 2 | 30 | 0 | 0 | 0 |
| WS | M | 65 | Welder COPD "0 | 30.5 | 0 | 0 | 1 | 0 | -1 | -1 | 10 | 0 | 0 | 0 |
| WR | M | 160 | Welder COPD "0 | 56.9 | 0 | 2 | 0 | 1 | 1 | 1 | 30 | 0 | 0 | 0 |
| WIR | M | 125 | Welder COPD "0 | 63.4 | 0 | 0 | 0 | 1 | 1 | 2 | 45 | 2 | 3 | 2 |
| ZAE | M | 93 | Welder COPD "0 | 51.7 | 0 | 0 | 0 | 2 | 2 | 2 | 10 | 1 | 1 | 0 |
| ZE | M | 6 | Car/Bus driver COPD "0 | 45.7 | 0 | 0 | 0 | 1 | 1 | 1 | 35 | 4 | 4 | 4 |
| | n | 55 | Age (yrs, mean) | 50.0 | | | | | | PY (mean) | 32.2 | | | |

Fig. 3 (cont.)

C)

Manifest COPD at Visit 1

| Initials | Gender | ID | Clinical strata COPD (manifest) | Age | GOLD V1 | V2 | V3 | Intensity of Bronchitis V1 | V2 | V3 | Pack Years Total | Smoking habits V1 | V2 | V3 |
|---|---|---|---|---|---|---|---|---|---|---|---|---|---|---|
| CW | M | 45 | Driver COPD °I-III | 59.0 | 1 | 0 | 0 | 1 | 0 | 1 | 10 | 0 | 0 | 0 |
| DJ | M | 85 | Driver COPD °I-III | 41.6 | 1 | 0 | 0 | 1 | 1 | 1 | 8 | 1 | 2 | 2 |
| GW | M | 102 | Driver COPD °I-III | 55.9 | 1 | 0 | 0 | -1 | -1 | -1 | 30 | 0 | 0 | 0 |
| HP | M | 98 | Driver COPD °I-III | 70.2 | 1 | 1 | 2 | 1 | 1 | 1 | 20 | 0 | 0 | 0 |
| KA | M | 107 | Welder COPD °I-III | 48.8 | 1 | 0 | 1 | 2 | 2 | 1 | 30 | 3 | 3 | 3 |
| KW | M | 55 | Driver COPD °I-III | 54.1 | 1 | 0 | 0 | 1 | 1 | 1 | 50 | 2 | 2 | 2 |
| MM | F | 114 | Driver COPD °I-III | 57.3 | 1 | 0 | 0 | 1 | 1 | 4 | 35 | 5 | 5 | 5 |
| RH | M | 116 | Driver COPD °I-III | 71.6 | 1 | 1 | n.d | 2 | 2 | n.d. | 45 | 0 | 0 | 0 |
| WH | M | 92 | Welder COPD °I-III | 44.2 | 1 | 2 | 1 | 0 | 2 | 1 | 35 | 4 | 3 | 3 |
| DK | M | 87 | Welder COPD °I-III | 50.8 | 2 | 2 | 2 | -1 | -1 | -1 | 5 | 1 | 1 | 1 |
| GG | M | 133 | Driver COPD °I-III | 52.5 | 2 | 2 | n.d | 0 | 0 | n.d. | 30 | 0 | 0 | 0 |
| AG | M | 71 | Welder COPD °I-III | 56.5 | 2 | 2 | 2 | 1 | 1 | -1 | 20 | 0 | 0 | 0 |
| BD | M | 148 | Driver COPD °I-III | 43.2 | 2 | 2 | 1 | 2 | 3 | 3 | 25 | 0 | 0 | 0 |
| CA | M | 37 | Driver COPD °I-III | 65.8 | 2 | 3 | 4 | 1 | 1 | -1 | 40 | 5 | 2 | 5 |
| GG | M | 136 | Welder COPD °I-III | 51.8 | 2 | 0 | 2 | 1 | 1 | 2 | 30 | 3 | 3 | 3 |
| HAH | M | 96 | Driver COPD °I-III | 46.2 | 2 | 2 | 1 | 1 | 0 | 0 | 40 | 4 | 4 | 4 |
| HE | M | 99 | Driver COPD °I-III | 48.9 | 2 | 3 | 2 | 1 | 1 | 2 | 25 | 0 | 0 | 0 |
| HF | M | 147 | Driver COPD °I-III | 63.3 | 2 | 2 | 2 | 1 | 1 | 1 | 30 | 3 | 3 | 3 |
| HH | M | 151 | Driver COPD °I-III | 56.2 | 2 | 2 | 2 | 3 | 3 | 2 | 30 | 3 | 3 | 3 |
| KT | M | 94 | Driver COPD °I-III | 50.8 | 2 | 2 | 2 | 1 | 1 | 1 | 30 | 5 | 0 | 1 |
| LG | M | 109 | Driver COPD °I-III | 60.0 | 2 | 2 | 2 | 1 | 1 | 2 | 40 | 4 | 3 | 3 |
| MB | F | 113 | Driver COPD °I-III | 69.7 | 2 | 2 | 2 | 1 | 1 | 2 | 35 | 3 | 3 | 3 |
| MJ | M | 112 | Welder COPD °I-III | 68.2 | 2 | 2 | 2 | 0 | 0 | 1 | 80 | 5 | 5 | 5 |
| MJ | M | 68 | Welder COPD °I-III | 47.5 | 2 | 2 | 2 | 1 | 2 | 3 | 50 | 0 | 0 | 0 |
| MT | M | 171 | Welder COPD °I-III | 48.8 | 2 | 1 | 2 | 1 | 2 | 2 | 35 | 2 | 3 | 3 |
| RJ | M | 75 | Driver COPD °I-III | 49.8 | 2 | 2 | 2 | 1 | 1 | 1 | 40 | 3 | 3 | 3 |
| SCHR | M | 76 | Driver COPD °I-III | 51.1 | 2 | 2 | 2 | 1 | 1 | 1 | 30 | 3 | 1 | 1 |
| SCHS | F | 130 | Driver COPD °I-III | 53.0 | 2 | 2 | 3 | 1 | 2 | 2 | 30 | 4 | 4 | 3 |
| SE | F | 119 | Driver COPD °I-III | 52.5 | 2 | 2 | 2 | 1 | 1 | 0 | 40 | 0 | 0 | 0 |
| SS | M | 104 | Welder COPD °I-III | 39.9 | 2 | 0 | 0 | 2 | 2 | 2 | 15 | 2 | 2 | 2 |
| VA | M | 121 | Welder COPD °I-III | 49.8 | 2 | 2 | 3 | 1 | 1 | 1 | 30 | 3 | 3 | 3 |
| WM | M | 9 | Driver COPD °I-III | 48.2 | 2 | 2 | 2 | -1 | 0 | -1 | 25 | 3 | 3 | 3 |
| WT | M | 69 | Welder COPD °I-III | 47.5 | 2 | 2 | 0 | 1 | 1 | 1 | 60 | 2 | 2 | -1 |
| ZJ | M | 78 | Welder COPD °I-III | 60.2 | 2 | 2 | 2 | 1 | 1 | 2 | 35 | 0 | 0 | 2 |
| ZS | M | 127 | Driver COPD °I-III | 27.4 | 2 | 2 | 0 | 2 | 4 | 4 | 9 | 3 | 5 | 4 |
| BH | M | 2 | Driver COPD °I-III | 46.4 | 3 | 2 | 2 | 0 | 0 | -1 | 25 | 3 | 0 | 0 |
| CP | M | 100 | Welder COPD °I-III | 70.8 | 3 | 3 | 3 | 0 | 1 | 0 | 70 | 0 | 0 | 0 |
| FW | M | 132 | Driver COPD °I-III | 65.3 | 3 | 3 | 3 | 0 | 0 | 1 | 40 | 3 | 3 | 3 |
| BW | M | 38 | Driver COPD °I-III | 68.5 | 3 | 3 | 3 | 1 | 1 | 1 | 60 | 4 | 4 | 3 |
| KE | M | 108 | Welder COPD °I-III | 51.5 | 3 | 4 | 4 | 1 | 2 | 1 | 45 | 4 | 4 | 4 |
| KK | M | 73 | Welder COPD °I-III | 55.5 | 3 | 3 | 3 | 1 | 1 | 3 | 25 | 1 | 1 | 1 |
| LH | M | 80 | Welder COPD °I-III | 69.8 | 3 | 3 | n.d | 1 | 1 | n.d. | 70 | 3 | 3 | 3 |
| MC | F | 111 | Driver COPD °I-III | 62.2 | 3 | 3 | 4 | 0 | 0 | 0 | 40 | 0 | 0 | 0 |
| NP | M | 70 | Driver COPD °I-III | 64.2 | 3 | 3 | 4 | 1 | 1 | 2 | 100 | 0 | 0 | 0 |
| SCHB | M | 146 | Driver COPD °I-III | 57.8 | 3 | 3 | 3 | 2 | 2 | 2 | 60 | 3 | 4 | 3 |
| TG | M | 129 | Driver COPD °I-III | 62.5 | 3 | 2 | 2 | 1 | 2 | 2 | 50 | 2 | 2 | 2 |
| WJ | M | 63 | Driver COPD °I-III | 55.8 | 3 | 3 | 3 | 1 | 1 | 1 | 40 | 0 | 0 | 0 |
| HOH | M | 48 | Driver COPD °I-III | 70.8 | 4 | 3 | 3 | -1 | 0 | 2 | 100 | 0 | 0 | 0 |
| JR | M | 110 | Driver COPD °I-III | 55.3 | 4 | 3 | n.d | 1 | 1 | n.d. | 40 | 4 | 1 | n.d. |
| | | n 49 | Age (yrs, mean) | 55.5 | | | | | | | PY (mean) 38.7 | | | |

Fig. 3 (cont.)

D)

| | | Healthy | GOLD at risk | GOLD I | | GOLD II | | GOLD III | | GOLD IV | | | Total |
|---|---|---|---|---|---|---|---|---|---|---|---|---|---|
| No. of participants | | 16 | 55 | 9 | | 26 | | 12 | | 2 | | | 120 |
| Age | | 36 ± 12.2 | 50 ± 9.5 | 56 ± 10.4 | p=0.083 | 52 ± 9.0 | p=0.304 | 61 ± 7.6 | p=0.0004 | 63 ± 11.0 | p=0.054 | | |
| Packyears | | 0 | 32 ± 26 | 29 ± 15 | p=0.729 | 33 ± 15 | p=0.815 | 53 ± 21 | p=0.004 | 70 ± 42 | p=0.022 | | |
| Gender | F | 7 (44%) | 8 (15%) | 1 (11%) | | 3 (12%) | | 1 (88%) | | 0 | | p=0.931 | 20 (17%) |
| | M | 9 (56%) | 47 (85%) | 8 (89%) | | 23 (88%) | | 11 (92%) | | 2 (100%) | | | 100 (83%) |
| Occupation | Control (healthy) | 16 | 0 | 0 | | 0 | | 0 | | 0 | | | 16 (13%) |
| | Taxi/Bus driver | 0 | 31 (56%) | 7 (78%) | | 16 (62%) | | 8 (67%) | | 2 (100%) | | p=0.594 | 64 (53%) |
| | Welder | 0 | 24 (44%) | 2 (22%) | | 10 (38%) | | 4 (33%) | | 0 | | | 40 (33%) |
| Symptoms of chronic bronchitis (Cough & Phlegm) | No symptoms | 16 (100%) | 0 | 0 | | 0 | | 0 | | 0 | | | 16 (13%) |
| | frequently dry | 0 | 24 (44%) | 2 (22%) | | 4 (15%) | | 4 (33%) | | 1 (50%) | | p=0.054 | 35 (29%) |
| | productive | 0 | 16 (29%) | 5 (56%) | | 18 (69%) | | 7 (58%) | | 1 (50%) | | | 47 (39%) |
| | discolored | 0 | 15 (27%) | 2 (22%) | | 4 (15%) | | 1 (8%) | | 0 | | | 22 (18%) |
| Changes between baseline and visit 3 | | | | | | | | | | | | | |
| GOLD stage | deterioration | 0 | 7 (13%) | 1 (11%) | | 3 (12%) | | 3 (25%) | | 0 | | | 14 (12%) |
| | stable | 16 (100%) | 48 (87%) | 3 (33%) | | 18 (69%) | | 7 (58%) | | 1 (50%) | | p=0.001 | 93 (78%) |
| | improvement | 0 | 0 | 5 (56%) | | 5 (19%) | | 2 (17%) | | 1 (50%) | | | 13 (11%) |
| Cough & Phlegm | deterioration | 0 | 11 (20%) | 2 (22%) | | 9 (35%) | | 4 (33%) | | 1 (50%) | | | 27 (23%) |
| | stable | 16 (100%) | 26 (47%) | 5 (56%) | | 12 (46%) | | 7 (58%) | | 0 | | p=0.058 | 66 (55%) |
| | improvement | 0 | 18 (33%) | 2 (22%) | | 5 (19%) | | 1 (8%) | | 1 (50%) | | | 27 (23%) |
| Exacerbations (month 1-12) | yes | 0 | 12 (22%) | 3 (33%) | | 4 (15%) | | 5 (42%) | | 1 (50%) | | p=0.308 | 25 (21%) |
| | no | 16 (100%) | 43 (78%) | 6 (67%) | | 22 (85%) | | 7 (58%) | | 1 (50%) | | | 95 (79%) |
| Exacerbations (month 12-36) | yes | 0 | 10 (18%) | 3 (33%) | | 14 (54%) | | 5 (42%) | | 0 | | p=0.008 | 32 (27%) |
| | no | 16 (100%) | 45 (82%) | 6 (67%) | | 12 (46%) | | 7 (58%) | | 2 (100%) | | | 88 (73%) |

A)

B)

C)

D)

A)

B)

c)

D)

E)

F)

G)

Figure 5:
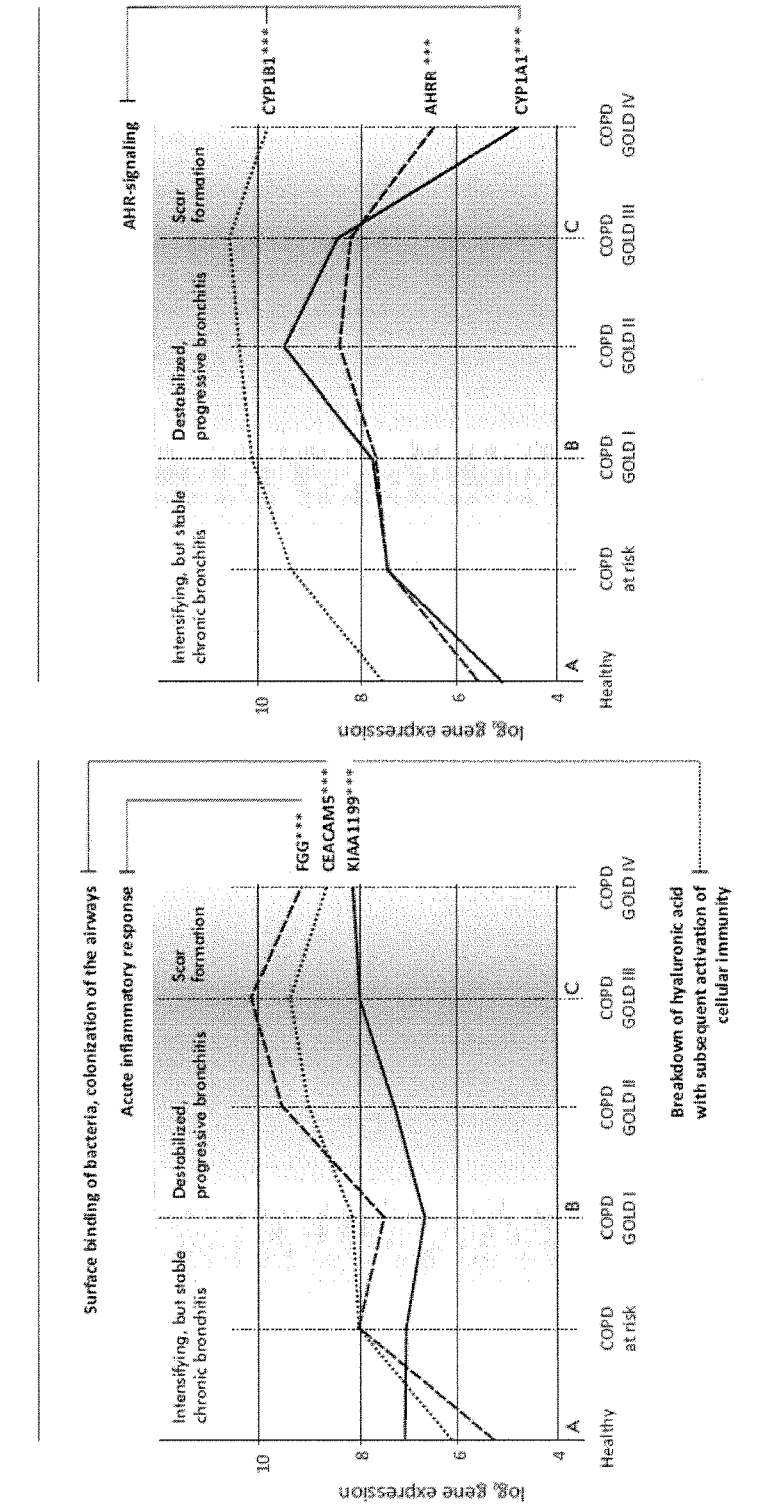
Figure 5:
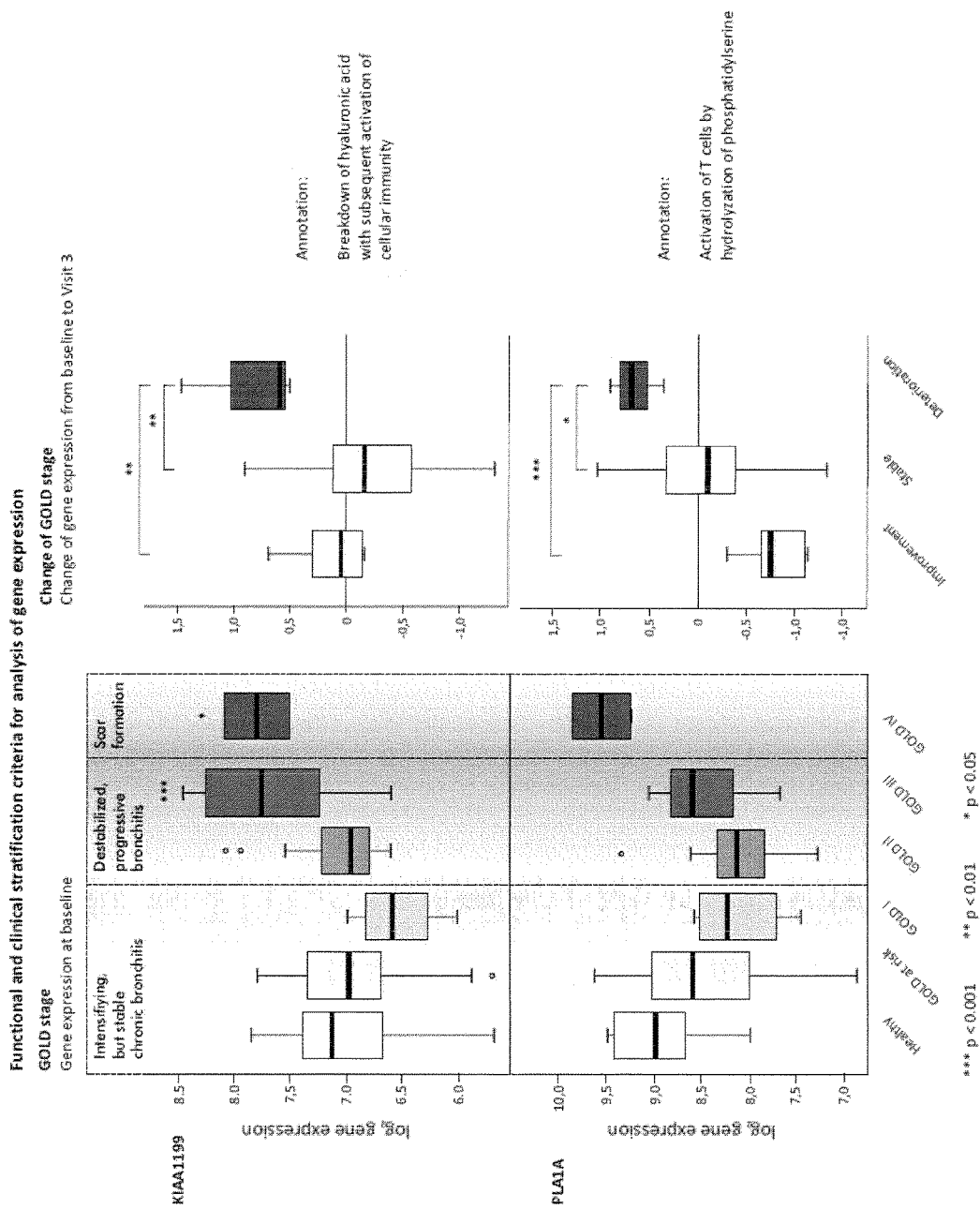
Figure 5:
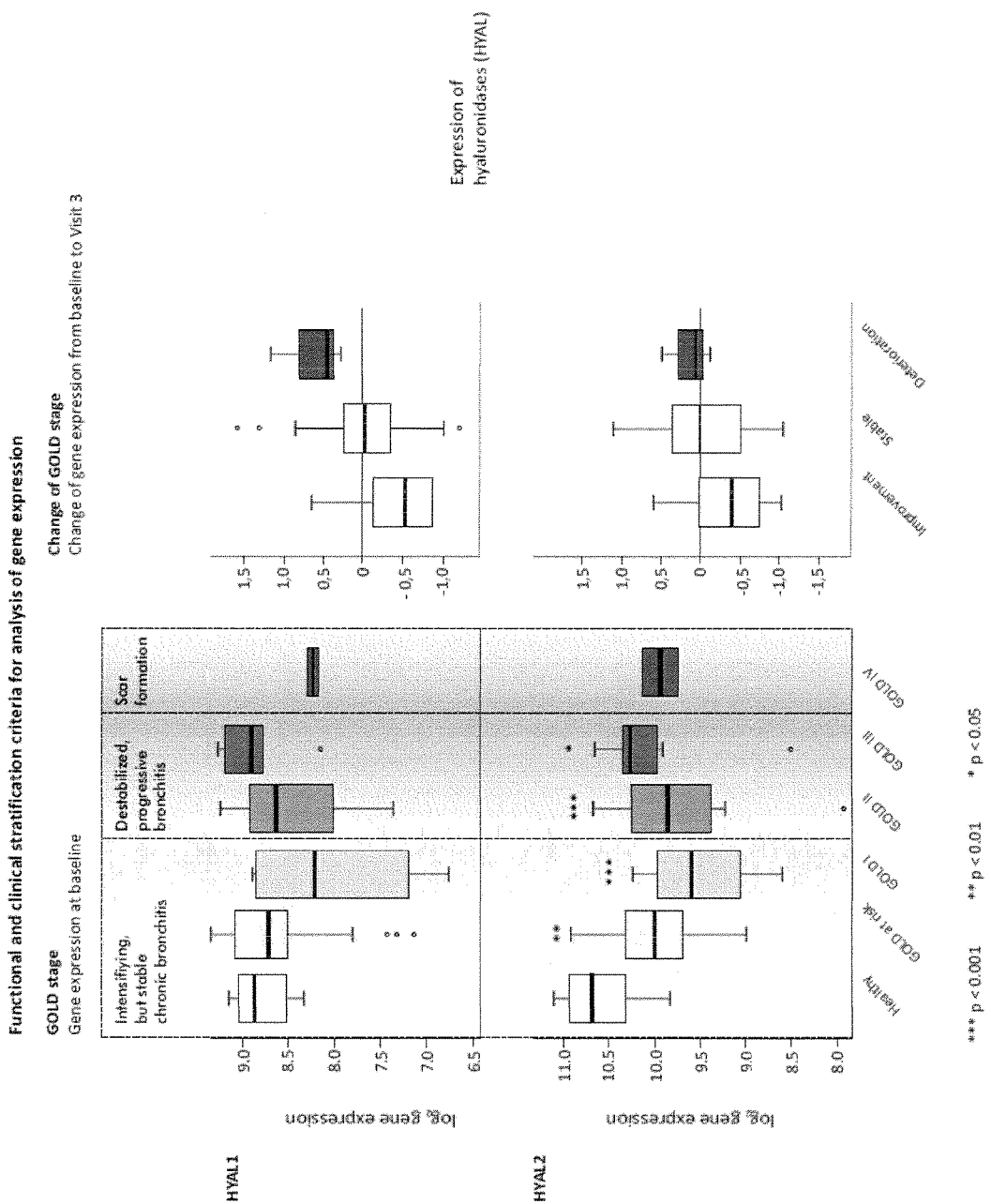
Figure 5:
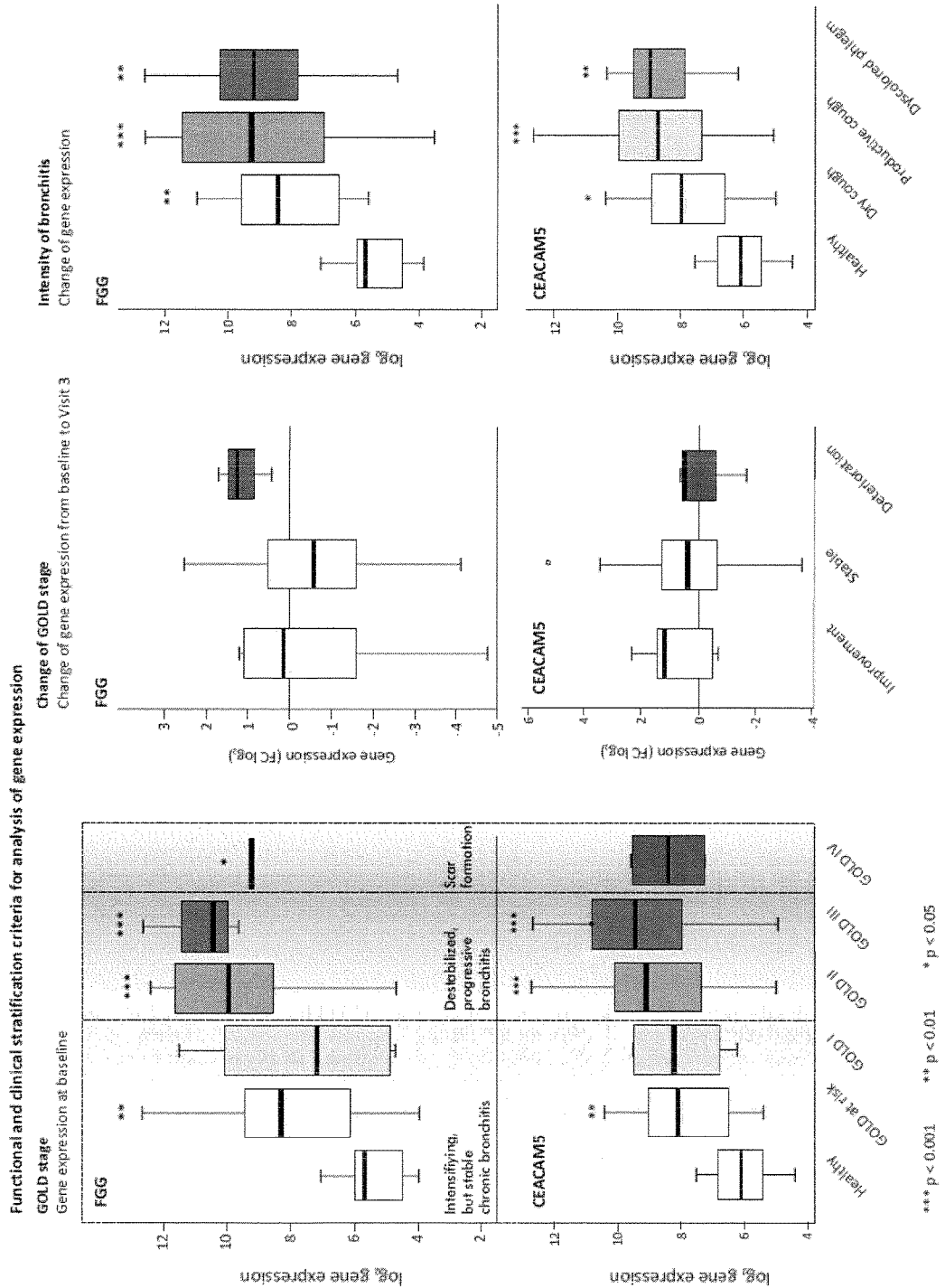
Figure 5:
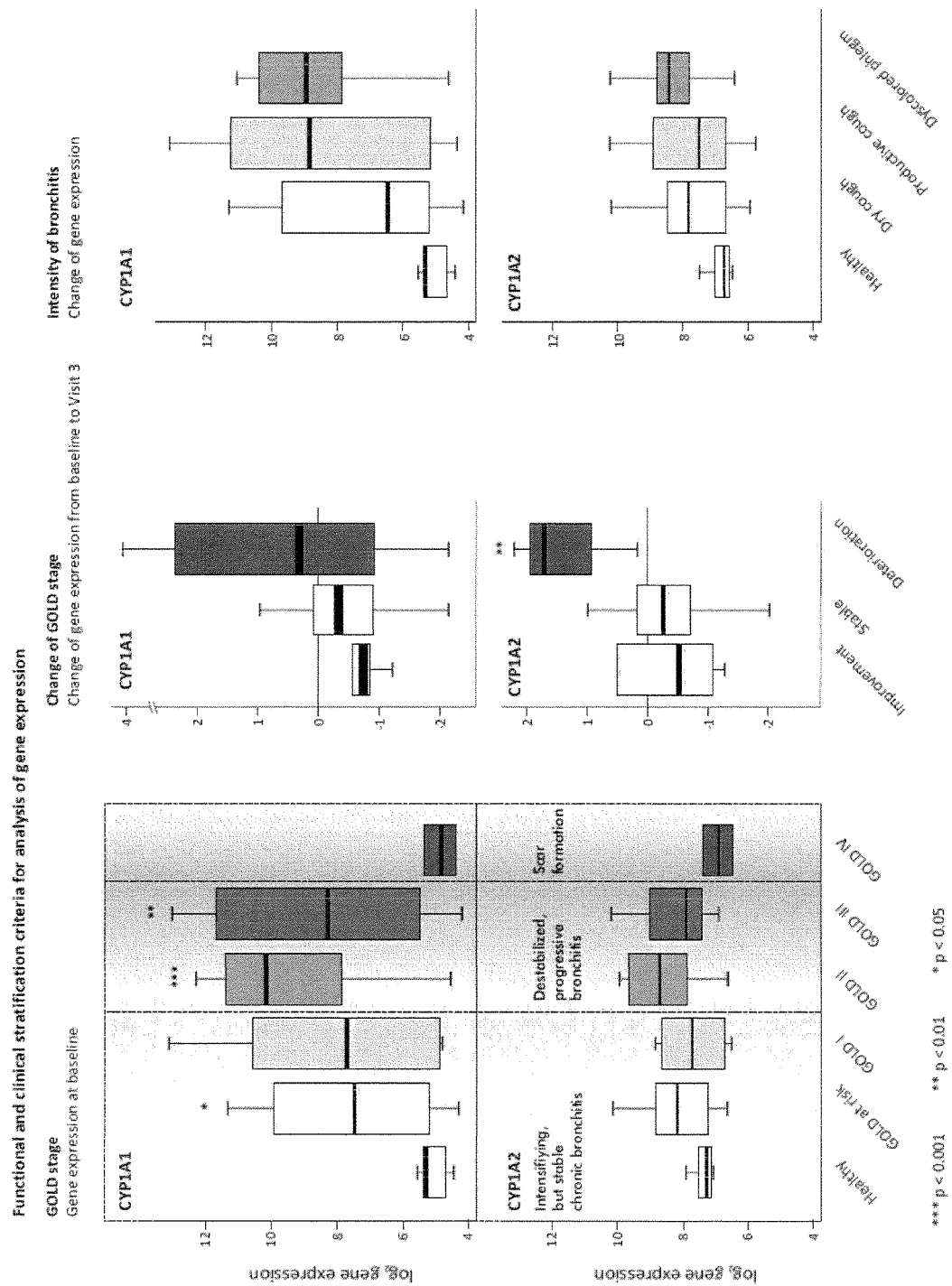
Figure 5:
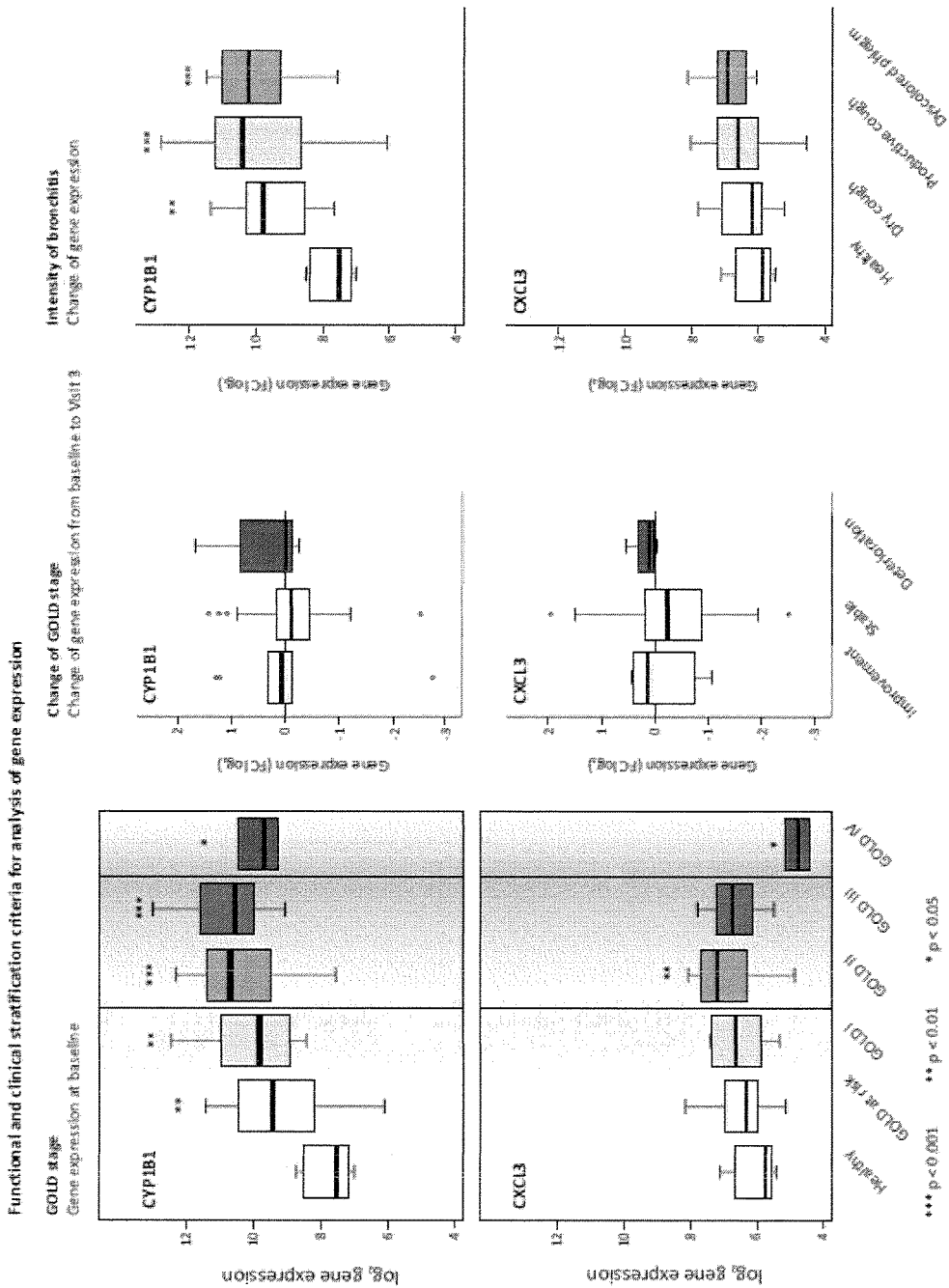
Figure 5:
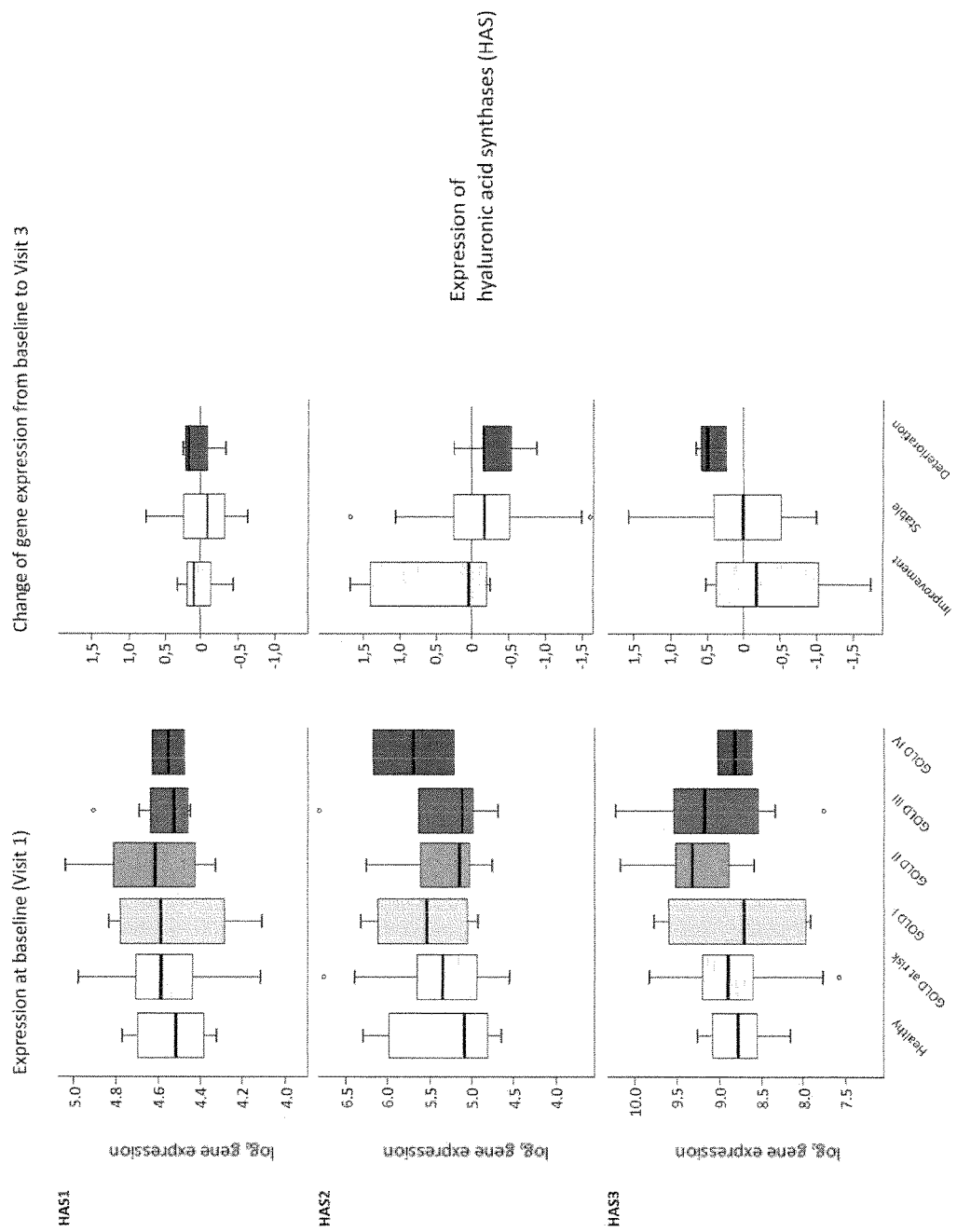

Fig. 5 (cont.)
H)
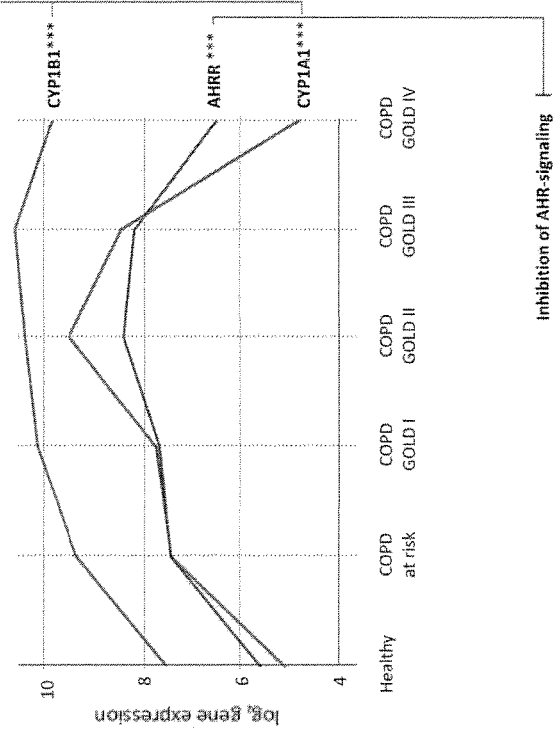
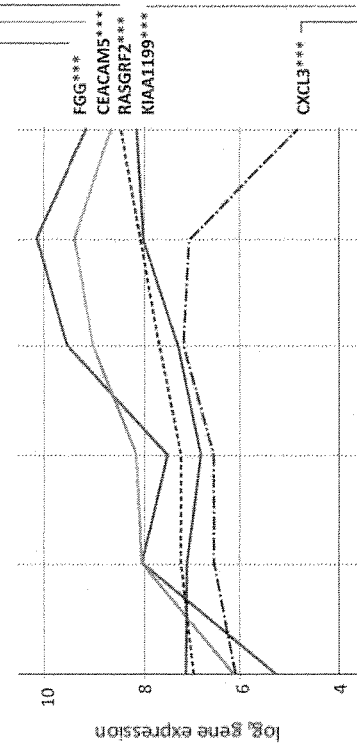

A)

B)

c)

D)

E)

Figure 8:
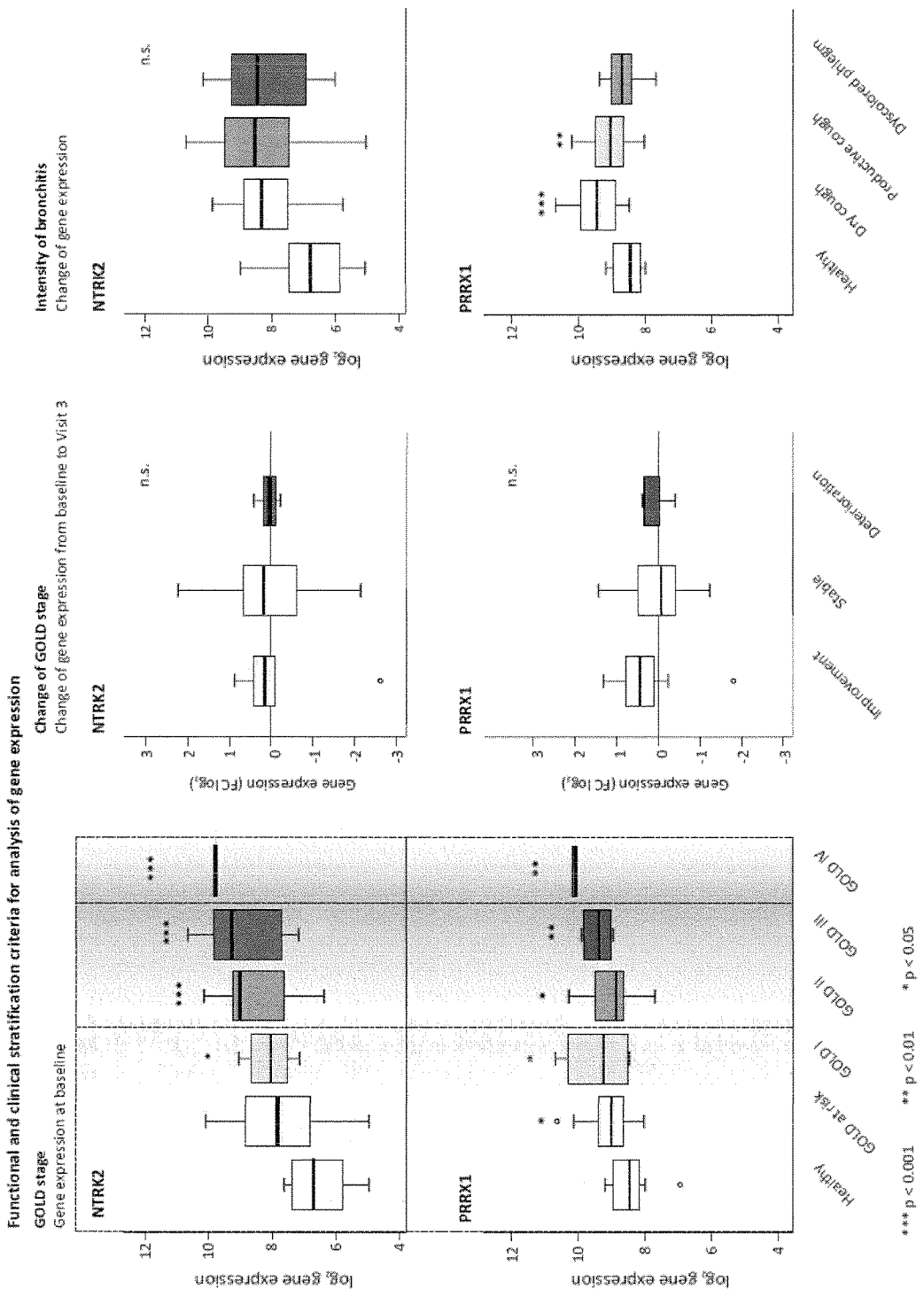
Figure 8:
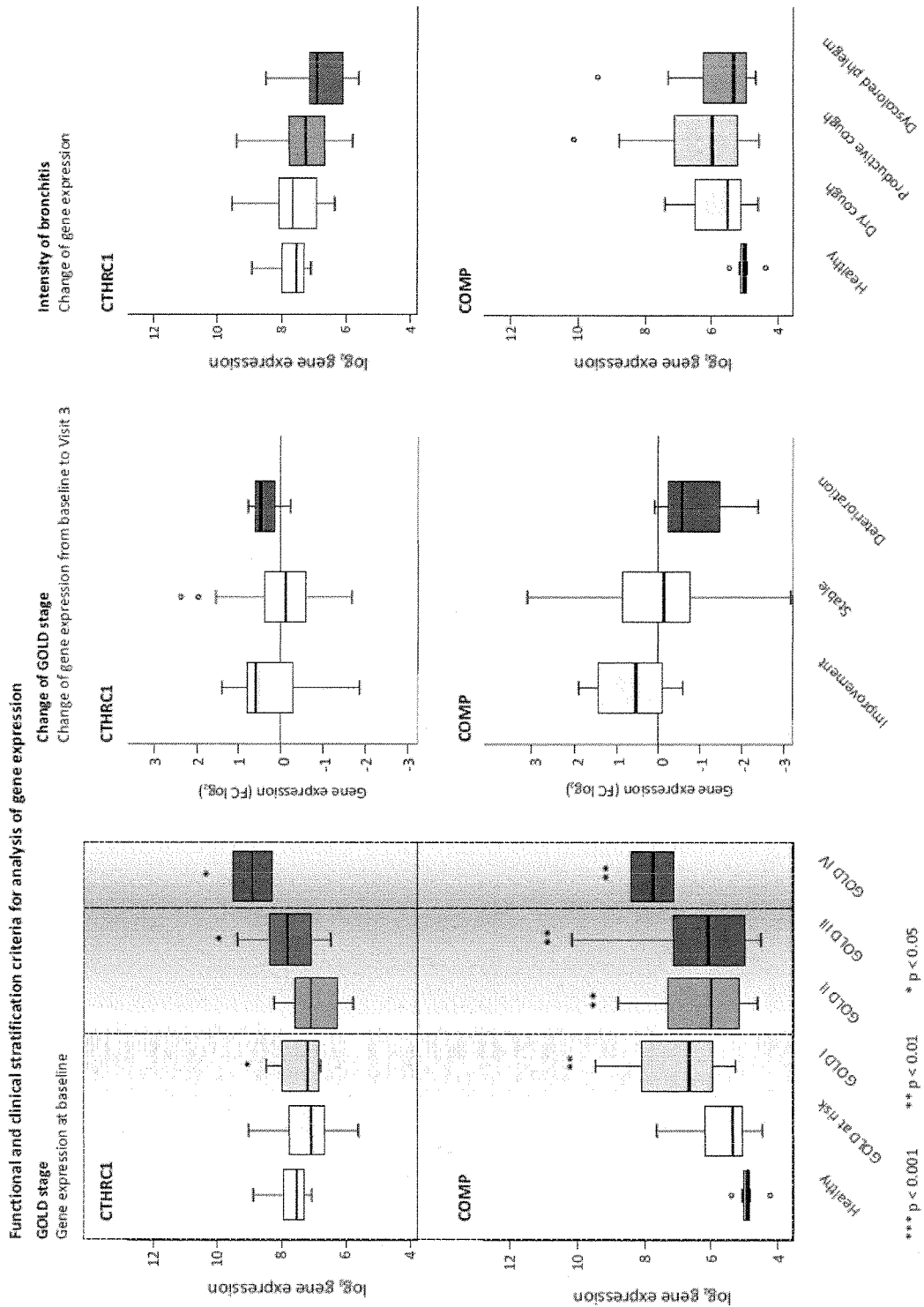
Figure 8:
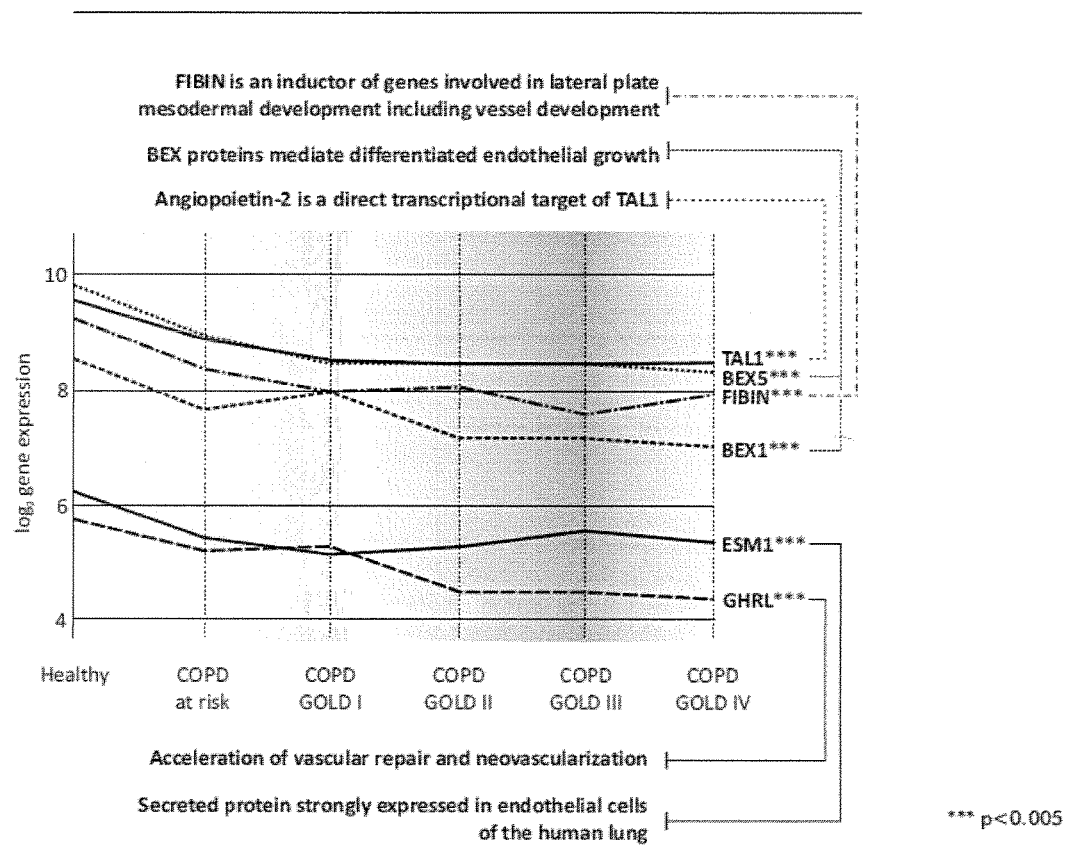

Fig. 8
A)
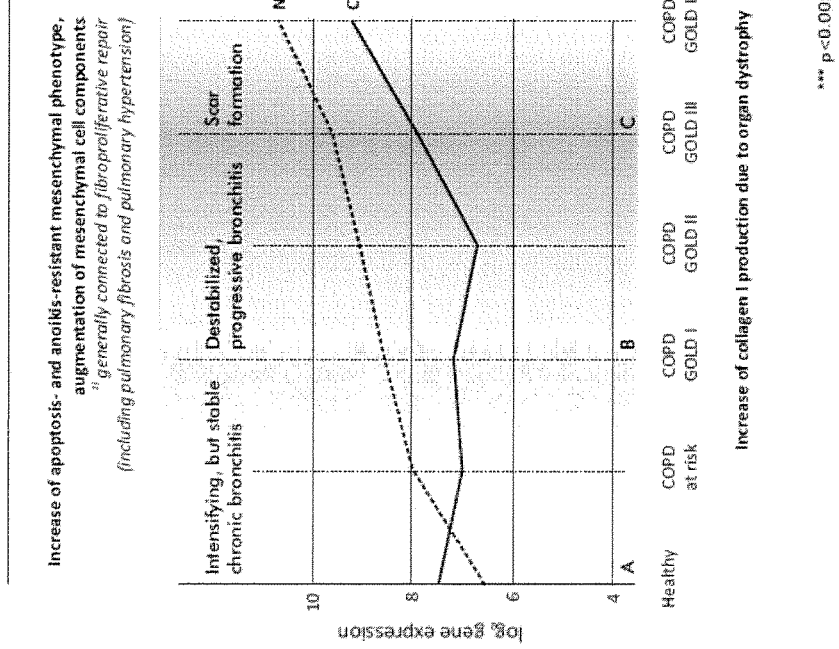
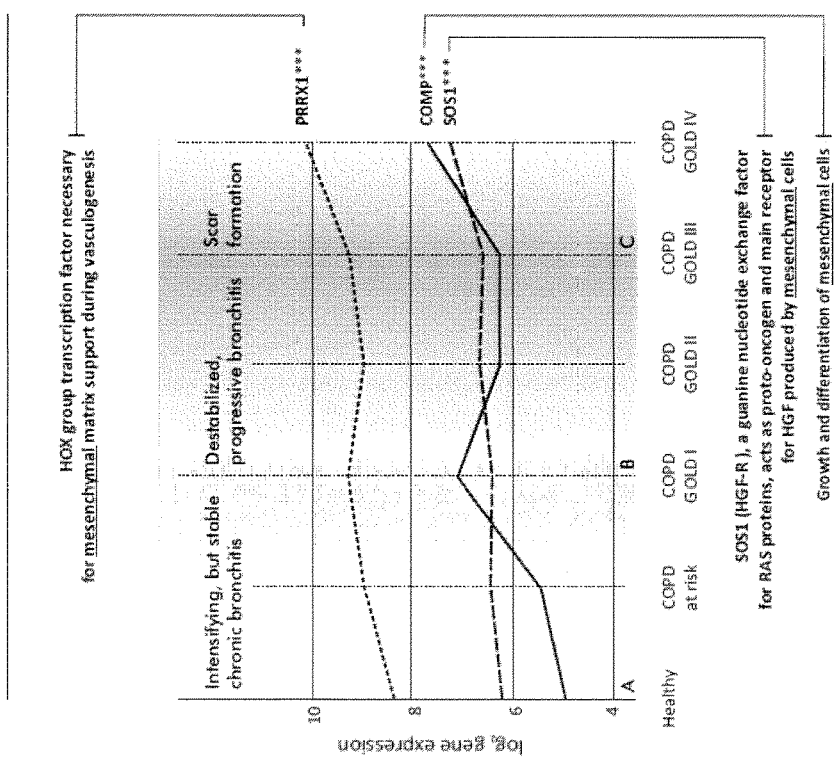

B)

c)

D)

```
                            SEQUENCE LISTING

<160> NUMBER OF SEQ ID NOS: 59

<210> SEQ ID NO 1
<211> LENGTH: 2471
<212> TYPE: DNA
<213> ORGANISM: Homo sapiens

<400> SEQUENCE: 1
agaaagcgag cagccaccca gctccccgcc accgccatgg tccccgacac cgcctgcgtt      60
cttctgctca ccctggctgc cctcggcgcg tccggacagg gccagagccc gttgggctca     120
gacctgggcc cgcagatgct tcgggaactg caggaaacca acgcggcgct gcaggacgtg     180
cgggagctgc tgcggcagca ggtcagggag atcacgttcc tgaaaaacac ggtgatggag     240
tgtgacgcgt gcgggatgca gcagtcagta cgcaccggcc tacccagcgt gcggcccctg     300
ctccactgcg cgcccggctt ctgcttcccc ggcgtggcct gcatccagac ggagagcggc     360
gcgcgctgcg gccctgccc cgcgggcttc acgggcaacg gctcgcactg caccgacgtc     420
aacgagtgca acgccaccc ctgcttcccc cgagtccgct gtatcaacac cagcccgggg     480
ttccgctgcg aggcttgccc gccggggtac agcggcccca cccaccaggg cgtggggctg     540
gctttcgcca aggccaacaa gcaggtttgc acggacatca cgagtgtga cccgggcaa      600 cataactgcg tccccaactc cgtgtgcatc aacacccggg gctccttcca gtgcggcccg     660
tgccagcccg gcttcgtggg cgaccaggcg tccggctgcc agcggcgcgc acagcgcttc     720
tgccccgacg gctcgcccag cgagtgccac gagcatgcag actgcgtcct agagcgcgat     780
ggctcgcggt cgtgcgtgtg tgccgttggc tgggccggca acgggatcct ctgtggtcgc     840
gacactgacc tagacggctt cccggacgag aagctgcgct gcccggagcg ccagtgccgt     900
aaggacaact gcgtgactgt gcccaactca gggcaggagg atgtggaccg cgatggcatc     960
ggagacgcct gcgatccgga tgccgacggg gacggggtcc ccaatgaaaa ggacaactgc    1020
ccgctggtgc ggaacccaga ccagcgcaac acggacgagg acaagtgggg cgatgcgtgc    1080
gacaactgcc ggtcccagaa gaacgacgac caaaaggaca cagaccagga cggccggggc    1140
gatgcgtgcg acgacgacat cgacggcgac cggatccgca accaggccga caactgccct    1200
agggtaccca actcagacca gaaggacagt gatggcgatg gtataggga tgcctgtgac    1260 aactgtcccc agaagagcaa cccggatcag gcggatgtgg accacgactt tgtgggagat    1320
gcttgtgaca gcgatcaaga ccaggatgga gacggacatc aggactctcg ggacaactgt    1380
cccacggtgc ctaacagtgc ccaggaggac tcagaccacg atggcagggg tgatgcctgc    1440
gacgacgacg acgacaatga cggagtccct gacagtcggg acaactgccg cctggtgcct    1500
```

| | |
|---|---|
| aaccccggcc aggaggacgc ggacagggac ggcgtgggcg acgtgtgcca ggacgacttt | 1560 |
| gatgcagaca aggtggtaga caagatcgac gtgtgtccgg agaacgctga agtcacgctc | 1620 |
| accgacttca gggccttcca gacagtcgtg ctggacccgg agggtgacgc gcagattgac | 1680 |
| cccaactggg tggtgctcaa ccagggaagg gagatcgtgc agacaatgaa cagcgaccca | 1740 |
| ggcctggctg tgggttacac tgccttcaat ggcgtggact tcgagggcac gttccatgtg | 1800 |
| aacacggtca cggatgacga ctatgcgggc ttcatctttg gctaccagga cagctccagc | 1860 |
| ttctacgtgg tcatgtggaa gcagatggag caaacgtatt ggcaggcgaa ccccttccgt | 1920 |
| gctgtggccg agcctggcat ccaactcaag gctgtgaagt cttccacagg ccccggggaa | 1980 |
| cagctgcgga acgtctgtg gcatacagga gacacagagt cccaggtgcg gctgctgtgg | 2040 |
| aaggacccgc gaaacgtggg ttggaaggac aagaagtcct atcgttggtt cctgcagcac | 2100 |
| cggcccaag tgggctacat cagggtgcga ttctatgagg gccctgagct ggtggccgac | 2160 |
| agcaacgtgg tcttggacac aaccatgcgg ggtggccgcc tgggggtctt ctgcttctcc | 2220 |
| caggagaaca tcatctgggc caacctgcgt taccgctgca atgacaccat cccagaggac | 2280 |
| tatgagaccc atcagctgcg gcaagcctag ggaccagggt gaggacccgc cggatgacag | 2340 |
| ccaccctcac cgcggctgga tggggctct gcacccagcc caaggggtg gccgtcctga | 2400 |
| gggggaagtg agaagggctc agagaggaca aaataaagtg tgtgtgcagg gaaaaaaaa | 2460 |
| aaaaaaaaa a | 2471 |

<210> SEQ ID NO 2
<211> LENGTH: 5160
<212> TYPE: DNA
<213> ORGANISM: Homo sapiens

<400> SEQUENCE: 2

| | |
|---|---|
| aaaacccgga ggagcgggat ggcgcgcttt gactctggag tgggagtggg agcgagcgct | 60 |
| tctgcgactc cagttgtgag agccgcaagg gcatgggaat tgacgccact caccgacccc | 120 |
| cagtctcaat ctcaacgctg tgaggaaacc tcgactttgc caggtcccca agggcagcgg | 180 |
| ggctcggcga gcgaggcacc cttctccgtc cccatcccaa tccaagcgct cctggcactg | 240 |
| acgacgccaa gagactcgag tgggagttaa agcttccagt gagggcagca ggtgtccagg | 300 |
| ccgggcctgc gggttcctgt tgacgtcttg ccctaggcaa aggtcccagt tccttctcgg | 360 |
| agccggctgt cccgcgccac tggaaaccgc acctccccgc agcatgggca ccagcctcag | 420 |
| cccgaacgac ccttggccgc taaacccgct gtccatccag cagaccacgc tcctgctact | 480 |
| cctgtcggtg ctggccactg tgcatgtggg ccagcggctg ctgaggcaac ggaggcggca | 540 |
| gctccggtcc gcgcccccgg gcccgtttgc gtggccactg atcggaaacg cggcggcggt | 600 |
| gggccaggcg gctcacctct cgttcgctcg cctggcgcgg cgctacggcg acgttttcca | 660 |
| gatccgcctg ggcagctgcc ccatagtggt gctgaatggc gagcgcgcca tccaccaggc | 720 |
| cctggtgcag cagggctcgg ccttcgccga ccggccggcc ttcgcctcct tccgtgtggt | 780 |
| gtccggcggc cgcagcatgg ctttcggcca ctactcggag cactggaagg tgcagcggcg | 840 |
| cgcagcccac agcatgatgc gcaacttctt cacgcgccag ccgcgcagcc gccaagtcct | 900 |
| cgagggccac gtgctgagcg aggcgcgcga gctggtggcg ctgctggtgc gcggcagcgc | 960 |
| ggacggcgcc ttcctcgacc cgaggccgct gaccgtcgtg gccgtggcca acgtcatgag | 1020 |
| tgccgtgtgt ttcggctgcc gctacagcca cgacgacccc gagttccgtg agctgctcag | 1080 |
| ccacaacgaa gagttcgggc gcacggtggg cgcgggcagc ctggtggacg tgatgccctg | 1140 |

```
gctgcagtac ttccccaacc cggtgcgcac cgttttccgc gaattcgagc agctcaaccg    1200
caacttcagc aacttcatcc tggacaagtt cttgaggcac tgcgaaagcc ttcggcccgg    1260
ggccgccccc cgcgacatga tggacgcctt tatcctctct gcggaaaaga aggcggccgg    1320
ggactcgcac ggtggtggcg cgcggctgga tttggagaac gtaccggcca ctatcactga    1380
catcttcggc gccagccagg acaccctgtc caccgcgctg cagtggctgc tcctcctctt    1440
caccaggtat cctgatgtgc agactcgagt gcaggcagaa ttggatcagg tcgtggggag    1500
ggaccgtctg ccttgtatgg gtgaccagcc caacctgccc tatgtcctgg ccttccttta    1560
tgaagccatg cgcttctcca gctttgtgcc tgtcactatt cctcatgcca ccactgccaa    1620
cacctctgtc ttgggctacc acattcccaa ggacactgtg ttttttgtca accagtggtc    1680
tgtgaatcat gacccactga agtggcctaa cccggagaac tttgatccag ctcgattctt    1740
ggacaaggat ggcctcatca acaaggacct gaccagcaga gtgatgattt tttcagtggg    1800
caaaaggcgg tgcattggcg aagaactttc taagatgcag cttttttctct tcatctccat    1860 cctggctcac cagtgcgatt tcagggccaa cccaaatgag cctgcgaaaa tgaatttcag    1920
ttatggtcta accattaaac ccaagtcatt taaagtcaat gtcactctca gagagtccat    1980
ggagctcctt gatagtgctg tccaaaattt acaagccaag gaaacttgcc aataagaagc    2040
aagaggcaag ctgaaatttt agaaatattc acatcttcgg agatgaggag taaaattcag    2100 ttttttttcca gttcctcttt tgtgctgctt ctcaattagc gtttaaggtg agcataaatc    2160
aactgtccat caggtgaggt gtgctccata cccagcggtt cttcatgagt agtgggctat    2220
gcaggagctt ctgggagatt ttttttgagtc aaagacttaa agggcccaat gaattattat    2280
atacatactg catcttggtt atttctgaag gtagcattct ttggagttaa atgcacata     2340 tagacacata cacccaaaca cttacaccaa actactgaat gaagcagtat tttggtaacc    2400
aggccatttt tggtgggaat ccaagattgg tctcccatat gcagaaatag acaaaaagta    2460
tattaaacaa gtttcagag tatattgttg aagagacaga acaagtaat ttcagtgtaa     2520 agtgtgtgat tgaaggtgat aagggaaaag ataaagacca gaaattccct tttcacctt    2580 tcaggaaaat aacttagact ctagtattta tgggtggatt tatcctttg ccttctggta    2640 tacttcctta cttttaagga taaatcataa agtcagttgc tcaaaagaa atcaatagtt    2700 gaattagtga gtatagtggg gttccatgag ttatcatgaa ttttaaagta tgcattatta    2760
aattgtaaaa ctccaaggtg atgttgtacc tctttgctt gccaaagtac agaatttgaa     2820
ttatcagcaa agaaaaaaaa aaagccagc caagctttaa attatgtgac cataatgtac    2880
tgatttcagt aagtctcata ggttaaaaaa aaagtcacc aaatagtgtg aaatatatta     2940
cttaactgtc cgtaagcagt atattagtat tatcttgttc aggaaaaggt tgaataatat    3000
atgccttgta taatattgaa aattgaaaag tacaactaac gcaaccaagt gtgctaaaaa    3060
tgagcttgat taaatcaacc acctattttt gacatgaaa tgaagcaggg tttcttttct    3120
tcactcaaat tttggcgaat ctcaaaatta gatcctaaga tgtgttctta ttttttataac   3180 atctttattg aaattctatt tataatacag aatcttgttt tgaaaataac ctaattaata    3240
tattaaaatt ccaaattcat ggcatgctta aattttaact aaattttaaa gccattctga    3300
ttattgagtt ccagttgaag ttagtggaaa tctgaacatt ctcctgtgga aggcagagaa    3360
atctaagctg tgtctgccca atgaataatg gaaaatgcca tgaattacct ggatgttctt    3420
tttacgaggt gacaagagtt ggggacagaa ctcccattac aactgaccaa gtttctcttc    3480
```

-continued

| | |
|---|---|
| tagatgattt tttgaaagtt aacattaatg cctgctttt ggaaagtcag aatcagaaga | 3540 |
| tagtcttgga agctgtttgg aaaagacagt ggagatgagg tcagttgtgt tttttaagat | 3600 |
| ggcaattact ttggtagctg ggaaagcata aagctcaaat gaaatgtatg cattcacatt | 3660 |
| tagaaaagtg aattgaagtt tcaagtttta aagttcattg caattaaact tccaaagaaa | 3720 |
| gttctacagt gtcctaagtg ctaagtgctt attacatttt attaagcttt ttggaatctt | 3780 |
| tgtaccaaaa ttttaaaaaa gggagttttt gatagttgtg tgtatgtgtg tgtgggtgg | 3840 |
| ggggatggta agagaaaaga gagaaacact gaaaagaagg aaagatggtt aaacattttc | 3900 |
| ccactcattc tgaattaatt aatttggagc acaaaattca aagcatggac atttagaaga | 3960 |
| aagatgtttg gcgtagcaga gttaaatctc aaataggcta ttaaaaaagt ctacaacata | 4020 |
| gcagatctgt tttgtggttt ggaatattaa aaaacttcat gtaatttat tttaaaattt | 4080 |
| catagctgta cttcttgaat ataaaaaatc atgccagtat ttttaaaggc attagagtca | 4140 |
| actacacaaa gcaggcttgc ccagtacatt taaattttt ggcacttgcc attccaaaat | 4200 |
| attatgcccc accaaggctg agacagtgaa tttgggctgc tgtagcctat ttttttagat | 4260 |
| tgagaaatgt gtagctgcaa aaataatcat gaaccaatct ggatgcctca ttatgtcaac | 4320 |
| caggtccaga tgtgctataa tctgttttta cgtatgtagg cccagtcgtc atcagatgct | 4380 |
| tgcggcaaaa ggaaagctgt gtttatatgg aagaaagtaa ggtgcttgga gtttacctgg | 4440 |
| cttatttaat atgcttataa cctagttaaa gaaggaaaa gaaaacaaaa aacgaatgaa | 4500 |
| aataactgaa tttggaggct ggagtaatca gattactgct ttaatcagaa accctcattg | 4560 |
| tgtttctacc ggagagagaa tgtatttgct gacaaccatt aaagtcagaa gttttactcc | 4620 |
| aggttattgc aataaagtat aatgtttatt aaatgcttca tttgtatgtc aaagctttga | 4680 |
| ctctataagc aaattgcttt tttccaaaac aaaaagatgt ctcaggtttg ttttgtgaat | 4740 |
| tttctaaaag ctttcatgtc ccagaactta gcctttacct gtgaagtgtt actacagcct | 4800 |
| taatattttc ctagtagatc tatattagat caaatagttg catagcagta tatgttaatt | 4860 |
| tgtgtgtttt tagctgtgac acaactgtgt gattaaaagg tatactttag tagacattta | 4920 |
| taactcaagg ataccttctt atttaatctt ttcttatttt tgtactttat catgaatgct | 4980 |
| tttagtgtgt gcataatagc tacagtgcat agttgtagac aaagtacatt ctggggaaac | 5040 |
| aacatttata tgtagccttt actgtttgat ataccaaatt aaaaaaaaat tgtatctcat | 5100 |
| tacttatact gggacaccat taccaaaata ataaaaatca ctttcataat cttgaaaaaa | 5160 |

<210> SEQ ID NO 3
<211> LENGTH: 2608
<212> TYPE: DNA
<213> ORGANISM: Homo sapiens

<400> SEQUENCE: 3

| | |
|---|---|
| ctcaccctga aggtgacagt tccttggaac cttccctgat ccttgtgatc ccaggctcca | 60 |
| agagtccacc cttcccagct cagctcagta cctcagccac ctccaagatc cctacactga | 120 |
| tcatgctttt cccaatctcc atgtcggcca cggagtttct tctggcctct gtcatcttct | 180 |
| gtctggtatt ctgggtaatc agggcctcaa gacctcaggt ccccaaaggc ctgaagaatc | 240 |
| caccagggcc atggggctgg cctctgattg ggcacatgct gaccctggga aagaacccgc | 300 |
| acctggcact gtcaaggatg agccagcagt atgggacgt gctgcagatc cgaattggct | 360 |
| ccacacccgt ggtggtgctg agcggcctgg acaccatccg gcaggcctg gtgcggcagg | 420 |
| gcgatgattt caagggccgg cccgacctct acaccttcac cctcatcagt aatggtcaga | 480 |

```
gcatgtcctt cagcccagac tctggaccag tgtgggctgc ccgccggcgc ctggcccaga    540
atggcctgaa aagtttctcc attgcctctg acccagcctc ctcaacctcc tgctacctgg    600
aagagcatgt gagcaaggag gctgaggtcc tgataagcac gttgcaggag ctgatggcag    660
ggcctgggca cttttaacccc tacaggtatg tggtggtatc agtgaccaat gtcatctgtg    720
ccatttgctt tggccggcgc tatgaccaca accaccaaga actgcttagc ctagtcaacc    780
tgaataataa tttcggggag gtggttggct ctggaaaccc agctgacttc atccctattc    840
ttcgctacct acccaacccT tccctgaatg ccttcaagga cctgaatgag aagttctaca    900
gcttcatgca agatggtc aaggagcact acaaaacctt tgagaagggc cacatccggg    960
acatcacaga cagcctgatt gagcactgtc aggagaagca gctggatgag aacgccaatg    1020
tccagctgtc agatgagaag atcattaaca tcgtcttgga cctctttgga gctgggtttg    1080
acacagtcac aactgctatc tcctggagcc tcatgtattt ggtgatgaac cccagggtac    1140
agagaaagat ccaagaggag ctagacacag tgattggcag gtcacggcgg ccccggctct    1200
ctgacagatc ccatctgccc tatatggagg ccttcatcct ggagaccttc cgacactctt    1260
ccttcgtccc cttcaccatc ccccacagca caacaagaga cacaagtttg aaaggctttt    1320
acatccccaa ggggcgttgt gtctttgtaa accagtggca gatcaaccat gaccagaagc    1380
tatgggtcaa cccatctgag ttcctacctg aacggtttct caccccctgat ggtgctatcg    1440 acaaggtgtt aagtgagaag gtgattatct ttggcatggg caagcggaag tgtatcggtg    1500
agaccattgc ccgctgggag gtcttttctct tcctggctat cctgctgcaa cgggtggaat    1560
tcagcgtgcc actgggcgtg aaggtggaca tgaccccccat ctatgggcta accatgaagc    1620
atgcctgctg tgagcacttc caaatgcagc tgcgctctta ggtgcttgag agccctgagg    1680
cctagactct gtctacctgg tctggttggg cagccagacc agcaggctgg cctatgtggt    1740
ctaaggttca gcctgaaaact catagacact gatctggctg cagttttgct atctgggctg    1800
tgggcaagcc taagggatcc tgcctgcccc taccctggac ttgcctctgc acaccctcca    1860
gagacaacag gtaaaacagg gccacataga tgctgatgga gccttcccaa gttgtgcttg    1920
agccaggagg cctgctaggg ttaggaggtc cttaggcctc tgagaagctc tgaagaactc    1980
tctggaagcc cctgggccca gtacctagct ggctctgtga gggtgctgac tggcttcagc    2040
aagttagaac tagccaaacc aggaccctgt ccaatctttg acaattggga gctgccaaga    2100
gtgaagggaa gagacagccc aggatactgg cacagaggta gtctcactgc ttgaactagg    2160
ctgagcaatc tgaccctatg ggtctaggac acagttcctg ggaacatcac attcctctgc    2220
ccttcctgca ggcaggaaca aacagggctg ccttctggcc ttgtaagacc cttattgctg    2280
tcctggaggg gctggggact tgtgtctgcg gggatcagag cgcacaggga gtgcacatat    2340
ccaggcacca ggactagggc tggagtgagg ggggggtatt tcaattacct tctattggtc    2400
tcccttctct acactcttgt aataaaatgt ctattttaa tgtttgtaca caacaatcct    2460
tctattctag cctgcattga gcttgcatgc ttgcataaga gcttaagaac cattgattta    2520
atgtaatagg gaaaattcta acccaggtat ccaaaaatgt gtaagaacaa ctacctgagc    2580
taaataaaga tattgttcag aaatccta                                      2608
```

<210> SEQ ID NO 4
<211> LENGTH: 1665
<212> TYPE: DNA
<213> ORGANISM: Homo sapiens

```
<400> SEQUENCE: 4
cttctggtaa ggaggccccg tgatcagctc cagccatttg cagtcctggc tatcccagga      60
gcttacataa agggacaatt ggagcctgag aggtgacagt gctgacacta caaggctcgg     120
agctccgggc actcagacat catgagttgg tccttgcacc cccggaattt aattctctac     180
ttctatgctc tttatttct ctcttcaaca tgtgtagcat atgttgctac cagagacaac      240
tgctgcatct tagatgaaag attcggtagt tattgtccaa ctacctgtgg cattgcagat     300
ttcctgtcta cttatcaaac caaagtagac aaggatctac agtctttgga agacatctta     360
catcaagttg aaaacaaaac atcagaagtc aaacagctga taaaagcaat ccaactcact     420
tataatcctg atgaatcatc aaaaccaaat atgatagacg ctgctacttt gaagtccagg     480
aaaatgttag aagaaattat gaaatatgaa gcatcgattt taacacatga ctcaagtatt     540
cgatatttgc aggaaatata taattcaaat aatcaaaaga ttgttaacct gaaagagaag     600
gtagcccagc ttgaagcaca gtgccaggaa ccttgcaaag acacggtgca atccatgat      660
atcactggga aagattgtca agacattgcc aataagggag ctaaacagag cgggctttac     720
tttattaaac ctctgaaagc taaccagcaa ttcttagtct actgtgaaat cgatgggtct     780
ggaaatggat ggactgtgtt tcagaagaga cttgatggca gtgtagattt caagaaaaac     840
tggattcaat ataagaagg atttggacat ctgtctccta ctggcacaac agaattttgg      900
ctgggaaatg agaagattca tttgataagc acacagtctg ccatcccata tgcattaaga     960
gtggaactgg aagactggaa tggcagaacc agtactgcag actatgccat gttcaaggtg    1020
ggacctgaag ctgacaagta ccgcctaaca tatgcctact cgctggtgg ggatgctgga    1080
gatgcctttg atggctttga ttttggcgat gatcctagtg acaagttttt cacatcccat    1140
aatggcatgc agttcagtac ctgggacaat gacaatgata gtttgaagg caactgtgct    1200
gaacaggatg gatctggttg gtggatgaac aagtgtcacg ctggccatct caatggagtt    1260
tattaccaag gtggcactta ctcaaaagca tctactccta tggttatga taatggcatt    1320
atttgggcca cttggaaaac ccggtggtat tccatgaaga aaaccactat gaagataatc    1380
ccattcaaca gactcacaat ggagaagga cagcaacacc acctgggggg agccaaacag    1440
gctggagacg tttaaaagac cgtttcaaaa gagatttact tttttaaagg actttatctg    1500
aacagagaga tataatattt ttcctattgg acaatggact tgcaaagctt cacttcattt    1560
taagagcaaa agaccccatg ttgaaaactc cataacagtt ttatgctgat gataatttat    1620
ctacatgcat ttcaataaac cttttgtttc ctaagactag aaaaa                    1665

<210> SEQ ID NO 5
<211> LENGTH: 840
<212> TYPE: DNA
<213> ORGANISM: Homo sapiens

<400> SEQUENCE: 5
agacccagag ccaatgcgtg gattagtccc tcctcctagt tgcagtctgg tagttgtcgc      60
tggccgtgtg acggctcgct gttgccctga aggcaggcga gccagctgcc caggaaaggt     120
ggaaagtggt agaagctgac ccctgagccc tgcaggtct ttaagtgcgt ttgtgcagcc      180
gatttcaagg ctaagagaga aagactgcct ctgatccctg aaggaagaaa aaaaaaaaa      240
aaacaggaaa aaaactcaac atggaaaatg tccccaagga aaacaaagtt gtggagaagg     300
ccccagtgca gaatgaagcc cccgctttag gaggtggtga ataccaggag cctggaggaa     360
atgttaaagg ggtttgggct ccacctgccc cgggttttgg agaggatgtg cccaataggc     420
```

| ttgtcgataa cattgatatg atagatggag atggagatga tatggaacgg ttcatggagg | 480 |
| agatgagaga gctaaggagg aaaattaggg aacttcagtt gaggtacagt ctgcgcattc | 540 |
| ttatagggga ccctcctcac catgatcatc atgatgagtt ttgccttatg ccttgaatct | 600 |
| tgaggttaat aatcataaaa tccctgcttt ctaaattcgc atttttcctg gtgtaccttt | 660 |
| aatgtgaacc ttttggcatt cttctgcaat tttctgattg agattgcat tttgacctag | 720 |
| tctgtaagtt tttctgtcag aagaggactt tcatcaactt tcatggaaag atgtttattg | 780 |
| catactgtaa agttaataaa gcaatttaaa agcagtctaa aaaaaaaaaa aaaaaaaaa | 840 |

<210> SEQ ID NO 6
<211> LENGTH: 8340
<212> TYPE: DNA
<213> ORGANISM: Homo sapiens

<400> SEQUENCE: 6

| actaattttc tggagtttct gcccctgctc tgcgtcagcc ctcacgtcac ttcgccagca | 60 |
| gtagcagagg cggcggcggc ggctcccgga attgggttgg agcaggagcc tcgctggctg | 120 |
| cttcgctcgc gctctacgcg ctcagtcccc ggcggtagca ggagcctgga cccaggcgcc | 180 |
| gccggcgggc gtgaggcgcc ggagcccggc ctcgaggtgc ataccggacc cccattcgca | 240 |
| tctaacaagg aatctgcgcc ccagagagtc ccggagcgc cgccggtcgg tgcccggcgc | 300 |
| gccgggccat gcagcgacgg ccgccgcgga gctccgagca gcggtagcgc ccccctgtaa | 360 |
| agcggttcgc tatgccgggg ccactgtgaa ccctgccgcc tgccgaaca ctcttcgctc | 420 |
| cggaccagct cagcctctga taagctggac tcggcacgcc cgcaacaagc accgaggagt | 480 |
| taagagagcc gcaagcgcag ggaaggcctc cccgcacggg tgggggaaag cggccggtgc | 540 |
| agcgcgggga caggcactcg ggctggcact ggctgctagg gatgtcgtcc tggataaggt | 600 |
| ggcatggacc cgccatggcg cggctctggg gcttctgctg gctggttgtg ggcttctgga | 660 |
| gggccgcttt cgcctgtccc acgtcctgca aatgcagtgc ctctcggatc tggtgcagcg | 720 |
| acccttctcc tggcatcgtg gcatttccga gattggagcc taacagtgta gatcctgaga | 780 |
| acatcaccga aattttcatc gcaaaccaga aaaggttaga aatcatcaac gaagatgatg | 840 |
| ttgaagctta tgtgggactg agaaatctga caattgtgga ttctggatta aaatttgtgg | 900 |
| ctcataaagc atttctgaaa aacagcaacc tgcagcacat caattttacc cgaaacaaac | 960 |
| tgacgagttt gtctaggaaa catttccgtc accttgactt gtctgaactg atcctggtgg | 1020 |
| gcaatccatt tacatgctcc tgtgacatta tgtggatcaa gactctccaa gaggctaaat | 1080 |
| ccagtccaga cactcaggat ttgtactgcc tgaatgaaag cagcaagaat attcccctgg | 1140 |
| caaacctgca gataccaat tgtggttttgc catctgcaaa tctggccgca cctaacctca | 1200 |
| ctgtggagga aggaaagtct atcacattat cctgtagtgt ggcaggtgat ccggttccta | 1260 |
| atatgtattg gatgttggt aacctggttt ccaaacatat gaatgaaaca gccacacac | 1320 |
| agggctcctt aaggataact aacatttcat ccgatgacag tgggaagcag atctcttgtg | 1380 |
| tggcggaaaa tcttgtagga gaagatcaag attctgtcaa cctcactgtg cattttgcac | 1440 |
| caactatcac atttctcgaa tctccaacct cagaccacca ctggtgcatt ccattcactg | 1500 |
| tgaaaggcaa ccccaaacca gcgcttcagt ggttctataa cgggccaata ttgaatgagt | 1560 |
| ccaaatacat ctgtactaaa atacatgtta ccaatcacac ggagtaccac ggctgcctcc | 1620 |
| agctggataa tcccactcac atgaacaatg gggactacac tctaatagcc aagaatgagt | 1680 |

```
atgggaagga tgagaaacag atttctgctc acttcatggg ctggcctgga attgacgatg    1740
gtgcaaaccc aaattatcct gatgtaattt atgaagatta tggaactgca gcgaatgaca    1800
tcggggacac cacgaacaga agtaatgaaa tcccttccac agacgtcact gataaaaccg    1860
gtcgggaaca tctctcggtc tatgctgtgg tggtgattgc gtctgtggtg ggattttgcc    1920
ttttggtaat gctgtttctg cttaagttgg caagacactc caagtttggc atgaaagatt    1980
tctcatggtt tggatttggg aaagtaaaat caagacaagg tgttggccca gcctccgtta    2040
tcagcaatga tgatgactct gccagcccac tccatcacat ctccaatggg agtaacactc    2100
catcttcttc ggaaggtggc ccagatgctg tcattattgg aatgaccaag atccctgtca    2160
ttgaaaatcc ccagtacttt ggcatcacca acagtcagct caagccagac acatggccca    2220
gaggttcccc caagaccgcc tgataataat ttggtatttg gaggctcctg tgtcactgca    2280
ggaactaaag gaggctaaat ccatgcctga tggaggagaa gagttctatg gttatctgca    2340
aattctggcc agacaacatc ttgacgtcac tccttagctt ccataaccta gccaagcaag    2400
aagttgcctt tccaagacaa agcagtgtgc tctaatgact aacccctcaa agtactatgc    2460
cactttaact atagacccat ctcctcgatc aatcaggatg gcaagatgga gctgaggagc    2520
tcagcaacat caagtctgga gttggtcttt aactcaacta gctcgtttag acgtgtctga    2580
acaccacatc acctgacagc acggggtggt ttcccagtaa aatttacaaa ctcagctcaa    2640
gggcagctgt gttgctttcc tttccttgac tgctgagaaa cttttgaca gggaacaatg    2700
gaaacacacc ttctgagctg aaacaaacaa acagaaacaa aacatactaa ccagcaaaat    2760
cccccaaatca tcaatcttgg gttctcttga agggcaggag tgtgttttat cttctcccgt    2820
cggagcaaac actatagatg tcctccctaa aattctgtct tccctagagc agccttgtaa    2880
attagctagg gtcctagggt tgaggcctaa atcaacttaa aattgtctct aaatatgtac    2940
ctggatgtgt ttgtacttgc agagcatgcc ctcttcatgt gcctagggct agtaactccc    3000
tgtggcagag gcatgtaaag tattctgact ttttttttt caacttaatt ccatttccaa    3060
tgaaatggat ttttaaaaat tttctccaga gtgtgccata cttctccagc tattatagtt    3120
aatgtgtgtg tatccttgtg tatatgtgtg tttgtgtgtg catatgtgtt ttcctagtgg    3180
ttacatgctt actaggcaat tatgtaaata agcacagatt cataggccag ctaggcctga    3240
ggaaagaaga cattataaag ggagggagta ttttaacatt agctaaagct atcacacaag    3300
gcacccattc tgctcccctc aacagccaca gcccacttcg tccttgtctt accaataagg    3360
ggaaaggctg gaggtgatat ttttcacaga accgcagagg ttttgaacat atttgcaaca    3420
ttactttgag tacacatgag caaaaattct gaattacatc caggaccccca gaagctcatt    3480
agatcaaaga gtgcggggcc cctcagagtt accagagatt atctgcagac ttcagtgcaa    3540
tcgaatgacc atggtccatt tgatggtca gaggtaggac tgaaaaacgg gtagaaacaa    3600
ttgcttttagc gcttccttct gtactttgcc tattaatgtt ttgtctttca aaatatatt    3660
ttctcctaat tgtttaattg gccaaataat ggctgctttg ggagttgttt gtatgccttg    3720
gaaggccatg gcctgcactt taaaaataag ctaagtccat tctgcccagc acgagcatta    3780
ggacagagaa tgcacttatt ttaggatcct taaaaattgc ttcttttatg gcacactggg    3840
ttgacgactc atctcgtggg agccttcatg gcacattgct gctgttctgc aggtcccaat    3900
acaattcctt cccctctca gtgccacggc ccccccattg ctagctacaa caatttgata    3960
tcatattccc ttttcaactc caagggagat gataagaagc tatcaaataa tgctttaaaa    4020
aagcaacttg agtttcttaa aagaaaggaa atgaatacat gctgcataat tacatttaaa    4080
```

```
atgtaagcca tgttattata agccgcactg agatgaagat ttgttagcaa accagtttca   4140
agcacactca cagtgaagta aaatcatgtt tttagcatct gaccattggg taatattatt   4200
ctttgttatc aaaagagaaa tatcacccaa gtatagtata cttagacctc ctagaggaaa   4260
cactccagtc ctaagcttgg tgtctgaaaa gaaaaacaaa aataaagatt atggatttag   4320
gtcagggaga cagagtgata ttctgaagac tgtgtttact ccctcatcat cggccaacca   4380
agatggagtt ctgcatcctg cacatatcag acatttcagt ccaatttcac caaagcatca   4440
gtgatgttct agaagcatcc cagcagatgg aggatcctaa tgtatttgtt ctgggtattt   4500
cccaaggccc agcctgactg gagtgtgtgt accaacagga tgaatccaat caagctacgc   4560
ccccattttg gtttcggatt ggccactctt gcatgtgcta gtagattgtg gaccaggacc   4620
agctgagcaa acacagttgc agagtagcct cctatgttgc taagaagctc ctgctaccca   4680
ggtgctttga acaattgagt gctccctctg gttaagtaga gatggcacca ccggagtttt   4740
tcttggatgt gaggctcaat cctttacggc agctattata acaaagtgaa ggttttctcc   4800
ctgggaaatg cagcttttct ctgtctttac taattctgcc agcctgtgag agtaaccacc   4860
gtagctgggc ttcttctcag attaattgtc atgccaggtc tccttcctgg ggagctgtga   4920
tgctgctctg aggttgattg ctgaggttgt agtgggtttt tgtttgtttt tgtttagttt   4980
ttcttgattg ttcttctttc tcttgaatgg caagagaaga aacactttct ctaacccacg   5040
gccaggaagg aaatggggag agagctactt cttagttcaa cctggttgcc acataaagga   5100
atctctctcc ttggactcag cccctaactg gaagcaagag ccactgccct ctgagactga   5160
gagagcagcc cgaggaggag atgaatccat tctgcccttt gtttgggttt gcttcctgtc   5220
agtgagagaa tgctgaggca gttcctgtta tgtgaaactt tcatttttaa aaccaggaca   5280
gtcctaaaca gactggaatg agttggtcaa tcccagttgg tataggccca atgattttg    5340 ctagtaagat aggattgtct tcctcaccca aaatgccttc aagtgcccta aaatgggtat   5400
tttaaaataa gaataaataa tgtagattta gtagaaaacc tggaaaacat aagaaacaaa   5460
gatgaaacga aaagtcccat gtaattccac cagttagagt taaccactga tatcgtttgg   5520
atatatggct ttctagtctt gtggatatcc ttttaatctc ttgtaatata aagtctgacc   5580
atatgtgtcc ttgcatttgt ttgtactgga ctctgttaat atttctatag taatggctca   5640
cttttgggag attgtgctgc acagtgtgta ggaagcacat tgggtgtatt attcccagtt   5700
ttgtattttg tatttccttg gagatgtgca ggggttaaga gcgggggtct ggccatagct   5760
ggccacgtca gactctcata tggtaagtat cacagagcac atgaggcctg tgttatgcgc   5820
tggaaagact caggaaatga gaggctctct tgttctgaca aggcaggctg agagctctca   5880
tttagggtca tcactccaga taactccaaa tgcagtttat tgctcaactg aagcagatga   5940
tcactttttg cctccaagtt cttcacccta gctagctcct ttcaaagagc cgagtatgct   6000
ggatcttaaa gggccaaact agttacatct catacatttc ctgatgttta gggatgcctt   6060
cacttccatc aaggatacct tggctgtgca aggacctctg atagctggag tctccttttg   6120
gtcactccca gctttgctta aacttgatgg agtttgctgt ccagtgatcc ccggatcttt   6180
catcatgaaa gccttccttc ctctcctgat gtctcaggcc tctagaccta gactgggtt    6240 ctggcaagga ggcctctatc aatagtatga catccaataa tatgttagtg ttgatatttt   6300
gcacagtaat attaagttta agagattata aaaatgagtt caaatgaata agttcctgtg   6360
atgtaagaga ttagatatgt gtgatttcag aaccaaaggc agggggaat cccagaaaga    6420
```

| | | | | |
|---|---|---|---|---|
| aaacaataat | ataatcctag | tttctatata | ttatttttat | tcattactgt | atatgggtag | 6480 |
| agatcaatat | tctttcttat | gctgttacta | ttaattaaca | cattttttaa | ccatgccatt | 6540 |
| gaacttttgg | gtgcattaaa | gtggaaccca | agctcctcat | tagataataa | tggcatttgg | 6600 |
| actgagtgcc | atattcctaa | atttccaata | aagtggttga | tatagagagg | acaggataaa | 6660 |
| gccctatagt | gtgcagttat | atcaaaacag | ctagtctcca | ctttagggaa | tgcctttact | 6720 |
| agagattaca | tgaaatgtct | gcttataaaa | taagcagaga | tggcaccact | aagcagccac | 6780 |
| ctgaattgtt | ttcctacagg | aatgattact | tttcagatcc | atttatgttt | tcatgctcaa | 6840 |
| tacttactcc | ccttccctgc | aacacccaaa | gagtttactt | ttgcaagtca | tttggtcttc | 6900 |
| agtctactac | tgaggaatag | agaggcacta | actgctttac | ccaggatcag | aactcatgtt | 6960 |
| cttaccttct | attaatagag | tacttgagcc | agatggacta | actggtctca | cattttctct | 7020 |
| atcttggttt | tacttccata | aacatcaata | tctttaccca | catgattttt | ccatcctccc | 7080 |
| atttttttcc | atatgtatta | gggttcagga | actatgatgc | taatgatcac | atttcttcct | 7140 |
| agttcctaat | ttcattagtg | ccatttcctg | atatctacag | aaacaattat | caatacatgt | 7200 |
| agctgcttga | gccttattta | gaaggctagc | cttttctttt | caagtgctgt | cagaatgtat | 7260 |
| acatttagtc | tgtctttttc | ccttttagga | gtctttgttc | tgggttgatg | gcaaaattcc | 7320 |
| tcttttttaca | tgtgagattt | ttgatttcac | tgaattctac | ctagattttt | atggacattg | 7380 |
| gattttaaag | aggaaaacac | tcattttctt | agtaagatat | tggtgataca | tagctatgcc | 7440 |
| attgatttcc | atactcctga | gctttgggga | gggagacagt | ggccaagtag | caggcagaat | 7500 |
| aagatcatca | ctcatgtcct | gaatcaatca | cactttcctt | ctcggattgt | gtatatgctc | 7560 |
| tgccacttcc | tacatattac | atcctgagtt | tttaagtaaa | gtggatctta | gccagatttg | 7620 |
| agtctaatgg | ctgattcatc | ggcatagttc | ttggcgttaa | catctcagtg | tcctctttag | 7680 |
| ttctctttga | ggattcatgt | cattgagggc | ctttgtgcct | ccacttgtct | cagtatgagg | 7740 |
| aagaactttg | gtgtgagggc | ggagctatgt | gaagggttgc | tgggttgggg | gattagttca | 7800 |
| tatggtcccc | atgccatcta | tttacttttg | gagagagggg | actttgagtg | ggtgggtatg | 7860 |
| gatagatgtt | cctcaaggaa | accctgctgg | ctaatgggca | ctacatctgt | gtattactgt | 7920 |
| gattctctct | gtaagctccc | catgtggcca | aggacccccc | tcctaccagg | gcacttcctg | 7980 |
| ccacctcatt | gcactggtct | caaccattca | gcctgctgct | gctgcaccat | gttgggctgc | 8040 |
| ggtaggatag | ggaaggggtt | ctgttgattg | ctaaatgttg | cctaactttta | tttccctctc | 8100 |
| ccacatttca | tgcaagggag | cggacctaac | acatgacttg | cattctcttc | ctatgttcag | 8160 |
| aaactccagg | gcttgcccac | gtgtatgtat | gagtgaccaa | tggagcttgg | aattcttttat | 8220 |
| ctatatgatc | tgtccgaaaa | tgagatcttt | tgtactggaa | tttgtgatgt | agttgatcat | 8280 |
| tcagagccaa | acgcatatac | caataaagac | aagactgtca | tataaaaaaa | aaaaaaaaaa | 8340 |

<210> SEQ ID NO 7
<211> LENGTH: 8292
<212> TYPE: DNA
<213> ORGANISM: Homo sapiens

<400> SEQUENCE: 7

| | | | | |
|---|---|---|---|---|
| actaattttc | tggagtttct | gccctgctc | tgcgtcagcc | ctcacgtcac | ttcgccagca | 60 |
| gtagcagagg | cggcggcggc | ggctcccgga | attgggttgg | agcaggagcc | tcgctggctg | 120 |
| cttcgctcgc | gctctacgcg | ctcagtcccc | ggcggtagca | ggagcctgga | cccaggcgcc | 180 |
| gccggcgggc | gtgaggcgcc | ggagcccggc | ctcgaggtgc | ataccggacc | cccattcgca | 240 |

```
tctaacaagg aatctgcgcc ccagagagtc ccgggagcgc cgccggtcgg tgcccggcgc    300
gccgggccat gcagcgacgg ccgccgcgga gctccgagca gcggtagcgc cccctgtaa    360 agcggttcgc tatgccgggg ccactgtgaa ccctgccgcc tgccggaaca ctcttcgctc    420
cggaccagct cagcctctga taagctggac tcggcacgcc cgcaacaagc accgaggagt    480
taagagagcc gcaagcgcag ggaaggcctc cccgcacggg tgggggaaag cggccggtgc    540
agcgcgggga caggcactcg ggctggcact ggctgctagg gatgtcgtcc tggataaggt    600
ggcatggacc cgccatggcg cggctctggg gcttctgctg gctggttgtg ggcttctgga    660
gggccgcttt cgcctgtccc acgtcctgca aatgcagtgc ctctcggatc tggtgcagcg    720 accccttctcc tggcatcgtg gcatttccga gattggagcc taacagtgta gatcctgaga    780
acatcaccga aattttcatc gcaaaccaga aaggttaga aatcatcaac gaagatgatg    840
ttgaagctta tgtgggactg agaaatctga caattgtgga ttctggatta aaatttgtgg    900
ctcataaagc atttctgaaa aacagcaacc tgcagcacat caattttacc cgaaacaaac    960
tgacgagttt gtctaggaaa catttccgtc accttgactt gtctgaactg atcctggtgg   1020
gcaatccatt tacatgctcc tgtgacatta tgtggatcaa gactctccaa gaggctaaat   1080
ccagtccaga cactcaggat ttgtactgcc tgaatgaaag cagcaagaat attcccctgg   1140
caaacctgca gatacccaat tgtggtttgc catctgcaaa tctggccgca cctaacctca   1200
ctgtggagga aggaaagtct atcacattat cctgtagtgt ggcaggtgat ccggttccta   1260
atatgtattg ggatgttggt aacctggttt ccaaacatat gaatgaaaca agccacacac   1320
agggctcctt aaggataact aacatttcat ccgatgacag tgggaagcag atctcttgtg   1380
tggcggaaaa tcttgtagga gaagatcaag attctgtcaa cctcactgtg cattttgcac   1440
caactatcac atttctcgaa tctccaacct cagaccacca ctggtgcatt ccattcactg   1500
tgaaaggcaa ccccaaacca gcgcttcagt ggttctataa cggggcaata ttgaatgagt   1560
ccaaatacat ctgtactaaa atacatgtta ccaatcacac ggagtaccac ggctgcctcc   1620
agctggataa tcccactcac atgaacaatg gggactacac tctaatagcc aagaatgagt   1680
atgggaagga tgagaaacag atttctgctc acttcatggg ctggcctgga attgacgatg   1740
gtgcaaaccc aaattatcct gatgtaattt atgaagatta tggaactgca gcgaatgaca   1800
tcggggacac cacgaacaga agtaatgaaa tcccttccac agacgtcact gataaaaccg   1860
gtcgggaaca tctctcggtc tatgctgtgg tggtgattgc gtctgtggtg ggattttgcc   1920 tttttggtaat gctgtttctg cttaagttgg caagacactc caagtttggc atgaaaggcc   1980
cagcctccgt tatcagcaat gatgatgact ctgccagccc actccatcac atctccaatg   2040
ggagtaacac tccatcttct tcggaaggtg gcccagatgc tgtcattatt ggaatgacca   2100
agatccctgt cattgaaaat ccccagtact ttggcatcac caacagtcag ctcaagccag   2160
acacatggcc cagaggttcc cccaagaccg cctgataata tttggtatt tggaggctcc   2220 tgtgtcactg caggaactaa aggaggctaa atccatgcct gatggaggag aagagttcta   2280
tggttatctg caaattctgg ccagacaaca tcttgacgtc actccttagc ttccataacc   2340
tagccaagca agaagttgcc tttccaagac aaagcagtgt gctctaatga ctaacccctc   2400
aaagtactat gccactttaa ctatagaccc atctcctcga tcaatcagga tggcaagatg   2460
gagctgagga gctcagcaac atcaagtctg gagttggtct ttaactcaac tagctcgttt   2520
agacgtgtct gaacaccaca tcacctgaca gcacggggtg gtttcccagt aaaatttaca   2580
```

```
aactcagctc aagggcagct gtgttgcttt cctttccttg actgctgaga aacttttga   2640 cagggaacaa tggaaacaca ccttctgagc tgaaacaaac aaacagaaac aaaacatact   2700
aaccagcaaa atccccaaat catcaatctt gggttctctt gaagggcagg agtgtgtttt   2760
atcttctccc gtcggagcaa acactataga tgtcctccct aaaattctgt cttccctaga   2820
gcagccttgt aaattagcta gggtcctagg gttgaggcct aaatcaactt aaaattgtct   2880
ctaaatatgt acctggatgt gtttgtactt gcagagcatg ccctcttcat gtgcctaggg   2940
ctagtaactc cctgtggcag aggcatgtaa agtattctga cttttttttt ttcaacttaa   3000
ttccatttcc aatgaaatgg attttaaaa attttctcca gagtgtgcca tacttctcca   3060
gctattatag ttaatgtgtg tgtatccttg tgtatatgtg tgtttgtgtg tgcatatgtg   3120
ttttcctagt ggttacatgc ttactaggca attatgtaaa taagcacaga ttcataggcc   3180
agctaggcct gaggaaagaa gacattataa agggagggag tattttaaca ttagctaaag   3240
ctatcacaca aggcacccat tctgctcccc tcaacagcca cagcccactt cgtccttgtc   3300
ttaccaataa ggggaaaggc tggaggtgat atttttcaca gaaccgcaga ggttttgaac   3360
atatttgcaa cattactttg agtacacatg agcaaaaatt ctgaattaca tccaggaccc   3420
cagaagctca ttagatcaaa gagtgcgggg cccctcagag ttaccagaga ttatctgcag   3480
acttcagtgc aatcgaatga ccatggtcca ttttgatggt cagaggtagg actgaaaaac   3540
gggtagaaac aattgcttta cgcttccttt ctgtactttg cctattaatg ttttgtcttt   3600
caaaaatata ttttctccta attgtttaat tggccaaata atggctgctt gggagttgt    3660 ttgtatgcct tggaaggcca tggcctgcac tttaaaaata agctaagtcc attctgccca   3720
gcacgagcat taggacagag aatgcactta ttttaggatc cttaaaaatt gcttctttta   3780
tggcacactg ggttgacgac tcatctcgtg ggagccttca tggcacattg ctgctgttct   3840
gcaggtccca atacaattcc ttccccctct cagtgccacg gcccccccat tgctagctac   3900
aacaatttga tatcatattc ccttttcaac tccaaaggag atgataagaa gctatcaaat   3960
aatgctttaa aaaagcaact tgagtttctt aaaagaaagg aaatgaatac atgctgcata   4020
attacattta aaatgtaagc catgttatta taagccgcac tgagatgaag atttgttagc   4080
aaaccagttt caagcacact cacagtgaag taaaatcatg ttttagcat ctgaccattg    4140 ggtaatatta ttcttgtta tcaaaagaga aatatcaccc aagtatagta tacttagacc    4200
tcctagagga aacactccag tcctaagctt ggtgtctgaa aagaaaaaca aaaataaaga   4260
ttatggattt aggtcaggga gacagagtga tattctgaag actgtgttta ctccctcatc   4320
atcggccaac caagatggag ttctgcatcc tgcacatatc agacatttca gtccaatttc   4380
accaaagcat cagtgatgtt ctagaagcat cccagcagat ggaggatcct aatgtatttg   4440
ttctgggtat ttcccaaggc ccagcctgac tggagtgtgt gtaccaacag gatgaatcca   4500
atcaagctac gccccccattt tggtttcgga ttggccactc ttgcatgtgc tagtagattg   4560
tggaccagga ccagctgagc aaacacagtt gcagagtagc ctcctatgtt gctaagaagc   4620
tcctgctacc caggtgcttt gaacaattga gtgctccctc tggttaagta gagatggcac   4680
caccggagtt tttcttggat gtgaggctca atcctttacg gcagctatta taacaaagtg   4740
aaggttttct ccctgggaaa tgcagctttt ctctgtcttt actaattctg ccagcctgtg   4800
agagtaacca ccgtagctgg gcttcttctc agattaattg tcatgccagg tctccttcct   4860
ggggagctgt gatgctgctc tgaggttgat tgctgaggtt gtagtgggtt tttgtttgtt   4920
tttgtttagt ttttcttgat tgttcttctt tctcttgaat ggcaagagaa gaaacacttt   4980
```

```
ctctaaccca cggccaggaa ggaaatgggg agagagctac ttcttagttc aacctggttg   5040
ccacataaag gaatctctct ccttggactc agcccctaac tggaagcaag agccactgcc   5100
ctctgagact gagagagcag cccgaggagg agatgaatcc attctgccct ttgtttgggt   5160
ttgcttcctg tcagtgagag aatgctgagg cagttcctgt tatgtgaaac tttcattttt   5220
aaaaccagga cagtcctaaa cagactggaa tgagttggtc aatcccagtt ggtataggcc   5280
caatgatttt tgctagtaag ataggattgt cttcctcacc caaaatgcct tcaagtgccc   5340
taaaatgggt attttaaaat aagaataaat aatgtagatt tagtagaaaa cctggaaaac   5400
ataagaaaca aagatgaaac gaaaagtccc atgtaattcc accagttaga gttaaccact   5460
gatatcgttt ggatatatgg cttctagtc ttgtggatat cctttaatc tcttgtaata    5520 taaagtctga ccatatgtgt ccttgcattt gtttgtactg gactctgtta atatttctat   5580
agtaatggct cactttgggg agattgtgct gcacagtgtg taggaagcac attgggtgta   5640
ttattcccag ttttgtattt tgtatttcct tggagatgtg caggggttaa gagcgggggt   5700
ctggccatag ctggccacgt cagactctca tatggtaagt atcacagagc acatgaggcc   5760
tgtgttatgc gctggaaaga ctcaggaaat gagaggctct cttgttctga caaggcaggc   5820
tgagagctct catttagggt catcactcca gataactcca aatgcagttt attgctcaac   5880
tgaagcagat gatcactttt tgcctccaag ttcttcaccc tagctagctc ctttcaaaga   5940
gccgagtatg ctggatctta aagggccaaa ctagttacat ctcatacatt tcctgatgtt   6000
tagggatgcc ttcacttcca tcaaggatac cttggctgtg caaggacctc tgatagctgg   6060
agtctccttt tggtcactcc cagctttgct taaacttgat ggagtttgct gtccagtgat   6120
ccccggatct ttcatcatga aagccttcct tcctctcctg atgtctcagg cctctagacc   6180
tagactgggg ttctggcaag gaggcctcta tcaatagtat gacatccaat aatatgttag   6240
tgttgatatt ttgcacagta atattaagtt taagagatta taaaaatgag ttcaaatgaa   6300
taagttcctg tgatgtaaga gattagatat gtgtgatttc agaaccaaag gcaggggga   6360 atcccagaaa gaaaacaata atataatcct agtttctata tattattttt attcattact   6420
gtatatgggt agagatcaat attctttctt atgctgttac tattaattaa cacattttt   6480 aaccatgcca ttgaactttt gggtgcatta aagtggaacc caagctcctc attagataat   6540
aatggcattt ggactgagtg ccatattcct aaatttccaa taaagtggtt gatatagaga   6600
ggacaggata aagccctata gtgtgcagtt atatcaaaac agctagtctc cactttaggg   6660 aatgcccttta ctagagatta catgaaatgt ctgcttataa aataagcaga gatggcacca   6720
ctaagcagcc acctgaattg ttttcctaca ggaatgatta cttttcagat ccatttatgt   6780
tttcatgctc aatacttact ccccttccct gcaacaccca aagagtttac ttttgcaagt   6840
catttggtct tcagtctact actgaggaat agagaggcac taactgcttt acccaggatc   6900
agaactcatg ttcttacctt ctattaatag agtacttgag ccagatggac taactggtct   6960
cacattttct ctatcttggt tttacttcca taaacatcaa tatctttacc cacatgattt   7020
ttccatcctc ccattttttt ccatatgtat tagggttcag gaactatgat gctaatgatc   7080
acatttcttc ctagttccta atttcattag tgccatttcc tgtatcctac agaaacaatt   7140
atcaatacat gtagctgctt gagccttatt tagaaggcta gcctttcttt tccaagtgct   7200
gtcagaatgt atacatttag tctgtctttt tccctttag gagtctttgt tctgggttga   7260
tggcaaaatt cctcttttta catgtgagat ttttgatttc actgaattct acctagattt   7320
```

| | |
|---|---:|
| ttatggacat tggattttaa agaggaaaac actcattttc ttagtaagat attggtgata | 7380 |
| catagctatg ccattgattt ccatactcct gagctttggg gagggagaca gtggccaagt | 7440 |
| agcaggcaga ataagatcat cactcatgtc ctgaatcaat cacactttcc ttctcggatt | 7500 |
| gtgtatatgc tctgccactt cctacatatt acatcctgag tttttaagta aagtggatct | 7560 |
| tagccagatt tgagtctaat ggctgattca tcggcatagt tcttggcgtt aacatctcag | 7620 |
| tgtcctcttt agttctcttt gaggattcat gtcattgagg ccttttgtgc ctccacttgt | 7680 |
| ctcagtatga ggaagaactt tggtgtgagg gcggagctat gtgaagggtt gctgggttgg | 7740 |
| gggattagtt catatggtcc ccatgccatc tatttacttt tggagagagg ggactttgag | 7800 |
| tgggtgggta tggatagatg ttcctcaagg aaaccctgct ggctaatggg cactacatct | 7860 |
| gtgtattact gtgattctct ctgtaagctc cccatgtggc caaggacccc cctcctacca | 7920 |
| gggcacttcc tgccacctca ttgcactggt ctcaaccatt cagcctgctg ctgctgcacc | 7980 |
| atgtttgggct gcggtaggat agggaagggg ttctgttgat tgctaaatgt tgcctaactt | 8040 |
| tatttccctc tcccacattt catgcaaggg agcggaccta acacatgact tgcattctct | 8100 |
| tcctatgttc agaaactcca gggcttgccc acgtgtatgt atgagtgacc aatggagctt | 8160 |
| ggaattcttt atctatatga tctgtccgaa atgagatcct tttgtactgg aatttgtgat | 8220 |
| gtagttgatc attcagagcc aaacgcatat accaataaag acaagactgt catataaaaa | 8280 |
| aaaaaaaaaa aa | 8292 |

<210> SEQ ID NO 8
<211> LENGTH: 549
<212> TYPE: DNA
<213> ORGANISM: Homo sapiens

<400> SEQUENCE: 8

| | |
|---|---:|
| acctccgcca ggaactgcag gcccacctgt ctgcaaccca gctgaggcca tgccctcccc | 60 |
| agggaccgtc tgcagcctcc tgctcctcgg catgctctgg ctggacttgg ccatggcagg | 120 |
| ctccagcttc ctgagccctg aacaccagag agtccagaga aaggagtcga agaagccacc | 180 |
| agccaagctg cagccccgag ctctagcagg ctggctccgc ccggaagatg gaggtcaagc | 240 |
| agaagggca gaggatgaac tggaagtccg gttcaacgcc ccctttgatg ttggaatcaa | 300 |
| gctgtcaggg gttcagtacc agcagcacag ccaggccctg ggaagtttc ttcaggacat | 360 |
| cctctgggaa gaggccaaag aggcccccagc cgacaagtga tcgcccacaa gccttactca | 420 |
| cctctctcta gtttagaag cgctcatctg gcttttcgct tgcttctgca gcaactccca | 480 |
| cgactgttgt acaagctcag gaggcgaata aatgttcaaa ctgtaaaaaa aaaaaaaaa | 540 |
| aaaaaaaaa | 549 |

<210> SEQ ID NO 9
<211> LENGTH: 501
<212> TYPE: DNA
<213> ORGANISM: Homo sapiens

<400> SEQUENCE: 9

| | |
|---|---:|
| agttccccaa agataacaca gctttgcaca gtggatgttt acttgctggt ggtcttatct | 60 |
| aagatcaaca ttggcagctg tgcccggaga ggcctccagg gtccagcaga gaaaggagtc | 120 |
| gaagaagcca ccagccaagc tgcagccccg agctctagca ggctggctcc gcccggaaga | 180 |
| tggaggtcaa gcagaagggg cagaggatga actggaagtc cggttcaacg ccccctttga | 240 |
| tgttggaatc aagctgtcag gggttcagta ccagcagcac agccaggccc tggggaagtt | 300 |

| | |
|---|---|
| tcttcaggac atcctctggg aagaggccaa agaggcccca gccgacaagt gatcgcccac | 360 |
| aagccttact cacctctctc taagtttaga agcgctcatc tggcttttcg cttgcttctg | 420 |
| cagcaactcc cacgactgtt gtacaagctc aggaggcgaa taaatgttca aactgtaaaa | 480 |
| aaaaaaaaaa aaaaaaaaaa a | 501 |

<210> SEQ ID NO 10
<211> LENGTH: 498
<212> TYPE: DNA
<213> ORGANISM: Homo sapiens

<400> SEQUENCE: 10

| | |
|---|---|
| agttccccaa agataacaca gctttgcaca gtggatgttt acttgctggt ggtcttatct | 60 |
| aagatcaaca ttggcagctg tgcccggaga ggcctccagg gtccagagaa aggagtcgaa | 120 |
| gaagccacca gccaagctgc agccccgagc tctagcaggc tggctccgcc cggaagatgg | 180 |
| aggtcaagca aaggggcag aggatgaact ggaagtccgg ttcaacgccc cctttgatgt | 240 |
| tggaatcaag ctgtcagggg ttcagtacca gcagcacagc caggccctgg ggaagtttct | 300 |
| tcaggacatc ctctgggaag aggccaaaga ggccccagcc gacaagtgat cgcccacaag | 360 |
| ccttactcac ctctctctaa gtttagaagc gctcatctgg cttttcgctt gcttctgcag | 420 |
| caactcccac gactgttgta caagctcagg aggcgaataa atgttcaaac tgtaaaaaaa | 480 |
| aaaaaaaaaa aaaaaaaa | 498 |

<210> SEQ ID NO 11
<211> LENGTH: 384
<212> TYPE: DNA
<213> ORGANISM: Homo sapiens

<400> SEQUENCE: 11

| | |
|---|---|
| agttccccaa agataacaca gctttgcaca gtggatgttt acttgctggt ggtcttatct | 60 |
| aagatcaaca ttggcagctg tgcccggaga ggcctccagg gtccagttca acgccccctt | 120 |
| tgatgttgga atcaagctgt caggggttca gtaccagcag cacagccagg ccctggggaa | 180 |
| gtttcttcag gacatcctct gggaagaggc caaagaggcc ccagccgaca agtgatcgcc | 240 |
| cacaagcctt actcacctct ctctaagttt agaagcgctc atctggcttt tcgcttgctt | 300 |
| ctgcagcaac tcccacgact gttgtacaag ctcaggaggc gaataaatgt tcaaactgta | 360 |
| aaaaaaaaaa aaaaaaaaaa aaaa | 384 |

<210> SEQ ID NO 12
<211> LENGTH: 1939
<212> TYPE: DNA
<213> ORGANISM: Homo sapiens

<400> SEQUENCE: 12

| | |
|---|---|
| agtttggacg gctgcttccc accagcaaag accacgactg agagccgag ccggaggcag | 60 |
| ctgggaaaca tgaagagcgt cttgctgctg accacgctcc tcgtgcctgc acacctggtg | 120 |
| gccgcctgga gcaataatta tgcggtggac tgccctcaac actgtgacag cagtgagtgc | 180 |
| aaaagcagcc cgcgctgcaa gaggacagtg ctcgacgact gtggctgctg ccgagtgtgc | 240 |
| gctgcagggc ggggagaaac ttgctaccgc acagtctcag gcatggatgg catgaagtgt | 300 |
| ggcccggggc tgaggtgtca gccttctaat ggggaggatc cttttggtga agagtttggt | 360 |
| atctgcaaag agcatgacat ggcatctgga gatggcaata ttgtgagaga agaagttgtg | 420 |

```
aaagagaatg ctgccgggtc tcccgtaatg aggaaatggt taaatccacg ctgatcccgg      480
ctgtgatttc tgagagaagg ctctatttc  gtgattgttc aacacacagc caacatttta      540
ggaactttct agattatagc ataaggacat gtaattttg  aagaccaaat gtgatgcatg      600
gtggatccag aaaacaaaaa gtaggatact tacaatccat aacatccata tgactgaaca      660
cttgtatgtg tttgttaaat attcgaatgc atgtagattt gttaaatgtg tgtgtatagt      720
aacactgaag aactaaaaat gcaatttagg taatcttacg tggagacagg tcaaccaaag      780
agggagctag gcaaagctga agaccgcagt gagtcaaatt agttctttga ctttgatgta      840
cattaatgtt gggatatgga atgaagactt aagagcagga gaagatgggg agggggtggg      900
agtgggaaat aaaatattta gcccttcctt ggtaggtagc ttctctagaa tttaattgtg      960
cttttttttt tttttttggc tttgggaaaa gtcaaaataa acaaccaga  aaaccccctga     1020 aggaagtaag atgtttgaag cttatggaaa tttgagtaac aaacagcttt gaactgagag     1080
caatttcaaa aggctgctga tgtagttccc gggttacctg tatctgaagg acggttctgg     1140
ggcataggaa acacatacac ttccataaat agctttaacg tatgccacct cagagataaa     1200
tctaagaagt atttacccca ctggtggttt gtgtgtgtat gaaggtaaat atttatatat     1260
ttttataaat aaatgtgtta gtgcaagtca tcttccctac ccatatttat catcctcttg     1320
aggaaagaaa tctagtatta tttgttgaaa atggttagaa taaaactatg actctataag     1380
gttttcaaac atctgaggca tgataaattt attatccata attatagtaa taataacctt     1440
aataagcata agaaaaacag agtcactctg gatttcaaaa atgtcaaaaa atgagcaaca     1500
gagggtcctt atttaaacat aagtgctgtg acttaggtga atttccaatt taaggtagaa     1560
aataagtttt taggaggttt gtaaaagaag aatcaatttt cagcagaaaa catgtcaact     1620
ttaaaatata gtttattttc atatttttttt cttttaaact tggttgataa gtggaattag     1680
gagtatattt gaaagaatct tagcacaaac aggactgttg tactagatgt tcttaggaaa     1740
tatctcagaa gtattttatt tgaagtgaag aacttattta agaattattt cagtatttac     1800 ctgtattta  ttcttgaagt tggccaacag agttgtgaat gtgtgtggga aggcctttga     1860
atgtaaagct gcataagctg ttaggttttg ttttaaaagg acatgtttat tattgttcaa     1920
taaaaaagaa caagataca                                                 1939
```

<210> SEQ ID NO 13
<211> LENGTH: 882
<212> TYPE: DNA
<213> ORGANISM: Homo sapiens

<400> SEQUENCE: 13

```
caccctttcc agatacacac ccgtttagtg cgagaaatgg agcggttggg gagaggatct       60
cccgaggggg ctggattgag aatgggtacc atttgagatc tcctaggagg ccggccatcg      120
ggcaatgtct gatggagtcc agccggtgga ggagactgaa aggaaacagc ctgcttcctg      180
caggtccgcg ggagggaggt ctttaagtgc gtttgtgcag ccgatttcaa ggctaagaga      240
gaaagactgc ctctgatccc tgaaggaaga aaaaaaaaa  aaaaacagga aaaaaactca      300
acatggaaaa tgtccccaag gaaaacaaag ttgtggagaa ggccccagtg cagaatgaag      360 ccccgctt   aggaggtggt gaataccagg agcctggagg aaatgttaaa ggggtttggg      420
ctccacctgc cccgggtttt ggagaggatg tgcccaatag gcttgtcgat aacattgata      480
tgatagatga agatggagat gatatggaac ggttcatgga ggagatgaga gagctaagga      540
ggaaaattag ggaacttcag ttgaggtaca gtctgcgcat tcttataggg gaccctcctc      600
```

```
accatgatca tcatgatgag ttttgcctta tgccttgaat cttgaggtta ataatcataa     660
aatccctgct ttctaaattc gcattttcc tggtgtacct ttaatgtgaa ccttttggca      720
ttcttctgca attttctgat tggagattgc attttgacct agtctgtaag tttttctgtc    780
agaagaggac tttcatcaac tttcatggaa agatgtttat tgcatactgt aaagttaata    840
aagcaattta aaagcagtct aaaaaaaaaa aaaaaaaaa aa                        882
```

<210> SEQ ID NO 14
<211> LENGTH: 1278
<212> TYPE: DNA
<213> ORGANISM: Homo sapiens

<400> SEQUENCE: 14

```
ccattggcct gtagattcac ctcccctggg cagggcccca ggacccagga taatatctgt     60
gcctcctgcc cagaaccctc caagcagaca caatggtaag aatggtgcct gtcctgctgt    120
ctctgctgct gcttctgggt cctgctgtcc cccaggagaa ccaagatggt cgttactctc    180
tgacctatat ctacactggg ctgtccaagc atgttgaaga cgtccccgcg tttcaggccc    240
ttggctcact caatgacctc cagttcttta gatacaacag taaagacagg aagtctcagc    300
ccatgggact ctggagacag gtggaaggaa tggaggattg gaagcaggac agccaacttc    360
agaaggccag ggaggacatc tttatggaga ccctgaaaga catcgtggag tattacaacg    420
acagtaacgg gtctcacgta ttgcagggaa ggtttggttg tgagatcgag aataacagaa    480
gcagcggagc attctggaaa tattactatg atggaaagga ctacattgaa ttcaacaaag    540
aaatcccagc ctgggtcccc ttcgacccag cagcccagat aaccaagcag aagtgggagg    600
cagaaccagt ctacgtgcag cgggccaagg cttacctgga ggaggagtgc cctgcgactc    660
tgcggaaata cctgaaatac agcaaaaata tcctggaccg gcaagatcct ccctctgtgg    720
tggtcaccag ccaccaggcc ccaggagaaa agaagaaact gaagtgcctg gcctacgact    780
tctacccagg gaaaattgat gtgcactgga ctcgggccgg cgaggtgcag gagcctgagt    840
tacggggaga tgttcttcac aatgaaaatg gcacttacca gtcctgggtg gtggtggcag    900 tgccccgca ggacacagcc ccctactcct gccacgtgca gcacagcagc ctggcccagc    960
ccctcgtggt gcctgggag gccagctagg aagcaagggt tggaggcaat gtgggatctc   1020
agacccagta gctgcccttc ctgcctgatg tgggagctga accacagaaa tcacagtcaa   1080
tggatccaca aggcctgagg agcagtgtgg ggggacagac aggaggtgga tttggagacc   1140
gaagactggg atgcctgtct tgagtagact tggacccaaa aaatcatctc accttgagcc   1200
cacccccacc ccattgtcta atctgtagaa gctaataaat aatcatccct ccttgcctag   1260
cataaaaaaa aaaaaaaa                                                  1278
```

<210> SEQ ID NO 15
<211> LENGTH: 1801
<212> TYPE: DNA
<213> ORGANISM: Homo sapiens

<400> SEQUENCE: 15

```
gggttatatg atctctttgg ctttagggaa ttactccata ccagctctga gatttccagc     60
tcagcgatgc ccccaggtcc ctgggagagc tgcttctggg tgggggcct cattttgtgg     120 ctcagcgttg gaagttcagg ggatgcacct cctaccccac agccaaagtg cgctgacttc    180
cagagcgcca accttttga aggcaccgat ctcaaagtcc agtttctcct ctttgtccct     240
```

```
tcgaatccta gctgtgggca gctagtagaa ggaagcagtg acctccaaaa ctctgggttc      300
aatgccactc tgggaaccaa actaattatc catggattca gggttttagg aacaaagcct      360
tcctggattg acacatttat tagaaccctt ctgcgtgcaa cgaatgctaa tgtgattgcc      420
gtggactgga tttatgggtc tacaggagtc tacttctcag ctgtgaaaaa tgtgctgggt      480
gtgtcggaat cctcaatcca catcattggt gttagcctgg gggcccacgt tgggggcatg      540
gtgggacagc tcttcggagg ccagctggga cagatcacag gcctgacccc gctggacct       600
gagtacacca gggccagtgt ggaagagcgc ttggatgctg gagatgccct cttcgtggaa      660
gccatccaca cagacaccga caatttgggt attcggattc cgttggaca tgtggactac       720
ttcgtcaacg gaggccaaga ccaacctggc tgccccacct tcttttacgc aggttatagt      780
tatctgatct gtgatcacat gagggctgtg cacctctaca tcagcgccct ggagaattcc      840
tgtccactga tggcctttcc ctgtgccagc tacaaggcct tccttgctgg acgctgtctg      900
gattgcttta acccttttct gctttcctgc ccaaggatag gactggtgga caaggtggt       960
gtcaagatag agccgctccc caaggaagtg aaagtctacc tcctgactac ttccagtgct     1020
ccgtactgca tgcatcacag cctcgtggag tttcacttga aggaactgag aaacaaggac     1080
accaacatcg aggttaccct ccttagcagt aacatcacct cttcatctaa gatcaccata     1140
cctaagcagc aacgctatgg gaaaggaatc atagcccatg ccaccccaca atgccagata     1200
aaccaagtga aattcaagtt tcagtcttcc aaccgagttt ggaaaaaaga ccggactacc     1260
attattggga agttctgcac tgccctttg cctgtcaatg acagagaaaa gatggtctgc      1320
ttacctgaac cagtgaactt acaagcaagt gtgactgttt cctgtgacct gaagatagcc     1380
tgtgtgtagt ttaacctggg caggacacat ctccctgcat ttttttttt tttttgagag      1440
agaggtgtga tgagggatgt gtgtgtgcag cttattgtag accattacta ctaaggagaa     1500
aagcaaagct ctttcttatt ttcctcataa tcagctaccc tggaggggag ggagaactca     1560
ttttacagaa cttggtttcc tttgccgatc ttatgtacat acccatttta gctttcccat     1620
gcatacttaa ctgcacttgc tttatctcct tgggcattcg tacttaggat tcaatagaaa     1680
catgtacagg gtaaacaatt ttttaaaaat aaaacttcat ggagtatctg aaaaaaaaaa     1740
aaaaaaaaaa aaaaaaaaaa aaaaaaaaaa aaaaaaaaaa aaaaaaaaaa aaaaaaaaaa     1800
a                                                                     1801

<210> SEQ ID NO 16
<211> LENGTH: 1647
<212> TYPE: DNA
<213> ORGANISM: Homo sapiens

<400> SEQUENCE: 16
gggttatatg atctctttgg ctttagggaa ttactccata ccagctctga gatttccagc       60
tcagcgatgc ccccaggtcc ctgggagagc tgcttctggg tggggggcct cattttgtgg      120
ctcagcgttg gaagttcagg gttttaggaa caaagccttc ctggattgac acatttatta      180
gaacccttct gcgtgcaacg aatgctaatg tgattgccgt ggactggatt tatgggtcta      240
caggagtcta cttctcagct gtgaaaaatg tgattaagtt gagcctcgag atctcccttt      300
tcctcaataa actcctggtg ctgggtgtgt cggaatcctc aatccacatc attggtgtta      360
gcctgggggc ccacgttggg ggcatggtgg acagctctt cggaggccag ctgggacaga       420
tcacaggcct ggacccgct ggacctgagt acaccagggc cagtgtggaa gagcgcttgg       480
atgctggaga tgccctcttc gtggaagcca tccacacaga caccgacaat ttgggtattc      540
```

```
ggattcccgt tggacatgtg gactacttcg tcaacggagg ccaagaccaa cctggctgcc      600
ccaccttctt ttacgcaggt tatagttatc tgatctgtga tcacatgagg gctgtgcacc      660
tctacatcag cgccctggag aattcctgtc cactgatggc ctttccctgt gccagctaca      720
aggccttcct tgctgacgc tgtctggatt gctttaaccc ttttctgctt tcctgcccaa       780
ggataggact ggtggaacaa ggtggtgtca agatagagcc gctccccaag gaagtgaaag      840
tctacctcct gactacttcc agtgctccgt actgcatgca tcacagcctc gtggagtttc      900
acttgaagga actgagaaac aaggacacca acatcgaggt taccttcctt agcagtaaca      960
tcacctcttc atctaagatc accataccta agcagcaacg ctatgggaaa ggaatcatag     1020
cccatgccac cccacaatgc cagataaacc aagtgaaatt caagtttcag tcttccaacc     1080
gagtttggaa aaaagaccgg actaccatta ttgggaagtt ctgcactgcc cttttgcctg     1140
tcaatgacag agaaaagatg gtctgcttac ctgaaccagt gaacttacaa gcaagtgtga     1200
ctgtttcctg tgacctgaag atagcctgtg tgtagtttaa cctgggcagg acacatctcc     1260
ctgcattttt tttttttttt tgagagagag gtgtgatgag ggatgtgtgt gtgcagctta     1320
ttgtagacca ttactactaa ggagaaaagc aaagctcttt cttatttttcc tcataatcag     1380 ctaccctgga ggggagggag aactcatttt acagaacttg gtttcctttg ccgatcttat     1440
gtacataccc attttagctt tcccatgcat acttaactgc acttgcttta tctccttggg     1500
cattcgtact taggattcaa tagaaacatg tacagggtaa acaatttttt aaaaataaaa     1560
cttcatggag tatctgaaaa aaaaaaaaaa aaaaaaaaaa aaaaaaaaaa aaaaaaaaaa     1620
aaaaaaaaaa aaaaaaaaaa aaaaaaa                                         1647

<210> SEQ ID NO 17
<211> LENGTH: 5622
<212> TYPE: DNA
<213> ORGANISM: Homo sapiens

<400> SEQUENCE: 17
ggcacgtgga ctccctttaa tccagtgact gtcaggtcga tcatatgccg aggacgatga       60
tcccgccggg ggagtgcacg tacgcgggcc ggaagcggag gaggcccctg cagaaacaga      120
ggcccgccgt gggggcagag aagtccaacc cctccaagcg acaccgggac cgcctcaacg      180
ccgagttgga ccacctggcc agcctgctgc cgttcccgcc tgacatcatc tccaagctgg      240
acaagctttc tgtcctgcgc ctcagtgtca gttacctccg ggtgaagagc ttcttccaag      300
tcgtgcagga gcagagctca cggcagcctg cggccggcgc cccctcgccc ggagacagct      360
gtcctcttgc agggtctgcc gtgctggagg gaaggctgct gttggagtct cttaatggct      420
ttgctctggt cgtgagtgca gaagggacga tattttatgc atcagcaacg atcgtggact      480
atctgggctt ccatcagacg gatgtaatgc accagaacat ttatgactac atccacgtgg      540
acgaccgcca ggacttctgc cggcagctcc actgggccat ggaccctccc caggtggtgt      600
ttgggcagcc ccgcccttg gagacaggag atgatgctat cctggggagg ctgctcaggg      660
cccaggagtg gggcacaggc acgcccaccg agtactcggc cttcctgacc cgctgcttca     720
tctgccgtgt gcgctgcctg ctggacagca cctcgggctt cctgacgatg cagtttcaag      780
gaaaactaaa attcctgttt ggacagaaga agaaggcgcc gtcaggagcc atgctcccgc      840
cgcggctgtc gctgttctgc attgcggcac ccgttctcct cccctccgca gcggagatga      900
aaatgaggag cgcgctcctg agggcaaaac ccagagcaga caccgcagcc accgcggatg      960
```

```
caaaagtaaa agccaccacc agtctgtgcg aatcggaact gcatggaaaa cccaattact    1020
cagcaggaag gagcagcaga gagagcggcg ttttggtgct cagggaacag actgacgctg    1080
gccgatgggc acaggttccc gccagggccc catgcctgtg cctccggggt ggccctgacc    1140
ttgtccttga ccccaagggg ggctcagggg acagggagga ggagcagcac aggatgctga    1200
gcagggcctc tggagtgaca gggcggaggg agactccagg acccacaaag cccctgccct    1260
ggacagcggg aaagcacagt gaggatggtg ccaggccgag gctgcagccc agcaagaatg    1320
acccgccctc cctgcgcccc atgccccgcg gctcctgcct gccctgcccg tgtgtccagg    1380
gcactttcag gaactcgccc atctctcacc cgccgagccc gtccccagt gcctactcca     1440 gccggaccag cagacccatg cgggatgtcg gtgaggacca ggtgcaccct cccctctgcc    1500
actttcccca gaggagcctg cagcaccagc tccctcagcc tggagctcag cgttttgcca    1560 cgagggcta tcccatggag acatgaagc tgcaaggtgt accgatgcct ccggggggacc     1620 tgtgtggtcc gacgctgctg ctagatgtgt ccatcaagat ggagaaggac tctgggtgtg    1680
agggtgctgc agacggctgt gtgcccagcc aggtgtggct gggggccagt gacaggagcc    1740
acccagccac cttccctacc aggatgcacc tgaaaacaga gccagactct cggcaacagg    1800
tgtacatctc gcacctgggg cacggcgtgc gggggggctca gccccatggg agggccactg    1860
ctgggcgcag cagggagctg accccttttcc accctgcaca ctgtgcctgc ctggagccca    1920
cagacggcct tccccagtcg gagcctcccc accagctctg tgcacgggc cgaggtgaac     1980 agtcctgcac ctgcagagct gctgaggccg cccctgtggt caagcgggag cccttggact    2040 cacccccagtg ggctactcac agccaggaa tggtgcccgg gatgttgccc aaaagtgcct     2100
tggccacgct ggtcccgccc caagcttcgg ggtgcacatt cctgccatag cgcagtgacc    2160
accatccaag ctcagatctg tgtgtctacg ctcagatgcg tcgtggctg ggctgccctg     2220 ctcctggtca ggccggagcc cgtcctaaga cacacgcttt gcagagctgt gcatgcgcag    2280
tctgctagtg tgtgtgtgca gcatacgcag gagcctatcc tgaattttgt aaaatatccc    2340
aacagttctt aaatgaaaac tggccttaag tctattcaag catgacagca tttctctttg    2400
aggaattaaa atctttagga aagtgatcat ggctggacag cttcatgccc cagaggcagc    2460
gagcacccgt cccatggctg ccaagtccac agtcgggat gaagcagtcg ggtgatgctc      2520
ccaagtccgc agtcggggat gaagcggtcg ggtgatgctc ccaagtccgc agtcggggat    2580
gaagcggtcg ggtgacacac ctagctcagc cctcccaggc cacctgcagc tcccagcctg    2640
tgctgtgcag gcagggtcag cccatcgcca cagtgcactg tagaggccag cacacggcaa    2700
attagaaata caacacgcgg agaaagggt ccgtgagccc actcatagag gaatctagaa      2760
cgttccaggc agcagaggct ggcagcgtgg gtcccacact gccccacacc gtgcggcagg    2820
tgctccatgg cgccatgaca gagtctgagg ccagacctgg actggaattg acagcataac    2880
ccctgttcct tctggacatc tcccgagttc tcagtgggtc tctgcggacg gttcttccta    2940
atctgcctct tggtacatca cgtaatacag agttcacaga ctccgggttt ggaagtacag    3000
agaaacacac aacgtagaga aagacacag gaaactgcgc tgcctgtggg ggtttctctc     3060
tggctggctg tacagttcac tcaaatgagg gttcccattg ccatcctagg agaataatta    3120
gggacaagac agacaagtat taatagcatt aaaacagttg taaggcgat attttctgag     3180 agtaggaaat ttggatacaa aagcataagt cagaaagtga aggtcaccaa tccaccaacc    3240
cgagaaccta cagctgatgg tgcatttcag gcttcttcca cggtctggcc tggaacccca    3300
cccggctggt gcaggcatca gatcagggtg tagaagtcac cccaagcaag aggaagccag    3360
```

```
gcagtgaggc cctggggtgt ggctgcagct gggcccacct gtgcggggt gggaaggccc    3420 catcctcagg gagagggcat cggcgccctg acgtcagctc cactgggagt ggcaggagct    3480
gtgggagccc atgggtgagg gacccaccac cccgctgcac tgtgcattgt gcctcccgtg    3540
tggacgccct ctctgttgtt ggcccgcggg tgagggaccc accaccccta gggacccacc    3600
accccgccgc actgtgcatt ctgcctcctg tgtggacgcc ctctctgttg tcagtggctt    3660
tgaggtgtca gtgcttactt agatgctggt ttaatgctgg acccatttgt taaacgcacc    3720
ttcactttgt caaacccag gtttggttgg caggactggg tcttctgccc aatgccaggt    3780
gcctgcgcct cagtggcc tggttcttgg acagtttgcc cccatgtggc agggataggg    3840
ataaggatct cctctcagta ctggaagaga acagccaacc atctgagccc agagtcacag    3900
atccatcgtg gccccctatg acccccaagc cctaccgagg gggcactcac tctctgctta    3960 gccaggggc gtctttcaaa aggtgacctc catgctgtgc tgtcgtgggt gtgagacgtg    4020
ctcatggcct tccactgcca tctctccctt atctgatgcc taaagtcacg atggggacag    4080
agctacccag gggccagcca tggggtgacc agccacctga gggtcagtca cctgtggaga    4140
gcaggcacct gtgaagacca ggcacctgag gactggcgcc tacttcccac tttggcccta    4200
cactggcaca gagcccctct ttattcattt ctcatgctga gcatggcaca cttctggcct    4260
ctgggcattt atggatttaa gaccaggatg gtatttcaga agcttcccac ttccttccta    4320
ttctaaccga gtgcccagct cctttgctga tcatggaaag acccttaata attaggcctg    4380
caggccaggc gcagtggctc atgcctataa tcccagcact ttaggaggtc aaggtaggag    4440
gatcgcttaa gcccaggagt tcaagaccag cctgggcaac acaggaagaa tgtgtctcta    4500
caaaaaataa ttaaaaatca gatctgctgt atccctgaaa aagtctcaat caacatgcat    4560
gttccactct tggagttccc tgttctgagg gccagccacg tcctgtgtcc tggagcttag    4620
ccctcagcag ctcccttcag cctgggcgcc gcctgggtcc caaacgtggc agctgctctt    4680
ccagtctcgg ggccgaggag ggcagggagc tcagtgactg agagtcttgt gtatcacatg    4740
tcttgagtgt cctggagcca acggctgtca ctgggaaaaa caccaggccc caaagatcga    4800
atcagagacg tggctgcgtg tttgcgattg tagccaggcc cttcagtgtc atcaaaggag    4860
cactggggcc tccttaagca cagacggcag cccctgccca ggaggcttct tcaccacgtc    4920
ctgccctgca gcctcccaga cctttagatg cgccctgcc caaggccctc ctggtgacag    4980
gtgccagatt gagtggtggg ttgctgccag gcaggccacg ctgtgttgac gctgcactca    5040
gcacgtgggt gttggctctg ccggttttgt ggtgtgggga ccctacagga ggctgcggcc    5100
ctgagagcct gggatcagcg aggtgtccga catcccttcc tcaacggcaa caaaaactcc    5160
ccaagtcagc actttggtta ttttatagcc acaaccctct tggaaaacag tggggaagac    5220
tatggaacat agaaagtgtg gatgtatcac ttctctctaa aatgtcattg ttagcactaa    5280
ttacaggttc atgtttttct gtgtatgtag cttttcccta tatagctgaa aaagtattaa    5340
agtcaaatat aaggtgggaa tgggatggaa gggaggagat caatacaact tatatttttg    5400
cagtttctac tggaagaaaa aagttttcaa tacctagacc aacttgttga atttttaaaa    5460
cttatgcact ataaatgcaa ctttctctac tgctttctca gtgcctttag gaagctttca    5520

aatttttttg tactgtggtt tgtattaaat ttgcaatatt gatgtaaaat acatgacatg    5580
ctagtacatg tttaacaaaa atttaaaaaa aaaaaaaaaa aa    5622
```

<210> SEQ ID NO 18

<211> LENGTH: 2039
<212> TYPE: DNA
<213> ORGANISM: Homo sapiens

<400> SEQUENCE: 18

| | | | | | |
|---|---|---|---|---|---|
| gtaggtgtca | cttatatcac | aaggctacag | gtgtctttat | ttccactgca | cgctggtgct | 60 |
| gggagcgcct | gccttctctt | gccttgaaag | cctcctcttt | ggacctagcc | accgctgccc | 120 |
| tcacggtaat | gttggactcg | gtgacacaca | gcaccttcct | gcctaatgca | tccttctgcg | 180 |
| atcccctgat | gtcgtggact | gatctgttca | gcaatgaaga | gtactaccct | gcctttgagc | 240 |
| atcagacaga | tgctgattcc | aactgcttga | aaacaagtgg | catcaaaagt | caagactgtc | 300 |
| acagtcatag | tagaacaagc | ctccaaagtt | ctcatctatg | ggaatttgta | cgagacctgc | 360 |
| ttctatctcc | tgaagaaaac | tgtggcattc | tggaatggga | agatagggaa | caaggaattt | 420 |
| ttcgggtggt | taaatcggaa | gccctggcaa | agatgtgggg | acaaaggaag | aaaaatgaca | 480 |
| gaatgacata | tgaaaagttg | agcagagccc | tgagatacta | ctataaaaca | ggaattttgg | 540 |
| agcgggttga | ccgaaggtta | gtgtacaaat | ttggaaaaaa | tgcacacggg | tggcaggaag | 600 |
| acaagctatg | atctgctcca | ggcatcaagc | tcattttatg | gatttctgtc | ttttaaaaca | 660 |
| atcagattgc | aatagacatt | cgaaaggctt | cattttcttc | tcttttttt | taacctgcaa | 720 |
| acatgctgat | aaaatttctc | cacatctcag | cttacatttg | gattcagagt | tgttgtctac | 780 |
| ggagggtgag | agcagaaact | cttaagaaat | cctttcttct | ccctaagggg | atgaggggat | 840 |
| gatcttttgt | ggtgtcttga | tcaaacttta | ttttcctaga | gttgtggaat | gacaacagcc | 900 |
| catgccattg | atgctgatca | gagaaaaact | attcaattct | gccattagag | acacatccaa | 960 |
| tgctcccatc | ccaaaggttc | aaaagttttc | aaataactgt | ggcagctcac | caaaggtggg | 1020 |
| ggaaagcatg | attagtttgc | aggttatggt | aggagagggt | gagatataag | acatacatac | 1080 |
| tttagatttt | aaattattaa | agtcaaaaat | ccatagaaaa | gtatcccttt | ttttttttt | 1140 |
| gagacgggtt | ctcactatgt | tgcccagggc | tggtcttgaa | ctcctatgct | caagtgatcc | 1200 |
| tcccacctcg | gcctcccaaa | gtactgtgat | tacaagcgtg | agccacggca | cctgggcaga | 1260 |
| aaagtatctt | aattaatgaa | agagctaagc | catcaagctg | ggacttaatt | ggatttaaca | 1320 |
| taggttcaca | gaaagtttcc | taaccagagc | atctttttga | ccactcagca | aaacttccac | 1380 |
| agacatcctt | ctggacttaa | acacttaaca | ttaaccacat | tattaattgt | tgctgagttt | 1440 |
| attcccccctt | ctaactgatg | gctggcatct | gatatgcaga | gttagtcaac | agacactggc | 1500 |
| atcaattaca | aaatcactgc | tgtttctgtg | attcaagctg | tcaacacaat | aaaatcgaaa | 1560 |
| ttcattgatt | ccatctctgg | tccagatgtt | aaacgtttat | aaaaccggaa | atgtcctaac | 1620 |
| aactctgtaa | tggcaaatta | aattgtgtgt | ctttttttgtt | ttgtctttct | acctgatgtg | 1680 |
| tattcaagcg | ctataacacg | tatttccttg | acaaaaatag | tgacagtgaa | ttcacactaa | 1740 |
| taaatgttca | taggttaaag | tctgcactga | catttctca | tcaatcactg | gtatgtaagt | 1800 |
| tatcagtgac | tgacagctag | gtggactgcc | cctaggactt | ctgtttcacc | agagcaggaa | 1860 |
| tcaagtggtg | aggcactgaa | tcgctgtaca | ggctgaagac | ctccttatta | gagttgaact | 1920 |
| tcaaagtaac | ttgttttaaa | aaatgtgaat | tactgtaaaa | taatctatt | tggattcatg | 1980 |
| tgttttccag | gtggatatag | tttgtaaaca | atgtgaataa | agtatttaac | atgtaaaaa | 2039 |

<210> SEQ ID NO 19
<211> LENGTH: 2222
<212> TYPE: DNA
<213> ORGANISM: Homo sapiens

<400> SEQUENCE: 19

```
ggctgagtgg tttgctcctt ccctctctc tgggaggctg agcagggtg ccggttgct     60
caggccatgg gagccacacc tgttattgct gcctctgatt tgtgtgacac tgagaagccc    120
acaggcctgt ccctccaact cggtggaccc tctctgtgtg catttggtgt gtgagccagc    180
tctgagaagg gttcagaagc cactggaggc atctgggac ctcagcttcc atgccatctc    240
tgcctcactc ccacagggta atgttggact cggtgacaca cagcaccttc ctgcctaatg    300
catccttctg cgatcccctg atgtcgtgga ctgatctgtt cagcaatgaa gagtactacc    360
ctgcctttga gcatcagaca ggttactcct tttttaatga cgctgaagaa agcaaggcca    420
ccatcaaaga ctatgctgat ccaactgct tgaaaacaag tggcatcaaa agtcaagact    480
gtcacagtca tagtagaaca agcctccaaa gttctcatct atgggaattt gtacgagacc    540
tgcttctatc tcctgaagaa aactgtggca ttctggaatg gaagatagg gaacaaggaa    600
tttttcgggt ggttaaatcg gaagccctgg caaagatgtg gggacaaagg aagaaaaatg    660
acagaatgac atatgaaaag ttgagcagag ccctgagata ctactataaa acaggaattt    720
tggagcgggt tgaccgaagg ttagtgtaca aatttggaaa aaatgcacac gggtggcagg    780
aagacaagct atgatctgct ccaggcatca agctcatttt atggatttct gtcttttaaa    840
acaatcagat tgcaatagac attcgaaagg cttcattttc ttctcttttt ttttaacctg    900
caaacatgct gataaaattt ctccacatct cagcttacat ttggattcag agttgttgtc    960
tacggagggt gagagcagaa actcttaaga aatcctttct tctccctaag gggatgaggg   1020
gatgatcttt tgtggtgtct tgatcaaact ttattttcct agagttgtgg aatgacaaca   1080
gcccatgcca ttgatgctga tcagagaaaa actattcaat tctgccatta gagacacatc   1140
caatgctccc atcccaaagg ttcaaaagtt ttcaaataac tgtggcagct caccaaaggt   1200
gggggaaagc atgattagtt tgcaggttat ggtaggagag ggtgagatat aagcataca   1260
tactttagat tttaaattat taaagtcaaa aatccataga aaagtatccc ttttttttt   1320
tttgagacgg gttctcacta tgttgcccag ggctggtctt gaactcctat gctcaagtga   1380
tcctcccacc tcggcctccc aaagtactgt gattacaagc gtgagccacg gcacctgggc   1440
agaaaagtat cttaattaat gaaagagcta agccatcaag ctgggactta attggattta   1500
acataggttc acagaaagtt tcctaaccag agcatctttt tgaccactca gcaaaacttc   1560
cacagacatc cttctggact taaacactta acattaacca cattattaat tgttgctgag   1620
tttattcccc cttctaactg atggctggca tctgatatgc agagttagtc aacagacact   1680
ggcatcaatt acaaaatcac tgctgttct gtgattcaag ctgtcaacac aataaaatcg   1740
aaattcattg attccatctc tggtccagat gttaaacgtt tataaaaccg gaaatgtcct   1800
aacaactctg taatggcaaa ttaaattgtg tgtctttttt gttttgtctt tctacctgat   1860
gtgtattcaa gcgctataac acgtatttcc ttgacaaaaa tagtgacagt gaattcacac   1920
taataaatgt tcataggtta aagtctgcac tgacattttc tcatcaatca ctggtatgta   1980
agttatcagt gactgacagc taggtggact gccctagga cttctgtttc accagagcag   2040
gaatcaagtg gtgaggcact gatcgctgt acaggctgaa gacctcctta ttagagttga   2100
acttcaaagt aacttgtttt aaaaaatgtg aattactgta aataatctca ttttggattc   2160
atgtgttttc caggtggata tagtttgtaa acaatgtgaa taaagtattt aacatgtaaa   2220
aa                                                                  2222
```

<210> SEQ ID NO 20
<211> LENGTH: 1214
<212> TYPE: DNA
<213> ORGANISM: Homo sapiens

<400> SEQUENCE: 20

| | | | | | |
|---|---|---|---|---|---|
| agaaggttta | aggccggaaa | gggaaatgaa | ggggcccggc | gctaaccctc | taaggacctg | 60 |
| ttttgcttct | gtttaaacca | aatgggcagt | ctgtcattac | acacaccctg | ggtcttcata | 120 |
| tgtggccgcc | aggtaggagc | atcacagtca | agctacggga | gaaaacagtt | tccaggaaac | 180 |
| tggaaatgaa | cggcccgagt | gctttccagg | ggctcatctg | tgggaagtat | aatggaatgt | 240 |
| gcttacaagg | gccagcagga | gtgcctggtc | gagacgggag | ccctgggggcc | aatggcattc | 300 |
| cgggtacacc | tgggatccca | ggtcgggatg | gattcaaagg | agaaaagggg | gaatgtctga | 360 |
| gggaaagctt | tgaggagtcc | tggacaccca | actacaagca | gtgttcatgg | agttcattga | 420 |
| attatggcat | agatcttggg | aaaattgcgg | agtgtacatt | tacaaagatg | cgttcaaata | 480 |
| gtgctctaag | agttttgttc | agtggctcac | ttcggctaaa | atgcagaaat | gcatgctgtc | 540 |
| agcgttggta | tttcacattc | aatggagctg | aatgttcagg | acctcttccc | attgaagcta | 600 |
| taatttattt | ggaccaagga | agccctgaaa | tgaattcaac | aattaatatt | catcgcactt | 660 |
| cttctgtgga | aggactttgt | gaaggaattg | gtgctggatt | agtggatgtt | gctatctggg | 720 |
| ttggtacttg | ttcagattac | ccaaaaggag | atgcttctac | tggatggaat | tcagtttctc | 780 |
| gcatcattat | tgaagaacta | ccaaaataaa | tgctttaatt | ttcatttgct | acctcttttt | 840 |
| ttattatgcc | ttggaatggt | tcacttaaat | gacattttaa | ataagtttat | gtatacatct | 900 |
| gaatgaaaag | caaagctaaa | tatgtttaca | gaccaaagtg | tgatttcaca | ctgtttttaa | 960 |
| atctagcatt | attcattttg | cttcaatcaa | aagtggtttc | aatatttttt | ttagttggtt | 1020 |
| agaatacttt | cttcatagtc | acattctctc | aacctataat | ttggaatatt | gttgtggtct | 1080 |
| tttgtttttt | ctcttagtat | agcattttta | aaaaaatata | aaagctacca | atctttgtac | 1140 |
| aatttgtaaa | tgttaagaat | ttttttata | tctgttaaat | aaaaattatt | tccaacaacc | 1200 |
| ttaatatctt | taaa | | | | | 1214 |

<210> SEQ ID NO 21
<211> LENGTH: 618
<212> TYPE: DNA
<213> ORGANISM: Homo sapiens

<400> SEQUENCE: 21

| | | | | | |
|---|---|---|---|---|---|
| gcggccgcaa | gctcggcact | cacggctctg | agggctccga | cggcactgac | ggccatggcg | 60 |
| cgttcgaacc | tcccgctggc | gctgggcctg | gccctggtcg | cattctgcct | cctggcgctg | 120 |
| ccacgcgacg | cccgggcccg | gccgcaggag | cgcatggtcg | gagaactccg | ggacctgtcg | 180 |
| cccgacgacc | cgcaggtgca | gaaggcggcc | caggcggccg | tggccagcta | caacatgggc | 240 |
| agcaacagca | tctactactt | ccgagacacg | cacatcatca | aggcgcagag | ccagctggtg | 300 |
| gccggcatca | agtacttcct | gacgatggag | atggggagca | cagactgccg | caagaccagg | 360 |
| gtcactggag | accacgtcga | cctcaccact | tgcccccctgg | cagcagggc | gcagcaggag | 420 |
| aagctgcgct | gtgactttga | ggtccttgtg | gttccctggc | agaactcctc | tcagctccta | 480 |
| aagcacaact | gtgtgcagat | gtgataagtc | cccgagggcg | aaggccattg | gtttggggc | 540 |
| catggtggag | ggcacttcag | gtccgtgggc | cgtatctgtc | acaataaatg | gccagtgctg | 600 |
| cttcttgcaa | aaaaaaaa | | | | | 618 |

<210> SEQ ID NO 22
<211> LENGTH: 2324
<212> TYPE: DNA
<213> ORGANISM: Homo sapiens

<400> SEQUENCE: 22

| | | | | | | |
|---|---|---|---|---|---|---|
| gtaggtgtca | cttatatcac | aaggctacag | gtgtctttat | ttccactgca | cgctggtgct | 60 |
| gggagcgcct | gccttctctt | gccttgaaag | cctcctcttt | ggacctagcc | accgctgccc | 120 |
| tcacggtaat | gttggactcg | gtgacacaca | gcaccttcct | gcctaatgca | tccttctgcg | 180 |
| atcccctgat | gtcgtggact | gatctgttca | gcaatgaaga | gtactaccct | gcctttgagc | 240 |
| atcagacagc | ctgtgactca | tactggacat | cagtccaccc | tgaatactgg | actaagcgcc | 300 |
| atgtgtggga | gtggctccag | ttctgctgcg | accagtacaa | gttggacacc | aattgcatct | 360 |
| ccttctgcaa | cttcaacatc | agtggcctgc | agctgtgcag | catgacacag | gaggagttcg | 420 |
| tcgaggcagc | tggcctctgc | ggcgagtacc | tgtacttcat | cctccagaac | atccgcacac | 480 |
| aaggttactc | cttttttaat | gacgctgaag | aaagcaaggc | caccatcaaa | gactatgctg | 540 |
| attccaactg | cttgaaaaca | gtggcatca | aagtcaaga | ctgtcacagt | catagtagaa | 600 |
| caagcctcca | aagttctcat | ctatgggaat | tgtacgaga | cctgcttcta | tctcctgaag | 660 |
| aaaactgtgg | cattctggaa | tgggaagata | gggaacaagg | aattttttcgg | gtggttaaat | 720 |
| cggaagccct | ggcaaagatg | tggggacaaa | ggaagaaaaa | tgacagaatg | acatatgaaa | 780 |
| agttgagcag | agccctgaga | tactactata | aacaggaat | tttggagcgg | gttgaccgaa | 840 |
| ggttagtgta | caaatttgga | aaaaatgcac | acgggtggca | ggaagacaag | ctatgatctg | 900 |
| ctccaggcat | caagctcatt | ttatggattt | ctgtctttta | aaacaatcag | attgcaatag | 960 |
| acattcgaaa | ggcttcattt | tcttctcttt | tttttaacc | tgcaaacatg | ctgataaaat | 1020 |
| ttctccacat | ctcagcttac | atttggattc | agagttgttg | tctacggagg | gtgagagcag | 1080 |
| aaactcttaa | gaaatccttt | cttctcccta | aggggatgag | gggatgatct | tttgtggtgt | 1140 |
| cttgatcaaa | cttttatttc | ctagagttgt | ggaatgacaa | cagcccatgc | cattgatgct | 1200 |
| gatcagagaa | aaactattca | attctgccat | tagagacaca | tccaatgctc | ccatcccaaa | 1260 |
| ggttcaaaag | ttttcaaata | actgtggcag | ctcaccaaag | gtgggggaaa | gcatgattag | 1320 |
| tttgcaggtt | atggtaggag | agggtgagat | ataagacata | catactttag | attttaaatt | 1380 |
| attaaagtca | aaaatccata | gaaaagtatc | cctttttttt | ttttgagac | gggttctcac | 1440 |
| tatgttgccc | agggctggtc | ttgaactcct | atgctcaagt | gatcctccca | cctcggcctc | 1500 |
| ccaaagtact | gtgattacaa | gcgtgagcca | cggcacctgg | gcagaaaagt | atcttaatta | 1560 |
| atgaaagagc | taagccatca | agctgggact | taattggatt | taacataggt | tcacagaaag | 1620 |
| ttcctaacc | agagcatctt | tttgaccact | cagcaaaact | tccacagaca | tccttctgga | 1680 |
| cttaaacact | taacattaac | cacattatta | attgttgctg | agtttattcc | cccttctaac | 1740 |
| tgatggctgg | catctgatat | gcagagttag | tcaacagaca | ctggcatcaa | ttacaaaatc | 1800 |
| actgctgttt | ctgtgattca | agctgtcaac | acaataaaat | cgaaattcat | tgattccatc | 1860 |
| tctggtccag | atgttaaacg | tttataaaac | cggaaatgtc | ctaacaactc | tgtaatggca | 1920 |
| aattaaattg | tgtgtctttt | ttgttttgtc | tttctacctg | atgtgtattc | aagcgctata | 1980 |
| acacgtattt | ccttgacaaa | aatagtgaca | gtgaattcac | actaataaat | gttcataggt | 2040 |
| taaagtctgc | actgacattt | tctcatcaat | cactggtatg | taagttatca | gtgactgaca | 2100 |

| | | |
|---|---|---|
| gctaggtgga ctgcccctag gacttctgtt tcaccagagc aggaatcaag tggtgaggca | 2160 |
| ctgaatcgct gtacaggctg aagacctcct tattagagtt gaacttcaaa gtaacttgtt | 2220 |
| ttaaaaaatg tgaattactg taaaataatc tattttggat tcatgtgttt tccaggtgga | 2280 |
| tatagtttgt aaacaatgtg aataaagtat taacatgta aaaa | 2324 |

<210> SEQ ID NO 23
<211> LENGTH: 1166
<212> TYPE: DNA
<213> ORGANISM: Homo sapiens

<400> SEQUENCE: 23

| | |
|---|---|
| gctccgggaa tttccctggc ccggccgctc cgggctttcc agtctcaacc atgcataaaa | 60 |
| agggttcgcc gatcttgggg agccacacag cccgggtcgc aggcacctcc ccgccagctc | 120 |
| tcccgcttct cgcacagctt cccgacgcgt ctgctgagcc ccatggccca cgccacgctc | 180 |
| tccgccgccc ccagcaatcc ccggctcctg cgggtggcgc tgctgctcct gctcctggtg | 240 |
| gccgccagcc ggcgcgcagc aggagcgtcc gtggtcactg aactgcgctg ccagtgcttg | 300 |
| cagacactgc agggaattca cctcaagaac atccaaagtg tgaatgtaag gtcccccgga | 360 |
| ccccactgcg cccaaaccga agtcatagcc acactcaaga atgggaagaa agcttgtctc | 420 |
| aaccccgcat cccccatggt tcagaaaatc atcgaaaaga tactgaacaa ggggagcacc | 480 |
| aactgacagg agaagagtaa aagcttatca gcgtatcat tgacacttcc tgcagggtgg | 540 |
| tccctgccct taccagagct gaaaatgaaa aagagaacag cagctttcta gggacagctg | 600 |
| gaaaggactt aatgtgtttg actatttctt acgagggttc tacttattta tgtatttatt | 660 |
| tttgaaagct tgtatttaa tattttacat gctgttattt aaagatgtga gtgtgtttca | 720 |
| tcaaacatag ctcagtcctg attatttaat tggaatatga tgggttttaa atgtgtcatt | 780 |
| aaactaatat ttagtgggag accataatgt gtcagccacc ttgataaatg acagggtggg | 840 |
| gaactggagg gtgggggat tgaaatgcaa gcaattagtg gatcactgtt agggtaaggg | 900 |
| aatgtatgta cacatctatt ttttatactt tttttttaaa aaagaatgt cagttgttat | 960 |
| ttattcaaat tatctcacat tatgtgttca acatttttat gctgaagttt cccttagaca | 1020 |
| ttttatgtct tgcttgtagg gcataatgcc ttgtttaatg tccattctgc agcgtttctc | 1080 |
| tttcccttgg aaaagagaat ttatcattac tgttacattt gtacaaatga catgataata | 1140 |
| aaagttttat gaaaaaaaaa aaaaaa | 1166 |

<210> SEQ ID NO 24
<211> LENGTH: 5189
<212> TYPE: DNA
<213> ORGANISM: Homo sapiens

<400> SEQUENCE: 24

| | |
|---|---|
| gggaaagtga agaaaacaga aaaggagagg gacagaggcc agaggacttc tcatactgga | 60 |
| cagaaaccga tcaggcatgg aactccccctt cgtcactcac ctgttcttgc ccctggtgtt | 120 |
| cctgacaggt ctctgctccc cctttaacct ggatgaacat cacccacgcc tattcccagg | 180 |
| gccaccagaa gctgaatttg gatacagtgt cttacaacat gttgggggtg gacagcgatg | 240 |
| gatgctggtg ggcgccccct gggatgggcc ttcaggcgac cggagggggg acgtttatcg | 300 |
| ctgccctgta ggggggccc acaatgcccc atgtgccaag ggccacttag gtgactacca | 360 |
| actgggaaat tcatctcatc ctgctgtgaa tatgcacctg gggatgtctc tgttagagac | 420 |
| agatggtgat gggggattca tggcctgtgc ccctctctgg tctcgtgctt gtggcagctc | 480 |

```
tgtcttcagt tctgggatat gtgcccgtgt ggatgcttca ttccagcctc agggaagcct      540
ggcacccact gcccaacgct gcccaacata catggatgtt gtcattgtct tggatggctc      600
caacagcatc taccoctggt ctgaagttca gaccttccta cgaagactgg tagggaaact      660
gtttattgac ccagaacaga tacagtgggg actggtacag tatggggaga gccctgtaca      720
tgagtggtcc ctgggagatt tccgaacgaa ggaagaagtg gtgagagcag caaagaacct      780
cagtcggcgg gagggacgag aaacaaagac tgcccaagca ataatggtgg cctgcacaga      840
agggttcagt cagtcccatg ggggccgacc cgaggctgcc aggctactgg tggttgtcac      900
tgatggagag tccatgatg gagaggagct tcctgcagca ctaaaggcct gtgaggctgg      960
aagagtgaca cgctatggga ttgcagtcct tggtcactac ctccggcggc agcgagatcc     1020
cagctctttc ctgagagaaa ttagaactat tgccagtgat ccagatgagc gattcttctt     1080
caatgtcaca gatgaggctg ctctgactga cattgtggat gcactaggag atcggatttt     1140
tggccttgaa gggtcccatg cagaaaacga aagctccttt gggctggaaa tgtctcagat     1200
tggtttctcc actcatcggc taaaggatgg gattcttttt gggatggtgg gggcctatga     1260
ctggggaggc tctgtgctat ggcttgaagg aggccaccgc cttttccccc cacgaatggc     1320 actgaagac gagttccccc ctgcactgca gaaccatgca gcctacctgg gttactctgt     1380
ttcttccatg cttttgcggg gtggacgccg cctgtttctc tctggggctc ctcgatttag     1440
acatcgagga aaagtcatcg ccttccagct taagaaagat ggggctgtga gggttgccca     1500
gagcctccag ggggagcaga ttggttcata ctttggcagt gagctctgcc cattggatac     1560
agatagggat ggaacaactg atgtcttact tgtggctgcc cccatgttcc tgggacccca     1620
gaacaaggaa acaggacgtg tttatgtgta tctggtaggc cagcagtcct tgctgaccct     1680
ccaaggaaca cttcagccag aaccccccca ggatgctcgg tttggctttg ccatgggagc     1740
tcttcctgat ctgaaccaag atggttttgc tgatgtggct gtggggcgc ctctggaaga     1800 tgggcaccag ggagcactgt acctgtacca tggaacccag agtggagtca ggccccatcc     1860
tgcccagagg attgctgctg cctccatgcc acatgccctc agctactttg gccgaagtgt     1920
ggatggtcgg ctagatctgg atggagatga tctggtcgat gtggctgtgg gtgcccaggg     1980
ggcagccatc ctgctcagct cccggcccat tgtccatctg acccatcac tggaggtgac     2040 cccacaggcc atcagtgtgg ttcagaggga ctgtaggcgg cgaggccaag aggcagtctg     2100
tctgactgca gccctttgct tccaagtgac ctcccgtact cctggtcgct gggatcacca     2160
attctacatg aggttcaccg catcactgga tgaatggact gctggggcac gtgcagcatt     2220
tgatggctct ggccagaggt tgtcccctcg gaggctccgg ctcagtgtgg ggaatgtcac     2280
ttgtgagcag ctacacttcc atgtgctgga tacatcagat tacctccggc cagtggcctt     2340
gactgtgacc tttgccttgg acaatactac aaagccaggg cctgtgctga atgagggctc     2400
acccacctct atacaaaagc tggtccccttt tcaaaggat tgtggccctg acaatgaatg     2460
tgtcacagac ctggtgcttc aagtgaatat ggacatcaga ggctccagga aggccccatt     2520
tgtggttcga ggtggccggc ggaaagtgct ggtatctaca actctggaga acagaaagga     2580
aaatgcttac aatacgagcc tgagtctcat cttctctaga aacctccacc tggccagtct     2640
cactcctcag agagagagcc aataaaggt ggaatgtgcc gcccttctg ctcatgcccg     2700 gctctgcagt gtggggcatc ctgtcttcca gactggagcc aaggtgacct ttctgctaga     2760
gtttgagttt agctgctcct ctctcctgag ccaggtcttc gtgaagctga ctgccagcag     2820
```

```
tgacagcctg gagagaaatg ggacccttca agataacaca gcccagacct cagcctacat    2880
ccaatatgag ccccacctcc tgttctctag tgagtctacc ctgcaccgct atgaggttca    2940
cccatatggg accctcccag tgggtcctgg cccagaattc aaaaccactc tcagggttca    3000
gaacctaggc tgctatgtgg tcagtggcct catcatctca gccctccttc cagctgtggc    3060
ccatggggc aattacttcc tatcactgtc tcaagtcatc actaacaatg caagctgcat     3120
agtgcagaac ctgactgaac ccccaggccc acctgtgcat ccagaggagc ttcaacacac    3180
aaacagactg aatgggagca atactcagtg tcaggtggtg aggtgccacc ttgggcagct    3240
ggcaaagggg actgaggtct ctgttggact attgaggctg gttcacaatg aattttccg     3300
aagagccaag ttcaagtccc tgacggtggt cagcaccttt gagctgggaa ccgaagaggg    3360
cagtgtccta cagctgactg aagcctcccg ttggagtgag agcctcttgg aggtggttca    3420
gacccggcct atcctcatct ccctgtggat cctcataggc agtgtcctgg agggttgct     3480
cctgcttgct ctccttgtct tctgcctgtg gaagcttggc ttctttgccc ataagaaaat    3540
ccctgaggaa gaaaaaagag aagagaagtt ggagcaatga atgtagaata agggtctaga    3600
aagtcctccc tggcagcttc ttcaagagac ttgcataaaa gcagaggttt gggggctcag    3660
atgggacaag aagccgcctc tggactatct ccccagacca gcagcctgac ttgactttg     3720
agtcctaggg atgctgctgg ctagagatga ggctttacct cagacaagaa gagctggcac    3780
caaaactagc catgctccca ccctctgctt ccctcctcct cgtgatcctg gttccatagc    3840
caacactggg gcttttgttt ggggtccttt tatccccagg aatcaataat tttttttgcct   3900
aggtgcctga ctcctttcag attccctctt tatcttccct cacagtttgg aaaggatgag    3960
ggttatcttc ctcgattctt ccaccctctc actttcctgc ctgttccca ctccacagga     4020
gggagctgac gttggcttga aaggagtaaa gtcaacatct gctgctttcc tgtggactct    4080
ggtgattcat agagccggat ggggagagtc aacaggaaaa aaggagggag gaggaaaagc    4140
cacaagagac attctgtaca attccaagga acagagaagc ctttagacag gcaactgcca    4200
tcccccctga aacctgagac ctgtagtgca ctcgaccgcc ctcaggtgtt ggtgaaacag    4260
agctgccccc aggctcgctg ggcataggct tcctgattcc aagccttttc tgggagcaaa    4320
gccagggcct ggtgcctgat tttctgaagc caggagccct caggtggctg gagctggaat    4380
agcagggagg actgggtgta cctaggcagt attttctcta cttctctcaa gtcttatact    4440
cactcttgag ccctccttgg ggcctgctta gaaagcagac aggagagaga gtactgctac    4500
ttgatgatgg gaaatgcttt cactttacca gctttgggaa gcagcagccc catgggatct    4560
aaaagtgtgg agtctgcatt aagaaaccta catgggtggc atgggctct ggggagcaag     4620
cccttacttg ctcagcactg gttatgtagc acaaatagct cctaggaaaa tgtttctggg    4680
gcaaccctag aaccctggtc atattttgca gggtttctct ggtggaatca gtttgccagc    4740
ccttgcttga tgcttactgg aaatctccag gttaatttct atctctgatc cctccccaac    4800
ccactccata tttgggtcat ggacagtaaa ggcagttgga ttctcataga caactgggta    4860
acttatattt ctttgtaatc aagacttgag atatcgaagt cagttattgg tctccagagt    4920
gcagctctgg gagcctttg aagaatcagc actcattaag agctgagaag agagaagacc     4980
tgattgggtg gttgactagc agtcacagaa cctgtcctcc caggctgttc ctgaggcctg    5040
accacagtat ttattttggc atgtctctgg ccttctgcag aggcccaccc tcatgggcat    5100
tgtctctgtt tcccagtggg gtggacagta tatcagatgg tcagaacaaa taaagttcag    5160
tgtcaaatga aaaaaaaaaa aaaaaaaa                                      5189
```

<210> SEQ ID NO 25
<211> LENGTH: 2005
<212> TYPE: DNA
<213> ORGANISM: Homo sapiens

<400> SEQUENCE: 25

| | | | | | |
|---|---|---|---|---|---|
| tttcctctca | gggggcagca | ggaagtgagg | agaaagggct | gggatgggag | gcgggagcgg | 60 |
| atgggaggga | atggggttta | tcaagtcctc | ggcgagctgc | ccaacgggca | gcagctggcg | 120 |
| caagtagcct | agctggagag | gctcacccca | ggaaggaggg | aggccaccga | cctactgggc | 180 |
| cgacggactc | ccacacagtt | cctgagctgg | tgccaggcag | gtgacacctc | ctgcagcccc | 240 |
| cagcatgcgg | gcaggcccag | gccccaccgt | tacattggcc | ctggtgctgg | cggtgtcatg | 300 |
| ggccatggag | ctcaagccca | cagcaccacc | catcttcact | ggccggccct | ttgtggtagc | 360 |
| gtgggacgtg | cccacacagg | actgtggccc | acgcctcaag | gtgccactgg | acctgaatgc | 420 |
| ctttgatgtg | caggcctcac | ctaatgaggg | ttttgtgaac | cagaatatta | ccatcttcta | 480 |
| ccgcgaccgt | ctaggcctgt | atccacgctt | cgattctgcc | ggaaggtctg | tgcatggtgg | 540 |
| tgtgccacag | aatgtcagcc | tttgggcaca | ccggaagatg | ctgcagaaac | gtgtggagca | 600 |
| ctacattcgg | acacaggagt | ctgcggggct | ggcggtcatc | gactgggagg | actggcgacc | 660 |
| tgtgtgggtg | cgcaactggc | aggacaaaga | tgtgtatcgc | cggttatcac | gccagctagt | 720 |
| ggccagtcgt | caccctgact | ggcctccaga | ccgcatagtc | aaacaggcac | aatatgagtt | 780 |
| tgagttcgca | gcacagcagt | tcatgctgga | gacactgcgt | tatgtcaagg | cagtgcggcc | 840 |
| ccggcacctc | tggggcttct | acctctttcc | tgactgctac | aatcatgatt | atgtgcagaa | 900 |
| ctgggagagc | tacacaggcc | gctgccctga | tgttgaggtg | gcccgcaatg | accagctggc | 960 |
| ctggctgtgg | gctgagagca | cggccctctt | cccgtctgtc | tacctggacg | agacacttgc | 1020 |
| ttcctcccgc | catggccgca | actttgtgag | cttccgtgtt | caggaggccc | ttcgtgtggc | 1080 |
| tcgcacccac | catgccaacc | atgcactccc | agtctacgtc | ttcacacgac | ccacctacag | 1140 |
| ccgcaggctc | acggggctta | gtgagatgga | cctcatctct | accattggcg | agagtgcggc | 1200 |
| cctgggcgca | gctggtgtca | tcctctgggg | tgacgcgggg | tacaccacaa | gcacggagac | 1260 |
| ctgccagtac | ctcaaaagatt | acctgacacg | gctgctggtc | ccctacgtgg | tcaatgtgtc | 1320 |
| ctgggccacc | aatattgca | gccgggccca | gtgccatggc | catgggcgct | gtgtgcgccg | 1380 |
| caacccagt | gccagtacct | tcctgcatct | cagcaccaac | agtttccgcc | tagtgcctgg | 1440 |
| ccatgcacct | ggtgaacccc | agctgcgacc | tgtgggggag | ctcagttggg | ccgacattga | 1500 |
| ccacctgcag | acacacttcc | gctgccagtg | ctacttgggc | tggagtggtg | agcaatgcca | 1560 |
| gtgggaccat | aggcaggcag | ctggaggtgc | cagcgaggcc | tgggctgggt | cccacctcac | 1620 |
| cagtctgctg | gctctggcag | ccctggcctt | tacctggacc | ttgtaggggt | ctcctgccta | 1680 |
| gctgcctagc | aagctggcct | ctaccacaag | ggctctctta | ggcatgtagg | accctgcagg | 1740 |
| gggtggacaa | actggagtct | ggagtgggca | gagcccccag | gaagcccagg | agggcatcca | 1800 |
| taccagctcg | cacccccctg | ttctaagggg | gaggggaagt | ccctgggagg | ccccttctct | 1860 |
| ccctgccaga | ggggaaggag | ggtacagctg | ggctggggag | gacctgaccc | tactcccttg | 1920 |
| ccctagatag | tttattatta | ttattatttt | ggggtctctt | ttgtaaatta | aacataaaac | 1980 |
| aattgcttct | ctgcttggat | tttgt | | | | 2005 |

<210> SEQ ID NO 26

<211> LENGTH: 5802
<212> TYPE: DNA
<213> ORGANISM: Homo sapiens

<400> SEQUENCE: 26

```
tttatagcag cagtagaaat ataccaccct agaggacaca cctccttta gctaggtacc      60
tataaatgtc caggattttc tattcaattg agaagaaccc agcaaaatgg ggatctccac     120
agtcatcctt gaaatgtgtc ttttatgggg acaagttcta tctacaggtg ggtggatccc     180
aaggactaca gactacgctt cactgattcc ctcggaggtg cccttggatc caactgtagc     240
agaaggttct ccatttccct cggagtcgac cctggagtca actgtagcag aaggttctcc     300
gatttccttg gagtcaaccc tggagtcaac cgtagcagaa ggttctctga ttccctcaga     360
gtcaaccctg gagtcaactg tagcagaagg atctgattct ggtttggccc tgaggctggt     420
gaatggagat ggcaggtgtc agggccgagt ggagatccta taccgaggct cctggggcac     480
cgtgtgtgat gacagctggg acaccaatga tgccaacgtg gtctgtaggc agctgggttg     540
tggctgggcc atgtcagctc caggaaatgc ctggtttggc cagggctcag acccattgc      600
cctggatgat gtgcgctgct caggacacga atcctacctg tggagctgcc cccacaatgg     660
ctggctctcc cataactgtg gccatggtga agatgctggt gttatctgct cagctgccca     720
gcctcagtca acactcaggc cagaaagttg gcctgtcagg atatcaccac ctgtacccac     780
agaaggatct gaatccagtt tggccctgag gctggtgaat ggaggcgaca ggtgtcgagg     840
ccgagtggag gtcctatacc gaggctcctg ggcaccgtg tgtgatgact actgggacac      900
caatgatgcc aatgtggtct gcaggcagct gggctgtggc tgggccatgt cagccccagg     960
aaatgcccag tttggccagg gctcaggacc cattgtcctg gatgatgtgc gctgctcagg    1020
acatgagtcc tacctgtgga gctgcccca caatggctgg ctcacccaca actgtggcca     1080
tagtgaagac gctggtgtca tctgctcagc tccccagtcc cggccgacac ccagcccaga    1140
tacttggccg acctcacatg catcaacagc aggacctgaa tccagtttgg ccctgaggct    1200
ggtgaatgga ggtgacaggt gtcagggccg agtggaggtc ctataccgag ctcctgggg     1260
caccgtgtgt gatgatagct gggacaccag tgacgccaat gtggtctgcc ggcagctggg    1320
ctgtggctgg ccacgtcag ccccaggaaa tgcccggttt ggccagggtt caggacccat     1380
tgtcctggat gacgtgcgct gctcaggcta tgagtcctac ctgtggagct gcccccacaa    1440
tggctggctc tcccataact gtcagcacag tgaagacgct ggtgtcatct gctcagctgc    1500
ccactcctgg tcgacgccca gtccagacac attgccgacc atcaccttgc ctgcatcgac    1560
agtaggatct gaatccagtt tggccctgag gctggtgaat ggaggtgaca ggtgtcaggg    1620
ccgagtggag gtcctatacc aaggctcctg ggcaccgtg tgcgatgaca gctgggacac     1680
caatgatgcc aatgtcgtct gcaggcaact gggctgtggc tgggccatgt cagccccagg    1740
aaatgcccgg tttggtcagg gctcaggacc cattgtcctg gatgatgtgc gctgctcagg    1800
acacgagtct tacctgtgga gctgcccca caatggctgg ctctcccaca actgtggcca     1860
tagtgaagac gctggtgtca tctgctcagc ttcccagtcc cggccaacac ctagtccaga    1920
cacttggcca acctcacatg catcaacagc aggatctgaa tccagtttgg ccctgaggct    1980
ggtgaatgga ggtgacaggt gtcagggccg agtggaggtc ctataccgag ctcctggggg    2040
caccgtgtgt gatgactact gggacaccaa tgatgccaat gtggtttgca ggcagctggg    2100
ctgtggctgg gccatgtcag ccccaggaaa tgcccggttt ggccagggtt caggacccat    2160
tgtcctggat gatgtgcgct gctcaggaca tgagtcctat ctgtggagct gcccccacaa    2220
```

```
tggctggctc tcccacaact gtggccatca tgaagacgct ggtgtcatct gctcagcttc    2280
ccagtcccag ccgacaccca gcccagacac ttggccaacc tcacatgcat caacagcagg    2340
atctgaatcc agtttggccc tgaggctggt gaatggaggt gacaggtgtc agggccgagt    2400
ggaggtccta taccgaggct cctggggcac cgtgtgtgat gactactggg acaccaatga    2460
tgccaatgtg gtttgcaggc agctgggctg tggctgggcc acgtcagccc aggaaatgc     2520 ccggtttggc cagggttcag gacccattgt cctggatgat gtgcgctgct caggacatga    2580
gtcctatctg tggagctgcc cccacaatgg ctggctctcc cacaactgtg gccatcatga    2640
agacgctggt gtcatctgct cagcttccca gtcccagccg acaccagcc cagacacttg     2700 gccaacctct cgtgcatcaa cagcaggatc tgaatccact ttggccctga ctggtgaa      2760 tggaggtgac aggtgtcgag gccgagtgga ggtcctatac caaggctcct ggggcaccgt    2820
gtgtgatgac tactgggaca ccaatgatgc caacgtggtc tgcaggcagc tgggctgtgg    2880
ctgggccatg tcagcccag gaaatgccca gtttggccag gctcaggac ccattgtcct      2940 ggatgatgtg cgctgctcag gacacgagtc ttacctgtgg agctgccccc acaatggctg    3000
gctctcccac aactgtggcc atcatgaaga tgctggtgtc atctgctcag ctgctcagtc    3060
ccagtcaacg cccaggccag atacttggct gaccaccaac ttaccggcat tgacagtagg    3120
atctgaatcc agtttggctc tgaggctggt gaatggaggt gacaggtgtc gaggccgagt    3180
ggaggtcctg tatcgaggct cctggggaac cgtgtgtgat gacagctggg acaccaatga    3240
tgccaatgtg gtctgcaggc agctgggctg tggctgggcc atgtcggccc aggaaatgc     3300 ccggtttggc cagggctcag gacccattgt cctggatgat gtgcgctgct cagggaatga    3360
gtcctacctg tggagctgcc cccacaaagg ctggctcacc cacaactgtg gccatcacga    3420
agacgctggt gtcatctgct cagccaccca aataaattct actacgacag attggtggca    3480
tccaacaact acaaccactg caagaccctc ttcaaattgt ggtggcttct tattctatgc    3540
cagtgggaca ttctccagcc catcctaccc tgcatactac cccaacaatg ctaagtgtgt    3600
ttgggaaata gaagtgaatt ctggttatcg cataaacctg gcttcagta atctgaaatt     3660 ggaggcacac cataactgca gttttgatta tgttgaaatc tttgatggat cattgaatag    3720
cagtctcctg ctggggaaaa tctgtaatga taccaggcaa atatttacat cttcttacaa    3780
ccgaatgacc attcactttc gaagtgacat cagtttccaa aacactggct ttttggcttg    3840
gtataactcc ttcccaagcg atgccaacctt gaggttggtc aatttaaatt catcctatgg    3900
tctatgtgcc gggcgtgtag aaatttacca tggtggcacc tggggggacag tttgtgatga    3960 ctcctggacc attcaggaag ctgaggtggt ctgcagacag ctagggtgtg gacgtgcagt    4020 ttcagcccttt ggaaatgcat attttggctc tggctctggc cccatcaccc tggacgatgt    4080
agagtgctca gggacggaat ccactctctg gcagtgccgg aaccgaggct ggttctccca    4140
caactgtaat catcgtgaag atgctggtgt catctgctca ggaaaccatc tatcgacacc    4200
tgctcctttt ctcaacatca cccgtccaaa cacagattat tcctgcggag cttcctatc     4260 ccaaccatca ggggacttttt ccagcccatt ctatcccggg aactatccaa acaatgccaa    4320
gtgtgtgtgg gacattgagg tgcaaaacaa ctaccgtgtg actgtgatct tcagagatgt    4380
ccagcttgaa ggtggctgca actatgatta tattgaagtt ttcgatggcc cctaccgcag    4440 ttccctctc attgctcgag tttgtgatgg ggccagagg ccttcacttt cttcctccaa      4500
cttcatgtcc attcgcttca tcagtgacca cagcatcaca aggagagggt tccgggctga    4560
```

| | | | | |
|---|---|---|---|---|
| gtactactcc | agtccctcca | atgacagcac | caacctgctc | tgtctgccaa atcacatgca | 4620 |
| agccagtgtg | agcaggagct | atctccaatc | cttgggcttt | tctgccagtg accttgtcat | 4680 |
| ttccacctgg | aatggatact | acgagtgtcg | gccccagata | acgccgaacc tggtgatatt | 4740 |
| cacaattccc | tactcaggct | gcggcacctt | caagcaggca | gacaatgaca ccatcgacta | 4800 |
| ttccaacttc | ctcacagcag | ctgtctcagg | tggcatcatc | aagaggagga cagacctccg | 4860 |
| tattcacgtc | agctgcagaa | tgcttcagaa | cacctgggtc | gacaccatgt acattgctaa | 4920 |
| tgacaccatc | cacgttgcta | ataacaccat | ccaggtcgag | gaagtccagt atggcaattt | 4980 |
| tgacgtgaac | atttccttt | atacttcctc | atctttcttg | tatcctgtga ccagccgccc | 5040 |
| ttactacgtg | gacctgaacc | aggacttgta | cgttcaggct | gaaatcctcc attctgatgc | 5100 |
| tgtactgacc | ttgtttgtgg | acacctgcgt | ggcatcacca | tactccaatg acttcacgtc | 5160 |
| tttgacttat | gatctaatcc | ggagtggatg | cgtgagggat | gacacctacg gaccctactc | 5220 |
| ctcgccatct | cttcgcattg | cccgcttccg | gttcagggcc | ttccacttcc tgaaccgctt | 5280 |
| ccccctccgtg | tacctgcgtt | gtaaaatggt | ggtgtgcaga | gcgtatgacc cctcttcccg | 5340 |
| ctgctaccga | ggctgtgtgt | tgaggtcgaa | gagggatgtg | ggctcctacc aggaaaaggt | 5400 |
| ggacgtcgtc | ctgggtccca | tccagctgca | gacccccca | cgccgagaag aggagcctcg | 5460 |
| gtaggtggtc | gctctcagac | cccactgtcc | accggggcgc | agacccctga ctcggggact | 5520 |
| tgggatgttc | ctcttggtgt | catattccaa | ctcagattga | gccctacatt gtgctgcacc | 5580 |
| tggtcatacg | gagttgaatc | agacctggtt | cccgcctccc | ccaaggctca tggtccttgg | 5640 |
| aggacccgtt | gcagggtgag | gtcaagagag | ttctgacctg | gatggcccat agacctgacg | 5700 |
| tcccagaatc | catgcttctc | atctgcaaaa | tgaaaatgtc | aatacttact tcttagcact | 5760 |
| gttgagaggg | ttacttacat | aaaggaattt | tggtgaaact | gc | 5802 |

<210> SEQ ID NO 27
<211> LENGTH: 1220
<212> TYPE: DNA
<213> ORGANISM: Homo sapiens

<400> SEQUENCE: 27

| | | | | |
|---|---|---|---|---|
| agtcccagct | cagagccgca | acctgcacag | ccatgcccgg | gcaagaactc aggacggtga | 60 |
| atggctctca | gatgctcctg | gtgttgctgg | tgctctcgtg | gctgccgcat gggggcgccc | 120 |
| tgtctctggc | cgaggcgagc | cgcgcaagtt | tcccgggacc | ctcagagttg cactccgaag | 180 |
| actccagatt | ccgagagttg | cggaaacgct | acgaggacct | gctaaccagg ctgcgggcca | 240 |
| accagagctg | ggaagattcg | aacaccgacc | tcgtcccggc | ccctgcagtc cggatactca | 300 |
| cgccagaagt | gcggctggga | tccggcggcc | acctgcacct | gcgtatctct cgggccgccc | 360 |
| ttcccgaggg | gctccccgag | gcctcccgcc | ttcaccgggc | tctgttccgg ctgtccccga | 420 |
| cggcgtcaag | gtcgtgggac | gtgacacgac | cgctgcggcg | tcagctcagc cttgcaagac | 480 |
| cccaggcgcc | cgcgctgcac | ctgcgactgt | cgccgccgcc | gtcgcagtcg gaccaactgc | 540 |
| tggcagaatc | ttcgtccgca | cggccccagc | tggagttgca | cttgcggccg caagccgcca | 600 |
| gggggcgccg | cagagcgcgt | gcgcgcaacg | gggaccactg | tccgctcggg cccgggcgtt | 660 |
| gctgccgtct | gcacacggtc | cgcgcgtcgc | tggaagacct | gggctgggcc gattgggtgc | 720 |
| tgtcgccacg | ggaggtgcaa | gtgaccatgt | gcatcggcgc | gtgccgagc cagttccggg | 780 |
| cggcaaacat | gcacgcgcag | atcaagacga | ggcctgcaccg | cctgaagccc gacacggtgc | 840 |
| cagcgccctg | ctgcgtgccc | gccagctaca | atcccatggt | gctcattcaa aagaccgaca | 900 |

```
ccggggtgtc gctccagacc tatgatgact tgttagccaa agactgccac tgcatatgag      960
cagtcctggt ccttccactg tgcacctgcg cggaggacgc gacctcagtt gtcctgccct     1020
gtggaatggg ctcaaggttc ctgagacacc cgattcctgc ccaaacagct gtatttatat     1080
aagtctgtta tttattatta atttattggg gtgaccttct tggggactcg ggggctggtc     1140
tgatggaact gtgtatttat ttaaaactct ggtgataaaa ataaagctgt ctgaactgtt     1200
aaaaaaaaaa aaaaaaaaaa                                                 1220

<210> SEQ ID NO 28
<211> LENGTH: 1882
<212> TYPE: DNA
<213> ORGANISM: Homo sapiens

<400> SEQUENCE: 28
agcgctccta taagggagc caccagcgct ggaggccgct gctcgctgcg ccaccgcctc        60
ccgccacccc tgcccgcccg acagcgccgc cgcctgcccc gccatgggtc gacagaagga      120
gctggtgtcc cgctgcgggg agatgctcca catccgctac cggctgctcc gacaggcgct      180
ggccgagtgc ctggggaccc tcatcctggt gatgtttggc tgtggctccg tgcccaggt      240 tgtgctcagc cggggcaccc acggtggttt cctcaccatc aacctggcct ttggctttgc      300
tgtcactctg gcatcctca tcgctggcca ggtctctggg gcccacctga acctgccgt       360 gacctttgcc atgtgcttcc tggctcgtga gccctggatc aagctgccca tctacaccct      420
ggcacagacg ctgggagcct tcttgggtgc tggaatagtt tttgggctgt attatgatgc      480
aatctggcac ttcgccgaca accagctttt tgtttcgggc cccaatggca cagccggcat      540
ctttgctacc taccccctg acacttgga tatgatcaat ggcttctttg accagttcat       600
aggcacagcc tcccttatcg tgtgtgtgct ggccattgtt gacccctaca caacccccgt      660
ccccccgagc ctggaggcct tcaccgtggg cctggtggtc ctggtcattg cacctccat      720 gggcttcaac tccggctatg ccgtcaaccc tgcccgggac tttggccccc gccttttac       780 agcccttgcg ggctggggct ctgcagtctt cacgaccggc cagcattggt ggtgggtgcc      840
catcgtgtcc ccactcctgg gctccattgc gggtgtcttc gtgtaccagc tgatgatcgg      900
ctgccacctg gagcagcccc caccctccaa cgaggaagag aatgtgaagc tggcccatgt      960
gaagcacaag gagcagatct gagtgggcag gggccatctc cccactccgc tgccctggcc     1020
ttgagcatcc actgactgtc caagggccac tcccaagaag ccccttcac gatccaccct     1080 ttcaggctaa ggagctccct atctaccctc accccacgag acagccccttt caggatttcc     1140 actggacctt gcccaaatag caccttaggc cactgccct aagctggggt ggaaccggaa      1200
tttgggtcaa tacatccttt tgtctcccaa gggaagagaa tgggcagcag gtatgtgtgt     1260
gtgtgcatgt gtgtgcatgt gtgtgcatgt gtgtgcaggg gtgtgtgtgt gtgggggggg     1320
ttcccagata ttcagggcaa gggaccagtc ggaagggatt ctggctattg ggggagccca     1380
gagacagggg aaggcagcct gtccatctgt gcataaggag aggaaagttc cagggtgtgt     1440
atgtttcagg ggcttcacat ggaggagctg cagatagata tgtgttttctg tgtatgtgta     1500 tgtctgcctt ttttttctaag tggggcttc tacaggcttt tggaagtag ggtggatgtg     1560 ggtagggctg ggaggagggg gccacagctt aggtttggag ctctggatgt acatacataa     1620
gtaggagcag tgggacgtgt ttctgtcata atgcaggcat gaagggtgga gtgaagtcag     1680
gtcataagtt tcatgtttgc ttttgttttg ttttgttttt aatgtatgta gcagatgtta     1740
```

| | |
|---|---:|
| cagtcttagg gatccgggat gggagacccc actttagaaa gggtcgtcac tcctttaatc | 1800 |
| ctctactcaa caatgtactc ttttactttt atattaaaaa aaataaaata aatatgtgcc | 1860 |
| taaaacctcc aaaaaaaaaa aa | 1882 |

<210> SEQ ID NO 29
<211> LENGTH: 1336
<212> TYPE: DNA
<213> ORGANISM: Homo sapiens

<400> SEQUENCE: 29

| | |
|---|---:|
| gagagacaca gagtccggca ttggtcccag gcagcagtta gcccgccgcc cgcctgtgtg | 60 |
| tccccagagc catggagaga gccagtctga tccagaaggc caagctggca gagcaggccg | 120 |
| aacgctatga ggacatggca gccttcatga aggcgccgt ggagaagggc gaggagctct | 180 |
| cctgcgaaga gcgaaacctg ctctcagtag cctataagaa cgtggtgggc ggccagaggg | 240 |
| ctgcctggag ggtgctgtcc agtattgagc agaaaagcaa cgaggagggc tcggaggaga | 300 |
| aggggcccga ggtgcgtgag taccgggaga aggtggagac tgagctccag ggcgtgtgcg | 360 |
| acaccgtgct gggcctgctg gacagccacc tcatcaagga ggccggggac gccgagagcc | 420 |
| gggtcttcta cctgaagatg aagggtgact actaccgcta cctggccgag gtggccaccg | 480 |
| gtgacgacaa gaagcgcatc attgactcag cccggtcagc ctaccaggag gccatggaca | 540 |
| tcagcaagaa ggagatgccg cccaccaacc ccatccgcct gggcctggcc ctgaactttt | 600 |
| ccgtcttcca ctacgagatc gccaacagcc ccgaggaggc catctctctg gccaagacca | 660 |
| cttttcgacga ggccatggct gatctgcaca ccctcagcga ggactcctac aaagacagca | 720 |
| ccctcatcat gcagctgctg cgagacaacc tgacactgtg gacggccgac aacgccgggg | 780 |
| aagagggggg cgaggctccc caggagcccc agagctgagt gttgcccgcc accgccccgc | 840 |
| cctgccccct ccagtccccc accctgccga gggactagt atggggtggg aggccccacc | 900 |
| cttctcccct aggcgctgtt cttgctccaa agggctccgt ggagagggac tggcagagct | 960 |
| gaggccacct ggggctgggg atcccactct tcttgcagct gttgagcgca cctaaccact | 1020 |
| ggtcatgccc ccacccctgc tctccgcacc cgcttcctcc cgaccccagg accaggctac | 1080 |
| ttctcccctc ctcttgcctc cctcctgccc ctgctgcctc tgatcgtagg aattgaggag | 1140 |
| tgtcccgcct tgtggctgag aactggacag tggcagggc tggagatggg tgtgtgtgtg | 1200 |
| tgtgtgtgtg tgtgtgtgtg tgtgcgcgcg cgccagtgca agaccgagat tgagggaaag | 1260 |
| catgtctgct gggtgtgacc atgtttcctc tcaataaagt tcccctgtga cactcaaaaa | 1320 |
| aaaaaaaaaa aaaaaa | 1336 |

<210> SEQ ID NO 30
<211> LENGTH: 8171
<212> TYPE: DNA
<213> ORGANISM: Homo sapiens

<400> SEQUENCE: 30

| | |
|---|---:|
| gaggcagggg tgagaccggc ggccacccgt gagccctccg caccgcacc atgcagaaga | 60 |
| gcgtgcgcta caacgagggg cacgcccgt acctggccctt tctggcgcgc aaggagggca | 120 |
| ccaagcgcgg cttcctgagt aagaagacgg ccgaggcgag ccgctggcac gagaagtggt | 180 |
| tcgccctcta ccagaatgtg ctcttctact tcgagggcga gcagagctgc gcccggcgg | 240 |
| gcatgtacct cctggagggc tgcagctgcg aacgaacgcc cgcgccaccc agggccggcg | 300 |
| ccgggcaggg aggcgtccga gacgcgctgg acaagcagta ttactttact gttcttttg | 360 |

```
gccatgaagg tcagaagcca ctggagctgc gctgtgagga ggagcaggat ggtaaagagt    420
ggatggaggc cattcaccaa gccagttatg cagacatttt gattgagagg gaagtattaa    480
tgcagaagta cattcatcta gttcagatcg tagagacaga aaaaattgca gctaaccaac    540
tccgacatca acttgaagat caagacacag aaatcgaaag gcttaaatca gagattattg    600
ctcttaataa aaccaaagaa cgaatgcgac cttaccaaag caaccaagaa gacgaagatc    660
cagacatcaa gaagattaaa aaggttcaga gcttcatgcg aggatggttg tgcagaagga    720
aatggaagac catcgtgcag gattacattt gttctcctca tgctgaaagt atgaggaaga    780
gaaaccagat tgtgttcacc atggtggagg cagagtcaga gtacgttcac cagctctaca    840
tcctggtcaa tggctttctc cggccctgc gtatggccgc cagctccaag aagccccca    900 tcagccacga cgacgtcagc agtatttttc ttaacagtga acaatcatg tttcttcatg    960 aaatatttca tcaaggacta aaggcaagga tagcaaactg gcccacttta attttagctg   1020
atctgtttga tattttgctc cccatgctga acatttatca agaatttgtg cgtaatcacc   1080
agtacagcct gcaagttctc gccaattgta agcaaaacag agattttgac aaactcttaa   1140
aacagtatga agccaatcca gcctgtgagg ggaggatgct ggagacattc ttgacctatc   1200
ccatgtttca gatccccaga tatatcatca cactccatga gctccttgct cacacacccc   1260
atgagcatgt ggaaaggaaa agcctggagt ttgccaaatc aaagctagag aactatccaa   1320
gagtaatgca cgatgaagtc agcgacactg aaaacataag gaaaaaccctt gccatcgaaa   1380 gaatgatcgt ggagggctgt gacatcttgc tggacaccag ccaaacgttc atccgccaag   1440
gttctcttat tcaagtacct tccgttgaga gggggaaact tagtaaagtt cgcctgggtt   1500
cgttgtcttt gaaaaaggaa ggagagagac aatgcttctt atttacaaaa cacttttaa   1560 tatgtacaag aagttcagga gggaagcttc atctgctcaa gacaggtggg ttctgtctc   1620 taatagactg cacattgatt gaggagccag atgcaagcga tgatgactct aaaggttctg   1680
ggcaagtgtt tgggcacctg gatttttaaaa tagtggtgga gcctcctgac gctgccgcct   1740
tcactgttgt cttgttagca ccctcacgcc aggagaaagc tgcctggatg agtgacatca   1800
gtcagtgtgt ggacaatata cgatgtaatg gtttaatgac tatagtgttt gaagagaatt   1860
ccaaagtcac tgtgccacat atgattaagt ctgatgcccg tcttcataaa gacgacactg   1920
acatttgctt cagtaaaaca ctcaactcct gcaaagtgcc ccagatccgt tatgccagcg   1980
tggagcgcct cttggaacga ctgacagact gcggtttct tagtattgat ttcctcaaca   2040
cctttctgca cacctatcgt attttcacta ctgccgctgt ggtgctgggg aaactctccg   2100
acatatacaa gaggcctttc acctccatcc ctgtcaggtc attggaattg tttttttgcta   2160 ccagccagaa caacagaggt gaacatttgg tggatggcaa atccccacgt ctgtgtcgca   2220
aattctcttc cccgccacca ctggctgtgt ccagaacatc ttccccagtg agggccagaa   2280
agctgtcttt gacttctccc ttgaactcaa agataggagc attggacctg acaacttcca   2340
gcagtcccac caccaccacc cagagtcccg ctgcgtctcc accaccacac actggtcaga   2400
taccactgga tctcagcaga ggcctctctt ctccagagca agcccggga acggtagaag   2460 agaatgtcga taacccacgc gtggatctgt gtaacaagct aaaacgaagt attcaaaaag   2520
cagtcctaga gtctgcacca gcggaccgag caggagtgga aagctcccct gcagcggaca   2580
ccacagaact ttcaccttgc agatccccct caactcctcg gcacctccgc tatcgacagc   2640
ctggaggaca gacggcggac aatgcccact gctctgtttc accggcttct gcttttgcaa   2700
```

-continued

```
tagccacagc tgcagcagga catgggagtc caccaggctt taacaacacc gagagaacat    2760
gtgataaaga gtttattata cggagaacgg ctaccaatcg agttctgaac gtcctccgtc    2820
actgggtctc aaagcacgca caggatttcg aactcaacaa tgaactaaag atgaatgtcc    2880
taaatttgct agaagaagtt ttgcgagacc cagaccttct tccccaagaa aggaaagccg    2940
ccgcgaatat cctcagggcc cttttcacaag atgaccaaga tgacatccac ctaaaattag    3000
aggatataat tcaaatgact gactgcatga aggccgaatg ctttgagtcc ttgtcggcca    3060
tggagctggc agaacagatc accctcctgg accatgtcat tttcagaagc attccctacg    3120
aggagtttct tgggcagggg tggatgaagc tggataaaaa cgaaagaact ccttacatta    3180
tgaaaaccag ccaacacttc aatgacatga gtaacctggt ggcctcccag ataatgaact    3240
atgctgatgt cagctcccgt gccaacgcca tcgagaaatg ggtggcagtg gcggacatct    3300
gccgatgcct gcacaactac aacggcgtgc tggagatcac ctcggcctta aacagaagtg    3360
ccatctacag gctgaagaaa acctgggcca aggtctctaa gcagacaaaa gctctaatgg    3420
acaaacttca aaagactgtt tcctctgaag gaagatttaa aaatcttaga gaaacccttta    3480 aaaattgtaa ccctcctgca gttccttatc ttgggatgta cttgacagac ctggcattta    3540
ttgaagaagg aacaccaaac tttactgagg aaggccttgt caatttctcc aaaatgagaa    3600
tgatatcaca catcatcaga gagatacgcc agttccagca gacttcctac agaatagatc    3660
atcagccaaa ggtcgcacag tacttgcttg acaaagacct tatcatagat gaagatacgc    3720
tatatgagct gtcactaaaa attgaacctc gactccctgc ttgaagatct ggccttgccc    3780
ctgagtccac gggatgttca tggaaagcag gacagacaga attgtgtatg ccttgcctat    3840
cacggtacag cacgaagcca ggctcctttc tccaccaaag aagatggaac cagactggaa    3900
ttctgtctcc agagagaaac ccagctgttt gggtcaaaga cagatgcttc agacttgggt    3960
gggaaggtga agatggcta tttagaaagc tggtggcacg ttttacataa gggaatgtca    4020
gatgggagat gctagttgcc attttaacaa agcaggtaaa tcggtaaatt ttaaactctg    4080
tccatgttct gttagaactc agggacaagg atccatgaaa aagacctgtg atgtttctct    4140
ggcgctttac tggcctgggc acacctacca atcttctagg atttgactgg ttccattaca    4200
tttccttttg gtataagctt cacagaaaag ctgacacttc ctctacagag atggaccaaa    4260
acataagcaa tttcagtcta cagcatgtgc atggttgtca gtgcattcta aatatttcta    4320
tgtgaggaat ggtaccttct gaaactgcct ttccagtctt taggcaatgg gataggaaag    4380
aaagaatgaa acacaaatgg atttgtatgt aacatttcct taattaaatg cagtaggctg    4440
tgccccagag gattccagac agtggctggc tgaggtgggt ggggagcttt tccttgagac    4500
tgttggtcct aagaagccag ccctttggga gaggcagctg caaaaggtg cacgcccatc    4560 tcaccgacaa aactgtggaa cagaaggcca ccaagtgctg tggggaatca tgggtttcag    4620
tgctgagtga aaatctatac ctaaaaatca tctctgcacc ttgctttgtt tgttttcttt    4680
ccccactcat agtactgcag gaatctattc tcatttacac agaccttttt ttaggcttac    4740
tatgaacatt ggctgtattt tttttaaaca gtttagtgaa attttctttt caaaacccac    4800
acttccatat gctgttcgta gatctctttc tttaaaaact gatgttgaga gatctctgag    4860
aatattataa gtgcatggga atgggccca accaccgaac agctcttaca ttacaaaacc    4920
aaatgcaagg gttagtcctg ctacctgagg ctggggaagt gacctccctt ttcccaagat    4980
tgtcagttgt tgaagaaata gggctatctc attgttacc tccctcttct cttctcaggg    5040
agactgctgc tttaaaagaa ggaagagaaa aaatatagtt ctatttccct gaacctgttg    5100
```

```
cacctgacat tttctcttag cagcatgaaa cttattgatg ctgacaatga aaaatggatc    5160
tgtctggctg ctttccctct ttccttgcac tttaattatg ttgctagagc taacagacta    5220
ataaattcca cctgctggct cttaagactc agtgaaagag ctagcattgg taatgcacca    5280
tagaggtaga gaatgtacac tttctgcacg gtaagtgcca tctctgtatg taactatata    5340
gtgaaatatc aactaagtaa aagaaaatat aatatttgaa gaccattccc aaaatatttt    5400
caatagttca tattagccaa cagtgtagca ctcaacccaa ggagggttcc ttatggatgc    5460 tttcttttc tttttaaag ttgcttgttt gttctcttta gtttcaaata agaggttgac       5520
gcatcttgat gcatgatgag aagcatgggc tgtttggatc ctaacaacgc ataacttgtg    5580
atttatttct cagtgctcca gaaactgagg gtttgaaata atatgtatca gttgcaccaa    5640
acacctcaag gtcttgcaga agaaaagtaa aggttagctt tcatggctca aaagcatagt    5700
cctgaagggt gaactaaaac cgggacaaat ctgtgagagg accacacaca tactagtttc    5760
gggccaaaca acacgtggaa aggtgcatgc attctactct gccttggagt tgccagagtc    5820
cttcagaggg aaagggatgg ttctgtgtgc acttttctg gaagttcgga ctcatttctt      5880
tgacccaaat gttccagaga cactgcagcc attcttatta acaaaaaata agacaggagt    5940
ttccaaatgc tccttccctt ttggatcgca gcttttcttc aactagtgac aaagcttttg    6000
cgcctatttc ctgcaggatg ttggaactgc cccgcactgg tcatattagg cactgtcaat    6060
tgctatgctg acttttaggg ggttttttgtt tgtttgaaaa acagggtctc accatgttgc    6120
ccaggctggt ctcgaactcc tggactcaag caatcttcct gcctcagcct ctcaagcagc    6180
tgggactgca ggggtgtgcc actcactagc ctttcgcatt tttgtttgag aattacacca    6240 cttctggag tctgcagcct tcctggagct gcaagagggc aagagagaga gctccacctc      6300
tgagggagtg tctgttgatg acctgcacta ttcgtgtgcc agctgggaga ggaatgcaca    6360
ttttaaaatc ccttcaattt ggtcaaatta aaaatcccca agagcaattt gcagtgtttt    6420
ttctggtcgt taaagtaccc atcctcttct gcctacacac aaagcatgca ttcccagctg    6480
catctgcctc tagtccatta tggagaccca tttctaagag gagatgggag gtcaacctct    6540
aacagccaag tagcgaacat gtatactgta aaattaacct agaaaatcag aagaaaaatc    6600
caatttcatg ctttcgaatg aatgcccaca ttttgtactg tcaacgaaat tatcttggag    6660
cttttagggg atgccttttc gttattaact gagacatcta gttttgctac agggacaaat    6720
ctcttaccta atccaatata ttatttgaca gattcaggca tgaagtaaaa cgtcgtcact    6780
tttccttagt gcttttctga aggaatttaa agacggaatt ttaaacggcc attgcaatat    6840
tttcaagtgg ctctcatacc aagtcccatt actgtttgtt aaatttcagt acgtcttaaa    6900
gtactactta taaacaaatg aaactcagag aaactgaatc acctggaaga gaaaaatcca    6960
ttatggtccc atgtggagtg aataatgatg gatcagcacc ctttctctca tgttattgta    7020
taagacgaga cttttgggcc agcagcgatt gggcagcttt taaattctta actgaaagaa    7080
gtaatgcaat acagggatta ttcccaataa aattaacttt tatttaaaag caagagattt    7140
tacttagctt ttttttttca agtttgatt ttatccccctt gaaaaaaaat ctcttcactt     7200
taaagtataa aggtttttaa aaatccaatt gcaaatgta ttatttttac aactatcgaa      7260
aaggcataaa agagaacata ctatttatgg ctgaagggta tagccaggct aatgtgcaca    7320
gagggaatca ataaataaaa ctcttttca tttcagtaag aaatcagatt gtaagtttaa      7380
tggctccatt atagatacca ccgtgtaata gaagacttaa gtcaatgaaa tctaatcagt    7440
```

```
gtgtcatttc tcagcggcca ttggtgactt aaaattaaga tgaggcagag ccaaaatgga    7500
aaacagtcat tttgttgtag gtataaacac atgaacgatt cagaaaatta ttcatctcag    7560
ctgccatgca gcatgacatt aacattagga ttgatagcac tagtctgatc tgctcaagga    7620
aaataatagt tctattatac ttaatgatgt tggttttac acagctcatt tcattttca     7680 ctagaaagcc agttatgaaa gagagctggc ctaggcatcc cggccctgag tcctaggccc    7740
agtctccaac tggaaaacct taggctggtg tttacacatc cctgagcctc agtttcctca    7800
tctgcaaaac ggtgtgaata gtaatccctg tgctgcttat ctcacagggc tattgtgagg    7860
accaaatgga ttagactgta aactgcaaag tgctgtccgc acatgaggtc atctgattac    7920
tgtcctcaga tctcttttgt agaggatttc aatgtatttc tttatcattt gagtgtgtgt    7980
gtgatggacg aatatgtgtg tgagtttgag aagcatatcg ttcgtgtcca gttactttgc    8040
aaatttgtgg acatttgtga ttggacagag gggtttgtgc tgtggcctaa cacttgccaa    8100
gtgaggtgta ggttatgcct atatgcaaat taaacttcac ctttcttgaa tattcaaaaa    8160
aaaaaaaaaa a                                                          8171

<210> SEQ ID NO 31
<211> LENGTH: 2089
<212> TYPE: DNA
<213> ORGANISM: Homo sapiens

<400> SEQUENCE: 31
agtttggacg gctgcttccc accagcaaag accacgactg gagagccgag ccggaggcag      60
ctgggaaaca tgaagagcgt cttgctgctg accacgctcc tcgtgcctgc cacctggtg     120 gccgcctgga gcaataatta tgcggtggac tgccctcaac actgtgacag cagtgagtgc    180
aaaagcagcc cgcgctgcaa gaggacagtg ctcgacgact gtggctgctg ccgagtgtgc    240
gctgcagggc ggggagaaac ttgctaccgc acagtctcag gcatggatgg catgaagtgt    300
ggccccgggc tgaggtgtca gccttctaat ggggaggatc cttttggtga agagtttggt    360
atctgcaaag actgtcccta cggcaccttc gggatggatt gcagagagac ctgcaactgc    420
cagtcaggca tctgtgacag ggggacggga aaatgcctga attccccctt cttccaatat    480
tcagtaacca agtcttccaa cagatttgtt tctctcacgg agcatgacat ggcatctgga    540
gatggcaata ttgtgagaga agaagttgtg aaagagaatg ctgccgggtc tcccgtaatg    600
aggaaatggt taaatccacg ctgatcccgg ctgtgatttc tgagagaagg ctctattttc    660
gtgattgttc aacacacagc caacatttta ggaactttct agattatagc ataaggacat    720
gtaatttttg aagaccaaat gtgatgcatg gtggatccag aaaacaaaaa gtaggatact    780
tacaatccat aacatccata tgactgaaca cttgtatgtg tttgttaaat attcgaatgc    840
atgtagattt gttaaatgtg tgtgtatagt aacactgaag aactaaaaat gcaatttagg    900
taatcttacg tggagacagg tcaaccaaag agggagctag gcaaagctga agaccgcagt    960
gagtcaaatt agttctttga ctttgatgta cattaatgtt gggatatgga atgaagactt   1020
aagagcagga gaagatgggg aggggtggg agtgggaaat aaaatattta gcccttcctt   1080
ggtaggtagc ttctctagaa tttaattgtg cttttttttt ttttttttggc tttgggaaaa   1140 gtcaaaataa acaaccaga aaccccctga aggaagtaag atgtttgaag cttatggaaa   1200
tttgagtaac aaacagcttt gaactgagag caatttcaaa aggctgctga tgtagttccc   1260
gggttacctg tatctgaagg acggttctgg ggcataggaa acacatacac ttccataaat   1320
agctttaacg tatgccacct cagagataaa tctaagaagt attttaccca ctggtggttt   1380
```

-continued

| | |
|---|---|
| gtgtgtgtat gaaggtaaat atttatatat ttttataaat aaatgtgtta gtgcaagtca | 1440 |
| tcttccctac ccatatttat catcctcttg aggaaagaaa tctagtatta tttgttgaaa | 1500 |
| atggttagaa taaaactatg actctataag gttttcaaac atctgaggca tgataaattt | 1560 |
| attatccata attatagtaa taataacctt aataagcata agaaaaacag agtcactctg | 1620 |
| gatttcaaaa atgtcaaaaa atgagcaaca gagggtcctt atttaaacat aagtgctgtg | 1680 |
| acttaggtga attttcaatt taaggtagaa aataagtttt taggaggttt gtaaaagaag | 1740 |
| aatcaatttt cagcagaaaa catgtcaact ttaaaatata gtttattttc atattttttt | 1800 |
| cttttaaact tggttgataa gtggaattag gagtatattt gaaagaatct tagcacaaac | 1860 |
| aggactgttg tactagatgt tcttaggaaa tatctcagaa gtattttatt tgaagtgaag | 1920 |
| aacttattta agaattattt cagtatttac ctgtatttta ttcttgaagt tggccaacag | 1980 |
| agttgtgaat gtgtgtggga aggcctttga atgtaaagct gcataagctg ttaggttttg | 2040 |
| ttttaaaagg acatgtttat tattgttcaa taaaaaagaa caagataca | 2089 |

<210> SEQ ID NO 32
<211> LENGTH: 7686
<212> TYPE: DNA
<213> ORGANISM: Homo sapiens

<400> SEQUENCE: 32

| | |
|---|---|
| tttatagcag cagtagaaat ataccaccct agaggacaca cctccttta gctaggtacc | 60 |
| tataaatgtc caggattttc tattcaattg agaagaaccc agcaaaatgg ggatctccac | 120 |
| agtcatcctt gaaatgtgtc ttttatgggg acaagttcta tctacaggtg ggtggatccc | 180 |
| aaggactaca gactacgctt cactgattcc ctcggaggtg cccttggatc caactgtagc | 240 |
| agaaggttct ccatttccct cggagtcgac cctggagtca actgtagcag aaggttctcc | 300 |
| gatttccttg gagtcaaccc tggagtcaac cgtagcagaa ggttctctga ttccctcaga | 360 |
| gtcaaccctg gagtcaactg tagcagaagg atctgattct ggtttggccc tgaggctggt | 420 |
| gaatggagat ggcaggtgtc agggccgagt ggagatccta taccgaggct cctgggcac | 480 |
| cgtgtgtgat gacagctggg acaccaatga tgccaacgtg gtctgtaggc agctgggttg | 540 |
| tggctgggcc atgtcagctc caggaaatgc ctggtttggc cagggctcag gacccattgc | 600 |
| cctggatgat gtgcgctgct caggacacga atcctacctg tggagctgcc ccacacaatgg | 660 |
| ctggctctcc cataactgtg gccatggtga agatgctggt gttatctgct cagctgccca | 720 |
| gcctcagtca acactcaggc cagaaagttg gcctgtcagg atatcaccac ctgtacccac | 780 |
| agaaggatct gaatccagtt tggccctgag gctggtgaat ggaggcgaca ggtgtcgagg | 840 |
| ccgagtggag gtcctatacc gaggctcctg gggcaccgtg tgtgatgact actgggacac | 900 |
| caatgatgcc aatgtggtct gcaggcagct gggctgtggc tgggccatgt cagccccagg | 960 |
| aaatgcccag tttggccagg gctcaggacc cattgtcctg gatgatgtgc gctgctcagg | 1020 |
| acatgagtcc tacctgtgga gctgccccca caatggctgg ctcacccaca actgtggcca | 1080 |
| tagtgaagac gctggtgtca tctgctcagc tccccagtcc cggccgacac ccagcccaga | 1140 |
| tacttggccg acctcacatg catcaacagc aggacctgaa tccagtttgg ccctgaggct | 1200 |
| ggtgaatgga ggtgacaggt gtcagggccg agtggaggtc ctataccgag gctcctgggg | 1260 |
| caccgtgtgt gatgatagct gggacaccag tgacgccaat gtggtctgcc ggcagctggg | 1320 |
| ctgtggctgg gccacgtcag ccccaggaaa tgcccggttt ggccagggtt caggacccat | 1380 |

```
tgtcctggat gacgtgcgct gctcaggcta tgagtcctac ctgtggagct gcccccacaa    1440
tggctggctc tcccataact gtcagcacag tgaagacgct ggtgtcatct gctcagctgc    1500
ccactcctgg tcgacgccca gtccagacac gttgccgacc atcaccttac ctgcatcgac    1560
agtaggatct gaatccagtt tggccctgag gctggtgaat ggaggtgaca ggtgtcaggg    1620
ccgagtggag gtcctatacc gaggctcctg gggcaccgtg tgtgatgaca gctgggacac    1680
caatgatgcc aatgtggtct gcaggcagct gggctgtggc tgggccatgt tggccccagg    1740
aaatgcccgg tttggtcagg gctcaggacc cattgtcctg gatgacgtgc gctgctcagg    1800
gaatgagtcc tacttgtgga gctgccccca aatggctggg ctctcccata actgtggcca    1860
tagtgaagac gctggtgtca tctgctcagg acctgaatcc agtttggccc tgaggctggt    1920
gaatggaggt gacaggtgtc agggccgagt ggaggtccta taccgaggct cttggggcac    1980
cgtgtgtgat gacagctggg acaccaatga tgccaatgtg gtctgcaggc agctgggctg    2040
tggctgggcc acgtcagccc caggaaatgc ccggtttggt cagggctcag gacccattgt    2100
cctggatgat gtgcgctgct caggacatga gtcctacctg tggagctgcc ccaacaatgg    2160
ctggctctcc cacaactgtg gccatcatga agatgctggt gtcatctgct cagctgccca    2220
gtcccggtcg acgcccaggc cagacacgtt gtcgaccatc acgttacctc catcgacagt    2280
aggatctgaa tccagtttga ccctgaggct ggtgaatgga agtgacaggt gtcagggccg    2340
agtagaggtc ctataccgag gctcctgggg caccgtgtgt gatgacagct gggataccaa    2400
tgatgccaat gtggtctgca ggcagctggg ctgtggctgg ccacgtcgg ccccaggaaa    2460 tgcccggttt ggccagggct caggacccat tgttctggat gatgtgcgct gctcaggaca    2520
cgagtcctac ctgtggagct gcccccacaa tggctggctc tcccacaact gtggccatca    2580
tgaagatgct ggtgtcatct gctcagtttc ccagtcccgg ccgacaccca gtccagatac    2640
ttggccgacc tcacatgcat caacagcagg acctgaatcc agtttggccc tgaggctggt    2700
gaatggaggt gacaggtgtc agggccgagt ggaggtccta taccgaggct cctggggcac    2760
cgtgtgtgat gatagctggg acaccagtga cgccaatgtg gtctgccggc agctgggctg    2820
tggctgggcc acgtcagccc caggaaatgc ccggtttggc cagggttcag gacccattgt    2880
cctggatgac gtgcgctgct caggctatga gtcctacctg tggagctgcc cccacaatgg    2940
ctggctctcc cataactgtc agcacagtga agacgctggt gtcatctgct cagctgccca    3000
ctcctggtcg acgcccagtc cagacacatt gccgaccatc accttgcctg catcgacagt    3060
aggatctgaa tccagtttgg ccctgaggct ggtgaatgga ggtgacaggt gtcagggccg    3120
agtggaggtc ctataccaag gctcctgggg caccgtgtgc gatgacagct gggacaccaa    3180
tgatgccaat gtcgtctgca ggcaactggg ctgtggctgg ccatgtcag ccccaggaaa    3240 tgcccggttt ggtcagggct caggacccat tgtcctggat gatgtgcgct gctcaggaca    3300
cgagtcttac ctgtggagct gcccccacaa tggctggctc tcccacaact gtggccatag    3360
tgaagacgct ggtgtcatct gctcagcttc ccagtcccgg ccaacaccta gtccagacac    3420
ttggccaacc tcacatgcat caacagcagg atctgaatcc agtttggccc tgaggctggt    3480
gaatggaggt gacaggtgtc agggccgagt ggaggtccta taccgaggct cctggggcac    3540
cgtgtgtgat gactactggg acaccaatga tgccaatgtg gtttgcaggc agctgggctg    3600
tggctgggcc atgtcagccc caggaaatgc ccggtttggc cagggttcag gacccattgt    3660
cctggatgat gtgcgctgct caggacatga gtcctatctg tggagctgcc ccacaatgg    3720 ctggctctcc cacaactgtg gccatcatga agacgctggt gtcatctgct cagcttccca    3780
```

```
gtcccagccg acacccagcc cagacacttg gccaacctca catgcatcaa cagcaggatc   3840
tgaatccagt ttggccctga ggctggtgaa tggaggtgac aggtgtcagg gccgagtgga   3900
ggtcctatac cgaggctcct ggggcaccgt gtgtgatgac tactgggaca ccaatgatgc   3960
caatgtggtt tgcaggcagc tgggctgtgg ctggccacg tcagcccag gaaatgcccg    4020
gtttggccag ggttcaggac ccattgtcct ggatgatgtg cgctgctcag acatgagtc    4080
ctatctgtgg agctgccccc acaatggctg gctctcccac aactgtggcc atcatgaaga   4140
cgctggtgtc atctgctcag cttcccagtc ccagccgaca cccagcccag acacttggcc   4200
aacctcacat gcatcaacag caggatctga atccagtttg ccctgaggc tggtgaatgg    4260
aggtgacagg tgtcagggcc gagtggaggt cctataccga ggctcctggg gcaccgtgtg   4320
tgatgactac tgggacacca atgatgccaa tgtggtttgc aggcagctgg gctgtggctg   4380
ggccacgtca gccccaggaa atgcccggtt tggccaggt tcaggaccca ttgtcctgga    4440
tgatgtgcgc tgctcaggac atgagtccta tctgtggagc tgcccccaca atggctggct   4500
ctcccacaac tgtggccatc atgaagacgc tggtgtcatc tgctcagctt cccagtccca   4560
gccgacaccc agcccagaca cttggccaac ctctcgtgca tcaacagcag gatctgaatc   4620
cactttggcc ctgagactgg tgaatggagg tgacaggtgt cgaggccgag tggaggtcct   4680
ataccaaggc tcctgggca ccgtgtgtga tgactactgg gacaccaatg atgccaacgt    4740
ggtctgcagg cagctgggct gtggctgggc catgtcagcc ccaggaaatg cccagtttgg   4800
ccagggctca ggacccattg tcctggatga tgtgcgctgc tcaggacacg agtcttacct   4860
gtggagctgc cccacaatg ctggctctc ccacaactgt ggccatcatg aagatgctgg     4920
tgtcatctgc tcagctgctc agtcccagtc aacgcccagg ccagatactt ggctgaccac   4980
caacttaccg gcattgacag taggatctga atccagtttg gctctgaggc tggtgaatgg   5040
aggtgacagg tgtcgaggcc gagtggaggt cctgtatcga ggctcctggg gaaccgtgtg   5100
tgatgacagc tgggacacca atgatgccaa tgtggtctgc aggcagctgg gctgtggctg   5160
ggccatgtcg gccccaggaa atgcccggtt tggccagggc tcaggaccca ttgtcctgga   5220
tgatgtgcgc tgctcaggga atgagtccta cctgtggagc tgcccccaca aaggctggct   5280
cacccacaac tgtggccatc acgaagacgc tggtgtcatc tgctcagcca cccaaataaa   5340
ttctactacg acagattggt ggcatccaac aactacaacc actgcaagac cctcttcaaa   5400
ttgtggtggc ttcttattct atgccagtgg gacattctcc agcccatcct accctgcata   5460
ctaccccaac aatgctaagt gtgtttggga aatagaagtg aattctggtt atcgcataaa   5520
cctgggcttc agtaatctga aattggaggc acaccataac tgcagttttg attatgttga   5580
aatctttgat ggatcattga atagcagtct cctgctgggg aaaatctgta atgataccag   5640
gcaaatattt acatcttctt acaaccgaat gaccattcac tttcgaagtg acatcagttt   5700
ccaaaacact ggcttttgg cttggtataa ctccttccca agcgatgcca ccttgaggtt    5760
ggtcaattta aattcatcct atggtctatg tgccgggcgt gtagaaattt accatggtgg   5820
cacctggggg acagtttgtg atgactcctg gaccattcag gaagctgagg tggtctgcag   5880
acagctaggg tgtggacgtg cagtttcagc ccttggaaat gcatattttg gctctggctc   5940
tggccccatc accctggacg atgtagagtg ctcaggacg gaatccactc tctggcagtg    6000
ccggaaccga ggctggttct cccacaactg taatcatcgt gaagatgctg gtgtcatctg   6060
ctcaggaaac catctatcga cacctgctcc ttttctcaac atcacccgtc caaacacaga   6120
```

| | |
|---|---|
| ttattcctgc ggaggcttcc tatcccaacc atcaggggac tttttccagcc cattctatcc | 6180 |
| cgggaactat ccaaacaatg ccaagtgtgt gtgggacatt gaggtgcaaa acaactaccg | 6240 |
| tgtgactgtg atcttcagag atgtccagct tgaaggtggc tgcaactatg attatattga | 6300 |
| agttttcgat ggcccctacc gcagttcccc tctcattgct cgagtttgtg atggggccag | 6360 |
| aggctccttc acttcttcct ccaacttcat gtccattcgc ttcatcagtg accacagcat | 6420 |
| cacaaggaga gggttccggg ctgagtacta ctccagtccc tccaatgaca gcaccaacct | 6480 |
| gctctgtctg ccaaatcaca tgcaagccag tgtgagcagg agctatctcc aatccttggg | 6540 |
| cttttctgcc agtgaccttg tcatttccac ctggaatgga tactacgagt gtcggcccca | 6600 |
| gataacgccg aacctggtga tattcacaat tccctactca ggctgcggca ccttcaagca | 6660 |
| ggcagacaat gacaccatcg actattccaa cttcctcaca gcagctgtct caggtggcat | 6720 |
| catcaagagg aggacagacc tccgtattca cgtcagctgc agaatgcttc agaacacctg | 6780 |
| ggtcgacacc atgtacattg ctaatgacac catccacgtt gctaataaca ccatccaggt | 6840 |
| cgaggaagtc cagtatggca attttgacgt gaacatttcc ttttatactt cctcatcttt | 6900 |
| cttgtatcct gtgaccagcc gcccttacta cgtggacctg aaccaggact tgtacgttca | 6960 |
| ggctgaaatc ctccattctg atgctgtact gaccttgttt gtggacacct gcgtggcatc | 7020 |
| accatactcc aatgacttca cgtctttgac ttatgatcta atccggagtg gatgcgtgag | 7080 |
| ggatgacacc tacggaccct actcctcgcc atctcttcgc attgcccgct tccggttcag | 7140 |
| ggccttccac ttcctgaacc gcttcccctc cgtgtacctg cgttgtaaaa tggtggtgtg | 7200 |
| cagagcgtat gaccctctt cccgctgcta ccgaggctgt gtgttgaggt cgaagaggga | 7260 |
| tgtgggctcc taccaggaaa aggtggacgt cgtcctgggt cccatccagc tgcagacccc | 7320 |
| cccacgccga gaagaggagc ctcggtaggt ggtcgctctc agaccccact gtccaccggg | 7380 |
| gcgcagaccc ctgactcggg gacttgggat gttcctcttg gtgtcatatt ccaactcaga | 7440 |
| ttgagcccta cattgtgctg cacctggtca tacggagttg aatcagacct ggttcccgcc | 7500 |
| tcccccaagg ctcatggtcc ttggaggacc cgttgcaggg tgaggtcaag agagttctga | 7560 |
| cctggatggc ccatagacct gacgtcccag aatccatgct tctcatctgc aaaatgaaaa | 7620 |
| tgtcaatact tacttcttag cactgttgag agggttactt acataaagga atttttggtga | 7680 |
| aactgc | 7686 |

<210> SEQ ID NO 33
<211> LENGTH: 1665
<212> TYPE: DNA
<213> ORGANISM: Homo sapiens

<400> SEQUENCE: 33

| | |
|---|---|
| agttggaggg aggcagggaa tctggcttga ttggcgtgct gagacgcacc tggcgcaacc | 60 |
| ctcccttctg aatcgaagtt caagtcccgc ggacactgca accatgaagg agagacgggc | 120 |
| cccccagcca gtcgtggcca gatgtaagct cgttctggtc ggggacgtgc agtgtgggaa | 180 |
| gaccgcgatg ttgcaagtgt tagcgaagga ttgctatcca gagacctatg tgcccaccgt | 240 |
| gttcgaaaat tacacagcct gttttggagac agaggaacag agggtggagc ttagtctctg | 300 |
| ggatacctca ggatctccct actacgataa tgtccgtcca ctctgctaca gcgactcgga | 360 |
| tgcagtatta ctatgttttg acatcagccg tccagagaca gtggacagcg cactcaagaa | 420 |
| gtggaggaca gaaatcctag attattgtcc cagcacccgc gttttgctca ttggctgcaa | 480 |
| gacagacctg cgaacagacc tgagtactct gatggagctg tcccaccaga agcaggcgcc | 540 |

| | |
|---|---|
| catctcctat gagcagggtt gtgcaatagc aaagcagctg ggtgcagaaa tctacctgga | 600 |
| aggctcagct ttcacctcag aaaagagcat ccacagcatc tttcggacgg catccatgct | 660 |
| gtgtctgaac aagcctagcc cactgcccca gaagagccct gtccgaagcc tctccaaacg | 720 |
| actgctccac ctcccagtc gctctgaact catctcttct accttcaaga aggaaaaggc | 780 |
| caaaagctgt tccattatgt gaagtggaaa ttgaggggg gagacaaccc cctacttcct | 840 |
| cccttggggt gcagaggcac ggggagaggg aggatgagac aatttaggac actggacatg | 900 |
| agttttcag atggccacgg tgagggcttg aaggagaca ggaatggggc gaggaaggag | 960 |
| ccaggcccgg catgaggacc tgacgctgag agagaaccat catccccaa gccaggcact | 1020 |
| agattttgga gggggcgact accccagtgc ccccccgct ccagaggaag aaagctgtg | 1080 |
| ggggacgggg ggcatgctgg cctcatgggc ttggggcct acagcagcct caccttcagc | 1140 |
| ttcatgcctc ttccacacag cgtttccatg caggtcaggg gatgggaggg gtccctgagc | 1200 |
| ccttcccttc ccctctaagg aggcagcaac ggagagtggg gaagtggagc ggcagctccc | 1260 |
| ttggggggctt agcccaggtg cttcgtaact gcaatcggaa gtgcaggagc tggtcagagc | 1320 |
| caatgagaag gaaacctcat cttttgcatag cccatgcctc atggagaggt gacatcatac | 1380 |
| attcacatgc ttctcaccta agtccccagg gtccaaggga gaagccccag accccttct | 1440 |
| cttgcagagt gtggggtgg tggtgctgca ggggcagggc tgggtggggg tcaccagact | 1500 |
| ttttctgccc ttagggtagt acagctggca tttgttttat agactcttgt ctttggaatt | 1560 |
| ggggggaggg gggagtgtt tcaatctgtt atatgttctg tgtttaatga agaaaaccta | 1620 |
| tttattaatg aaaaatataa tacatataaa gaatttggct ccgta | 1665 |

<210> SEQ ID NO 34
<211> LENGTH: 1849
<212> TYPE: DNA
<213> ORGANISM: Homo sapiens

<400> SEQUENCE: 34

| | |
|---|---|
| gggttatatg atctctttgg ctttagggaa ttactccata ccagctctga gatttccagc | 60 |
| tcagcgatgc cccaggtcc ctgggagagc tgcttctggg tgggggcct cattttgtgg | 120 |
| ctcagcgttg gaagttcagg ggatgcacct cctaccccac agccaaagtg cgctgacttc | 180 |
| cagagcgcca acctttttga aggcaccgat ctcaaagtcc agtttctcct cttttgtccct | 240 |
| tcgaatccta gctgtgggca gctagtagaa ggaagcagtg acctccaaaa ctctgggttc | 300 |
| aatgccactc tgggaaccaa actaattatc catggattca gggttttagg aacaaagcct | 360 |
| tcctggattg acacatttat tagaaccctt ctgcgtgcaa cgaatgctaa tgtgattgcc | 420 |
| gtggactgga tttatgggtc tacaggagtc tacttctcag ctgtgaaaaa tgtgattaag | 480 |
| ttgagcctcg agatctccct tttcctcaat aaactcctgg tgctgggtgt gtcggaatcc | 540 |
| tcaatccaca tcattggtgt tagcctgggg gcccacgttg ggggcatggt gggacagctc | 600 |
| ttcggaggcc agctgggaca gatcacaggc ctggaccccg ctggacctga gtacaccagg | 660 |
| gccagtgtgg aagagcgctt ggatgctgga gatgccctct tcgtggaagc catccacaca | 720 |
| gacaccgaca atttgggtat tcggattccc gttggacatg tggactactt cgtcaacgga | 780 |
| ggccaagacc aacctggctg ccccaccttc ttttacgcag gttatagtta tctgatctgt | 840 |
| gatcacatga gggctgtgca cctctacatc agcgccctgg agaattcctg tccactgatg | 900 |
| gcctttccct gtgccagcta caaggccttc cttgctggac gctgtctgga ttgctttaac | 960 |

| | |
|---|---|
| ccttttctgc tttcctgccc aaggatagga ctggtggaac aaggtggtgt caagatagag | 1020 |
| ccgctcccca aggaagtgaa agtctacctc ctgactactt ccagtgctcc gtactgcatg | 1080 |
| catcacagcc tcgtggagtt tcacttgaag gaactgagaa acaaggacac caacatcgag | 1140 |
| gttaccttcc ttagcagtaa catcacctct tcatctaaga tcaccatacc taagcagcaa | 1200 |
| cgctatggga aggaatcat agcccatgcc accccacaat gccagataaa ccaagtgaaa | 1260 |
| ttcaagtttc agtcttccaa ccgagtttgg aaaaagacc ggactaccat tattgggaag | 1320 |
| ttctgcactg ccctttttgcc tgtcaatgac agagaaaaga tggtctgctt acctgaacca | 1380 |
| gtgaacttac aagcaagtgt gactgtttcc tgtgacctga agatagcctg tgtgtagttt | 1440 |
| aacctgggca ggacacatct ccctgcattt ttttttttt tttgagagag aggtgtgatg | 1500 |
| agggatgtgt gtgtgcagct tattgtagac cattactact aaggagaaaa gcaaagctct | 1560 |
| ttcttatttt cctcataatc agctaccctg gaggggaggg agaactcatt ttacagaact | 1620 |
| tggtttcctt tgccgatctt atgtacatac ccattttagc tttcccatgc atacttaact | 1680 |
| gcacttgctt tatctccttg ggcattcgta cttaggattc aatagaaaca tgtacagggt | 1740 |
| aaacaatttt ttaaaaataa aacttcatgg agtatctgaa aaaaaaaaaa aaaaaaaaaa | 1800 |
| aaaaaaaaaa aaaaaaaaaa aaaaaaaaaa aaaaaaaaa aaaaaaaa | 1849 |

<210> SEQ ID NO 35
<211> LENGTH: 7656
<212> TYPE: DNA
<213> ORGANISM: Homo sapiens

<400> SEQUENCE: 35

| | |
|---|---|
| tttatagcag cagtagaaat ataccaccct agaggacaca cctcctttta gctaggtacc | 60 |
| tataaatgtc caggattttc tattcaattg agaagaaccc agcaaaatgg ggatctccac | 120 |
| agtcatcctt gaaatgtgtc ttttatgggg acaagttcta tctacaggtg ggtggatccc | 180 |
| aaggactaca gactacgctt cactgattcc ctcggaggtg cccttggatc caactgtagc | 240 |
| agaaggttct ccatttccct cggagtcgac cctggagtca actgtagcag aaggttctcc | 300 |
| gatttccttg gagtcaaccc tggagtcaac cgtagcagaa ggttctctga ttccctcaga | 360 |
| gtcaaccctg gagtcaactg tagcagaagg atctgattct ggtttggccc tgaggctggt | 420 |
| gaatggagat ggcaggtgtc agggccgagt ggagatccta taccgaggct cctggggcac | 480 |
| cgtgtgtgat gacagctggg acaccaatga tgccaacgtg gtctgtaggc agctgggttg | 540 |
| tggctgggcc atgtcagctc caggaaatgc ctggttttggc cagggctcag gacccattgc | 600 |
| cctggatgat gtgcgctgct caggacacga atcctacctg tggagctgcc cccacaatgg | 660 |
| ctggctctcc cataactgtg gccatggtga agatgctggt gttatctgct cagctgccca | 720 |
| gcctcagtca acactcaggc cagaaagttg gcctgtcagg atatccacac ctgtacccac | 780 |
| agaaggatct gaatccagtt tggccctgag gctggtgaat ggaggcgaca ggtgtcgagg | 840 |
| ccgagtggag gtcctatacc gaggctcctg gggcaccgtg tgtgatgact actgggacac | 900 |
| caatgatgcc aatgtggtct gcaggcagct gggctgtggc tgggccatgt cagccccagg | 960 |
| aaatgcccag tttggccagg gctcaggacc cattgtcctg gatgatgtgc gctgctcagg | 1020 |
| acatgagtcc tacctgtgga gctgcccca caatggctgg ctcacccaca actgtggcca | 1080 |
| tagtgaagac gctggtgtca tctgctcagc tccccagtcc cggccgacac ccagcccaga | 1140 |
| tacttggccg acctcacatg catcaacagc aggacctgaa tccagtttgg ccctgaggct | 1200 |
| ggtgaatgga ggtgacaggt gtcagggccg agtggaggtc ctataccgag ctcctgggg | 1260 |

```
caccgtgtgt gatgatagct gggacaccag tgacgccaat gtggtctgcc ggcagctggg    1320
ctgtggctgg gccacgtcag ccccaggaaa tgcccggttt ggccagggtt caggacccat    1380
tgtcctggat gacgtgcgct gctcaggcta tgagtcctac ctgtggagct gcccccacaa    1440
tggctggctc tcccataact gtcagcacag tgaagacgct ggtgtcatct gctcagacac    1500
gttgccgacc atcaccttac ctgcatcgac agtaggatct gaatccagtt tggccctgag    1560
gctggtgaat ggaggtgaca ggtgtcaggg ccgagtggag gtcctatacc gaggctcctg    1620
gggcaccgtg tgtgatgaca gctgggacac caatgatgcc aatgtggtct gcaggcagct    1680
gggctgtggc tgggccatgt tggccccagg aaatgcccgg tttggtcagg gctcaggacc    1740
cattgtcctg gatgacgtgc gctgctcagg gaatgagtcc tacttgtgga gctgccccca    1800
caatggctgg ctctcccata actgtggcca tagtgaagac gctggtgtca tctgctcagg    1860
acctgaatcc agtttggccc tgaggctggt gaatggaggt gacaggtgtc agggccgagt    1920
ggaggtccta taccgaggct cttggggcac cgtgtgtgat gacagctggg acaccaatga    1980
tgccaatgtg gtctgcaggc agctgggctg tggctgggcc acgtcagccc aggaaatgc    2040 ccggtttggt cagggctcag gacccattgt cctggatgat gtgcgctgct caggacatga    2100
gtcctacctg tggagctgcc caacaatgg ctggctctcc cacaactgtg ccatcatga    2160 agatgctggt gtcatctgct cagctgccca gtcccggtcg acgccaggc cagacacgtt    2220 gtcgaccatc acgttacctc catcgacagt aggatctgaa tccagtttga ccctgaggct    2280
ggtgaatgga agtgacaggt gtcagggccg agtagaggtc ctataccgag gctcctgggg    2340
caccgtgtgt gatgacagct gggataccaa tgatgccaat gtggtctgca ggcagctggg    2400
ctgtggctgg gccacgtcgg ccccaggaaa tgcccggttt ggccagggct caggacccat    2460
tgttctggat gatgtgcgct gctcaggaca cgagtcctac ctgtggagct gcccccacaa    2520
tggctggctc tcccacaact gtggccatca tgaagatgct ggtgtcatct gctcagtttc    2580
ccagtcccgg ccgacaccca gtccagatac ttggccgacc tcacatgcat caacagcagg    2640
acctgaatcc agtttggccc tgaggctggt gaatggaggt gacaggtgtc agggccgagt    2700
ggaggtccta taccgaggct cctggggcac cgtgtgtgat gatagctggg acaccagtga    2760
cgccaatgtg gtctgccggc agctgggctg tggctgggcc acgtcagccc aggaaatgc    2820 ccggtttggc cagggttcag gacccattgt cctggatgac gtgcgctgct caggctatga    2880
gtcctacctg tggagctgcc ccacaatgg ctggctctcc cataactgtc agcacagtga    2940
agacgctggt gtcatctgct cagctgccca ctcctggtcg acgccagtc cagacacatt    3000 gccgaccatc accttgcctg catcgacagt aggatctgaa tccagtttgg ccctgaggct    3060
ggtgaatgga ggtgacaggt gtcagggccg agtggaggtc ctataccaag gctcctgggg    3120
caccgtgtgc gatgacagct gggacaccaa tgatgccaat gtcgtctgca ggcaactggg    3180
ctgtggctgg gccatgtcag ccccaggaaa tgcccggttt ggtcagggct caggacccat    3240
tgtcctggat gatgtgcgct gctcaggaca cgagtcttac ctgtggagct gcccccacaa    3300
tggctggctc tcccacaact gtggccatag tgaagacgct ggtgtcatct gctcagcttc    3360
ccagtcccgg ccaacaccta gtccagacac ttggccaacc tcacatgcat caacagcagg    3420
atctgaatcc agtttggccc tgaggctggt gaatggaggt gacaggtgtc agggccgagt    3480
ggaggtccta taccgaggct cctggggcac cgtgtgtgat gactactggg acaccaatga    3540
tgccaatgtg gtttgcaggc agctgggctg tggctgggcc atgtcagccc aggaaatgc    3600
```

```
ccggtttggc cagggttcag gacccattgt cctggatgat gtgcgctgct caggacatga   3660
gtcctatctg tggagctgcc cccacaatgg ctggctctcc cacaactgtg gccatcatga   3720
agacgctggt gtcatctgct cagcttccca gtcccagccg acacccagcc cagacacttg   3780
gccaacctca catgcatcaa cagcaggatc tgaatccagt ttggccctga ggctggtgaa   3840
tggaggtgac aggtgtcagg gccgagtgga ggtcctatac cgaggctcct ggggcaccgt   3900
gtgtgatgac tactgggaca ccaatgatgc caatgtggtt tgcaggcagc tgggctgtgg   3960
ctgggccacg tcagccccag gaaatgcccg gtttggccag ggttcaggac ccattgtcct   4020
ggatgatgtg cgctgctcag gacatgagtc ctatctgtgg agctgccccc acaatggctg   4080
gctctcccac aactgtggcc atcatgaaga cgctggtgtc atctgctcag cttcccagtc   4140
ccagccgaca cccagcccag acacttggcc aacctcacat gcatcaacag caggatctga   4200
atccagtttg ccctgaggc tggtgaatgg aggtgacagg tgtcagggcc gagtggaggt   4260
cctataccga ggctcctggg gcaccgtgtg tgatgactac tgggacacca atgatgccaa   4320
tgtggtttgc aggcagctgg gctgtggctg gccacgtca gccccaggaa atgcccggtt   4380
tggccagggt tcaggaccca ttgtcctgga tgatgtgcgc tgctcaggac atgagtccta   4440
tctgtggagc tgcccccaca atggctggct cccacacaac tgtggccatc atgaagacgc   4500
tggtgtcatc tgctcagctt cccagtccca gccgacaccc agcccagaca cttggccaac   4560
ctctcgtgca tcaacagcag gatctgaatc cactttggcc ctgagactgg tgaatggagg   4620
tgacaggtgt cgaggccgag tggaggtcct ataccaaggc tctggggca ccgtgtgtga   4680
tgactactgg gacaccaatg atgccaacgt ggtctgcagg cagctgggct gtggctgggc   4740
catgtcagcc caggaaatg cccagtttgg ccagggctca ggacccattg tcctggatga   4800
tgtgcgctgc tcaggacacg agtcttacct gtggagctgc ccccacaatg ctggctctc   4860
ccacaactgt ggccatcatg aagatgctgg tgtcatctgc tcagctgctc agtcccagtc   4920
aacgcccagg ccagatactt ggctgaccac caacttaccg gcattgacag taggatctga   4980
atccagtttg gctctgaggc tggtgaatgg aggtgacagg tgtcgaggcc gagtggaggt   5040
cctgtatcga ggctcctggg gaaccgtgtg tgatgacagc tgggacacca atgatgccaa   5100
tgtggtctgc aggcagctgg gctgtggctg gccatgtcg gccccaggaa atgcccggtt   5160
tggccagggt tcaggaccca ttgtcctgga tgatgtgcgc tgctcaggga tgagtccta   5220
cctgtggagc tgcccccaca aaggctggct cacccacaac tgtggccatc acgaagacgc   5280
tggtgtcatc tgctcagcca cccaaataaa ttctactacg acagattggt ggcatccaac   5340
aactacaacc actgcaagac cctcttcaaa ttgtggtggc ttcttattct atgccagtgg   5400
gacattctcc agcccatcct accctgcata ctacccaac aatgctaagt gtgtttggga   5460
aatagaagtg aattctggtt atcgcataaa cctgggcttc agtaatctga aattggaggc   5520
acaccataac tgcagttttg attatgttga aatctttgat ggatcattga atagcagtct   5580
cctgctgggg aaaatctgta atgataccag gcaaatattt acatcttctt acaaccgaat   5640
gaccattcac tttcgaagtg acatcagttt ccaaaacact ggcttttggg cttggtataa   5700
ctccttccca agcgatgcca ccttgaggtt ggtcaattta aattcatcct atggtctatg   5760
tgccgggcgt gtagaaattt accatggtgg cacctggggg acagtttgtg atgactcctg   5820
gaccattcag gaagctgagg tggtctgcag acagctaggg tgtggacgtg cagtttcagc   5880
ccttggaaat gcatatttg gctctggctc tggccccatc accctggacg atgtagagtc   5940
ctcagggacg gaatccactc tctggcagtg ccggaaccga ggctggttct cccacaactg   6000
```

```
taatcatcgt gaagatgctg gtgtcatctg ctcaggaaac catctatcga cacctgctcc   6060
ttttctcaac atcacccgtc caaacacaga ttattcctgc ggaggcttcc tatcccaacc   6120
atcaggggac ttttccagcc cattctatcc cgggaactat ccaaacaatg ccaagtgtgt   6180
gtgggacatt gaggtgcaaa acaactaccg tgtgactgtg atcttcagag atgtccagct   6240
tgaaggtggc tgcaactatg attatattga agttttcgat ggcccctacc gcagttcccc   6300
tctcattgct cgagtttgtg atggggccag aggctccttc acttcttcct ccaacttcat   6360
gtccattcgc ttcatcagtg accacagcat cacaaggaga gggttccggg ctgagtacta   6420
ctccagtccc tccaatgaca gcaccaacct gctctgtctg ccaaatcaca tgcaagccag   6480
tgtgagcagg agctatctcc aatccttggg cttttctgcc agtgaccttg tcatttccac   6540
ctggaatgga tactacgagt gtcggcccca gataacgccg aacctggtga tattcacaat   6600
tccctactca ggctgcggca ccttcaagca ggcagacaat gacaccatcg actattccaa   6660
cttcctcaca gcagctgtct caggtggcat catcaagagg aggacagacc tccgtattca   6720
cgtcagctgc agaatgcttc agaacacctg ggtcgacacc atgtacattg ctaatgacac   6780
catccacgtt gctaataaca ccatccaggt cgaggaagtc cagtatggca attttgacgt   6840
gaacatttcc ttttatactt cctcatcttt cttgtatcct gtgaccagcc gcccttacta   6900
cgtggacctg aaccaggact tgtacgttca ggctgaaatc ctccattctg atgctgtact   6960
gaccttgttt gtggacacct cgtggcatc accatactcc aatgacttca cgtctttgac   7020
ttatgatcta atccggagtg gatgcgtgag ggatgcacc tacggaccct actcctcgcc   7080
atctcttcgc attgcccgct tccggttcag ggccttccac ttcctgaacc gcttcccctc   7140
cgtgtacctg cgttgtaaaa tggtggtgtg cagagcgtat gaccctctt cccgctgcta   7200 ccgaggctgt gtgttgaggt cgaagaggga tgtgggctcc taccaggaaa aggtggacgt   7260
cgtcctgggt cccatccagc tgcagacccc cccacgccga aagaggagc ctcggtaggt   7320 ggtcgctctc agaccccact gtccaccggg gcgcagaccc ctgactcggg gacttgggat   7380
gttcctcttg gtgtcatatt ccaactcaga ttgagccta cattgtgctg cacctggtca   7440 tacgagttg aatcagacct ggttcccgcc tcccccaagg ctcatggtcc ttggaggacc   7500
cgttgcaggg tgaggtcaag agagttctga cctggatggc ccatagacct gacgtcccag   7560
aatccatgct tctcatctgc aaaatgaaaa tgtcaatact tacttcttag cactgttgag   7620
agggttactt acataaagga attttggtga aactgc                             7656
```

<210> SEQ ID NO 36
<211> LENGTH: 2413
<212> TYPE: DNA
<213> ORGANISM: Homo sapiens

<400> SEQUENCE: 36

```
cccgggctcg cgggcagacg gaggcgcctc tctttccccg ccctcgcct cggcccttc     60 tcttcccagc acctcggctg ttccccggcg gcggcagcgg cagcggcggc ccacacagca   120
gcgagaggcg agaggaggct gcctcgagga ggctgcctcg aggatgaagt gcaaacccaa   180
ccagacgcgg acctacgacc ccgagggggtt caagaagcgg gcggcgtgcc tgtgcttccg   240
gagcgaacgc gaggacgagg tcctgttagt gagtagcagc cggtacccgg accgctggat   300
cgtgccgggc gggggcatgg agcccgagga ggagccgggc ggtgcggcgg tccgagaggt   360
gtacgaagaa gcgggagtca aggggaagtt aggccggctc ctgggcgtct tcgaacagaa   420
```

| | |
|---|---|
| ccaggatcgc aagcacagaa cgtacgtgta tgtactgact gtcacggagc tgctggagga | 480 |
| ttgggaagat tcggttagca ttgggaggaa gcgagagtgg ttcaaagtcg aagatgccat | 540 |
| caaggttctc cagtgccaca agcccgtgca cgccgaatat ctggagaaac taaagctggg | 600 |
| cggttcccca accaatggaa actccatggc cccatcctcg ccagatagcg atccctaatg | 660 |
| aacagcaaag atgttcagta ttgtgctgaa agaaacattg atgtgaaccc agtgatcagt | 720 |
| ggaattgtca agtacaggtg agcacttctg tgttcccaag aagacagctc atctggtttc | 780 |
| ttcctgcatc ttgggacact ccttccctgt ctataccact gactcttgct ctggttgttg | 840 |
| tactcttata cgtgaataga ctcttaattc agcacctata gccttttgtt gtgcttttt | 900 |
| gatgtgtctg ccttcattag actatgatgt ctttgagagc aaagactatt tttccttact | 960 |
| ctttgcatat tctgcatctg agacactact tgaaatatgg ttggcatcac tgaaggttct | 1020 |
| ttgattcaat taatatttg taatcaccgt gtggcaaaac attcccctc caatctggtg | 1080 |
| ctagtagagt atatgctatc taggcaccat gtgtgtggct tttgtgtatc aggtgtttca | 1140 |
| gaaatatttc aagacagttg taagatgttt gaggacaaga attattactc ctatttctat | 1200 |
| gtcataccac acagtagctg cacagttta agattatgcc atcacctagg taatgtttt | 1260 |
| gtagaatcag tccttcgtgt aacaactcta gtgttttgt actgttgatg atttgcttaa | 1320 |
| attttattca aaaactatca cttgctataa aggtaattgt aaaaataaat acagtggacg | 1380 |
| caaaataatg ttgtgagttt ttataaaaat aaattttaaa atgatatata agacattttt | 1440 |
| ttgcaatgcc tgccctaacc acttcttaca tgtcatctta acatctcttt gaggaaacac | 1500 |
| tgtttcctca ttttacagat ttaacatact gtattatttg atgccagagc caacaggcta | 1560 |
| tatcataggc agtttccaaa cttaattatg ccatttagtt tgtctagatt tcttttgcct | 1620 |
| ctctcactga tccatttggc tgtagttttc atccctttc cagtacacac agctagctcc | 1680 |
| tcatcctacc tggttctgc atatgagaat gcagagggct gagagagggc aaaattgttg | 1740 |
| tcatttagaa aaggcattta ggaaagaggc tgctattaga ggggaacaca agtgaaggt | 1800 |
| ttttttaaaa aagaggactt gcatcagctg cctccagaac aattttaaga aaataacaaa | 1860 |
| gatgtttaga agaaatctta cggagtttgc catgggatgt gtgatatcag cagtcttcag | 1920 |
| ctccttacaa attaccaaaa gtggttctaa tatgctagtt tgtttgattt ttctttttat | 1980 |
| attataaagc aattgcatcg ataaaagctt ggactccatt ttagtgtgac actcttcctc | 2040 |
| atgataccag tgaaatgtat tgattgtgtc cccagttgtt acataatttg aaataaaaat | 2100 |
| ataacttctt gatttattgt tttttaagat gtgatatggt actgtggtta tgttgtttta | 2160 |
| aaaaatgatt atcttttaga aagtatact gaaaaatgta caggtgaaat gatatgttac | 2220 |
| tggtattcgc ttcaaaatca tctgagtgtg gggtaattga gtacatagat gaaacaagat | 2280 |
| tggccataaa ttggtaattg ctgaagctgt gtgatggatg tttgagagtt cattatacta | 2340 |
| ttctctatac ttttgtatat gtttgaaatt ttccataata aaattgaaa aagtaaaaa | 2400 |
| aaaaaaaaaa aaa | 2413 |

<210> SEQ ID NO 37
<211> LENGTH: 862
<212> TYPE: DNA
<213> ORGANISM: Homo sapiens

<400> SEQUENCE: 37

| | |
|---|---|
| cttggcggtg acgcacggcc ctcacgtgac cgggagctgc agagctacgc agccttcggt | 60 |
| gcagtcgtca ctcgtgtctc gctaccagct ccccgctgcc ctgcgctcgg cgggctggca | 120 |

```
tccggcccgg gggaaagcgg accagcccctt ctgcaggtct gcggggccaa gtgtcccggc      180
ggcgcacctc gtggcgagaa tcgggagaag gaggagacta caaggatagg cccaggagta      240
atggagtcca aagagaaacg agcagtaaac agtctcagca tggaaaatgc caaccaagaa      300
aatgaagaaa aggagcaagt tgctaataaa ggggagcct tggccctccc tttggatgct       360
ggtgaatact gtgtgcctag aggaaatcgt aggcggttcc gcgttaggca gcccatcctg      420
cagtatagat gggatatgat gcataggctt ggagaaccac aggcaaggat gagagaagag      480
aatatggaaa ggattgggga ggaggtgaga cagctgatgg aaaagctgag ggaaaagcag      540
ttgagtcata gtctgcgggc agtcagcact gacccccctc accatgacca tcatgatgag      600
ttttgcctta tgccctgaat cctgatggtt tccctaaagt tattacggaa acagacccct      660
gctttcgaat ttacatgttc atgatgtgcc cttgttgtaa acctttacct gtcacttgtt      720
tacgtgggtc tcctattacc agcttctaat tgaatattgt gttttttgaac cagtctgtaa      780 gattttttgtt agcagaagaa ttttacctat tgcatggaaa gatgctcatt atagtgaagt     840
taataaagca cctttaaaaa gc                                               862

<210> SEQ ID NO 38
<211> LENGTH: 7080
<212> TYPE: DNA
<213> ORGANISM: Homo sapiens

<400> SEQUENCE: 38
gagctagcgc tcaagcagag cccagcgcgg tgctatcgga cagagcctgg cgagcgcaag       60
cggcgcgggg agccagcggg gctgagcgcg gccagggtct gaacccagat tcccagact      120 agctaccact ccgcttgccc acgcccggg agctcgcggc gcctggcggt cagcgaccag      180
acgtccgggg ccgctgcgct cctggcccgc gaggcgtgac actgtctcgg ctacagaccc      240
agagggagca cactgccagg atgggagctg ctgggaggca ggacttcctc ttcaaggcca      300
tgctgaccat cagctggctc actctgacct gcttccctgg ggccacatcc acagtggctg      360
ctgggtgccc tgaccagagc cctgagttgc aaccctggaa ccctggccat gaccaagacc      420
accatgtgca tatcggccag ggcaagacac tgctgctcac ctcttctgcc acggtctatt      480
ccatccacat ctcagaggga ggcaagctgg tcattaaaga ccacgacgag ccgattgttt      540
tgcgaacccg gcacatcctg attgacaacg gaggagagct gcatgctggg agtgccctct      600 gcccttttcca gggcaatttc accatcattt tgtatggaag ggctgatgaa ggtattcagc      660 cggatccta ctatggtctg aagtacattg gggttggtaa aggaggcgct cttgagttgc      720
atggacagaa aaagctctcc tggacatttc tgaacaagac ccttcaccca ggtggcatgg      780
cagaaggagg ctatttttttt gaaaggagct ggggccaccg tggagttatt gttcatgtca      840
tcgaccccaa atcaggcaca gtcatccatt ctgaccggtt tgacacctat agatccaaga      900
aagagagtga acgtctggtc cagtatttga acgcggtgcc cgatggcagg atcctttctg      960
ttgcagtgaa tgatgaaggt tctcgaaatc tggatgacat ggccaggaag gcgatgacca     1020
aattgggaag caaacacttc ctgcaccttg gatttagaca cccttggagt tttctaactg     1080
tgaaaggaaa tccatcatct tcagtggaag accatattga atatcatgga catcgaggct     1140
ctgctgctgc ccgggtattc aaattgttcc agacagagca tggcgaatat tcaatgtttt     1200
ctttgtccag tgagtgggtt caagacgtgg agtggacgga gtggttcgat catgataaag     1260
tatctcagac taaaggtggg gagaaaattt cagacctctg gaaagctcac ccaggaaaaa     1320
```

```
tatgcaatcg tcccattgat atacaggcca ctacaatgga tggagttaac ctcagcaccg      1380
aggttgtcta caaaaaaggc caggattata ggtttgcttg ctacgaccgg ggcagagcct      1440
gccggagcta ccgtgtacgg ttcctctgtg ggaagcctgt gaggcccaaa ctcacagtca      1500
ccattgacac caatgtgaac agcaccattc tgaacttgga ggataatgta cagtcatgga      1560
aacctggaga taccctggtc attgccagta ctgattactc catgtaccag gcagaagagt      1620
tccaggtgct tccctgcaga tcctgcgccc caaccaggt caaagtggca gggaaaccaa       1680
tgtacctgca catcggggag gagatagacg gcgtggacat gcgggcggag gttgggcttc      1740
tgagccggaa catcatagtg atgggggaga tggaggacaa atgctacccc tacagaaacc      1800
acatctgcaa tttctttgac ttcgatacct ttgggggcca catcaagttt gctctgggat      1860
ttaaggcagc acacttggag ggcacggagc tgaagcatat gggacagcag ctggtgggtc      1920
agtacccgat tcacttccac ctggccggtg atgtagacga aggggaggt tatgacccac        1980
ccacatacat cagggacctc tccatccatc atacattctc tcgctgcgtc acagtccatg      2040
gctccaatgg cttgttgatc aaggacgttg tgggctataa ctctttgggc cactgcttct      2100
tcacggaaga tgggccggag gaacgcaaca cttttgacca ctgtcttggc ctccttgtca      2160
agtctggaac cctcctcccc tcggaccgtg acagcaagat gtgcaagatg atcacagagg      2220
actcctaccc ggggtacatc cccaagccca ggcaagactg caatgctgtg tccaccttct      2280
ggatggccaa tccaacaac aacctcatca actgtgccgc tgcaggatct gaggaaactg        2340
gattttggtt tatttttcac cacgtaccaa cgggcccctc cgtgggaatg tactccccag      2400
gttattcaga gcacattcca ctgggaaaat tctataacaa ccgagcacat tccaactacc      2460
gggctggcat gatcatagac aacggagtca aaccaccga ggcctctgcc aaggacaagc       2520
ggccgttcct ctcaatcatc tctgccagat acagccctca ccaggacgcc gacccgctga      2580
agccccggga gccggccatc atcagacact tcattgccta caagaaccag gaccacgggg      2640
cctggctgcg cggcggggat gtgtggctgg acagctgccg gtttgctgac aatggcattg      2700
gcctgaccct ggccagtggt ggaaccttcc gtatgacga cggctccaag caagagataa        2760
agaacagctt gtttgttggc gagagtggca acgtggggac ggaaatgatg gacaatagga      2820
tctggggccc tggcggcttg gaccatagcg gaaggaccct ccctataggc cagaattttc      2880
caattagagg aattcagtta tatgatggcc ccatcaacat ccaaaactgc actttccgaa      2940
agtttgtggc cctggagggc cggcacacca gcgccctggc cttccgcctg aataatgcct      3000
ggcagagctg ccccatagc aacgtgaccg gcattgcctt tgaggacgtt ccgattactt        3060
ccagagtgtt cttcggagag cctgggccct ggttcaacca gctggacatg gatggggata      3120
agacatctgt gttccatgac gtcgacggct ccgtgtccga gtaccctggc tcctacctca      3180
cgaagaatga caactggctg gtccggcacc cagactgcat caatgttccc gactggagag      3240
gggccatttg cagtgggtgc tatgcacaga tgtacattca gcctacaag accagtaacc        3300
tgcgaatgaa gatcatcaag aatgacttcc ccagccaccc tctttacctg gaggggcgc       3360
tcaccaggag cacccattac cagcaatacc aaccggttgt caccctgcag aagggctaca      3420
ccatccactg ggaccagacg gccccgccg aactcgccat ctggctcatc aacttcaaca        3480
agggcgactg gatccgagtg gggctctgct acccgcgagg caccacattc tccatcctct      3540
cggatgttca caatcgcctg ctgaagcaaa cgtccaagac gggcgtcttc gtgaggacct      3600
tgcagatgga caaagtggag cagagctacc ctggcaggag ccactactac tgggacgagg      3660
actcagggct gttgttcctg aagctgaaag ctcagaacga gagagagaag tttgctttct      3720
```

```
gctccatgaa aggctgtgag aggataaaga ttaaagctct gattccaaag aacgcaggcg    3780
tcagtgactg cacagccaca gcttacccca agttcaccga gagggctgtc gtagacgtgc    3840
cgatgcccaa gaagctcttt ggttctcagc tgaaaacaaa ggaccatttc ttggaggtga    3900
agatggagag ttccaagcag cacttcttcc acctctggaa cgacttcgct tacattgaag    3960
tggatgggaa gaagtacccc agttcggagg atggcatcca ggtggtggtg attgacggga    4020
accaagggcg cgtggtgagc cacacgagct caggaactc cattctgcaa ggcataccat    4080
ggcagctttt caactatgtg gcgaccatcc ctgacaattc catagtgctt atggcatcaa    4140
agggaagata cgtctccaga ggcccatgga ccagagtgct ggaaaagctt ggggcagaca    4200
ggggtctcaa gttgaaagag caaatggcat cgttggctt caaaggcagc ttccggccca    4260
tctgggtgac actggacact gaggatcaca aagccaaaat cttccaagtt gtgcccatcc    4320
ctgtggtgaa gaagaagaag ttgtgaggac agctgccgcc cggtgccacc tcgtggtaga    4380
ctatgacggt gactcttggc agcagaccag tggggatgg ctgggtcccc cagcccctgc    4440
cagcagctgc ctgggaaggc cgtgtttcag ccctgatggg ccaagggaag gctatcagag    4500
accctggtgt tgccacctgc ccctactcaa gtgtctacct ggagcccctg gggcggtgct    4560
ggccaatgct ggaaacattc actttcctgc agcctcttgg gtgcttctct cctatctgtg    4620
cctcttcagt gggggtttgg ggaccatatc aggagacctg ggtgtgctg acagcaaaga    4680 tccactttgg caggagccct gacccagcta ggaggtagtc tggagggctg gtcattcaca    4740
gatccccatg gtcttcagca gacaagtgag ggtggtaaat gtaggagaaa gagccttggc    4800
cttaaggaaa tctttactcc tgtaagcaag agccaaccctc acaggattag gagctggggt    4860
agaactggct atccttgggg aagaggcaag ccctgcctct ggccgtgtcc accttttcagg    4920 agactttgag tggcaggttt ggacttggac tagatgactc tcaaaggccc ttttagttct    4980
gagattccag aaatctgctg catttcacat ggtacctgga acccaacagt tcatggatat    5040
ccactgatat ccatgatgct gggtgcccca gcgcacacgg gatggagagg tgagaactaa    5100
tgcctagctt gaggggtctg cagtccagta gggcaggcag tcaggtccat gtgcactgca    5160
atgccaggtg gagaaatcac agagaggtaa aatggaggcc agtgccattt cagagggag    5220 gctcaggaag gcttcttgct tacaggaatg aaggctgggg gcattttgct gggggagat    5280 gaggcagcct ctggaatggc tcagggattc agccctccct gccgctgcct gctgaagctg    5340
gtgactacgg ggtcgccctt tgctcacgtc tctctggccc actcatgatg gagaagtgtg    5400
gtcagagggg agcaatgggc tttgctgctt atgagcacag aggaattcag tccccaggca    5460
gccctgcctc tgactccaag agggtgaagt ccacagaagt gagctcctgc cttagggcct    5520
catttgctct tcatccaggg aactgagcac aggggcctc caggagaccc tagatgtgct    5580
cgtactccct cggcctggga tttcagagct ggaaatatag aaaatatcta gcccaaagcc    5640
ttcattttaa cagatgggga aagtgagccc caagatgggg aaagaaccac acagctaagg    5700
gagggcctgg ggagccccac cctagcccctt gctgccacac cacattgcct caacaaccgg    5760
ccccagagtg cccaggcact cctgaggtag cttctggaaa tggggacaag tcccctcgaa    5820
ggaaaggaaa tgactagagt agaatgacag ctagcagatc tcttccctcc tgctcccagc    5880
gcacacaaac ccgccctccc cttggtgttg gcggtccctg tggccttcac tttgttcact    5940
acctgtcagc ccagcctggg tgcacagtag ctgcaactcc ccattggtgc tacctggctc    6000
tcctgtctct gcagctctac aggtgaggcc cagcagaggg agtagggctc gccatgtttc    6060
```

| | |
|---|---|
| tggtgagcca atttggctga tcttgggtgt ctgaacagct attgggtcca ccccagtccc | 6120 |
| tttcagctgc tgcttaatgc cctgctctct ccctggccca ccttatagag agcccaaaga | 6180 |
| gctcctgtaa gagggagaac tctatctgtg gtttataatc ttgcacgagg caccagagtc | 6240 |
| tccctgggtc ttgtgatgaa ctacatttat ccccttcct gccccaacca caaactcttt | 6300 |
| ccttcaaaga gggcctgcct ggctccctcc acccaactgc acccatgaga ctcggtccaa | 6360 |
| gagtccattc cccaggtggg agccaactgt cagggaggtc tttcccacca aacatctttc | 6420 |
| agctgctggg aggtgaccat agggctctgc ttttaaagat atggctgctt caaaggccag | 6480 |
| agtcacagga aggacttctt ccagggagat tagtggtgat ggagaggaga gttaaaatga | 6540 |
| cctcatgtcc ttcttgtcca cggttttgtt gagttttcac tcttctaatg caagggtctc | 6600 |
| acactgtgaa ccacttagga tgtgatcact ttcaggtggc caggaatgtt gaatgtcttt | 6660 |
| ggctcagttc atttaaaaaa gatatctatt tgaaagttct cagagttgta catatgtttc | 6720 |
| acagtacagg atctgtacat aaaagttttct ttcctaaacc attcaccaag agccaatatc | 6780 |
| taggcatttt cttggtagca caaattttct tattgcttag aaaattgtcc tccttgttat | 6840 |
| ttctgtttgt aagacttaag tgagttaggt ctttaaggaa agcaacgctc ctctgaaatg | 6900 |
| cttgtctttt ttctgttgcc gaaatagctg gtccttttc gggagttaga tgtatagagt | 6960 |
| gtttgtatgt aaacatttct tgtaggcatc accatgaaca agatatatt ttctatttat | 7020 |
| ttattatatg tgcacttcaa gaagtcactg tcagagaaat aaagaattgt cttaaatgtc | 7080 |

<210> SEQ ID NO 39
<211> LENGTH: 5676
<212> TYPE: DNA
<213> ORGANISM: Homo sapiens

<400> SEQUENCE: 39

| | |
|---|---|
| ggcacgtgga ctccctttaa tccagtgact gtcaggtcga tcatatgccg aggacgatga | 60 |
| tcccgccggg ggagtgcacg tacgcgggcc ggaagcggag gaggcccctg cagaaacaga | 120 |
| ggcccgccgt gggggcagag aagtccaacc cctccaagcg acaccgggac cgcctcaacg | 180 |
| ccgagttgga ccacctggcc agcctgctgc cgttcccgcc tgacatcatc tccaagctgg | 240 |
| acaagctttc tgtcctgcgc ctcagtgtca gttacctccg ggtgaagagc ttcttccaag | 300 |
| tcgtgcagga gcagagctca cggcagcctg cggccggcgc ccctcgccc ggagacagct | 360 |
| gtcctcttgc agggtctgcc gtgctggagg gaaggctgct gttggagtct cttaatggct | 420 |
| ttgctctggt cgtgagtgca gaagggacga tattttatgc atcagcaacg atcgtggact | 480 |
| atctgggctt ccatcagacg gatgtaatgc accagaacat ttatgactac atccacgtgg | 540 |
| acgaccgcca ggacttctgc cggcagctcc actgggccat ggaccctccc caggtggtgt | 600 |
| ttgggcagcc ccgcccttg gagacaggag atgatgctat cctggggagg ctgctcaggg | 660 |
| cccaggagtg gggcacaggc acgcccaccg agtactcggc cttcctgacc cgctgcttca | 720 |
| tctgccgtgt gcgctgcctg ctggacagca cctcgggctt cctggcccgg ggtcacagg | 780 |
| cttggcagct gcggctctgc tgtcccgagc cactcatgac gatgcagttt caaggaaaac | 840 |
| taaaattcct gtttggacag aagaagaagg cgccgtcagg agccatgctc ccgccgcggc | 900 |
| tgtcgctgtt ctgcattgcg gcacccgttc tcctccctc cgcagcggag atgaaaatga | 960 |
| ggagcgcgct cctgagggca aaacccagag cagacaccgc agccaccgcg gatgcaaaag | 1020 |
| taaaagccac caccagtctg tgcgaatcgg aactgcatgg aaaacccaat tactcagcag | 1080 |
| gaaggagcag cagagagagc ggcgtttttgg tgctcaggga acagactgac gctggccgat | 1140 |

```
gggcacaggt tcccgccagg gccccatgcc tgtgcctccg gggtggccct gaccttgtcc    1200
ttgaccccaa gggggggctca ggggacaggg aggaggagca gcacaggatg ctgagcaggg    1260
cctctggagt gacagggcgg agggagactc caggacccac aaagcccctg ccctggacag    1320
cgggaaagca cagtgaggat ggtgccaggc cgaggctgca gcccagcaag aatgacccgc    1380
cctccctgcg ccccatgccc cgcggctcct gcctgccctg cccgtgtgtc cagggcactt    1440
tcaggaactc gcccatctct cacccgccga gcccgtcccc cagtgcctac tccagccgga    1500
ccagcagacc catgcgggat gtcggtgagg accaggtgca ccctcccctc tgccactttc    1560
cccagaggag cctgcagcac cagctccctc agcctggagc tcagcgtttt gccacgaggg    1620
gctatcccat ggaggacatg aagctgcaag gtgtaccgat gcctccgggg acctgtgtg    1680 gtccgacgct gctgctagat gtgtccatca agatggagaa ggactctggg tgtgaggtg    1740 ctgcagacgg ctgtgtgccc agccaggtgt ggctgggggc cagtgacagg agccacccag    1800
ccaccttccc taccaggatg cacctgaaaa cagagccaga ctctcggcaa caggtgtaca    1860
tctcgcacct ggggcacggc gtgcgggggg ctcagcccca tgggagggcc actgctgggc    1920
gcagcaggga gctgacccct ttccaccctg cacactgtgc ctgcctggag cccacagacg    1980
gccttcccca gtcggagcct ccccaccagc tctgtgcacg gggccgaggt gaacagtcct    2040
gcacctgcag agctgctgag gccgcccctg tggtcaagcg ggagcccttg gactcacccc    2100
agtgggctac tcacagccag ggaatggtgc ccgggatgtt gcccaaaagt gccttggcca    2160
cgctggtccc gccccaagct tcggggtgca cattcctgcc atagcgcagt gaccaccatc    2220
caagctcaga tctgtgtgtc tacgctcaga tgcgtcggtg gctgggctgc cctgctcctg    2280
gtcaggccgg agcccgtcct aagacacacg ctttgcagag ctgtgcatgc gcagtctgct    2340
agtgtgtgtg tgcagcatac gcaggagcct atcctgaatt ttgtaaaata tcccaacagt    2400
tcttaaatga aaactggcct taagtctatt caagcatgac agcatttctc tttgaggaat    2460
taaaatcttt aggaaagtga tcatggctgg acagcttcat gccccagagg cagcgagcac    2520
ccgtcccatg gctgccaagt ccacagtcgg ggatgaagca gtcgggtgat gctcccaagt    2580
ccgcagtcgg ggatgaagcg gtcgggtgat gctcccaagt ccgcagtcgg ggatgaagcg    2640
gtcgggtgac acacctagct cagccctccc aggccacctg cagctcccag cctgtgctgt    2700
gcaggcaggg tcagcccatc gccacagtgc actgtagagg ccagcacacg gcaaattaga    2760
aatacaacac gcggagaaag gggtccgtga gcccactcat agaggaatct agaacgttcc    2820
aggcagcaga ggctggcagc gtgggtccca cactgcccca caccgtgcgg caggtgctcc    2880
atggcgccat gacagagtct gaggccagac ctggactgga attgacagca taaccctgt    2940 tccttctgga catctcccga gttctcagtg ggtctctgcg gacggttctt cctaatctgc    3000
ctcttggtac atcacgtaat acagagttca cagactccgg gtttggaagt acagagaaac    3060
acacaacgta gagagaagac acaggaaact gcgctgcctg tggggggttc tctctggctg    3120
gctgtacagt tcactcaaat gagggttccc attgccatcc taggagaata attagggaca    3180
agacagacaa gtattaatag cattaaaaca gttgtaaagg cgatattttc tgagagtagg    3240
aaatttggat acaaaagcat aagtcagaaa gtgaaggtcc caatccacc aacccgagaa    3300 cctacagctg atggtgcatt tcaggcttct tccacggtct ggcctggaac cccacccggc    3360
tggtgcaggc atcagatcag ggtgtagaag tcacccaag caagaggaag ccaggcagtg    3420
aggccctggg gtgtggctgc agctgggccc acctgtgcgg gggtgggaag gccccatcct    3480
```

```
cagggagagg gcatcggcgc cctgacgtca gctccactgg gagtggcagg agctgtggga    3540
gcccatgggt gagggaccca ccaccccgct gcactgtgca ttgtgcctcc cgtgtggacg    3600
ccctctctgt tgttggcccg cgggtgaggg acccaccacc cctagggacc caccaccccg    3660
ccgcactgtg cattctgcct cctgtgtgga cgccctctct gttgtcagtg gctttgaggt    3720
gtcagtgctt acttagatgc tggtttaatg ctggacccat ttgttaaacg caccttcact    3780
ttgtcaaaac ccaggtttgg ttggcaggac tgggtcttct gcccaatgcc aggtgcctgc    3840
gcctctcagt ggcctggttc ttggacagtt tgcccccatg tggcagggat agggataagg    3900
atctcctctc agtactggaa gagaacagcc aaccatctga gcccagagtc acagatccat    3960
cgtggccccc tatgaccccc aagccctacc gagggggcac tcactctctg cttagccagg    4020
gggcgtcttt caaaaggtga cctccatgct gtgctgtcgt gggtgtgaga cgtgctcatg    4080
gccttccact gccatctctc ccttatctga tgcctaaagt cacgatgggg acagagctac    4140
ccagggccca gccatggggt gaccagccac ctgagggtca gtcacctgtg gagagcaggc    4200
acctgtgaag accaggcacc tgaggactgg cgcctacttc ccactttggc cctacactgg    4260
cacagagccc ctctttattc atttctcatg ctgagcatgg cacacttctg gcctctgggc    4320
atttatggat ttaagaccag gatggtattt cagaagcttc ccacttcctt cctattctaa    4380
ccgagtgccc agctcctttg ctgatcatgg aaagacccct aataattagg cctgcaggcc    4440
aggcgcagtg gctcatgcct ataatcccag cactttagga ggtcaaggta ggaggatcgc    4500
ttaagcccag gagttcaaga ccagcctggg caacacagga gaatgtgtc tctacaaaaa     4560 ataattaaaa atcagatctg ctgtatccct gaaaagtct caatcaacat gcatgttcca     4620
ctcttggagt tccctgttct gagggccagc cacgtcctgt gtcctggagc ttagccctca    4680
gcagctccct tcagcctggg cgccgcctgg gtcccaaacg tggcagctgc tcttccagtc    4740
tcggggccga ggagggcagg gagctcagtg actgagagtc ttgtgtatca catgtcttga    4800
gtgtcctgga gccaacggct gtcactggga aaaacaccag gccccaaaga tcgaatcaga    4860
gacgtggctg cgtgtttgcg attgtagcca ggcccttcag tgtcatcaaa ggagcactgg    4920
ggcctcctta agcacagacg gcagccctg cccaggagge ttcttcacca cgtcctgccc      4980
tgcagcctcc cagacccttta gatgcgcccc tgcccaaggc cctcctggtg acaggtgcca    5040
gattgagtgg tgggttgctg ccaggcaggc cacgctgtgt tgacgctgca ctcagcacgt    5100
gggtgttggc tctgccggtt ttgtggtgtg gggaccctac aggaggctgc ggccctgaga    5160
gcctgggatc agcgaggtgt ccgacatccc ttcctcaacg gcaacaaaaa ctccccaagt    5220
cagcactttg gttattttat agccacaacc ctcttggaaa acagtgggga agactatgga    5280
acatagaaag tgtggatgta tcacttctct ctaaaatgtc attgttagca ctaattacag    5340
gttcatgttt ttctgtgtat gtagcttttc cctatatagc tgaaaaagta ttaaagtcaa    5400
atataaggtg ggaatgggat ggaagggagg agatcaatac aacttatatt tttgcagttt    5460
ctactggaag aaaaaagttt tcaataccta gaccaacttg ttgaattttt aaaacttatg    5520
cactataaat gcaactttct ctactgcttt ctcagtgcct ttaggaagct ttcaaatttt    5580
tttgtactgt ggtttgtatt aaatttgcaa tattgatgta aaatacatga catgctagta    5640
catgtttaac aaaaatttaa aaaaaaaaa aaaaaa                                5676
```

<210> SEQ ID NO 40
<211> LENGTH: 1763
<212> TYPE: DNA
<213> ORGANISM: Homo sapiens

<400> SEQUENCE: 40

```
cttctggtaa ggaggccccg tgatcagctc cagccatttg cagtcctggc tatcccagga      60
gcttacataa agggacaatt ggagcctgag aggtgacagt gctgacacta caaggctcgg     120
agctccgggc actcagacat catgagttgg tccttgcacc cccggaattt aattctctac     180
ttctatgctc tttatttct ctcttcaaca tgtgtagcat atgttgctac cagagacaac      240
tgctgcatct tagatgaaag attcggtagt tattgtccaa ctacctgtgg cattgcagat     300
ttcctgtcta cttatcaaac caaagtagac aaggatctac agtctttgga agacatctta     360
catcaagttg aaaacaaaac atcagaagtc aaacagctga taaaagcaat ccaactcact     420
tataatcctg atgaatcatc aaaaccaaat atgatagacg ctgctacttt gaagtccagg     480
aaaatgttag aagaaattat gaaatatgaa gcatcgattt taacacatga ctcaagtatt     540
cgatatttgc aggaaatata taattcaaat aatcaaaaga ttgttaacct gaaagagaag     600
gtagcccagc ttgaagcaca gtgccaggaa ccttgcaaag acacggtgca atccatgat     660
atcactggga agattgtca agacattgcc aataagggag ctaaacagag cgggctttac     720
tttattaaac ctctgaaagc taaccagcaa ttcttagtct actgtgaaat cgatgggtct     780
ggaaatggat ggactgtgtt tcagaagaga cttgatggca gtgtagattt caagaaaaac     840
tggattcaat ataagaagg atttggacat ctgtctccta ctggcacaac agaattttgg     900
ctgggaaatg agaagattca tttgataagc acacagtctg ccatcccata tgcattaaga     960
gtggaactgg aagactggaa tgcagaacc agtactgcag actatgccat gttcaaggtg    1020
ggacctgaag ctgacaagta ccgcctaaca tatgcctact cgctggtgg ggatgctgga    1080
gatgcctttg atggctttga ttttggcgat gatcctagtg acaagttttt cacatcccat    1140
aatggcatgc agttcagtac ctgggacaat gacaatgata agtttgaagg caactgtgct    1200
gaacaggatg gatctggttg gtggatgaac aagtgtcacg ctggccatct caatggagtt    1260
tattaccaag gtggcactta ctcaaaagca tctactccta atggttatga taatggcatt    1320
atttgggcca cttggaaaac ccggtggtat tccatgaaga aaccactat gaagataatc    1380
ccattcaaca gactcacaat tggagaagga cagcaacacc acctgggggg agccaaacag    1440
gtcagaccag agcaccctgc ggaaacagaa tatgactcac tttaccctga ggatgatttg    1500
tagaaaatta actgctaact tctattgacc cacaaagttt cagaaattct ctgaaagttt    1560
cttcctttt tctcttacta tatttattga tttcaagtct tctattaagg acatttagcc    1620
ttcaatggaa attaaaactc atttaggact gtatttccaa attactgata tcagagttat    1680
ttaaaaattg tttatttgag gagataacat ttcaactttg ttcctaaata tataataata    1740
aaatgattga ctttatttgc aaa                                           1763
```

<210> SEQ ID NO 41
<211> LENGTH: 666
<212> TYPE: DNA
<213> ORGANISM: Homo sapiens

<400> SEQUENCE: 41

```
gggtggctta gcactgcagg gctctgcgcg ggaacgctaa cctggtccgg agcgagtctg      60
ggtctcagcc ccgcgaacag cctttcacga gtcttcaagc tttcaggcta tcttctagtc     120
aagatgagtg ataagccaga cttgtcggaa gtggagaagt ttgacaggtc aaaactgaag     180
aaaactaata ctgaagaaaa aaatactctt ccctcaaagg aaactatcca gcaagagaaa     240
```

```
gagtgtgttc aaacatcata aaatggggat cgcctcccaa cagcagattt cgacattacc      300
tgagagtctt gatttttaggc ttgttttttg taaacccatg tgtttgtaga gattttaggc      360
gtcttcggat atcttctcac ctatgttccc tggctaagaa gtcagaggta gccaatgttt      420
ccttaaattc attttaaac ttaccattgg tgcatatgtt ccagatggca gatgctgtca       480
ataatctcac cattgatgac ctttgtgtat gtagttcttg catcctatac tggataagcc      540
tgttttaacc tgctatgatg ggtgcttcca ttgcttcata atcttcatga agttgcatgc      600
ttttgcagct tttcacagtt tatttgcatt tctaatgtag aataaagta accaatataa        660 tcatta                                                                  666

<210> SEQ ID NO 42
<211> LENGTH: 1437
<212> TYPE: DNA
<213> ORGANISM: Homo sapiens

<400> SEQUENCE: 42
attgctgatg gatcagtgag cctgtgttca tgccagtgag ctgctgtggc tcagatactg       60
atactttctt tccaaacagc ataagaagtg attgagccac aagtatactg aaggaagggc      120
tccctcgagt tctggtgtga agagataaat caccagtcac agactatgca cccgactgct      180
gctgttcagt ccagggaaaa tgaaagttgg agtgctgtgg ctcatttctt tcttcacctt      240
cactgacggc cacggtggct tcctggggaa aaatgatggc atcaaaacaa aaaagaact      300 cattgtgaat aagaaaaaac atctaggccc agtcgaagaa tatcagctgc tgcttcaggt      360
gacctataga gattccaagg agaaaagaga tttgagaaat tttctgaagc tcttgaagcc      420
tccattatta tggtcacatg ggctaattag aattatcaga gcaaaggcta ccacagactg      480
caacagcctg aatggagtcc tgcagtgtac ctgtgaagac agctacacct ggtttcctcc      540
ctcatgcctt gatccccaga actgctacct tcacacggct ggagcactcc caagctgtga      600
atgtcatctc aacaacctca gccagagtgt caatttctgt gagagaacaa agatttgggg      660
cactttcaaa attaatgaaa ggtttacaaa tgaccttttg aattcatctt ctgctatata      720
ctccaaatat gcaaatggaa ttgaaattca acttaaaaaa gcatatgaaa gaattcaagg      780
ttttgagtcg gttcaggtca cccaatttcg aatgtcactc ttgtcgccca agttggagtg      840
caatggcaca atctaggctc actgcaaccc tgcaacctct gcctaccggg ttcaagagat      900 tccctgcct cagcctccca gtagctgga attacaggca cctgccacca catccagcta       960
actttttttg tattttact agagacaggg tttcaccatg ttggccacac tggtctcaaa      1020
ctcctgacct caggtgatcc gcctgcctcg gcccccaaag tgctgggatt acaggcatga      1080
gccaccacat ctggcctagg accttaaata ttggaaagca tcctcaaaac tgtgggtcag      1140
tgagtagaac tacaaaacaa tagcagtagg gcagaaactt gaaagaaggc aggagatcat      1200
ggtgacagtg gatgggaaaa agtgagggtt ggggataagg gttgcgggtt gtcgaagggt      1260
ggattttctc cttcagcaac tacaggagat atgatgcctc ataattcgga gccagaagtg      1320
gggctttggg tgagatatct ttgcacagat aacatgtata catcatagtt caaaacccag      1380
tagtcattgt ttacagcaaa taagaaaata tttagtaaat taaaaaaaaa aaaaaaa       1437

<210> SEQ ID NO 43
<211> LENGTH: 2413
<212> TYPE: DNA
<213> ORGANISM: Homo sapiens

<400> SEQUENCE: 43
```

```
tttcctctca gggggcagca ggaagtgagg agaaagggct gggatgggag gcgggagcgg    60
atgggaggga atgggggttta tcaagtcctc ggcgagctgc ccaacgggca gcagctggcg   120
caagtagcct agctggagag gctcacccca ggaaggaggg aggccaccga cctactgggc   180
cgacggactc ccacacaggg ctggcggcgc cgcggagctg ggaggactga accaccggcc   240
tcgggctgca ggggaaacat ttcaggctga ctggcgctcg tggctgagac tcccatagaa   300
agcccggctc agaggggcat tagggtccta aatgggcggc cacgtccctc tgcagaggac   360
ctggggctct tcgagcccga aacgaggcac cggcaccgag aaaggtggac cacaccttcc   420
cgccccgtcc gcaagtccaa tcccgggccc acctccgcac tggagtctta aagggccagc   480
gtgcctgggg gcggagccag cagaggcgct gagccgggcc gcgcctgggc gaacggccgg   540
agcgggctgg gctgggcccg ggatggcggt ggccctggcg ccggtcccgg tggcgccccg   600
cgcgagttcc tgagctggtg ccaggcaggt gacacctcct gcagccccca gcatgcgggc   660
aggcccaggc cccaccgtta cattggccct ggtgctggcg tgtcatggg ccatggagct    720
caagcccaca gcaccaccca tcttcactgg ccggcccttt gtggtagcgt gggacgtgcc   780
cacacaggac tgtggcccac gcctcaaggt gccactggac ctgaatgcct ttgatgtgca   840
ggcctcacct aatgagggtt ttgtgaacca gaatattacc atcttctacc gcgaccgtct   900
aggcctgtat ccacgcttcg attctgccgg aaggtctgtg catggtggtg tgccacagaa   960
tgtcagcctt tgggcacacc ggaagatgct gcagaaacgt gtggagcact acattcggac  1020
acaggagtct gcggggctgg cggtcatcga ctgggaggac tggcgacctg tgtgggtgcg  1080
caactggcag gacaaagatg tgtatcgccg gttatcacgc cagctagtgg ccagtcgtca  1140
ccctgactgg cctccagacc gcatagtcaa acaggcacaa tatgagtttg agttcgcagc  1200
acagcagttc atgctggaga cactgcgtta tgtcaaggca gtgcggcccc ggcacctctg  1260
gggcttctac ctctttcctg actgctacaa tcatgattat gtgcagaact gggagagcta  1320
cacaggccgc tgccctgatg ttgaggtggc ccgcaatgac cagctggcct ggctgtgggc  1380
tgagagcacg gccctcttcc cgtctgtcta cctggacgag acacttgctt cctcccgcca  1440
tggccgcaac tttgtgagct tccgtgttca ggaggccctt cgtgtggctc gcacccacca  1500
tgccaaccat gcactcccag tctacgtctt cacacgaccc acctacagcc gcaggctcac  1560
ggggcttagt gagatggacc tcatctctac cattggcgag agtgcggccc tgggcgcagc  1620
tggtgtcatc ctctggggtg acgcggggta caccacaagc acggagacct gccagtacct  1680
caaagattac ctgacacggc tgctggtccc ctacgtggtc aatgtgtcct gggccaccca  1740
atattgcagc cgggcccagt gccatggcca tgggcgctgt gtgcgccgca accccagtgc  1800
cagtaccttc ctgcatctca gcaccaacag tttccgccta gtgcctggcc atgcacctgg  1860
tgaaccccag ctgcgacctg tggggagct cagttgggcc gacattgacc acctgcagac  1920
acacttccgc tgccagtgct acttgggctg gagtggtgag caatgccagt gggaccatag  1980
gcaggcagct ggaggtgcca gcgaggcctg ggctgggtcc cacctcacca gtctgctggc  2040
tctggcagcc ctggccttta cctggaccct gtaggggtct cctgcctagc tgcctagcaa  2100
gctggcctct accacaaggg ctctcttagg catgtaggac cctgcagggg gtggacaaac  2160
tggagtctgg agtgggcaga gcccccagga agcccaggag ggcatccata ccagctcgca  2220
ccccctgtt ctaagggga ggggaagtcc ctgggaggcc ccttctctcc ctgccagagg    2280
ggaaggaggg tacagctggg ctggggagga cctgacccta ctcccttgcc ctagatagtt  2340
```

| | |
|---|---:|
| tattattatt attattttgg ggtctctttt gtaaattaaa cataaaacaa ttgcttctct | 2400 |
| gcttggattt tgt | 2413 |

<210> SEQ ID NO 44
<211> LENGTH: 1279
<212> TYPE: DNA
<213> ORGANISM: Homo sapiens

<400> SEQUENCE: 44

| | |
|---|---:|
| gggagggaga gaggcgcgcg ggtgaaaggc gcattgatgc agcctgcggc ggcctcggag | 60 |
| cgcggcggag ccagacgctg accacgttcc tctcctcggt ctcctccgcc tccagctccg | 120 |
| cgctgcccgg cagccgggag ccatgcgacc ccagggcccc gccgcctccc cgcagcggct | 180 |
| ccgcggcctc ctgctgctcc tgctgctgca gctgcccgcg ccgtcgagcg cctctgagat | 240 |
| ccccaagggg aagcaaaagg cgcagctccg gcagagggag gtggtggacc tgtataatgg | 300 |
| aatgtgctta caagggccag caggagtgcc tggtcgagac gggagccctg gggccaatgg | 360 |
| cattccgggt acacctggga tcccaggtcg ggatggattc aaaggagaaa aggggaatg | 420 |
| tctgagggaa agctttgagg agtcctggac acccaactac aagcagtgtt catggagttc | 480 |
| attgaattat ggcatagatc ttgggaaaat tgcggagtgt acatttacaa agatgcgttc | 540 |
| aaatagtgct ctaagagttt tgttcagtgg ctcacttcgg ctaaaatgca gaaatgcatg | 600 |
| ctgtcagcgt tggtatttca cattcaatgg agctgaatgt tcaggacctc ttcccattga | 660 |
| agctataatt tatttggacc aaggaagccc tgaaatgaat tcaacaatta atattcatcg | 720 |
| cacttcttct gtgaaggac tttgtgaagg aattggtgct ggattagtgg atgttgctat | 780 |
| ctgggttggt acttgttcag attacccaaa aggagatgct tctactggat ggaattcagt | 840 |
| ttctcgcatc attattgaag aactaccaaa ataaatgctt taattttcat ttgctacctc | 900 |
| ttttttttatt atgccttgga atggttcact taaatgacat tttaaataag tttatgtata | 960 |
| catctgaatg aaaagcaaag ctaaatatgt ttacagacca aagtgtgatt tcacactgtt | 1020 |
| tttaaatcta gcattattca ttttgcttca atcaaaagtg gtttcaatat tttttttagt | 1080 |
| tggttagaat actttcttca tagtcacatt ctctcaacct ataatttgga atattgttgt | 1140 |
| ggtcttttgt ttttttctctt agtatagcat ttttaaaaaa atataaaagc taccaatctt | 1200 |
| tgtacaattt gtaaatgtta agaattttt ttatatctgt taaataaaaa ttatttccaa | 1260 |
| caaccttaat atctttaaa | 1279 |

<210> SEQ ID NO 45
<211> LENGTH: 4571
<212> TYPE: DNA
<213> ORGANISM: Homo sapiens

<400> SEQUENCE: 45

| | |
|---|---:|
| gcagtcagag ctgcctctcg ccctcgctag ctgggctcgc agcctcttcc tccctccctg | 60 |
| gctcctggct ttttgtttaa agcaacaccc accctccatc caggcttttt ttctttcttt | 120 |
| ctttattggt agcggccaaa aagagttgat tgctattggg atccgctgag taaagacacg | 180 |
| ggcaggggtg cgcggaggtg agaaaactga agacctggaa gattttttt tccttcaaaa | 240 |
| acccgtttcc atccagtctt cagccagtcc agtctacttt aatcctcacc aggacaatgg | 300 |
| attaagtttc tcttccctgg accagaagtc gggttcggac ttggggcaaa atgaaggaaa | 360 |
| aggccatgat caagaccgct aagatgcagg ggaacgtgat ggagctggtg gggagtaacc | 420 |
| ctccgcagag gaattggaaa ggaatagcaa ttgcactgct tgtcattctg gtcatctgct | 480 |

```
ccttgatcgt cacctcggtc atacttctga caccagcgga agataatagt ctgtctcaaa    540
agaagaaggt cactgtagaa gatctcttca gtgaagactt caaaattcat gaccccgagg    600
ctaagtggat aagtgataca gaattcatct acagagaaca gaaaggaaca gtgagactgt    660
ggaatgttga aacaaatact tctactgtct aatagaagg caaaaaaatt gaatcattaa     720
gagccatcag atatgaaata tctccagata gagagtatgc actttttttca tacaatgtgg   780 aacccatata tcaacactcg tatactggat attacgtcct gagcaaaatt cctcatgggg    840
atcctcaaag tctggaccca ccagaagtca gcaatgcaaa acttcagtat gcaggatggg    900
gccctaaagg ccaacagctg atatttattt ttgaaaacaa tatctactac tgtgcacatg    960
tcgggaaaca ggccatccgt gtggtctcca ctggcaagga aggtgtgatt tacaatggcc   1020
tcagtgactg gctgtatgaa gaggagattt tgaagacaca catcgcacac tggtggtctc   1080
cggatggcac gagactcgcc tacgccgcca tcaatgattc ccgtgtcccc atcatggagc   1140
tcccaactta caccggctcc atctacccca ccgtgaagcc ctaccactat cccaaggctg   1200
gaagtgagaa ccccagcatt tccctacacg ttattggctt aaatggaccc acccatgatc   1260
tggagatgat gccgcctgat gatccacgga tgagggagta ctacatcacc atggtgaagt   1320
gggccaccag caccaaggtc gccgtgacct ggctgaaccg ggcgcagaac gtgtccatcc   1380
tcaccctctg cgacgccacc acgggggtct gcacgaagaa acacgaggat gaaagtgagg   1440
cctggctcca cagacagaat gaagaacctg tgttctccaa ggatggccga aagttttttct   1500 tcatcagagc catcccccag ggaggacgag ggaaattcta tcacatcacg gtgtcctcgt   1560
cccagcccaa cagcagcaac gacaacatcc agtccatcac ctccggggac tgggacgtga   1620
ccaagatcct agcctacgat gagaaggga ataagatcta cttcctgagc acggaggacc    1680
tgcctcggag acgacaactc tacagtgcca acacggtggg caacttcaac aggcagtgcc   1740
tctcctgtga cctggttgag aactgcacct acttcagcgc ttccttcagc catagcatgg   1800
acttcttcct gctcaagtgc gaaggtcctg gtgttcctat ggtgacggtg cacaacacaa   1860
cagataagaa aaaaatgttt gacctagaaa caaatgaaca tgtcaagaag gccataaatg   1920
accgacagat gcctaaagtg aatacaggg acattgagat tgatgattac aacctgccca   1980
tgcagatact gaagccagca accttcaccg acaccaccca ctaccctctg ctcctggtgg   2040
tggatggcac cccaggcagc cagagtgtgg ctgagaagtt cgaggtgagc tgggagacgg   2100
tgatggtgag cagccacggc gcggtggtgg taaagtgtga cggccgtggc agcggcttcc   2160
aagggaccaa gctcctgcac gaagtgaggc ggcggctggg cttgctggag agaaggacc    2220 agatggaggc cgtgcggacg atgctgaagg agcagtacat tgacaggacg cgcgtggccg   2280
tgtttgggaa ggattacggt ggctacctga gcacctacat cctcccagca aagggagaaa   2340
atcaaggcca gacattcacc tgcggctctg ctctctctcc aataacagac ttcaaactct   2400
atgcctctgc gttttccgag aggtacttgg gcctccatgg acttgacaac agagcatacg   2460
agatgaccaa ggtagcccat cgagtctccg cgctggaaga acagcagttc ctgatcattc   2520
atcccactgc cgatgaaaaa attcattttcc agcacacagc agaactcatt acacaactaa   2580
ttagggggaa ggctaattac agcttacaga tttacccgga cgaaagccat tactttacca   2640
gctccagcct caaacagcat ctgtaccggt ccatcatcaa cttcttcgtg gaatgcttca   2700
ggatccagga caaactgctg acagtcacag cgaaagagga cgaggaggag gactaagctc   2760
aggtcgctct aagcacaaac gtggctcttt ctacaaccag atgcaaccga gggatttccc   2820
```

| | |
|---|---:|
| tgccctccct cttccctcgg aggggcgggg cggggcgggg ccgggtgttc catagcatgt | 2880 |
| gtgtctcgga tgcggaaggc agttttgctt gggaaacaag ctccttcccc ggggtcatca | 2940 |
| ctcacggcct ccatggcacc agggacaacg ctgtccccgc agcagcgcct cctcccggcg | 3000 |
| cccgagagac cggcacgcca cggcccctcc cccaaggaac agagcaaagg atggtggccg | 3060 |
| caggccccac gcgagcccac aggacaccgg cccctagatt ccagccacca agcggaagca | 3120 |
| tgagacccgc ccacactagc ctctgtgttc ccgttaggga catcacaccc tgtctcacgt | 3180 |
| cgcagtgcca tggacgcagc agttacagca ccattgtttt agcagtgcgt gttcatatat | 3240 |
| gggcttgcta cttcctgtaa tgaggacgtt caacatggtg aggggctaca agaaaacgct | 3300 |
| tttctgtaca gagtcttact gtagctacgc taatggttaa cctgatagaa ttaactcgta | 3360 |
| tttttctatg gttttaacct gatgctccac tgtctccgtc atggggttgt tttgctgttt | 3420 |
| ggggttgggc cttgtttccc tttcctttct ccagtccacg tgtagacttt gcgcttgatg | 3480 |
| aagaagcaga tcggaagtaa ctgctccctc ctcaaggttg tcttcagacg tcttggggac | 3540 |
| gttcctaaac actgaggggg aagacagcca atagcaccca ttaaaagaaa tacctaaata | 3600 |
| aaacctctct cccactcagc tatgctaggg cttggctgta ggtgtgcact gtctatttac | 3660 |
| atccgtcctt acaaccatcc ttgtcctcct tggtaccgta tcaagctctt tcccatgaca | 3720 |
| tttggtttaa aaaaaaaaaa aaaaaaaaaa aaaaaacaga aaaaagacaa agcgtcaact | 3780 |
| ccacccacag gcccgctgtg tgtgctcggg ccacgggagt cctgagggtt ctgtgggcct | 3840 |
| gcgcgcatcc ctctcccatc gtggggtgg ctccgtgacc ttcctgccac gagcaggagg | 3900 |
| ttgatgatgt gctacgttag ccttgtaaga tacacccca ccaaatgtgc agccggtgtt | 3960 |
| cccagtgtat atttcattct cttgtatata aaggaagcaa tgtgtgtcag gcctctgtgc | 4020 |
| agtcaaccca gcctcctccc gccagtgcta acccgtgtt gagcctgcat gctgacactg | 4080 |
| tggccgatct ggactctaga agtgctagtt tgaaatatat ccattactgt catttccttt | 4140 |
| tgagcttgtg acaagctga atgtcaggac tgacttcgcc agctcccagc cctgcggggg | 4200 |
| tgtccttggc atcccatcag cagaggagat gcgtccctgt tgcatttttgg cgtttgggc | 4260 |
| tttgggttta tccacatgag ctctgaacgt ccgttatagt tagggtgatt ggaaggtctc | 4320 |
| catcactggg tgttttaaag gtgattcacc accatttgtg aaaggaccaa cgtgctgata | 4380 |
| aacaggaccg atccgagtgc tacatgactg tgcgtttgct attcaatgg gcctgaacga | 4440 |
| ctacaaagcc agctaggtct ggaaggggaa gccagctctg gccacgacat ctggtcggag | 4500 |
| ggaagtgggg atgtggcatg gtagcgtctg ttcatccatg gaataaaaca ttattttacc | 4560 |
| aaaaaaaaaa a | 4571 |

```
<210> SEQ ID NO 46
<211> LENGTH: 4460
<212> TYPE: DNA
<213> ORGANISM: Homo sapiens

<400> SEQUENCE: 46
```

| | |
|---|---:|
| actaagcagc ggcagcttcc tgcttcggat cctctctctg ctgcttgcat ttaaagagca | 60 |
| aactcgtctt gtctacccac cctccctccc ccatcctccc caaatagcc ttgtgatttc | 120 |
| ggaagtatgg actaaaatca cactcctcct taccttaccg cttggactct ggtggctccc | 180 |
| aactcgccgt cagaccccac ctgccccggt ggtgggaagc gcctggacag accatgacca | 240 |
| cagccaagga gccaagcgct tcggggaaat ccgtgcagca gcaggaacag gagctggtgg | 300 |
| ggagtaaccc tccgcagagg aattggaaag gaatagcaat tgcactgctt gtcattctgg | 360 |

```
tcatctgctc cttgatcgtc acctcggtca tacttctgac accagcggaa gataatagtc    420
tgtctcaaaa gaagaaggtc actgtagaag atctcttcag tgaagacttc aaaattcatg    480
accccgaggc taagtggata agtgatacag aattcatcta cagagaacag aaaggaacag    540
tgagactgtg gaatgttgaa acaaatactt ctactgtctt aatagaaggc aaaaaaattg    600
aatcattaag agccatcaga tatgaaatat ctccagatag agagtatgca cttttttcat    660
acaatgtgga acccatatat caacactcgt atactggata ttacgtcctg agcaaaattc    720
ctcatgggga tcctcaaagt ctggacccac cagaagtcag caatgcaaaa cttcagtatg    780
caggatgggg ccctaaaggc caacagctga tatttatttt tgaaaacaat atctactact    840
gtgcacatgt cgggaaacag gccatccgtg tggtctccac tggcaaggaa ggtgtgattt    900
acaatggcct cagtgactgg ctgtatgaag aggagatttt gaagcacac atcgcacact    960 ggtggtctcc ggatggcacg agactcgcct acgccgccat caatgattcc cgtgtcccca   1020
tcatggagct cccaacttac accgctcca tctaccccac cgtgaagccc taccactatc   1080
ccaaggctgg aagtgagaac cccagcattt ccctacacgt tattggctta aatggaccca   1140
cccatgatct ggagatgatg ccgcctgatg atccacggat gagggagtac tacatcacca   1200
tggtgaagtg ggccaccagc accaaggtcg ccgtgacctg gctgaaccgg cgcagaacg   1260 tgtccatcct caccctctgc gacgccacca cggggggtctg cacgaagaaa cacgaggatg   1320
aaagtgaggc ctggctccac agacagaatg aagaacctgt gttctccaag gatggccgaa   1380
agttttcttt catcagagcc atccccccagg gaggacgagg gaaattctat cacatcacgg   1440
tgtcctcgtc ccagcccaac agcagcaacg acaacatcca gtccatcacc tccggggact   1500
gggacgtgac caagatccta gcctacgatg agaaggggaa taagatctac ttcctgagca   1560
cggaggacct gcctcggaga cgacaactct acagtgccaa cacggtgggc aacttcaaca   1620
ggcagtgcct ctcctgtgac ctggttgaga actgcaccta cttcagcgct tccttcagcc   1680
atagcatgga cttcttcctg ctcaagtgcg aaggtcctgg tgttcctatg gtgacggtgc   1740
acaacacaac agataagaaa aaaatgtttg acctagaaac aaatgaacat gtcaagaagg   1800
ccataaatga ccgacagatg cctaaagtgg aatacaggga cattgagatt gatgattaca   1860
acctgcccat gcagatactg aagccagcaa ccttcaccga caccaccac taccctctgc   1920 tcctggtggt ggatggcacc ccaggcagcc agagtgtggc tgagaagttc gaggtgagct   1980
gggagacggt gatggtgagc agccacggcg cggtggtggt aaagtgtgac ggccgtggca   2040
gcggcttcca agggaccaag ctcctgcacg aagtgaggcg gcggctgggc ttgctggagg   2100
agaaggacca gatggaggcc gtgcggacga tgctgaagga gcagtacatt gacaggacgc   2160
gcgtggccgt gtttgggaag gattacggtg gctacctgag cacctacatc ctcccagcaa   2220
agggagaaaa tcaaggccag acattcacct gcggctctgc tctctctcca ataacagact   2280
tcaaactcta tgcctctgcg ttttccgaga ggtacttggg cctccatgga cttgacaaca   2340
gagcatacga gatgaccaag gtagcccatc gagtctccgc gctggaagaa cagcagttcc   2400
tgatcattca tcccactgcc gatgaaaaaa ttcatttcca gcacacagca gaactcatta   2460
cacaactaat taggggaaag gctaattaca gcttacagat ttacccggac gaaagccatt   2520
actttaccag ctccagcctc aaacagcatc tgtaccggtc catcatcaac ttcttcgtgg   2580
aatgcttcag gatccaggac aaactgctga cagtcacagc gaaagaggac gaggaggagg   2640
actaagctca ggtcgctcta agcacaaacg tggctctttc tacaaccaga tgcaaccgag   2700
```

```
ggatttccct gccctccctc ttccctcgga ggggcggggc ggggcggggc cgggtgttcc    2760
atagcatgtg tgtctcggat gcggaaggca gttttgcttg ggaaacaagc tccttccccg    2820
gggtcatcac tcacggcctc catggcacca gggacaacgc tgtccccgca gcagcgcctc    2880
ctcccggcgc ccgagagacc ggcacgccac ggccctccc ccaaggaaca gagcaaagga     2940
tggtggccgc aggccccacg cgagcccaca ggacaccggc ccctagattc cagccaccaa    3000
gcggaagcat gagacccgcc cacactagcc tctgtgttcc cgttagggac atcacaccct    3060
gtctcacgtc gcagtgccat ggacgcagca gttacagcac cattgtttta gcagtgcgtg    3120
ttcatatatg ggcttgctac ttcctgtaat gaggacgttc aacatggtga ggggctacaa    3180
gaaaacgctt ttctgtacag agtcttactg tagctacgct aatggttaac ctgatagaat    3240
taactcgtat ttttctatgg ttttaacctg atgctccact gtctccgtca tgggggttgtt   3300 ttgctgtttg gggttgggcc ttgtttccct ttcctttctc cagtccacgt gtagactttg    3360
cgcttgatga agaagcagat cggaagtaac tgctccctcc tcaaggttgt cttcagacgt    3420
cttggggacg ttcctaaaca ctgaggggga agacagccaa tagcacccat taaagaaat     3480 acctaaataa aacctctctc ccactcagct atgctagggc ttggctgtag gtgtgcactg    3540
tctatttaca tccgtcctta caaccatcct tgtcctcctt ggtaccgtat caagctcttt    3600
cccatgacat ttggtttaaa aaaaaaaaa aaaaaaaaa aaaaacagaa aaaagacaaa      3660
gcgtcaactc cacccacagg cccgctgtgt gtgctcgggc cacgggagtc ctgagggttc    3720
tgtgggcctg cgcgcatccc tctcccatcg tgggggtggc tccgtgacct tcctgccacg    3780
agcaggaggt tgatgatgtg ctacgttagc cttgtaagat acacccccac caaatgtgca    3840
gccggtgttc ccagtgtata tttcattctc ttgtatataa aggaagcaat gtgtgtcagg    3900
cctctgtgca gtcaacccag cctcctcccg ccagtgctaa ccccgtgttg agcctgcatg    3960
ctgacactgt ggccgatctg gactctagaa gtgctagttt gaaatatatc cattactgtc    4020
atttcctttt gagcttgtgg acaagctgaa tgtcaggact gacttcgcca gctcccagcc    4080 ctgcggggt gtccttggca tcccatcagc agaggagatg cgtccctgtt gcattttggc     4140 gtttgggct tgggtttat ccacatgagc tctgaacgtc cgttatagtt agggtgattg       4200
gaaggtctcc atcactgggt gttttaaagg tgattcacca ccatttgtga aaggaccaac    4260
gtgctgataa acaggaccga tccgagtgct acatgactgt gcgtttgcta tttcaatggg    4320
cctgaacgac tacaaagcca gctaggtctg gaaggggaag ccagctctgg ccacgacatc    4380
tggtcggagg gaagtgggga tgtggcatgg tagcgtctgt tcatccatgg aataaaacat    4440
tattttacca aaaaaaaaa                                                  4460
```

<210> SEQ ID NO 47
<211> LENGTH: 4542
<212> TYPE: DNA
<213> ORGANISM: Homo sapiens

<400> SEQUENCE: 47

```
gctgctgctg ctgctgcctc cccaccgcct ttttttttt ttaatctgga gcggggtggg       60
gagtgggaac cggagagaaa gcaaaatatt aaaaagcccc aaagacagcc agcaggagcg     120
cggtgcccga tggcttcgct gtaccagagg ttcactggca agatcaacac ctcgaggtcc    180
ttccccgcgc cccggaggc gagtcacctc ctgggcggcc aggggcccga ggaggacggc     240
ggcgcaggag ccaagcccct cggccgcgg gcgcaggcgg cggcgcccg ggagcgcggc      300 ggcgcggcg gcggcgcggg tggccggccc cggttccagt accaggcgcg gagcgatggt    360
```

```
gacgaggagg acgagctggt ggggagtaac cctccgcaga ggaattggaa aggaatagca      420
attgcactgc ttgtcattct ggtcatctgc tccttgatcg tcacctcggt catacttctg      480
acaccagcgg aagataatag tctgtctcaa aagaagaagg tcactgtaga agatctcttc      540
agtgaagact tcaaaattca tgaccccgag gctaagtgga taagtgatac agaattcatc      600
tacagagaac agaaaggaac agtgagactg tggaatgttg aaacaaatac ttctactgtc      660
ttaatagaag gcaaaaaaat tgaatcatta agagccatca gatatgaaat atctccagat      720
agagagtatg cactttttc atacaatgtg gaacccatat atcaacactc gtatactgga      780
tattacgtcc tgagcaaaat tcctcatggg gatcctcaaa gtctggaccc accagaagtc      840
agcaatgcaa aacttcagta tgcaggatgg ggccctaaag ccaacagct gatatttatt      900 tttgaaaaca atatctacta ctgtgcacat gtcgggaaac aggccatccg tgtggtctcc      960
actggcaagg aaggtgtgat ttacaatggc ctcagtgact ggctgtatga agaggagatt     1020
ttgaagacac acatcgcaca ctggtggtct ccggatggca cgagactcgc ctacgccgcc     1080
atcaatgatt cccgtgtccc catcatggag ctcccaactt acaccggctc catctacccc     1140
accgtgaagc cctaccacta tcccaaggct ggaagtgaga accccagcat ttccctacac     1200
gttattggct taaatggacc cacccatgat ctggagatga tgccgcctga tgatccacgg     1260
atgggggagt actacatcac catggtgaag tgggccacca gcaccaaggt cgccgtgacc     1320
tggctgaacc gggcgcagaa cgtgtccatc ctcaccctct gcgacgccac cacggggggtc     1380 tgcacgaaga aacacgagga tgaaagtgag gcctggctcc acagacagaa tgaagaacct     1440
gtgttctcca aggatggccg aaagtttttc ttcatcagag ccatccccca gggaggacga     1500
gggaaattct atcacatcac ggtgtcctcg tcccagccca acagcagcaa cgacaacatc     1560
cagtccatca cctccgggga ctgggacgtg accaagatcc tagcctacga tgagaagggg     1620
aataagatct acttcctgag cacggaggac ctgcctcgga cgacaact ctacagtgcc     1680 aacacggtgg gcaacttcaa caggcagtgc ctctcctgtg acctggttga gaactgcacc     1740
tacttcagcg cttccttcag ccatagcatg gacttcttcc tgctcaagtg cgaaggtcct     1800
ggtgttccta tggtgacggt gcacaacaca acagataaga aaaaaatgtt tgacctagaa     1860
acaaatgaac atgtcaagaa ggccataaat gaccgacaga tgcctaaagt ggaatacagg     1920
gacattgaga ttgatgatta caacctgccc atgcagatac tgaagccagc aaccttcacc     1980
gacaccaccc actaccctct gctcctggtg gtggatggca cccccaggcag ccagagtgtg     2040 gctgagaagt tcgaggtgag ctgggagacg gtgatggtga gcagccacgg cgcggtggtg     2100
gtaaagtgtg acggccgtgg cagcggcttc caagggacca agctcctgca cgaagtgagg     2160
cggcggctgg gcttgctgga ggagaaggac cagatggagc ccgtgcggac gatgctgaag     2220
gagcagtaca ttgacaggac gcgcgtggcc gtgtttggga aggattacgg tggctacctg     2280
agcacctaca tcctcccagc aaagggagaa aatcaaggcc agacattcac ctgcggctct     2340
gctctctctc caataacaga cttcaaactc tatgcctctg cgttttccga gaggtacttg     2400
ggcctccatg gacttgacaa cagagcatac gagatgacca aggtagccca tcgagtctcc     2460
gcgctggaag aacagcagtt cctgatcatt catcccactg ccgatgaaaa aattcatttc     2520
cagcacacag cagaactcat tacacaacta attagggaa aggctaatta cagcttacag     2580
atttacccgg acgaaagcca ttactttacc agctccagcc tcaaacagca tctgtaccgg     2640
tccatcatca acttcttcgt ggaatgcttc aggatccagg acaaactgct gacagtcaca     2700
```

```
gcgaaagagg acgaggagga ggactaagct caggtcgctc taagcacaaa cgtggctctt    2760
tctacaacca gatgcaaccg agggatttcc ctgccctccc tcttccctcg gaggggcggg    2820
gcggggcggg gccgggtgtt ccatagcatg tgtgtctcgg atgcggaagg cagttttgct    2880
tgggaaacaa gctccttccc cggggtcatc actcacggcc tccatggcac cagggacaac    2940
gctgtccccg cagcagcgcc tcctcccggc gcccgagaga ccggcacgcc acggcccctc    3000
ccccaaggaa cagagcaaag gatggtggcc gcaggcccca cgcgagccca caggacaccg    3060
gcccctagat tccagccacc aagcggaagc atgagacccg cccacactag cctctgtgtt    3120
cccgttaggg acatcacacc ctgtctcacg tcgcagtgcc atggacgcag cagttacagc    3180
accattgttt tagcagtgcg tgttcatata tgggcttgct acttcctgta atgaggacgt    3240
tcaacatggt gagggctac aagaaaacgc ttttctgtac agagtcttac tgtagctacg    3300
ctaatggtta acctgataga attaactcgt attttttctat ggttttaacc tgatgctcca    3360
ctgtctccgt catgggttg ttttgctgtt tggggttggg ccttgtttcc ctttcctttc     3420
tccagtccac gtgtagactt tgcgcttgat gaagaagcag atcggaagta actgctccct    3480
cctcaaggtt gtcttcagac gtcttgggga cgttcctaaa cactgagggg gaagacagcc    3540
aatagcaccc attaaaagaa atacctaaat aaaacctctc tcccactcag ctatgctagg    3600
gcttggctgt aggtgtgcac tgtctattta catccgtcct tacaaccatc cttgtcctcc    3660
ttggtaccgt atcaagctct ttcccatgac atttggttta aaaaaaaaaa aaaaaaaaa     3720 aaaaaaacag aaaaaagaca aagcgtcaac tccacccaca ggcccgctgt gtgtgctcgg    3780
gccacgggag tcctgagggt tctgtgggcc tgcgcgcatc cctctcccat cgtggggtg     3840 gctccgtgac cttcctgcca cgagcaggag gttgatgatg tgctacgtta gccttgtaag    3900
atacaccccc accaaatgtg cagccggtgt tcccagtgta tatttcattc tcttgtatat    3960
aaaggaagca atgtgtgtca ggcctctgtg cagtcaaccc agcctcctcc cgccagtgct    4020
aaccccgtgt tgagcctgca tgctgacact gtggccgatc tggactctag aagtgctagt    4080
ttgaaatata tccattactg tcatttcctt ttgagcttgt ggacaagctg aatgtcagga    4140
ctgacttcgc cagctcccag ccctgcgggg gtgtccttgg catcccatca gcagaggaga    4200
tgcgtccctg ttgcattttg gcgtttgggg ctttgggttt atccacatga gctctgaacg    4260
tccgttatag ttagggtgat tggaaggtct ccatcactgg gtgttttaaa ggtgattcac    4320
caccatttgt gaaaggacca acgtgctgat aaacaggacc gatccgagtg ctacatgact    4380
gtgcgtttgc tatttcaatg ggcctgaacg actacaaagc cagctaggtc tggaagggga    4440
agccagctct ggccacgaca tctggtcgga gggaagtggg gatgtggcat ggtagcgtct    4500
gttcatccat ggaataaaac attattttac caaaaaaaaa aa                       4542
```

<210> SEQ ID NO 48
<211> LENGTH: 940
<212> TYPE: DNA
<213> ORGANISM: Homo sapiens

<400> SEQUENCE: 48

```
cctgggcgtg tgctaaggcc agagctacca gatgggtcca gctgccgcag gctctccagg      60
cactgtcccc taagtgacag ctgttactgc ctgggagagc tcaagtgcaa agactatcct     120
gttctcccat aaagaggagg aaaaggaaga tacagaaatc ggtgctgctc ccaacagcag     180
atcaaggcag tcgtcaggaa ctcaggatcc ggggggtctt cacggcttct ctgcccaggg     240
gccagaaccg aggaggccag gagggctgct ggggctaagg ggtctaagga cctcgttgca     300
```

```
cacgctacca ggagcagggg catggagcac agtgagggg ctcccggaga cccagccggt    360
actgtggtac cccaggagct gctggaagag atgctttggt tttttcgtgt ggaagatgca    420
tctccctgga atcattccat ccttgccctg gcagctgtgg tggtcattat aagcatggtc    480
ctcctgggaa gaagcatcca ggcaagcaga aagaaaaga tgcagccacc agaaaaagaa    540
actccagaag tcctgcattt ggatgaggcc aaggatcaca acagcctaaa caacctaaga    600
gaaactttgc tctcagaaaa gccaaacttg gcccaggtgg aacttgagtt aaaagagaga    660
gatgtgctgt cagttttcct tccggatgta ccagaaactg agagctagtg agggttcaga    720
gaagccccat cctaagccag acacatgatg tgggctcagc tcagtggcct gaaacctctc    780
aggttttaga gtctctccca agaagccgct tttttctttt tctttctttc ttttttttt    840 tcttagcaga tacaatgaat gaactgcaag caaactaaaa ttctgttatt aaaaaaaatc    900
ttttattaaa atgctcctgg aagggagcag gtggtattgc                         940

<210> SEQ ID NO 49
<211> LENGTH: 5018
<212> TYPE: DNA
<213> ORGANISM: Homo sapiens

<400> SEQUENCE: 49
gcccgggact atcccttcgc ggtgtagcgg cagccggaga cctggctgag gaggcaaccg     60
cgtagacacc tccctgctta gaaaacaaac actgaaccag accgatccca gttggagggt    120
tcgaaaatgt tccagacagc ctgtcgggag gggttgttgt tgctgttgga ctaaatagct    180
attcctgatt ggtcatgtat agggtttttt aaggcgggtg ggggaggag ggggtagagg    240 aaaggctcca acacctgca ggttggggc ggaaagctgt ttgcgattcc ctggactggt    300
tggtcgggga caggaggtaa ttcccagcca ttgaccccca tttctctctc tccctccctc    360
ttgccctgcc tctttctctc caccccatc tttcctggaa actcgctttg ggcgcggcag    420
atcgcccagg accacaccgc agcgtaactg caggcctctc agcgaaaag ggggaaagca    480 aagacccggg tgtgcatcct cttcctcggg ttccgcccct ttccggcgga gtggagatcc    540
tattcagagg ggccggtctc tctaaatatg ccccaggatg accgagcggc cgccgagcga    600
ggcggctcgc agtgaccccc agctagaggg acgggacgcg gccgaggcca gcatggcccc    660
cccgcacctg gtcctgctga acggcgtcgc caaggagacg agccgcgcgg ccgcagcgga    720
gcccccagtc atcgaactgg gcgcgcgcgg aggcccgggg ggcggccctg ccggtggggg    780
cggcgccgcg agagacttaa agggccgcga cgcggcgacg gccgaagcgc gccatcgggt    840
gcccaccacc gagctgtgca gacctcccgg gcccgccccg gccccgcgc ccgcctcggt    900 tacagcggag ctgccggcg acggccgcat ggtgcagctg agtcctcccg cgctggctgc    960 cccgccgcc cccggccgcg cgctgctcta cagcctcagc cagccgctgg cctctctcgg   1020
cagcgggttc tttgggggagc cggatgcctt ccctatgttc accaccaaca atcgagtgaa   1080
gaggagacct tcccccctatg agatggagat tactgatggt cccacacca aagttgtgcg   1140 gcgtatcttc accaacagcc gggagcgatg gcggcagcag aatgtgaacg gggccttgc    1200 cgagctccgc aagctgatcc ccacacatcc cccggacaag aagctcagca gaatgagat    1260 cctccgcctg gccatgaagt atatcaactt cttggccaag ctgctcaatg accaggagga   1320
ggagggcacc cagcggggcca agactggcaa ggaccctgtg gtggggctg gtggggtgg    1380 aggtggggga gggggcggcg cgcccccaga tgacctcctg caagacgtgc tttccccaa   1440
```

```
ctccagctgc ggcagctccc tggatggggc agccagcccg gacagctaca cggaggagcc   1500
cgcgcccaaa cacacggccc gcagcctcca tcctgccatg ctgcctgccg ccgatggagc   1560
cggccctcgg tgatgggtct gggccaccag gatcagccag gagggcgttc ttaggctgct   1620
gggatggtgg gcttcaggc aggtgggtg agaattgggc ggctctgaag caaggcggtg   1680
gacttgaact ttcctggatg tctgaacttt gggaagcctt tactgaccct ggggctggct   1740
tttctgtttc ctgtaccagt aggagatcag aaaaatggag caaagtggta ggtactttt   1800 gtgaagacgg cacggtcttc cctcttccct cagtcccaaa tccttcccaa gtaagaggct   1860
ggagttgtca ctgcttttgg cctggagttt gggatccctg tctttcctaa gacctggggt   1920
tgtcagctct catctgaggc atccagcagt tctgccttg cctttagccc ctcccaagct   1980
ggctggggtg gcctgtgtgg ccacttctgt ccatatttat aggtacccaa tagctgccca   2040
tttcgtgagc cccatcttca cccaggccta tgttgatcca tccagcttgc cagatgctgc   2100
agagtcacaa gcctcgaggt gccttcttca gggcctggtt gaagaagatg atcagtggac   2160
agtctgctct agatgagctg ggccggaggg tcaggaaacc cagtcgccct tacttcttgc   2220
cctggggatc aaagttctgc tttctcccca atgagacttg ccttcctaag cctgtggctg   2280
tggagacaat gtctgcagcc ctgagaaagc cctgtcgggc tttgtgtgaa ggcagagaaa   2340
gggacaatga tagtagagtg atatggagca agagatattt tgggcatgtg ggcttcaact   2400
cctcgacatc actgttcatg ctggcgagtg aatgccagtg tgctgatggg cgtacgctgg   2460
tgctgagtag atgcgcagcc ccatctgtgc attctcctgg atgcttagag ggatttcttt   2520
gctgtaagat gtctgtttgc tgatggtctg gtctatgttc cgaattgagc acaaaacctg   2580
tcctatgaat gctttgcatt tggaattttt gcttgacttc agttattggt ggaatcttta   2640
gcgctcaata ggaccaggat ccagcctcac ttctagggta tgggaaatcc aatcagagac   2700
caggccctgg ctaagaccca aacatatgca cattcactta gcagaacctt aaacacccct   2760
cagttgtgca gcttttggtc atcaagggtg cgtctgggag gttggtttaa tgcaatagaa   2820
gtgctcccct ctgaaagttg tacatgaaat ttttgtaaat cacatcctta tccttcatct   2880
tttaaagaaa taaccactgc aagtcctttt gtaaagtgaa gaatccttt gtagaatgaa   2940 ccactgcccc ttcattgatt tcctgtgtca atccagatgg tgggatgtgg ttttcttaag   3000
gtgaggcctg tctgtgacct gcatctaagc ccatgggaca aattgcacag aagtcctgta   3060
tgtctgtcat tgtacccta agtcacccta gccctctccc tctaggctct gccttcgagg   3120
tcagaggaga gatagcctgt ggccctgtcc tgccatgcaa gaactcatca ctgtggctgt   3180
ctggaaagcc ccccttata gtttgggctt cagcctagtg gcttgtcctc accatgatgg   3240
ggccctaatt cagccatgta cagacagaga atatgtctgc tcctttcccc ttccttttaa   3300
gtaaggtcca attctcgagc ttggggcaac attgttcacc tttgtagcac tcaggctctc   3360
cattcaattt caggctcccc agatcatgtt ttggtgaaaa ttagggttgg ttccttccca   3420
acgtttggaa gatcctgtga ggagcccat ctgtctaaag atagagtcat tgctgtagga   3480
tctaaggctg tttgcttcac cgtggattcg cttgagttag gaatgagaag tagccacagt   3540
atggatgggg ggatggggttt tatgagatgg atcacatatt ttattaagaa ctcaaacttc   3600
tggctccctc ttcttcaga cttgccatgt gactctggct tggcctatct cctagggcta   3660
tggtgtggac tgaatgggat catgaaagta gacagttttg agaacgtaaa gaactttttc   3720 ttttcccctca atctcaatcc tgcagtgggg tttcgcagcc tgagtccacg acctaggcag   3780
taggccggtg tgcctgactg cccagcattt gggtaattta gattgtaaac cgctttggcc   3840
```

```
tgagttattg agattgtcct catttctcca gattatctat ttgtgtgtgt gtgtgtgtgt    3900
gtgtgagaga cggtgtcttg ttctgtcact caggctggag tacagtggtg ccatcattgc    3960
tgtctgcagc cttgaactct gggctcaagc aatcctctca cctcagcctc ccgagtaggg    4020
aggaccacag gtgtgagcca ccacacctgg ctaattttta cttttttttt tttttggtag    4080
agatggagtc ttgctatatt gcccaggctg gtcttgaagt cctggcttca ggcaattctc    4140
ctgcctttgc ctccagaagc actgggatca caggtgtcag ccattgcacc cagcccagat    4200
tgtcttaatt tctatcttgt tccaaggcca gggacagtaa taagaatgga aaagagatat    4260
gggaacactg gcagactgtg taaaatgtaa tgcaactacc caaacaagc ctggtaggaa      4320 agggcaagtc tttaggtctt tgtaagaact aaagaagatc tgtaattttt attttcaccc    4380
tctgtacccc atgaccttat ccttcctctc cttccttgtt acccatgaaa aactggcaac    4440
attccaagaa tagcatctgt acaaggggaa agaacataa aggtaaaaca aaacaaaaca     4500 acatttgag aacaaagatg accataacca ctgaagggaa tcacatcttt taagacaaat     4560
tcatattctt ttatttgtta tggcagatga caagatggta caacctttat tcttttccaa    4620
aataaaacaa agggcacagc atctgtagtc agccgacaac tatttcggcc ttttgggggt    4680
gggtctggcc gtacttgtga tttcgatggt acgtgaccct ctgctgaaga cttgcccct      4740 gcccgtgtac atagtgcatt gtttctgtgg gcgggcccag cactttccgt caacgttgta    4800
ctgtatgtga tgaattgcgt tggtctctgc attttctgc agaagaggag taaccgctcc      4860
aggtaccttg accttgtac agcccagagg ccaacactgt gggtgtgtga ctctttagca     4920 aaaaaaccc atgtggtgat gatgtgtata tatatgtgag gatgtatcgg gaagatttct     4980
aaataaaagt tttacaaagg ggaaaaaaaa aaaaaaa                             5018

<210> SEQ ID NO 50
<211> LENGTH: 3024
<212> TYPE: DNA
<213> ORGANISM: Homo sapiens

<400> SEQUENCE: 50
aggatatctt tagccaaagg aaaagctccg cattcccacc cagtccagaa attgaaatac      60 tatcagggg caagagcctt tctctccagc tacacactcc atctcccggg agcaaggga     120 aactccgaga ggagggcaac agagccagca tcttgccagg gccccggagg aggggttccc    180
cgctacgcct gtgccggagg agttccagtc accgagcgag gggcgcaagg gtgggtgcat    240
cctgcgctgc ggcgggcgcg ctacccgac gctggtgtgc agagccacat gaagcctgct     300
ggggactggg ggccagggag cagcaagcca gctgggactg aggcggacgc tgtctcaggg    360
agacgctgac tcgcaaagac actcccttcc ttgtgcctgg gtaaaaagtc tcctcctggg    420
gtccctggcc atcctgaata tccagaatgg tgtttctgaa gttcttctgc atgagtttct    480
tctgccacct gtgtcaaggc tacttcgatg gcccctcta cccagagatg tccaatggga    540
ctctgcacca ctacttcgtg cccgatgggg actatgagga gaacgatgac cccgagaagt    600
gccagctgct cttcagggtg agtgaccaca ggcgctgctc ccaggggag gggagccagg     660 ttggcagcct gctgagcctc accctgcggg aggagttcac cgtgctgggc cgccaggtgg    720
aggatgctgg gcgcgtgctg gagggcatca gcaaaagcat ctcctacgac ctagacgggg    780
aagagagcta tggcaagtac ctgcggcggg agtccaccca gatcggggat gcctactcca    840
actcggacaa atccctcact gagctggaga gcaagttcaa gcagggccag gaacaggaca    900
```

```
gccggcagga gagcaggctc aacgaggact ttctgggaat gctggtccac accaggtccc    960
tgctgaagga gacactggac atctctgtgg ggctcaggga caaatacgag ctgctggccc   1020
tcaccattag gagccatggg acccgactag gtcggctgaa aaatgattat cttaaagtat   1080
aggtggaagg atacaaatgc tagaaagagg gaatcaaatc agccccgttt tggagggtgg   1140
gggacagaag atggggctac atttccccca tacctactat ttttttatat cccgatttgc   1200
actttgagaa tacatctaag gtcatctttc aaaagagaaa aattggacac ttgagtgact   1260
ttgtttttag ttttgttttt gtacattatt tatgtgattg ttatggaatt gtcacctgga   1320
aagaacaatt ttaagcaatg tcatttctag atgggtttct aattctgcag agacacccgt   1380
ttcagccaca tctaaaagag cacagtttat gtggtgcgga attaaacttc cccatcctgc   1440
agattatgtg gaaataccca agataaatag tgcatagctc ctttcagcct ctagccttca   1500
ctcctgggct ccaaaagcta tcccagttgc ctgttttttca aatgaggttc aaggtgctgc   1560
tttgcatgcc tgccaaccca tggaagttgt ttcttacttc ttttctctct tatttattaa   1620
ccatggtctg agagttgttt tgttctatg taacagtatt gccacaaaac tataggcaaa    1680
tcgtgtttgc agggagattt ctgatgcctc tgtgggtgtg tgtaagttaa agtggccaca   1740
tttaagaagg ccaagctttg tagtggttgc acagtcacac tgatatgctg atttgctctt   1800
tctcattgta tgtctatgct ttgtcatcag tgctatagta aattacaaag aaataggtag   1860
attgtatgaa catacccaca aatgcctatg atttaggtta ccaatgtatt ctttctcatt   1920
tggggttttg cttctgtctg tctgtttatt ggaaacttgt acttcaagta gggggaatcc   1980
taattctaat aactccttag ctaagtttta ttattcaggc aataaacatg ttttcatgta   2040
atactggctt actttgtaat ttacatctgt aactttcata tttctaaaag gggccaatgc   2100
aaaaggagag agaaggactg gatttaagcc agtttactta gagtatatga taagaaggc   2160
agaggaatag ctacatattt ggcaattctc ctctctgtag tcaccctgac atcctcacaa   2220
gaaaacaaat ctagccattg cccaaacttt aaatttgatc tctataggtc tgcttaaaga   2280
ctcaaatttt ctccagtttc tctcataaat tcaattgcaa aagtttctga caaggctcat   2340
accctgtacc cttatgcaga gcaagcattc catcctaagt tataaactac agtgatgttt   2400
aattttgaag ccaggtctac attatttaat taatggcttc aaaaggtgga gatgcacttt   2460
atttaatgtc tttccctagc taattcttac tctcaccta aatatgcttt cttgttgcat   2520
atatgcacag atacacacac acacacacac gaaaataaat aaatgttcat attcttctgt   2580
tcaacagaca tttatttct cctctcccctt gaataagaaa ataagttttc cattcctatg   2640
aactgtctaa tatctttcta ttacagaagg ggaaactgag gctgggaaag gctaaatgac   2700
ttatcctcca tcagttataa cagccctgg tcttcttaaa tttaaacacg ggacttcccg   2760
aactaatttt tttaaggata ctgaaaaatg agagagagtg gtcgaatgcc tgaaattttg   2820
cttaacttac tgtacttaaa atcaattata acttcttttt gttactcagg gccccacttt   2880
ttgttgcttt ctagacttgt gtgtagaaag aagattaatg atcacttaaa gtagtttcct   2940
tctttattct gaaaaaatga ggaaaaaata acaacagtgg caaataaaat catatttggt   3000
actaaaaaaa aaaaaaaaaa aaaa                                          3024
```

<210> SEQ ID NO 51
<211> LENGTH: 7111
<212> TYPE: DNA
<213> ORGANISM: Homo sapiens

<400> SEQUENCE: 51

```
gcgtcagccc tcacgtcact tcgccagcag tagcagaggc ggcggcggcg gctcccggaa    60
ttgggttgga gcaggagcct cgctggctgc ttcgctcgcg ctctacgcgc tcagtccccg   120
gcggtagcag gagcctggac ccaggcgccg ccggcgggcg tgaggcgccg gagcccggcc   180
tcgaggtgca taccggaccc ccattcgcat ctaacaagga atctgcgccc cagagagtcc   240
cgggagcgcc gccggtcggt gcccggcgcg ccgggccatg cagcgacggc cgccgcggag   300
ctccgagcag cggtagcgcc cccctgtaaa gcggttcgct atgccggggc cactgtgaac   360
cctgccgcct gccggaacac tcttcgctcc ggaccagctc agcctctgat aagctggact   420
cggcacgccc gcaacaagca ccgaggagtt aagagagccg caagcgcagg gaaggcctcc   480
ccgcacgggt gggggaaagc ggccggtgca gcgcggggac aggcactcgg gctggcactg   540
gctgctaggg atgtcgtcct ggataaggtg gcatggaccc gccatggcgc ggctctgggg   600
cttctgctgg ctggttgtgg gcttctggag ggccgctttc gcctgtccca cgtcctgcaa   660
atgcagtgcc tctcggatct ggtgcagcga cccttctcct ggcatcgtgg catttccgag   720
attggagcct aacagtgtag atcctgagaa catcaccgaa attttcatcg caaaccagaa   780
aaggttagaa atcatcaacg aagatgatgt tgaagcttat gtgggactga aaatctgac    840
aattgtggat tctggattaa aatttgtggc tcataaagca tttctgaaaa acagcaacct   900
gcagcacatc aattttaccc gaaacaaact gacgagtttg tctaggaaac atttccgtca   960
ccttgacttg tctgaactga tcctggtggg caatccattt acatgctcct gtgacattat  1020
gtggatcaag actctccaag aggctaaatc cagtccagac actcaggatt tgtactgcct  1080
gaatgaaagc agcaagaata ttcccctggc aaacctgcag atacccaatt gtggtttgcc  1140
atctgcaaat ctggccgcac ctaacctcac tgtggaggaa ggaaagtcta tcacattatc  1200
ctgtagtgtg gcaggtgatc cggttcctaa tatgtattgg gatgttggta acctggtttc  1260
caaacatatg aatgaaacaa gccacacaca gggctcctta aggataacta acatttcatc  1320
cgatgacagt gggaagcaga tctcttgtgt ggcggaaaat cttgtaggag aagatcaaga  1380
ttctgtcaac ctcactgtgc attttgcacc aactatcaca tttctcgaat ctccaacctc  1440
agaccaccac tggtgcattc cattcactgt gaaaggcaac cccaaaccag cgcttcagtg  1500
gttctataac gggcaatat tgaatgagtc caaatacatc tgtactaaaa tacatgttac  1560
caatcacacg gagtaccacg gctgcctcca gctggataat cccactcaca tgaacaatgg  1620
ggactacact ctaatagcca agaatgagta tgggaaggat gagaaacaga tttctgctca  1680
cttcatgggc tggcctggaa ttgacgatgg tgcaaaccca aattatcctg atgtaattta  1740
tgaagattat ggaactgcag cgaatgacat cggggacacc acgaacagaa gtaatgaaat  1800
ccctttccaca gacgtcactg ataaaaccgg tcgggaacat ctctcggtct atgctgtggt  1860
ggtgattgcg tctgtggtgg gatttttgcct tttggtaatg ctgtttctgc ttaagttggc  1920
aagacactcc aagtttggca tgaaaggttt tgttttgttt cataagatcc cactggatgg  1980
gtagctgaaa taaggaaaaa gacagagaaa ggggctgtgg tgcttgttgg ttgatgctgc  2040
catgtaagct ggactcctgg gactgctgtt ggcttatccc gggaagtgct gcttatctgg  2100
ggttttctgg tagatgtggg cggtgtttgg aggctgtact atatgaagcc tgcatatact  2160
gtgagctgtg attggggaac accaatgcag aggtaactct caggcagcta agcagcacct  2220
caagaaaaca tgttaaatta atgcttctct tcttacagta gttcaaatac aaaactgaaa  2280
tgaaatccca ttggattgta cttctcttct gaaaagtgtg cttttgacc ctactggaca   2340
```

```
tttattgact taattgcttc tgtttattaa aattgacctg caaagttaaa aaaaaattaa    2400
agttgagaac aggtataagt gcacactgaa tagtctaatc tacatgtaac acatatttta    2460
gtgtgatttt ctatactcta atcagcactg aattcagagg gtttgacttt ttcatctata    2520
acacagtgac taaagagtt aagggtatat ataccatcac tttgggactt ggtagtatta    2580
ttaaaaggtt atttccttca ctgtcaataa aagtccaaat gtttagctta ggtctgagag    2640
tcaaacaatg ttaaggattg tcttaaagtt ccttagccag caaacaaaa caaacaaaa    2700 caaacaaatg aaaaacgttt aaaaagaaga agaagaaaaa aaacaagaac aagcagcaac    2760
agctgttttg ttggggctat agatttaagt taggcatagt caatttcaga ataactaaga    2820
gtggaatata tgcatatggt gaaattataa ccttgcccct ttttatttgc cctctgcgat    2880
ccacctgctt tttagaagtc tgccgagtga aaggccaca gtatctcatg ctgtttgcat    2940
tacagaactg cagcttttct actctgaaaa ggcctgggag cagaatggct ggcctgctgt    3000
gagcaggaga ggagattcta agaaggatag tccccctac aacatactgt catactgctg    3060
ggttttcatg ggtaggaaag cttgtcctga ccccagcagc aaagaggtgg caggtcgcta    3120
atgaatatat gctttataat gtccttcttc attgctgaga gggcagcctt agagctgtgg    3180
atttctgcat ccccctgag tctgacccat ggacacctgt tcattcact ttagcatcac    3240 agtgaccttt gtatgctctg ttcagtctgt gtcaggcagt atgcttgtcc tgaagagagg    3300
tttggctatc cccaccccac cccaccccac cctgttcctt ttttatcagg aggacttcag    3360
agccaggcct gcagcatttt gtttgaaaac acaatcagct ctgacagtta gacatgcaca    3420
cagacgccat agctggattg gaaacattga tgttttaaaa atttattttt tttggaaata    3480
gttgcacaaa tgctgcaatt tagctttaag gttctataga ttttaacta gtccaacaca    3540 gtcagaaaca ttgttttgaa tcctctgtaa accaaggcat taatcttaat aaaccaggat    3600
ccatttaggt accacttgat ataaaagga tatccataat gaatatttta tactgcatcc    3660
tttacattag ccactaaata cgttattgct tgatgaagac ctttcacaga atcctatgga    3720
ttgcagcatt tcacttggct acttcatacc catgccttaa agagggcag tttctcaaaa    3780 gcagaaacat gccgcagtt ctcaagtttt cctcctaact ccatttgaat gtaagggcag    3840
ctggccccca atgtggggag gtccgaacat tttctgaatt cccatttct tgttcgcggc    3900 taaatgacag tttctgtcat tacttagatt ccgatcttc ccaaaggtgt tgatttacaa    3960
agaggccagc taatagcaga aatcatgacc ctgaaagaga gatgaaattc aagctgtgag    4020
ccaggcagga gctcagtatg gcaaaggttc ttgagaatca gccatttggt acaaaaaaga    4080
tttttaaagc ttttatgtta taccatggag ccatagaaag gctatggatt gtttaagaac    4140 tatttttaaag tgttccagac ccaaaaagga aaaataaaa aaaggaata tttgtaccca    4200 acagctagaa ggattgcaag gtagattttt gttttaaaat ggagagaagt ggacagataa    4260
ggccatttaa tatatcaaag atcagttgac atctcctagg gaatgatgaa acagcaggc    4320 tattagaaaa ttattcata tagttctcgt gttcttttct ttttttaat ccctgaaggg    4380 atgatcagta acatagcttc tcttttctgt actctagacc cccctttc atcattttgc    4440 tttttatgtc tcccataaga aatgtgcttt ttagagcttc ctaatgcatg tgttgcatta    4500
ttgcagcatt agaaaaggag aggtagcatt tttgctgaaa tcgggcctgt cactctccaa    4560
taaaggttct ggcacttcaa tgccaggcag gtctcctaaa tgaacagaat gatctgtgtg    4620
agccgatgcc tgcccttcca gaggggccac tgtccccagc cgcagccaac tgtgtcccac    4680
aggaatggga gcctaggttt ccaaatcttg tgattcttta ggagaaacat gaaacctgga    4740
```

-continued

```
tttcgtgtga aatgtcccga ttgttaaaaa gttggctcaa ttattttta aacattttgt    4800 aagccaacaa aagtctgtgg gctgccagtt tattactttt gtcttaaaac atgatcattg    4860
ttctctcacg gtatccttct gtcttcccgt tgcaaattca cttttctttc ttcctgacat    4920
tgccattgag ggctttgtta ccacaagcta agaaactgag tttaacagcc cagttatctg    4980
caacatgtca attacctttg ctcctctcct gtgattccca ccatgctgtg accctcagct    5040 gtctccctt gctgggaatt ctgcaccaat gtctcccctc aacccattcc ctggttggtc    5100
ctactcccgt gtggccagag acatcctagc aaatccttcc tcctattata tctgacacta    5160
atttcttttc aacagcgctc atgtctcttg gcccagtcag gtgctgccag gtttagatag    5220
gaaagtacat gtcccatttt catgggtgcc cttaatgtgg tccacgtcct atatcttatt    5280
atatttactc atggctcaat gggggcctcc agagaccctc tcaggctgct gagctagact    5340
aaggaatgca tccaccgtca tcacatgaga cactgactct gtgacgacaa aagtacaaac    5400
agtctgaggc taagaaaggt tcatctcaca acaggaaaaa caaatctcaa cacacattag    5460
agataattga ttcaggggtt ttctctccca gtctcccagc agggactgat ttcatttctg    5520
acccactagg ttttctttcc agaaataggt agcaaggaca agaactaaac aatcccagcc    5580
ccacccagca acacagaaca caggagtttg cttttggctt ctcactctcc aagtaaccct    5640
gaattaggcc cagaatggct gaggcttgga gcatctcctc agacagagca gaggcgacac    5700
ctcttcaggg gtgtgtggag taaatagctc gaagagctga agacagaaaa ccagtttcac    5760
gccaggtgcg agagagagca taatggaggg aagcccgctt tctctctcct cttctttct    5820 ctttatttct ttagagcact tgactttttt ttctctctct ctctagtatt ctaaactgac    5880
cccatgacca actgagaatt tattttttgtt tcattggttg tttcacagaa ttagaacaca    5940 cacgacttt tattcctcca ttgcaaaatg gaatcaagat actacacaag acctgtgctt    6000
tcttcctttg catgatttac acctccgcct gttttggtgc tagctgtcta gaacttctct    6060
cttggtttga atctgattcc ttcacactac actagaagtt tatttcatct tgttttgtct    6120
agactccaga tacagaggga cagctggact gaggacaagc aattccatct agcatagggt    6180
ctctcagggt tggtgcatcc agccacatgg gcagggccag tcacatctag tctatgtccc    6240
cagagccctt ggagttgcgc agcttagctg acttgactcc aaggaaatta gtacagaagt    6300
aaccactcta ttaagtgtgt tctgctatgt tcacatgcct gtagtacctg caaaccatgc    6360
caggttcatc taaagacata ggggaagatt aaggactctt ttggacagac catgaattga    6420
atttgctgcc aggtgctgcc agactgaatt tggctgacag aactcccagc ccaggaaagt    6480
tccatgacaa tgactgtcgc agaaggaaat ttcccactaa agtcagtcca ttttcaagtt    6540
ttggtcttca gagacaaaag aacgtcccag ccacctgatt ttgatggtga ggtaactcta    6600
agttgaattc aggctagtgt tgcagtatag ctttggcatg ttcatgagtg agcacccaga    6660
atgtgttgaa ccaacccca cccctaacta ctgactatga ctgcagtggg ttttatgggg    6720 gaaaaaagt gtgaaaagca aaagaaagg aacagagatt ttttatcacc tttattgtaa    6780
gacagtccat ttatgaattg agtataaaca catacaaagt aacaagagat tcctaagaaa    6840
cgcaaatcct tgagtttcac gcacttcatg ttcaaccatt tgctgtaatc cagaggcagc    6900
ctgtgaatca ttctcatgcc ctgttttttt tttttttttc ctataatgtt ctgggtttaa    6960
aagccatctt ttccacattt tctgtaaata atggataatc attttaaaaa ttttttatttt    7020 tagtgctgtt ttaacaatgt agatagatca taaatgtact tgctgaattc aatcattttt    7080
```
aacaagccaa taaagtttga taattcatct c                                7111

<210> SEQ ID NO 52
<211> LENGTH: 5560
<212> TYPE: DNA
<213> ORGANISM: Homo sapiens

<400> SEQUENCE: 52
aagacggatt ctcagacaag gcttgcaaat gccccgcagc catcatttaa ctgcacccgc    60
agaatagtta cggtttgtca cccgaccctc ccggatcgcc taatttgtcc ctagtgagac   120
cccgaggctc tgcccgcgcc tggcttcttc gtagctggat gcatatcgtg ctccgggcag   180
cgcgggcgca gggcacgcgt tcgcgcacac cctagcacac atgaacacgc gcaagagctg   240
aaccaagcac ggtttccatt tcaaaaaggg agacagcctc taccgcgatt gtagaagaga   300
ctgtggtgtg aattagggac cgggaggcgt cgaacggagg aacggttcat cttagagact   360
aattttctgg agtttctgcc cctgctctgc gtcagccctc acgtcacttc gccagcagta   420
gcagaggcgg cggcggcggc tcccggaatt gggttggagc aggagcctcg ctggctgctt   480
cgctcgcgct ctacgcgctc agtccccggc ggtagcagga gcctggaccc aggcgccgcc   540
ggcgggcgtg aggcgccgga gcccggcctc gaggtgcata ccggaccccc attcgcatct   600
aacaaggaat ctgcgcccca gagagtcccg ggagcgccgc cggtcggtgc ccggcgcgcc   660
gggccatgca gcgacggccg ccgcggagct ccgagcagcg gtagcgcccc cctgtaaagc   720
ggttcgctat gccggggcca ctgtgaaccc tgccgcctgc cggaacactc ttcgctccgg   780
accagctcag cctctgataa gctggactcg gcacgcccgc aacaagcacc gaggagttaa   840
gagagccgca agcgcaggga aggcctcccc gcacgggtgg gggaaagcgg ccggtgcagc   900
gcggggacag gcactcgggc tggcactggc tgctagggat gtcgtcctgg ataaggtggc   960
atggacccgc catggcgcgg ctctggggct tctgctggct ggttgtgggc ttctggaggg  1020
ccgctttcgc ctgtcccacg tcctgcaaat gcagtgcctc tcggatctgg tgcagcgacc  1080
cttctcctgg catcgtggca tttccgagat tggagcctaa cagtgtagat cctgagaaca  1140
tcaccgaaat tttcatcgca aaccagaaaa ggttagaaat catcaacgaa gatgatgttg  1200
aagcttatgt gggactgaga aatctgacaa ttgtggattc tggattaaaa tttgtggctc  1260
ataaagcatt tctgaaaaac agcaacctgc agcacatcaa ttttacccga acaaactga   1320
cgagtttgtc taggaaacat ttccgtcacc ttgacttgtc tgaactgatc ctggtgggca  1380
atccatttac atgctcctgt gacattatgt ggatcaagac tctccaagag gctaaatcca  1440
gtccagacac tcaggatttg tactgcctga atgaaagcag caagaatatt cccctggcaa  1500
acctgcagat acccaattgt ggtttgccat ctgcaaatct ggccgcacct aacctcactg  1560
tggaggaagg aaagtctatc acattatcct gtagtgtggc aggtgatccg gttcctaata  1620
tgtattggga tgttggtaac ctggtttcca acatatgaa tgaaacaagc cacacacagg  1680
gctccttaag gataactaac atttcatccg atgacagtgg gaagcagatc tcttgtgtgg  1740
cggaaaatct tgtaggagaa gatcaagatt ctgtcaacct cactgtgcat tttgcaccaa  1800
ctatcacatt tctcgaatct ccaacctcag accaccactg gtgcattcca ttcactgtga  1860
aaggcaaccc caaaccagcg cttcagtggt tctataacgg ggcaatattg aatgagtcca  1920
aatacatctg tactaaaata catgttacca atcacacgga gtaccacggc tgcctccagc  1980
tggataatcc cactcacatg aacaatgggg actcactct aatagccaag aatgagtatg  2040
ggaaggatga gaaacagatt tctgctcact tcatgggctg gcctggaatt gacgatggtg  2100

```
caaacccaaa ttatcctgat gtaatttatg aagattatgg aactgcagcg aatgacatcg    2160
gggacaccac gaacagaagt aatgaaatcc cttccacaga cgtcactgat aaaaccggtc    2220
gggaacatct ctcggtctat gctgtggtgg tgattgcgtc tgtggtggga ttttgccttt    2280
tggtaatgct gtttctgctt aagttggcaa gacactccaa gtttggcatg aaaggcccag    2340
cctccgttat cagcaatgat gatgactctg ccagcccact ccatcacatc tccaatggga    2400
gtaacactcc atcttcttcg gaaggtggcc cagatgctgt cattattgga atgaccaaga    2460
tccctgtcat tgaaaatccc cagtactttg gcatcaccaa cagtcagctc aagccagaca    2520
catttgttca gcacatcaag cgacataaca ttgttctgaa agggagcta ggcgaaggag    2580 cctttggaaa agtgttccta gctgaatgct ataacctctg tcctgagcag gacaagatct    2640
tggtggcagt gaagaccctg aaggatgcca gtgacaatgc acgcaaggac ttccaccgtg    2700
aggccgagct cctgaccaac ctccagcatg agcacatcgt caagttctat ggcgtctgcg    2760
tggagggcga ccccctcatc atggtctttg agtacatgaa gcatgggac ctcaacaagt    2820 tcctcagggc acacggccct gatgccgtgc tgatggctga gggcaacccg cccacggaac    2880
tgacgcagtc gcagatgctg catatagccc agcagatcgc cgcgggcatg gtctacctgg    2940
cgtcccagca cttcgtgcac cgcgatttgg ccaccaggaa ctgcctggtc ggggagaact    3000
tgctggtgaa aatcggggac tttgggatgt cccgggacgt gtacagcact gactactaca    3060
gggtcggtgg ccacacaatg ctgcccattc gctggatgcc tccagagagc atcatgtaca    3120
ggaaattcac gacggaaagc gacgtctgga gcctgggggt cgtgttgtgg gagattttca    3180
cctatggcaa acagccctgg taccagctgt caaacaatga ggtgatagag tgtatcactc    3240
agggccgagt cctgcagcga ccccgcacgt gccccagga ggtgtatgag ctgatgctgg    3300
ggtgctggca gcgagagccc cacatgagga agaacatcaa gggcatccat ccctccttc    3360 agaacttggc caaggcatct ccggtctacc tggacattct aggctagggc cttttccc    3420 agaccgatcc ttcccaacgt actcctcaga cgggctgaga ggatgaacat cttttaactg    3480
ccgctggagg ccaccaagct gctctccttc actctgacag tattaacatc aaagactccg    3540
agaagctctc gagggaagca gtgtgtactt cttcatccat agacacagta ttgacttctt    3600
tttggcatta tctctttctc tctttccatc tccttggtt gttcctttt cttttttaa    3660 atttctttt tctttttttt ttcgtcttcc ctgcttcacg attcttaccc tttcttttga    3720
atcaatctgg cttctgcatt actattaact ctgcatagac aaaggcctta acaaacgtaa    3780
tttgttatat cagcagacac tccagtttgc ccaccacaac taacaatgcc ttgttgtatt    3840
cctgcctttg atgtggatga aaaaaggga aacaaatat ttcacttaaa ctttgtcact    3900
tctgctgtac agatatcgag agtttctatg gattcacttc tatttattta ttattattac    3960
tgttcttatt gttttggat ggcttaagcc tgtgtataaa aagaaaact tgtgttcaat    4020 ctgtgaagcc tttatctatg ggagattaaa accagagaga aagaagattt attatgaacc    4080
gcaatatggg aggaacaaag acaaccactg ggatcagctg gtgtcagtcc ctacttagga    4140
aatactcagc aactgttagc tgggaagaat gtattcggca ccttcccctg aggacctttc    4200
tgaggagtaa aaagactact ggcctctgtg ccatggatga ttcttttccc atcaccagaa    4260
atgatagcgt gcagtagaga gcaaagatgg cttccgtgag acacaagatg gcgcatagtg    4320
tgctcggaca cagtttttgtc ttcgtaggtt gtgatgatag cactggttg tttctcaagc    4380 gctatccaca gaacctttgt caacttcagt tgaaaagagg tggattcatg tccagagctc    4440
```

```
atttcggggt caggtgggaa agccaagaac ttggaaaaga taagacaagc tataaattcg    4500
gaggcaagtt tcttttacaa tgaacttttc agatctcact tccctccgac ccctaacttc    4560
catgcccacc cgtcctttta actgtgcaag caaaattgtg catggtcttc gtcgattaat    4620
accttgtgtg cagacactac tgctccagac gtcgtttccc tgataggtag agcagatcca    4680
taaaaggta tgacttatac aattagggga agctaatgga gtttattagc tgagtatcaa     4740
tgtctctgcg ttgtacggtg gtgatgggtt ttaatgaata tggaccctga agcctggaaa    4800
tcctcatcca cgtcgaaccc acaggactgt gggaagggca gaatcaatcc ctaagggaaa    4860
ggaaacctca ccctgagggc atcacatgca ctcatgttca gtgtacacag gtcaagtccc    4920
ttgctctggg ctctagttgg gagagtggtt tcattccaag tgtactccat tgtcagtatg    4980
ctgtttttgt ttccttcact ccattcaaaa agtcaaaata caaaatttgg cacagcatgc    5040
caacgggagg ctgtgcccag accaagcact ggaagtgtgc ttctaggcat agtcattggt    5100
tttgcaaaaa gagggctcaa atttaaatag aaatttacag ctatttgaat ggtcagatat    5160
accaagaaag aaaaatattt ctgttcctca agaaaacttg ctaccctctg tgagggaat    5220
tttgctaaac ttgacatctt tataacatga gccagattga agggagtga ttttcattca    5280
tcttaggtca tgttatttca tatttgtttc tgaaggtgcg atagctctgt tttaggtttt    5340
gcttgcgcct gttaattact ggaacacctt attttcatt aaaggctttg aaagccaatt    5400
ctcaaaaatt caaagtgca aattaacaga acaaaggaa atccagtagc aactgcagtc    5460
aagcgaggga gttgacaaga taaaccttac gtccattcaa gttatatgct ggcctatgag    5520
agatgagagt tgggtcgttt gttctctttg ttgatgattt                          5560

<210> SEQ ID NO 53
<211> LENGTH: 5608
<212> TYPE: DNA
<213> ORGANISM: Homo sapiens

<400> SEQUENCE: 53
aagacggatt ctcagacaag gcttgcaaat gccccgcagc catcatttaa ctgcacccgc      60
agaatagtta cggtttgtca cccgacccte ccggatcgcc taatttgtcc ctagtgagac     120
cccgaggctc tgcccgcgcc tggcttcttc gtagctggat gcatatcgtg ctccgggcag    180
cgcgggcgca gggcacgcgt tcgcgcacac cctagcacac atgaacacgc gcaagagctg    240
aaccaagcac ggtttccatt tcaaaaaggg agacagcctc taccgcgatt gtagaagaga    300
ctgtggtgtg aattagggac cgggaggcgt cgaacggagg aacggttcat cttagagact    360
aattttctgg agtttctgcc cctgctctgc gtcagccctc acgtcacttc gccagcagta    420
gcagaggcgg cggcggcggc tcccggaatt gggttggagc aggagcctcg ctggctgctt    480
cgctcgcgct ctacgcgctc agtccccggc ggtagcagga gcctggaccc aggcgccgcc    540
ggcgggcgtg aggcgccgga gccggcctc gaggtgcata ccggaccccc attcgcatct    600
aacaaggaat ctgcgcccca gagagtcccg ggagcgccgc cggtcggtgc ccggcgcgcc    660
gggccatgca gcgacggccg ccgcggagct ccgagcagcg gtagcgcccc cctgtaaagc    720
ggttcgctat gccggggcca ctgtgaaccc tgccgcctgc cggaacactc ttcgctccgg    780
accagctcag cctctgataa gctggactcg gcacgcccgc aacaagcacc gaggagttaa    840
gagagccgca agcgcaggga aggcctcccc gcacgggtgg gggaaagcgg ccggtgcagc    900
gcggggacag gcactcgggc tggcactggc tgctagggat gtcgtcctgg ataaggtggc    960
atggacccgc catggcgcgg ctctgggggct tctgctggct ggttgtgggc ttctggaggg    1020
```

```
ccgctttcgc ctgtcccacg tcctgcaaat gcagtgcctc tcggatctgg tgcagcgacc    1080
cttctcctgg catcgtggca tttccgagat tggagcctaa cagtgtagat cctgagaaca    1140
tcaccgaaat tttcatcgca aaccagaaaa ggttagaaat catcaacgaa gatgatgttg    1200
aagcttatgt gggactgaga aatctgacaa ttgtggattc tggattaaaa tttgtggctc    1260
ataaagcatt tctgaaaaac agcaacctgc agcacatcaa ttttacccga aacaaactga    1320
cgagtttgtc taggaaacat ttccgtcacc ttgacttgtc tgaactgatc ctggtgggca    1380
atccatttac atgctcctgt gacattatgt ggatcaagac tctccaagag gctaaatcca    1440
gtccagacac tcaggatttg tactgcctga atgaaagcag caagaatatt ccctggcaa    1500
acctgcagat acccaattgt ggtttgccat ctgcaaatct ggccgcacct aacctcactg    1560
tggaggaagg aaagtctatc acattatcct gtagtgtggc aggtgatccg gttcctaata    1620
tgtattggga tgttggtaac ctggtttcca acatatgaa tgaaacaagc cacacacagg     1680
gctccttaag gataactaac atttcatccg atgacagtgg gaagcagatc tcttgtgtgg    1740
cggaaaatct tgtaggagaa gatcaagatt ctgtcaacct cactgtgcat tttgcaccaa    1800
ctatcacatt tctcgaatct ccaacctcag accaccactg gtgcattcca ttcactgtga    1860
aaggcaaccc caaaccagcg cttcagtggt tctataacgg ggcaatattg aatgagtcca    1920
aatacatctg tactaaaata catgttacca atcacacgga gtaccacggc tgcctccagc    1980
tggataatcc cactcacatg aacaatgggg actacactct aatagccaag aatgagtatg    2040
ggaaggatga gaaacagatt tctgctcact tcatgggctg gcctggaatt gacgatggtg    2100
caaacccaaa ttatcctgat gtaatttatg aagattatgg aactgcagcg aatgacatcg    2160
gggacaccac gaacagaagt aatgaaatcc cttccacaga cgtcactgat aaaaccggtc    2220
gggaacatct ctcggtctat gctgtggtgg tgattgcgtc tgtggtggga ttttgccttt    2280
tggtaatgct gtttctgctt aagttggcaa gacactccaa gttggcatg aaagattct     2340
catggtttgg atttgggaaa gtaaaatcaa gacaaggtgt tggcccagcc tccgttatca    2400
gcaatgatga tgactctgcc agcccactcc atcacatctc caatgggagt aacactccat    2460
cttcttcgga aggtggccca gatgctgtca ttattggaat gaccaagatc cctgtcattg    2520
aaaatcccca gtactttggc atcaccaaca gtcagctcaa gccagacaca tttgttcagc    2580
acatcaagcg acataacatt gttctgaaaa gggagctagg cgaaggagcc tttggaaaag    2640
tgttcctagc tgaatgctat aacctctgtc ctgagcagga caagatcttg gtggcagtga    2700
agaccctgaa ggatgccagt gacaatgcac gcaaggactt ccaccgtgag gccgagctcc    2760
tgaccaacct ccagcatgag cacatcgtca gttctatgg cgtctgcgtg agggcgacc     2820
ccctcatcat ggtctttgag tacatgaagc atggggacct caacaagttc ctcagggcac    2880
acggccctga tgccgtgctg atggctgagg gcaacccgcc cacggaactg acgcagtcgc    2940
agatgctgca tatagcccag cagatcgccg cgggcatggt ctacctggcg tcccagcact    3000
tcgtgcaccg cgatttggcc accaggaact gcctggtcgg ggagaacttg ctggtgaaaa    3060
tcggggactt tgggatgtcc cgggacgtgt acagcactga ctactacagg gtcggtggcc    3120
acacaatgct gcccattcgc tggatgcctc cagagagcat catgtacagg aaattcacga    3180
cggaaagcga cgtctggagc ctggggtcg tgttgtggga gattttcacc tatggcaaac    3240
agccctggta ccagctgtca aacaatgagg tgatagagtg tatcactcag ggccgagtcc    3300
tgcagcgacc ccgcacgtgc ccccaggagg tgtatgagct gatgctgggg tgctggcagc    3360
```

```
gagagcccca catgaggaag aacatcaagg gcatccatac cctccttcag aacttggcca    3420
aggcatctcc ggtctacctg gacattctag gctagggccc ttttccccag accgatcctt    3480
cccaacgtac tcctcagacg ggctgagagg atgaacatct tttaactgcc gctggaggcc    3540
accaagctgc tctccttcac tctgacagta ttaacatcaa agactccgag aagctctcga    3600
gggaagcagt gtgtacttct tcatccatag acacagtatt gacttctttt tggcattatc    3660
tctttctctc tttccatctc ccttggttgt tccttttttct ttttttaaat tttcttttttc   3720
ttttttttttt cgtcttccct gcttcacgat tcttacccctt tcttttgaat caatctggct   3780
tctgcattac tattaactct gcatagacaa aggccttaac aaacgtaatt tgttatatca    3840
gcagacactc cagtttgccc accacaacta acaatgcctt gttgtattcc tgcctttgat    3900
gtggatgaaa aaagggaaa acaaatattt cacttaaact ttgtcacttc tgctgtacag     3960
atatcgagag tttctatgga ttcacttcta tttatttatt attattactg ttcttattgt    4020
ttttggatgg cttaagcctg tgtataaaaa agaaaacttg tgttcaatct gtgaagcctt    4080
tatctatggg agattaaaac cagagagaaa gaagattat tatgaaccgc aatatgggag     4140
gaacaaagac aaccactggg atcagctggt gtcagtccct acttaggaaa tactcagcaa    4200
ctgttagctg ggaagaatgt attcggcacc ttccccctgag gaccttttctg aggagtaaaa   4260
agactactgg cctctgtgcc atggatgatt cttttcccat caccagaaat gatagcgtgc    4320
agtagagagc aaagatggct tccgtgagac acaagatggc gcatagtgtg ctcggacaca    4380
gttttgtctt cgtaggttgt gatgatagca ctggtttgtt tctcaagcgc tatccacaga    4440
accttttgtca acttcagttg aaaagaggtg gattcatgtc cagagctcat ttcggggtca    4500
ggtgggaaag ccaagaactt ggaaaagata agacaagcta taaattcgga ggcaagttc     4560
ttttacaatg aacttttcag atctcacttc cctccgaccc ctaacttcca tgcccacccg    4620
tcctttttaac tgtgcaagca aaattgtgca tggtcttcgt cgattaatac cttgtgtgca    4680
gacactactg ctccagacgt cgtttccctg ataggtagag cagatccata aaaaggtatg    4740
acttatacaa ttagggggaag ctaatggagt ttattagctg agtatcaatg tctctgcgtt   4800
gtacggtggt gatgggtttt aatgaatatg gaccctgaag cctggaaatc ctcatccacg    4860
tcgaacccac aggactgtgg gaagggcaga atcaatccct aagggaaagg aaacctcacc    4920
ctgagggcat cacatgcact catgttcagt gtacacaggt caagtccctt gctctgggct    4980
ctagttggga gagtggtttc attccaagtg tactccattg tcagtatgct gttttttgttt   5040
ccttcactcc attcaaaaag tcaaaataca aaatttggca cagcatgcca acgggaggct    5100
gtgcccagac caagcactgg aagtgtgctt ctaggcatag tcattggttt tgcaaaaaga    5160
gggctcaaat ttaaatagaa atttacagct atttgaatgg tcagatatac caagaaagaa    5220
aaatatttct gttcctcaag aaaacttgct accctctgtg aggggaattt tgctaaactt    5280
gacatcttta taacatgagc cagattgaaa gggagtgatt ttcattcatc ttaggtcatg    5340
ttatttcata tttgtttctg aaggtgcgat agctctgtttt taggttttgc ttgcgcctgt    5400
taattactgg aacaccttat ttttcattaa aggctttgaa agccaattct caaaaattca    5460
aaagtgcaaa ttaacagaac aaaaggaaat ccagtagcaa ctgcagtcaa gcagggagt    5520
tgacaagata aaccttacgt ccattcaagt tatatgctgg cctatgagag atgagagttg    5580
ggtcgtttgt tctctttgtt gatgatttt                                     5608

<210> SEQ ID NO 54
<211> LENGTH: 3600
```

<212> TYPE: DNA
<213> ORGANISM: Homo sapiens

<400> SEQUENCE: 54

| | | | | | |
|---|---|---|---|---|---|
| gaagagactc | agggcagagg | gaggaaggac | agcagaccag | acagtcacag | cagccttgac | 60 |
| aaaacgttcc | tggaactcaa | gctcttctcc | acagaggagg | acagagcaga | cagcagagac | 120 |
| catggagtct | ccctcggccc | ctccccacag | atggtgcatc | ccctggcaga | ggctcctgct | 180 |
| cacagcctca | cttctaacct | tctggaaccc | gcccaccact | gccaagctca | ctattgaatc | 240 |
| cacgccgttc | aatgtcgcag | aggggaagga | ggtgcttcta | cttgtccaca | atctgcccca | 300 |
| gcatcttttt | ggctacagct | ggtacaaagg | tgaaagagtg | gatggcaacc | gtcaaattat | 360 |
| aggatatgta | ataggaactc | aacaagctac | cccagggccc | gcatacagtg | gtcgagagat | 420 |
| aatatacccc | aatgcatccc | tgctgatcca | gaacatcatc | agaatgaca | caggattcta | 480 |
| caccctacac | gtcataaagt | cagatcttgt | gaatgaagaa | gcaactggcc | agttccgggt | 540 |
| atacccggag | ctgcccaagc | cctccatctc | cagcaacaac | tccaaacccg | tggaggacaa | 600 |
| ggatgctgtg | gccttcacct | gtgaacctga | gactcaggac | gcaacctacc | tgtggtgggt | 660 |
| aaacaatcag | agcctcccgg | tcagtccag | gctgcagctg | tccaatggca | acaggacccct | 720 |
| cactctattc | aatgtcacaa | gaaatgacac | agcaagctac | aaatgtgaaa | cccagaaccc | 780 |
| agtgagtgcc | aggcgcagtg | attcagtcat | cctgaatgtc | ctctatggcc | cggatgcccc | 840 |
| caccatttcc | cctctaaaca | catcttacag | atcagggaa | aatctgaacc | tctcctgcca | 900 |
| cgcagcctct | aacccacctg | cacagtactc | ttggtttgtc | aatgggactt | tccagcaatc | 960 |
| cacccaagag | ctctttatcc | ccaacatcac | tgtgaataat | agtggatcct | atacgtgcca | 1020 |
| agcccataac | tcagacactg | gcctcaatag | gaccacagtc | acgacgatca | cagtctatgc | 1080 |
| agagccaccc | aaaccccttca | tcaccagcaa | caactccaac | cccgtggagg | atgaggatgc | 1140 |
| tgtagcctta | acctgtgaac | ctgagattca | gaacacaacc | tacctgtggt | gggtaaataa | 1200 |
| tcagagcctc | ccggtcagtc | ccaggctgca | gctgtccaat | gacaacagga | ccctcactct | 1260 |
| actcagtgtc | acaaggaatg | atgtaggacc | ctatgagtgt | ggaatccaga | acaaattaag | 1320 |
| tgttgaccac | agcgacccag | tcatcctgaa | tgtcctctat | ggcccagacg | accccaccat | 1380 |
| ttcccccctca | tacacctatt | accgtccagg | ggtgaacctc | agcctctcct | gccatgcagc | 1440 |
| ctctaaccca | cctgcacagt | attcttggct | gattgatggg | aacatccagc | aacacacaca | 1500 |
| agagctcttt | atctccaaca | tcactgagaa | gaacagcgga | ctctatacct | gccaggccaa | 1560 |
| taactcagcc | agtggccaca | gcaggactac | agtcaagaca | atcacagtct | ctgcggagct | 1620 |
| gcccaagccc | tccatctcca | gcaacaactc | caaacccgtg | gaggacaagg | atgctgtggc | 1680 |
| cttcacctgt | gaacctgagg | ctcagaacac | aacctacctg | tggtgggtaa | atggtcagag | 1740 |
| cctcccagtc | agtcccaggc | tgcagctgtc | caatggcaac | aggaccctca | ctctattcaa | 1800 |
| tgtcacaaga | aatgacgcaa | gagcctatgt | atgtggaatc | cagaactcag | tgagtgcaaa | 1860 |
| ccgcagtgac | ccagtcaccc | tggatgtcct | ctatgggccg | gacacccca | tcatttcccc | 1920 |
| cccagactcg | tcttaccttt | cgggagcgaa | cctcaacctc | tcctgccact | ggcctctaa | 1980 |
| cccatccccg | cagtattctt | ggcgtatcaa | tgggatacccg | cagcaacaca | cacaagttct | 2040 |
| ctttatcgcc | aaaatcacgc | caaataataa | cgggacctat | gcctgttttg | tctctaactt | 2100 |
| ggctactggc | cgcaataatt | ccatagtcaa | gagcatcaca | gtctctgcat | ctggaacttc | 2160 |
| tcctggtctc | tcagctgggg | ccactgtcgg | catcatgatt | ggagtgctgg | ttgggggttgc | 2220 |

| | |
|---|---:|
| tctgatatag cagccctggt gtagtttctt catttcagga agactgacag ttgttttgct | 2280 |
| tcttccttaa agcatttgca acagctacag tctaaaattg cttctttacc aaggatattt | 2340 |
| acagaaaaga ctctgaccag agatcgagac catcctagcc aacatcgtga aaccccatct | 2400 |
| ctactaaaaa tacaaaaatg agctgggctt ggtggcgcgc acctgtagtc ccagttactc | 2460 |
| gggaggctga ggcaggagaa tcgcttgaac ccgggaggtg gagattgcag tgagcccaga | 2520 |
| tcgcaccact gcactccagt ctggcaacag agcaagactc catctcaaaa agaaaagaaa | 2580 |
| agaagactct gacctgtact cttgaataca agtttctgat accactgcac tgtctgagaa | 2640 |
| tttccaaaac tttaatgaac taactgacag cttcatgaaa ctgtccacca agatcaagca | 2700 |
| gagaaaataa ttaatttcat gggactaaat gaactaatga ggataatatt ttcataattt | 2760 |
| tttatttgaa attttgctga ttctttaaat gtcttgtttc ccagatttca ggaaactttt | 2820 |
| tttcttttaa gctatccaca gcttacagca atttgataaa atatactttt gtgaacaaaa | 2880 |
| attgagacat ttacattttc tccctatgtg gtcgctccag acttgggaaa ctattcatga | 2940 |
| atatttatat tgtatggtaa tatagttatt gcacaagttc aataaaaatc tgctctttgt | 3000 |
| atgacagaat acatttgaaa acattggtta tattaccaag actttgacta aatgtcgta | 3060 |
| tttgaggata taaacccata ggtaataaac ccacaggtac tacaaacaaa gtctgaagtc | 3120 |
| agccttggtt tggcttccta gtgtcaatta aacttctaaa agtttaatct gagattcctt | 3180 |
| ataaaaactt ccagcaaagc aactttaaaa aagtctgtgt gggccgggcg cggtggctca | 3240 |
| cgcctgtaat cccagcactt tgatccgccg aggcgggcgg atcacgaggt caggagatcc | 3300 |
| agaccatcct ggctaacaca gtgaaacccc gtctctacta aaaatacaaa aaagttagc | 3360 |
| cgggcgtggt ggtgggggcc tgtagtccca gctactcagg aggctgaggc aggagaacgg | 3420 |
| catgaacccg ggaggcaggg cttgcagtga gccaagatca tgccgctgca ctccagcctg | 3480 |
| ggagacaaag tgagactccg tcaaaaaaaa aaaaagtct atgtggtcag tcactactct | 3540 |
| tgctgcagtt atgaaaagaa tgaggccaag tctgatgaaa ataaacttat tttgaaaaca | 3600 |

<210> SEQ ID NO 55
<211> LENGTH: 3095
<212> TYPE: DNA
<213> ORGANISM: Homo sapiens

<400> SEQUENCE: 55

| | |
|---|---:|
| attgctgatg gatcagtgag cctgtgttca tgccagtgag ctgctgtggc tcagatactg | 60 |
| atactttctt tccaaacagc ataagaagtg attgagccac aagtatactg aaggaagggc | 120 |
| tccctcgagt tctggtgtga agagataaat caccagtcac agactatgca cccgactgct | 180 |
| gctgttcagt ccagggaaaa tgaaagttgg agtgctgtgg ctcatttctt tcttcacctt | 240 |
| cactgacggc cacggtggct tcctggggaa aaatgatggc atcaaaacaa aaaagaact | 300 |
| cattgtgaat aagaaaaaac atctaggccc agtcgaagaa tatcagctgc tgcttcaggt | 360 |
| gacctataga gattccaagg agaaaagaga tttgagaaat tttctgaagc tcttgaagcc | 420 |
| tccattatta tggtcacatg ggctaattag aattatcaga gcaaaggcta ccacagactg | 480 |
| caacagcctg aatggagtcc tgcagtgtac ctgtgaagac agctacacct ggtttcctcc | 540 |
| ctcatgcctt gatccccaga actgctacct tcacacggct ggagcactcc caagctgtga | 600 |
| atgtcatctc aacaacctca gccagagtgt caatttctgt gagagaacaa agatttgggg | 660 |
| cactttcaaa attaatgaaa ggtttacaaa tgaccttttg aattcatctt ctgctatata | 720 |
| ctccaaatat gcaaatggaa ttgaaattca acttaaaaaa gcatatgaaa gaattcaagg | 780 |

```
ttttgagtcg gttcaggtca cccaatttcg aaatggaagc atcgttgctg ggtatgaagt      840
tgttggctcc agcagtgcat ctgaactgct gtcagccatt gaacatgttg ccagaaaggc      900
taagacagcc cttcacaagc tgtttccatt agaagacggc tctttcagag tgttcggaaa      960
agcccagtgt aatgacattg tctttggatt tgggtccaag gatgatgaat atccctgcc     1020 ctgcagcagt ggctacaggg gaaacatcac agccaagtgt gagtcctctg ggtggcaggt     1080
catcagggag acttgtgtgc tctctctgct tgaagaactg aacaagaatt tcagtatgat     1140
tgtaggcaat gccactgagg cagctgtgtc atccttcgtg caaaatcttt ctgtcatcat     1200
tcggcaaaac ccatcaacca cagtggggaa tctggcttcg gtggtgtcga ttctgagcaa     1260
tatttcatct ctgtcactgg ccagccattt cagggtgtcc aattcaacaa tggaggatgt     1320
catcagtata gctgacaata tccttaattc agcctcagta accaactgga cagtcttact     1380
gcgggaagaa aagtatgcca gctcacggtt actagagaca ttagaaaaca tcagcactct     1440
ggtgcctccg acagctcttc ctctgaattt ttctcggaaa ttcattgact ggaaagggat     1500
tccagtgaac aaaagccaac tcaaaagggg ttacagctat cagattaaaa tgtgtcccca     1560
aaatacatct attcccatca gaggccgtgt gttaattggg tcagaccaat tccagagatc     1620
ccttccagaa actattatca gcatggcctc gttgactctg gggaacattc tacccgtttc     1680
caaaaatgga aatgctcagg tcaatggacc tgtgatatcc acggttattc aaaactattc     1740
cataaatgaa gttttcctat ttttttccaa gatagagtca aacctgagcc agcctcattg     1800
tgtgttttgg gatttcagtc atttgcagtg gaacgatgca ggctgccacc tagtgaatga     1860
aactcaagac atcgtgacgt gccaatgtac tcacttgacc tccttctcca tattgatgtc     1920 acctttgtc ccctctacaa tcttccccgt tgtaaaatgg atcacctatg tgggactggg     1980
tatctccatt ggaagtctca ttttatgcct gatcatcgag gctttgtttt ggaagcagat     2040 taaaaaagc caaacctctc acacacgtcg tatttgcatg gtgaacatag ccctgtccct     2100
cttgattgct gatgtctggt ttattgttgg tgccacagtg gacaccacgg tgaaccttc     2160 tggagtctgc acagctgctg tgttctttac acacttcttc tacctctctt tgttcttctg     2220
gatgctcatg cttggcatcc tgctggctta ccggatcatc ctcgtgttcc atcacatggc     2280
ccagcatttg atgatggctg ttggattttg cctgggttat gggtgccctc tcattatatc     2340
tgtcattacc attgctgtca cgcaacctag caataccta aaaaggaaag atgtgtgttg     2400
gcttaactgg tccaatggaa gcaaaccact cctggctttt gttgtccctg cactggctat     2460
tgtggctgtg aacttcgttg tggtgctgct agttctcaca aagctctgga ggccgactgt     2520
tggggaaaga ctgagtcggg atgacaaggc caccatcatc cgcgtgggga agagcctcct     2580
cattctgacc cctctgctag ggctcacctg gggctttgga ataggaacaa tagtggacag     2640
ccagaatctg gcttggcatg ttatttttgc tttactcaat gcattccagg gatttttat     2700 cttatgcttt ggaatactct tggacagtaa gctgcgacaa cttctgttca caagttgtc     2760 tgccttaagt tcttggaagc aaacagaaaa gcaaaactca tcagatttat ctgccaaacc     2820
caaattctca aagcctttca acccactgca aaacaaaggc cattatgcat tttctcatac     2880
tggagattcc tccgacaaca tcatgctaac tcagtttgtc tcaaatgaat aaggcaagga     2940
atcataaaat caagaaaaaa tttccagaac aacttgacat ttagagacaa atgtcaatga     3000
agaaattatg ctcagtattc gatcgggttt tctgatttag gggtctggga ataaaacaag     3060
aatgtctcag tggcttcaaa aaaaaaaaaa aaaaa                                3095
```

<210> SEQ ID NO 56
<211> LENGTH: 4071
<212> TYPE: DNA
<213> ORGANISM: Homo sapiens

<400> SEQUENCE: 56

| | | | | | | |
|---|---|---|---|---|---|---|
| tgattcgagc | gggaagaggg | gggtgggtgg | gatcggtggg | ggagaccatg | acctccagct | 60 |
| acgggcacgt | tctggagcgg | caaccggcgc | tgggcggccg | cttggacagc | ccggcaacc | 120 |
| tcgacaccct | gcaggcgaaa | aagaacttct | ccgtcagtca | cctgctagac | ctggaggaag | 180 |
| ccggggacat | ggtggcggca | caggcggatg | agaacgtggg | cgaggctggc | cggagcctgc | 240 |
| tggagtcgcc | gggactcacc | agcggcagcg | acaccccgca | gcaggacaat | gaccagctga | 300 |
| actcagaaga | aaaaagaag | agaaagcagc | gaaggaatag | gacaaccttc | aatagcagcc | 360 |
| agctgcaggc | tttggagcgt | gtctttgagc | ggacacacta | tcctgatgct | tttgtgcgag | 420 |
| aagaccttgc | ccgccgggtg | aacctcaccg | aggcgagagt | gcaggtgtgg | tttcagaacc | 480 |
| gaagagccaa | gttccgcagg | aatgagagag | ccatgctagc | caataaaaac | gcttccctcc | 540 |
| tcaaatccta | ctcaggagac | gtgactgctg | tggagcagcc | catcgtacct | cgtcctgctc | 600 |
| cgagacccac | cgattatctc | tcctggggga | cagcgtctcc | gtacagatcc | tcgtccctcc | 660 |
| caagatgttg | tttacacgag | gggcttcata | acggattcta | acggaagaca | ctgaaaagcg | 720 |
| ccatggctac | ttattctgcc | acatgtgcca | acaatagccc | tgcacagggc | atcaacatgg | 780 |
| ccaacagcat | tgccaacctg | agactgaagg | ccaaggaata | tagtttacag | aggaaccagg | 840 |
| tgccaacagt | caactgagga | aaaaaaataa | ttaaacaggc | taagaagaa | atcaaaaacc | 900 |
| ataagacacc | tatcctgctc | tgttatttct | tcatctgctg | ggggaaaaa | gtaaattaca | 960 |
| aacaaacaaa | caaagcagaa | ctaaaatatt | gggaccatgg | cagagaaaag | caggagagga | 1020 |
| gcaaaatgaa | aattagttaa | caaatgttcc | tcctccctct | gggataccac | caccacttgt | 1080 |
| ttctgtgtgt | gtttattttg | tttttctttc | attcatgctt | tgcttaatgt | actccaggct | 1140 |
| tcttcagata | ggttcagccc | acccacccc | atgattgtat | gaagttttaa | aaaaaactac | 1200 |
| agcagccaaa | gaaactatat | atatatatat | atatatatat | atccagaatg | attgcctcta | 1260 |
| ctgtcctcat | tgacttgttt | gaaccttagt | gccttacccct | gtcctcttcc | cagttctctt | 1320 |
| tatagaagct | ctaggagctt | tcgaaaagcc | aaagtctttc | tgaagaatct | gtgctggaca | 1380 |
| gacataattc | cctttctcat | tgtctccatc | tttgttggtc | atggtaaggt | ttttccatca | 1440 |
| gcctctgaaa | aaatagttgt | gcacaacatc | tgctcactgg | actgtctgat | ccaatgtaat | 1500 |
| tggctgcgtc | tggctaattc | taagcactaa | agtctacatc | taagctatag | atttaagctt | 1560 |
| gaagctacag | attatatcac | tatcaccacc | acccctcacc | ctatgcaatc | aatcaatcaa | 1620 |
| tcatcttaag | ttaaagatat | tgttgtctt | tgaatgattt | gctgtcacag | actatttggt | 1680 |
| agaagaaata | ttttcacct | gagagaggaa | gagaaatttc | tctagtaaca | caaagagtga | 1740 |
| gttctaaaag | gcatgcccac | atctctttcg | tgccttaagg | atagtgagat | gcacacttat | 1800 |
| atatatactg | tatatattta | tatatttata | tatatatttc | atatatatat | ataatattgc | 1860 |
| aagcttaagt | ttgcaatttc | ccaaacaata | caaaaagcaa | attacacacc | ctcaccactg | 1920 |
| ttcttatctc | tatagtgatg | aaacattaat | tagggatctt | gctgcttttc | ttttttctaca | 1980 |
| cgaagttttc | attaaagcca | cagaataatt | gatagggcag | ctgtttgaga | acaggtccca | 2040 |
| ttttcacatt | agggctttaa | atgaattaga | aactatttga | ggctataaaa | atgtccttga | 2100 |
| gtttggagcc | tgagctctgg | tgaaatgctg | atacatctga | tctatcatgg | gaattgcagt | 2160 |

```
tagagagagt aaggaatacc atttagtcat ctatccgttc ttcacttagc aggaatatga    2220
aagaaaggca catgtttaag aggaatacct aaaggttttt ctaaattcca acatttaaaa    2280
ggcaattgtg ggctattttt attttttaat attttgaaat aaagtttagt gtctagggct    2340
gggagccagg actgatcttc catttctttt tctttgttcc cagccatgct tttgtaactt    2400
gccaggtgga cttgaccaac tacattacca tgctgtgcct cagtttaccc atttgtaaaa    2460
tgggattaat aatacttacc tacctcacag gggtgttgtg aggctctatt catttgctcc    2520
tttattcttt cctgtattct ctgtatgtcc agcactttgt agccatggga ggaaagggac    2580
tataaaagtg tacaatgtta atggaatgat acggtacctg aaagccttgt tttctagtaa    2640
gaaaatgcta ccttgctgta catacttata accttgtatt tggaaatgag aaataggttt    2700
atattttcag atctctcaaa aatcacatca tttgaccaaa gaataattta agacacatag    2760
aacagatttt tttaatttat attttcatcc tgaccagctt agttctaata attttttagtt   2820 gtgagtgatt aaaaaacttt ggatcaattt tggtcaaaca tgccaacttt gtagtctgag    2880
tgacaggcaa ggattttttgg gtttaagatg cacttttagc acacatttgt atttcccttg   2940
gcatatcaga ttgagctaat ggtgatgtta tttcaatcta acagccacca atctgaaatt    3000
gtatttcaaa tgttgattct gtagttcttt aaataataat gaagctcatc ttatacattt    3060
tgctttcacc aattgattcc ttcttctttt agcccactat taaacatttt cttactgaat    3120
ggttcatgta ggcttgctga acagcacgca ttacttgctt cctgaagagt tcccccattc    3180
atccatttgt cccattagtt gctgtggatt atcaagtttt gaaggaactg tacatcccaa    3240
cagactgaaa cattctaagt gaaatgagta taatccaagt aactggtgaa ctttggaggt    3300
ttggagcttg aagagaatgg ctaagaagat ttgaattata gggagggaac agaaatcata    3360
catgaaaagg ttttactgag aaggggaaaa ccttagatag agggacatgt gaaacaaaat    3420
catttgaaat tttgattcag acatccatttt ccagtggcaa acagcaaagc ctgaacccat   3480
aaacccaaat gataggtgaa gttgggtggt tttatccaat gtctcaagca agcaatgtct    3540
gggaatatca tagagtaaca agtgctggtc agccaaagaa acattcactg ctggtgaacc    3600
aataccataa gcatgtatta tctaagcact tgatcaagaa atatacatgt tgtacaagct    3660
ctcaattttg ttcatttatt atcaaatttt taaaatacaa gtttggtatg tgatttggaa    3720
aagatgcctt ctggatctta agccagttgt cagtggaggt cctcagggct gcaaatgtca    3780
agacataacc ctgttcctca ccatcatgat accagataca ggtgaataca taggaactat    3840
ctgcctgtgt cctcaatctc ccttcaaaca agatgctgat ttgtagggta cttggcaggt    3900
taaattaaac cagaagaggt gacttaataa aaaagggaat gacatttagg gtataaagat    3960
ctcataagaa atgtaatatg taaattatat cttgctttat gttgtaaaat atacattgtt    4020
tgcgctagaa tagaaatgat ttcttttcaa taaaaagaaa gaaggactct a             4071
```

<210> SEQ ID NO 57
<211> LENGTH: 3999
<212> TYPE: DNA
<213> ORGANISM: Homo sapiens

<400> SEQUENCE: 57

```
tgattcgagc gggaagaggg gggtgggtgg gatcggtggg ggagaccatg acctccagct      60
acgggcacgt tctggagcgg caaccggcgc tgggcggccg cttggacagc ccgggcaacc     120
tcgacaccct gcaggcgaaa aagaacttct ccgtcagtca cctgctagac ctggaggaag     180
```

-continued

```
ccggggacat ggtggcggca caggcggatg agaacgtggg cgaggctggc cggagcctgc    240
tggagtcgcc gggactcacc agcggcagcg acaccccgca gcaggacaat gaccagctga    300
actcagaaga aaaaagaag agaaagcagc gaaggaatag acaaccttc aatagcagcc     360 agctgcaggt tttggagcgt gtctttgagc ggacacacta tcctgatgct tttgtgcgag    420
aagaccttgc ccgccgggtg aacctcaccg aggcgagagt gcaggtgtgg tttcagaacc    480
gaagagccaa gttccgcagg aatgagagag ccatgctagc caataaaaac gcttccctcc    540
tcaaatccta ctcaggagac gtgactgctg tggagcagcc catcgtacct cgtcctgctc    600
cgagacccac cgattatctc tcctggggga cagcgtctcc gtacagcgcc atggctactt    660
attctgccac atgtgccaac aatagccctg cacagggcat caacatggcc aacagcattg    720
ccaacctgag actgaaggcc aaggaatata gtttacagag gaaccaggtg ccaacagtca    780
actgaggaaa aaaataatt aaacaggcct aagaagaaat caaaaaccat aagacaccta    840
tcctgctctg ttatttcttc atctgctggg gggaaaagt aaattacaaa caaacaaaca    900
aagcagaact aaaatattgg gaccatggca gagaaaagca ggagaggagc aaaatgaaaa    960
ttagttaaca aatgttcctc ctccctctgg gataccacca ccacttgttt ctgtgtgtgt    1020
ttattttgtt tttctttcat tcatgctttg cttaatgtac tccaggcttc ttcagatagg    1080
ttcagcccac ccaccccat gattgtatga agttttaaaa aaaactacag cagccaaaga    1140
aactatatat atatatatat atatatatat ccagaatgat tgcctctact gtcctcattg    1200
acttgtttga accttagtgc cttaccctgt cctcttccca gttctctttt tagaagctct    1260
aggagctttc gaaaagccaa agtctttctg aagaatctgt gctggacaga cataattccc    1320
tttctcattg tctccatctt tgttggtcat ggtaaggttt ttccatcagc ctctgaaaaa    1380
atagttgtgc acaacatctg ctcactggac tgtctgatcc aatgtaattg ctgcgtctg    1440 gctaattcta agcactaaag tctacatcta agctatagat ttaagcttga agctacagat    1500
tatatcacta tcaccaccac ccctcaccct atgcaatcaa tcaatcaatc atcttaagtt    1560
aaagatattt gttgtctttg aatgatttgc tgtcacagac tatttggtag aagaaatatt    1620
tttcacctga gagaggaaga gaaatttctc tagtaacaca aagagtgagt tctaaaaggc    1680
atgcccacat ctctttcgtg ccttaaggat agtgagatgc acacttatat atatactgta    1740
tatatttata tatttatata tatatttcat atatatatat aatattgcaa gcttaagttt    1800
gcaatttccc aaacaataca aaaagcaaat tacacaccct caccactgtt cttatctcta    1860
tagtgatgaa acattaatta gggatcttgc tgcttttctt tttctacacg aagttttcat    1920
taaagccaca gaataattga tagggcagct gtttgagaac aggtcccatt ttcacattag    1980
ggctttaaat gaattagaaa ctatttgagg ctataaaaat gtccttgagt ttggagcctg    2040
agctctggtg aaatgctgat acatctgatc tatcatggga attgcagtta gagagagtaa    2100
ggaataccat ttagtcatct atccgttctt cacttagcag gaatatgaaa gaaaggcaca    2160
tgtttaagag gaatacctaa aggttttct aaattccaac atttaaaagg caattgtggg    2220 ctattttttat tttttaatat tttgaaataa agtttagtgt ctagggctgg gagccaggac    2280
tgatcttcca tttctttttc tttgttccca gccatgcttt tgtaacttgc caggtggact    2340
tgaccaacta cattaccatg ctgtgcctca gtttacccat ttgtaaaatg ggattaataa    2400
tacttaccta cctcacaggg gtgttgtgag gctctattca tttgctcctt tattctttcc    2460
tgtattctct gtatgtccag cactttgtag ccatgggagg aaagggacta taaagtgta    2520 caatgttaat ggaatgatac ggtacctgaa agccttgttt tctagtaaga aaatgctacc    2580
```

| | |
|---|---|
| ttgctgtaca tacttataac cttgtatttg gaaatgagaa ataggtttat attttcagat | 2640 |
| ctctcaaaaa tcacatcatt tgaccaaaga ataatttaag acacatagaa cagatttttt | 2700 |
| taatttatat tttcatcctg accagcttag ttctaataat ttttagttgt gagtgattaa | 2760 |
| aaaactttgg atcaatttg gtcaaacatg ccaactttgt agtctgagtg acaggcaagg | 2820 |
| attttggg ttaagatgca cttttagcac acatttgtat ttcccttggc atatcagatt | 2880 |
| gagctaatgg tgatgttatt tcaatctaac agccaccaat ctgaaattgt atttcaaatg | 2940 |
| ttgattctgt agttctttaa ataataatga agctcatctt atacattttg ctttcaccaa | 3000 |
| ttgattcctt cttcttttag cccactatta aaacatttct tactgaatgg ttcatgtagg | 3060 |
| cttgctgaac agcacgcatt acttgcttcc tgaagagttc ccccattcat ccatttgtcc | 3120 |
| cattagttgc tgtggattat caagttttga aggaactgta catcccaaca gactgaaaca | 3180 |
| ttctaagtga aatgagtata atccaagtaa ctggtgaact ttggaggttt ggagcttgaa | 3240 |
| gagaatggct aagaagattt gaattatagg gagggaacag aaatcataca tgaaaaggtt | 3300 |
| ttactgagaa ggggaaaacc ttagatagag ggacatgtga acaaaatca tttgaaattt | 3360 |
| tgattcagac atccatttcc agtggcaaac agcaaagcct gaacccataa acccaaatga | 3420 |
| taggtgaagt tgggtggttt tatccaatgt ctcaagcaag caatgtctgg gaatatcata | 3480 |
| gagtaacaag tgctggtcag ccaaagaaac attcactgct ggtgaaccaa taccataagc | 3540 |
| atgtattatc taagcacttg atcaagaaat atacatgttg tacagctct caattttgtt | 3600 |
| catttattat caaattttta aaatacaagt ttggtatgtg atttggaaaa gatgccttct | 3660 |
| ggatcttaag ccagttgtca gtggaggtcc tcagggctgc aaatgtcaag acataaccct | 3720 |
| gttcctcacc atcatgatac cagatacagg tgaatacata ggaactatct gcctgtgtcc | 3780 |
| tcaatctccc ttcaaacaag atgctgattt gtagggtact tggcaggtta aattaaacca | 3840 |
| gaagaggtga cttaataaaa aagggaatga catttagggt ataaagatct cataagaaat | 3900 |
| gtaatatgta aattatatct tgctttatgt tgtaaaatat acattgtttg cgctagaata | 3960 |
| gaaatgattt cttttcaata aaagaaaga aggactcta | 3999 |

<210> SEQ ID NO 58
<211> LENGTH: 2466
<212> TYPE: DNA
<213> ORGANISM: Homo sapiens

<400> SEQUENCE: 58

| | |
|---|---|
| ggctgagtgg tttgctcctt cccctctctc tgggaggctg agcaggggtg ccgggttgct | 60 |
| caggccatgg gagccacacc tgttattgct gcctctgatt tgtgtgacac tgagaagccc | 120 |
| acaggcctgt ccctccaact cggtggaccc tctctgtgtg catttggtgt gtgagccagc | 180 |
| tctgagaagg gttcagaagc cactggaggc atctgggac ctcagcttcc atgccatctc | 240 |
| tgcctcactc ccacagggta atgttggact cggtgacaca cagcaccttc ctgcctaatg | 300 |
| catccttctg cgatcccctg atgtcgtgga ctgatctgtt cagcaatgaa gagtactacc | 360 |
| ctgcctttga gcatcagaca gcctgtgact catactggac atcagtccac cctgaatact | 420 |
| ggactaagcg ccatgtgtgg gagtggctcc agttctgctg cgaccagtac aagttggaca | 480 |
| ccaattgcat ctccttctgc aacttcaaca tcagtggcct gcagctgtgc agcatgacac | 540 |
| aggaggagtt cgtcgaggca gctggcctct cggcgagta cctgtacttc atcctccaga | 600 |
| acatccgcac acaaggttac tccttttttta atgacgctga agaaagcaag gccaccatca | 660 |

```
aagactatgc tgattccaac tgcttgaaaa caagtggcat caaaagtcaa gactgtcaca      720
gtcatagtag aacaagcctc caaagttctc atctatggga atttgtacga gacctgcttc      780
tatctcctga agaaaactgt ggcattctgg aatgggaaga tagggaacaa ggaatttttc      840
gggtggttaa atcggaagcc ctggcaaaga tgtggggaca aaggaagaaa aatgacagaa      900
tgacatatga aaagttgagc agagccctga gatactacta taaaacagga attttggagc      960
gggttgaccg aaggttagtg tacaaatttg gaaaaaatgc acacgggtgg caggaagaca     1020
agctatgatc tgctccaggc atcaagctca ttttatggat ttctgtcttt taaaacaatc     1080
agattgcaat agacattcga aaggcttcat tttcttctct ttttttttaa cctgcaaaca     1140
tgctgataaa atttctccac atctcagctt acatttggat tcagagttgt tgtctacgga     1200
gggtgagagc agaaactctt aagaaatcct ttcttctccc taaggggatg agggggatgat   1260 cttttgtggt gtcttgatca aactttattt tcctagagtt gtggaatgac aacagcccat     1320
gccattgatg ctgatcagag aaaaactatt caattctgcc attagagaca catccaatgc     1380
tcccatccca aaggttcaaa agtttttcaaa taactgtggc agctcaccaa aggtggggga     1440
aagcatgatt agtttgcagg ttatggtagg agagggtgag atataagaca tacatacttt     1500 agatttttaaa ttattaaagt caaaaatcca tagaaaagta tcccttttt tttttttgag     1560 acgggtctct actatgttgc ccagggctgg tcttgaactc ctatgctcaa gtgatcctcc     1620
cacctcggcc tcccaaagta ctgtgattac aagcgtgagc cacggcacct gggcagaaaa    1680
gtatcttaat taatgaaaga gctaagccat caagctggga cttaattgga tttaacatag     1740
gttcacagaa agtttcctaa ccagagcatc ttttttgacca ctcagcaaaa cttccacaga   1800
catccttctg gacttaaaca cttaacatta accacattat taattgttgc tgagtttatt     1860
cccccttcta actgatggct ggcatctgat atgcagagtt agtcaacaga cactggcatc     1920
aattacaaaa tcactgctgt ttctgtgatt caagctgtca acacaataaa atcgaaattc     1980
attgattcca tctctggtcc agatgttaaa cgtttataaa accggaaatg tcctaacaac     2040
tctgtaatgg caaattaaat tgtgtgtctt ttttgttttg tctttctacc tgatgtgtat     2100
tcaagcgcta taacacgtat ttccttgaca aaaatagtga cagtgaattc acactaataa     2160
atgttcatag gttaaagtct gcactgacat tttctcatca atcactggta tgtaagttat     2220
cagtgactga cagctaggtg gactgcccct aggacttctg tttcaccaga gcaggaatca     2280
agtggtgagg cactgaatcg ctgtacaggc tgaagacctc cttattagag ttgaacttca     2340
aagtaacttg ttttaaaaaa tgtgaattac tgtaaaataa tctatttgg attcatgtgt      2400 tttccaggtg gatatagttt gtaaacaatg tgaataaagt atttaacatg taaaaaaaaa     2460
aaaaaa                                                               2466
```

<210> SEQ ID NO 59
<211> LENGTH: 3127
<212> TYPE: DNA
<213> ORGANISM: Homo sapiens

<400> SEQUENCE: 59

```
gaagctccac accagccatt acaaccctgc caatctcaag cacctgcctc tacagttggt       60
acagatggca ttgtcccagt ctgttccctt ctcggccaca gagcttctcc tggcctctgc      120
catcttctgc ctggtattct gggtgctcaa gggtttgagg cctcgggtcc ccaaaggcct      180
gaaaagtcca ccagagccat ggggctggcc cttgctcggg catgtgctga ccctgggaa      240 gaacccgcac ctggcactgt caaggatgag ccagcgctac ggggacgtcc tgcagatccg      300
```

```
cattggctcc acgcccgtgc tggtgctgag ccgcctggac accatccggc aggccctggt    360
gcggcagggc gacgatttca agggccggcc tgacctctac acctccaccc tcatcactga    420
tggccagagc ttgaccttca gcacagactc tggaccggtg tgggctgccc gccggcgcct    480
ggcccagaat gccctcaaca ccttctccat cgcctctgac ccagcttcct catcctcctg    540
ctacctggag gagcatgtga gcaaggaggc taaggccctg atcagcaggt tgcaggagct    600
gatggcaggg cctgggcact tcgacccctta caatcaggtg gtggtgtcag tggccaacgt    660
cattggtgcc atgtgcttcg gacagcactt ccctgagagt agcgatgaga tgctcagcct    720
cgtgaagaac actcatgagt tcgtggagac tgcctcctcc gggaaccccc tggacttctt    780
ccccatcctt cgctacctgc ctaaccctgc cctgcagagg ttcaaggcct tcaaccagag    840
gttcctgtgg ttcctgcaga aaacagtcca ggagcactat caggactttg acaagaacag    900
tgtccgggac atcacgggtg ccctgttcaa gcacagcaag aaggggccta gagccagcgg    960
caacctcatc ccacaggaga agattgtcaa ccttgtcaat gacatctttg agcaggatt    1020 tgacacagtc accacagcca tctcctggag cctcatgtac cttgtgacca gcctgagat    1080 acagaggaag atccagaagg agctggacac tgtgattggc agggagcggc ggccccggct    1140
ctctgacaga ccccagctgc cctacttgga ggccttcatc ctggagacct tccgacactc    1200
ctccttcttg cccttcacca tcccccacag cacaacaagg gacacaacgc tgaatggctt    1260
ctacatcccc aagaaatgct gtgtcttcgt aaaccagtgg caggtcaacc atgacccaga    1320
gctgtgggag gacccctctg agttccggcc tgagcggttc ctcaccgccg atggcactgc    1380
cattaacaag cccttgagtg agaagatgat gctgtttggc atgggcaagc gccggtgtat    1440
cggggaagtc ctggccaagt gggagatctt cctcttcctg gccatcctgc tacagcaact    1500
ggagttcagc gtgccgccgg cgtgaaagt cgacctgacc cccatctacg ggctgaccat    1560
gaagcacgcc cgctgtgaac atgtccaggc gcggctgcgc ttctccatca attgaagaag    1620
acaccaccat tctgaggcca gggagcgagt gggggccagc cacggggact cagcccttgt    1680
ttctcttcct ttctttttt aaaaaatagc agctttagcc aagtgcaggg cctgtaatcc    1740
cagcatttta ggaggccaag gttggaggat catttgagcc caggaattgg aaagcagcct    1800
ggccaacata gtgggaccct gtctctacaa aaaaaaatt tgccaagagc ctgagtgaca    1860
gagcaagacc ccatctcaaa aaaaaaaaca aacaaacaaa aaaaaaacca tatatataca    1920
tatatatata gcagctttat ggagatataa ttcttatgcc atataattca ccttctttt    1980 tttttttgt ctgagacaga atctcagtct gtcacccagg ttggagtgca gtggcgtgat    2040
ctcagctcac tgcaacctcc acctcgcagg ttcaagcaat cctcccactt cagcctccca    2100
agcacctggg attacaagca tgagtcacta cgcctggctg attttttgtag ttttagtgga    2160 gatggggttt caccatgttg gccaggcttg tctcgaactc ctgaccccaa gttatccacc    2220
tgccttggct tcccaaagtc ctgggattac aggtgtgagc caccacatcc agcctaactt    2280
acattcttaa agtgtcgaat gacttctagt gtagaattgt gcaaccatca ccagaattaa    2340
ttttattatt cttattattt ttgagacaga gtcttactct gttgccaggc tggagtgcag    2400
tggcgcgatc tcagctcact acaacctccg cctcccatgt tcaagcgatt ctcctgcctc    2460
agcctcccga gtagctggga ctataggcat gcgccaccat ggccagctaa tttttgtatt    2520
tttagtagag acgaggtttc actgtgttgg ccaggatggt ctccatctct tgacctcgtg    2580
atccacccgc ctcagcctcc caaagtgctg ggattaacag gtatgaacca ccgcgcccag    2640
```

```
ccttttttgtt  ttttttttttt  ttgagacaga  gtcttcctct  gtctcctaag  ctggagtgca   2700
gtggcatcat   ctcagctcac   tgcaacctct  gcctcccagg  ttcaagtgct  tctccagcct   2760
cagcctccca   agtagctgag   actacaggca  cacaccacca  cgcctggcta  atttttgtat   2820
ttttagtaga   gacgggtttc   accatgttgg  ctagactagt  ctcaaactcc  tgacctcaag   2880
tgatctgccc   gcctcgacct   ctctcaaagt  gctggcatta  caggtgtgag  ccacggtgcc   2940
cggcccacaa   ttaattttag   aacattttca  tcacccctaa  aagaaaccct  gcacccatta   3000
gcagtccctc   cacatttccc   cctagcctgc  ctcccctgcc  tcaccagccc  tggcaactgc   3060
taatctactt   tctgtgtcta   tggatttgcc  ttctctaaac  atttcatata  aatggaatta   3120
cacaatg                                                                    3127
```

METHODS OF DIAGNOSING CHRONIC OBSTRUCTIVE PULMONARY DISEASE (COPD) USING NOVEL MOLECULAR BIOMARKERS

This application is a national phase application under 35 U.S.C. § 371 of International Application No. PCT/EP2015/062431, filed Jun. 3, 2015, which claims benefit of European Application No. 14171388.3, filed Jun. 5, 2014, the entire contents of each of which are hereby incorporated by reference.

The present invention relates to in vitro methods for the diagnosis of chronic obstructive pulmonary disease (COPD), wherein the expression of the marker gene DMBT1 is determined. In particular, the invention relates to an in vitro diagnostic method of assessing the susceptibility of a subject to develop progressive COPD involving the appearance of irreversible lung damage, wherein the expression of the marker gene DMBT1 and optionally one or more further marker genes selected from KIAA1199, TMSB15A, DPP6, SLC51B, NUDT11, ELF5, AZGP1, PRRX1, AQP3, SFN, GPR110, GDF15, RASGRF2, RND1, PLA1A, FGG, CEACAM5, HYAL2, AHRR, CXCL3, CYP1A1, CYP1B1, CYP1A2, CST6, NTRK2, COMP, ITGA10, CTHRC1, TAL1, FIBIN, BEX5, BEX1, ESM1 and GHRL is determined. The invention also relates to an in vitro method of diagnosing stable COPD or assessing the susceptibility of a subject to develop stable COPD, wherein the expression of DMBT1 and optionally one or more further marker genes selected from KIAA1199, TMSB15A, DPP6, SLC51B, NUDT11, ELF5, AZGP1, PRRX1, AQP3, SFN, GPR110, GDF15, RASGRF2, RND1, PLA1A, FGG, CEACAM5, HYAL2, AHRR, CXCL3, CYP1A1, CYP1B1, CYP1A2, CST6, NTRK2, COMP, ITGA10, CTHRC1, TAL1, FIBIN, BEX5, BEX1, ESM1 and GHRL is determined. Furthermore, the invention relates to the use of primers for transcripts of the aforementioned marker genes, the use of nucleic acid probes to transcripts of these marker genes, the use of microarrays comprising nucleic acid probes to transcripts of these marker genes, and the use of antibodies against the proteins expressed from these marker genes in corresponding in vitro methods. In vitro methods of monitoring the progression of COPD are also provided, in which the expression of marker genes according to the invention is determined.

COPD represents one of the leading pathologies of the world's elderly population. Triggered by long-term exposure to combustion products, climatic conditions and repeated infections, COPD has become the fourth-leading cause of mortality in aged individuals. During the last decades, the worldwide prevalence of COPD has risen by more than 10%, particularly in active smokers beyond the age of 55 (Murray et al., 1997). Given the increasing number of elderly people in the world's population and the world-wide increase of inhalative hazards, both occupational and personal, COPD must be regarded as one of the most challenging threats to the world's health systems (Halbert et al., 2006; US Burden of Disease Collaborators, 2013). However, although the impact of COPD on health conditions is increasingly understood, the mechanisms that cause and maintain the progression of the disease are largely unknown. Based on clinical experience and results of controlled studies, COPD is regarded as a largely inflammatory disease. However, while long-term anti-inflammatory treatment may improve the outcome in COPD, its impact on the overall pathology of the disease is less clear. The TORCH (TOwards a Revolution in COPD Health) study has clearly shown that this unilateral view upon the pathophysiology of COPD is not entirely correct as patients who were under continuous treatment with inhaled corticosteroids did not have a better outcome than those without. In line with this, several well-defined clinical trials have tried to stratify patients according to relevant clinical phenotypes, the ECLIPSE (Evaluation of COPD Longitudinally to Identify Predictive Surrogate Endpoints) study being the latest and most important attempt thus far (Vestbo et al., 2011). While these attempts have proven the remarkable heterogeneity of the clinical manifestations of COPD, they unfortunately failed to improve the understanding of the disease's central driving forces, their mediators, and their hierarchy in evoking the clinical phenotypes of COPD.

Until recently, COPD has been largely defined by the limitation of the maximum volume of air exhaled in one second during forced expiration ($FEV_1$), as well as by the total amount of air exhaled (forced [expiratory] vital capacity, FVC), and their respective relationship (Wedzicha J A, 2000). However, the variability of the clinical presentation of COPD regardless of any individual degree of airflow limitation suggested that the disease comprises different mechanisms related to bronchial and peribronchial pathologies (Hurst et al., 2010; Han et al., 2010). As a consequence, further clinical measures have been added to the diagnostic process in COPD, such as the intensity of bronchial inflammation, the frequency of disease exacerbations or the presence of comorbidities (Vestbo et al., 2013).

Not surprisingly, $FEV_1$ does not correlate well with symptom development. However, many studies have clearly demonstrated that $FEV_1$ is a strong predictor of mortality and morbidity in COPD, suggesting a relevant correlation between the (morphologically fixed) obstruction of the peripheral airways and the pathophysiology of the disease. Given the probability that the morphology of the small airways is going to reflect the pathologic net result of all metabolic events within this lung compartment, including chronic inflammatory and regenerative activities, this is more than plausible. Based on these facts, it still seems appropriate to apply the symptoms of the most established clinical manifestations of COPD, i.e. fixed bronchial obstruction and intensity of bronchitis as the main clinical indicators for a first attempt to delineate mechanisms and mediators capable of driving the pathology of COPD. In view of the well-documented long-term history of COPD often covering periods of more than two decades, any attempt to delineate the pathology of the disease ought to a) cover the earliest phase of pathologic development, the establishment of chronic bronchitis (COPD "at risk" according to the GOLD (Global Initiative on Obstructive Lung Disease) criteria) likely to precede the first manifestation of "irreversible" bronchial obstruction, b) to include both long-term development of the disease preceding the controlled phase of clinical assessment and c) to span a period long enough to allow for the identification of important short-range effects on COPD pathology. Lastly, as the pathology of COPD is focused in the small airways (Hogg J C, et al., 2004 (a)), the initial biological assessment ought to be performed in this compartment, regardless of the fact that some characteristic symptoms, such as the production of phlegm as a sign of intensified bronchitis, will also reflect the metabolic activity of the more central airways.

COPD progressively debilitates patients, resulting in an increasing disability and worsening impact of exacerbations. In particular, the development of irreversible damage to the lungs commences and then gradually worsens when a patient suffering from COPD advances from the stable early disease stage into the progressive stage of COPD. Unfortunately, many patients with COPD remain undiagnosed and potentially unknown to healthcare providers until the more advanced stages of the disease. In such cases, the delayed diagnosis of COPD results in patients suffering from symptoms and limitations that could otherwise be alleviated by treatment (Price et al., 2011). It would therefore be highly desirable to be able to diagnose COPD at an early disease stage and, in particular, to identify patients who are at risk of developing progressive COPD in order to be able to prevent these patients from suffering significant irreversible damage.

It is therefore an object of the present invention to provide novel and/or improved methods that allow to diagnose COPD at an early disease stage or to assess the risk or susceptibility of a subject to develop COPD. It is furthermore an object of the invention to provide novel and/or improved methods that allow to assess the susceptibility of a subject to develop progressive COPD.

The present invention is based on the unexpected finding that the gene DMBT1 as well as the genes KIAA1199, TMSB15A, DPP6, SLC51B, NUDT11, ELF5, AZGP1, PRRX1, AQP3, SFN, GPR110, GDF15, RASGRF2, RND1, PLA1A, FGG, CEACAM5, HYAL2, AHRR, CXCL3, CYP1A1, CYP1B1, CYP1A2, CST6, NTRK2, COMP, ITGA10, CTHRC1, TAL1, FIBIN, BEX5, BEX1, ESM1 and GHRL are differentially expressed in samples from subjects suffering from progressive COPD or subjects at risk/prone to develop progressive COPD on the one hand, and in control samples from healthy subjects on the other hand. In particular, and as also described in Example 1, it has been found that the expression of the genes DMBT1, KIAA1199, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and COMP is upregulated in samples from patients suffering from progressive COPD or at risk of developing progressive COPD, while the expression of the genes TMSB15A, DPP6, SLC51B, NUDT11, PLA1A, HYAL2, CST6, ITGA10, CTHRC1, TAL1, FIBIN, BEX5, BEX1, ESM1 and GHRL is downregulated in samples from patients suffering from progressive COPD or at risk of developing progressive COPD, as compared to the expression of the corresponding genes in control samples from healthy patients. Therefore, in accordance with the present invention, these novel molecular biomarkers can advantageously be used for assessing the susceptibility/proneness of a subject to develop progressive COPD. It has further been surprisingly found that the genes DMBT1, KIAA1199, TMSB15A, DPP6, SLC51B, NUDT11, ELF5, AZGP1, PRRX1, AQP3, SFN, GPR110, GDF15, RASGRF2, RND1, PLA1A, FGG, CEACAM5, HYAL2, AHRR, CXCL3, CYP1A1, CYP1B1, CYP1A2, CST6, NTRK2, COMP, ITGA10, CTHRC1, TAL1, FIBIN, BEX5, BEX1, ESM1 and GHRL are differentially expressed in samples from subjects suffering from stable COPD or subjects at risk/prone to develop stable COPD on the one hand, and in control samples from healthy subjects on the other hand. In this connection, it has particularly been found that the expression of the genes KIAA1199, TMSB15A, DPP6, SLC51B, NUDT11, PLA1A, HYAL2, CST6, ITGA10, CTHRC1, TAL1, FIBIN, BEX5, BEX1, ESM1 and GHRL is downregulated in samples from patients having stable COPD or at risk of developing stable COPD, while the expression of the genes DMBT1, ELF5, AZGP1, PRRX1, AQP3, SFN, GPR110, GDF15, RASGRF2, RND1, FGG, CEACAM5, CXCL3, CYP1A1, CYP1B1, CYP1A2, NTRK2 and COMP is upregulated in samples from patients having stable COPD or at risk of developing stable COPD, as compared to the expression of the corresponding genes in control samples from healthy patients. In accordance with the present invention, these novel molecular biomarkers can thus be used for diagnosing stable COPD and/or assessing the susceptibility/proneness of a subject to develop stable COPD. Moreover, the biomarkers provided herein have excellent sensitivity and/or specificity.

Accordingly, in a first aspect the present invention provides an in vitro method for the diagnosis of COPD, the method comprising determining the level of expression of the gene DMBT1 in a sample obtained from a subject.

In accordance with this first aspect, the invention also relates to the use of DMBT1 as a marker for the in vitro diagnosis of COPD.

In a second aspect, the present invention provides an in vitro diagnostic method of assessing the susceptibility of a subject to develop progressive COPD involving the appearance of irreversible lung damage, the method comprising:
  determining the level of expression of the gene DMBT1 in a sample obtained from the subject;
  comparing the level of expression of DMBT1 in the sample from the subject to a control expression level of DMBT1 in a healthy subject; and
  determining whether or not the subject is prone to develop progressive COPD involving the appearance of irreversible lung damage, wherein an increase in the level of expression of DMBT1 in the sample from the subject as compared to the control expression level of DMBT1 is indicative of a proneness to develop progressive COPD.

It is preferred that in this second aspect the method further comprises:
  determining the level of expression of one or more further genes selected from KIAA1199, TMSB15A, DPP6, SLC51B, NUDT11, ELF5, AZGP1, PRRX1, AQP3, SFN, GPR110, GDF15, RASGRF2, RND1, PLA1A, FGG, CEACAM5, HYAL2, AHRR, CXCL3, CYP1A1, CYP1B1, CYP1A2, CST6, NTRK2, COMP, ITGA10, CTHRC1, TAL1, FIBIN, BEX5, BEX1, ESM1 and GHRL in the sample obtained from the subject;
  comparing the level of expression of the one or more further genes to a control expression level of the corresponding gene(s) in a healthy subject; and
  determining whether or not the subject is prone to develop progressive COPD involving the appearance of irreversible lung damage,
wherein an increase in the level of expression of DMBT1, KIAA1199, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or COMP in the sample from the subject as compared to the control expression level of the corresponding gene(s) is indicative of a proneness to develop progressive COPD, and wherein a decrease in the level of expression of TMSB15A, DPP6, SLC51B, NUDT11, PLA1A, HYAL2, CST6, ITGA10, CTHRC1, TAL1, FIBIN, BEX5, BEX1, ESM1 and/or GHRL in the sample from the subject as compared to the control expression level of the corresponding gene(s) is indicative of a proneness to develop progressive COPD.

In a third aspect, the invention provides an in vitro method of diagnosing stable COPD in a subject or assessing the susceptibility of a subject to develop stable COPD, the method comprising:
  determining the level of expression of the gene DMBT1 in a sample obtained from the subject;

comparing the level of expression of DMBT1 in the sample from the subject to a control expression level of DMBT1 in a healthy subject; and determining whether or not the subject suffers from stable COPD or is prone to suffer from stable COPD, wherein an increase in the level of expression of DMBT1 in the sample from the subject as compared to the control expression level of DMBT1 is indicative of stable COPD or a proneness to stable COPD.

The method according to this third aspect preferably further comprises:

determining the level of expression of one or more further genes selected from KIAA1199, TMSB15A, DPP6, SLC51B, NUDT11, ELF5, AZGP1, PRRX1, AQP3, SFN, GPR110, GDF15, RASGRF2, RND1, PLA1A, FGG, CEACAM5, HYAL2, AHRR, CXCL3, CYP1A1, CYP1B1, CYP1A2, CST6, NTRK2, COMP, ITGA10, CTHRC1, TAL1, FIBIN, BEX5, BEX1, ESM1 and GHRL in the sample obtained from the subject;

comparing the level of expression of the one or more further genes to a control expression level of the corresponding gene(s) in a healthy subject; and determining whether or not the subject suffers from stable COPD or is prone to suffer from stable COPD, wherein an increase in the level of expression of DMBT1, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or COMP in the sample from the subject as compared to the control expression level of the corresponding gene(s) is indicative of stable COPD or a proneness to stable COPD, and wherein a decrease in the level of expression of KIAA1199, TMSB15A, DPP6, SLC51B, NUDT11, PLA1A, HYAL2, CST6, ITGA10, CTHRC1, TAL1, FIBIN, BEX5, BEX1, ESM1 and/or GHRL in the sample from the subject as compared to the control expression level of the corresponding gene(s) is indicative of stable COPD or a proneness to stable COPD.

In a fourth aspect, the invention relates to an in vitro diagnostic method of assessing the susceptibility of a subject suffering from stable COPD to develop progressive COPD involving the appearance of irreversible lung damage, the method comprising:

determining the level of expression of the gene DMBT1 in a sample obtained from the subject;

comparing the level of expression of DMBT1 in the sample from the subject to a control expression level of DMBT1 in a subject suffering from stable COPD; and determining whether or not the subject is prone to develop progressive COPD involving the appearance of irreversible lung damage, wherein a decrease in the level of expression of DMBT1 in the sample from the subject as compared to the control expression level of DMBT1 is indicative of a proneness to develop progressive COPD.

It is preferred that the method of this fourth aspect further comprises:

determining the level of expression of one or more further genes selected from KIAA1199, ELF5, AZGP1, PRRX1, AQP3, GPR110, GDF15, RASGRF2, RND1, FGG, CEACAM5, HYAL2, AHRR, CXCL3, CYP1A1, CYP1B1, CYP1A2, CST6, NTRK2, COMP, ITGA10, CTHRC1, TAL1, BEX1 and GHRL in the sample obtained from the subject;

comparing the level of expression of the one or more further genes to a control expression level of the corresponding gene(s) in a subject suffering from stable COPD; and determining whether or not the subject is prone to develop progressive COPD involving the appearance of irreversible lung damage, wherein an increase in the level of expression of KIAA1199, GPR110, GDF15, RASGRF2, RND1, FGG, CEACAM5, HYAL2, AHRR, CXCL3, CYP1A1, CYP1B1, CYP1A2, CST6, NTRK2 and/or TAL1 in the sample from the subject as compared to the control expression level of the corresponding gene(s) is indicative of a proneness to develop progressive COPD, and wherein a decrease in the level of expression of DMBT1, ELF5, AZGP1, PRRX1, AQP3, COMP, ITGA10, CTHRC1, BEX1 and/or GHRL in the sample from the subject as compared to the control expression level of the corresponding gene(s) is indicative of a proneness to develop progressive COPD.

In a fifth aspect, the invention relates to the use of (i) a pair of primers for a transcript of the gene DMBT1, (ii) a nucleic acid probe to a transcript of the gene DMBT1, (iii) a microarray comprising a nucleic acid probe to the transcript of DMBT1 and optionally comprising nucleic acid probes to the transcripts of one or more further genes selected from KIAA1199, TMSB15A, DPP6, SLC51B, NUDT11, ELF5, AZGP1, PRRX1, AQP3, SFN, GPR110, GDF15, RASGRF2, RND1, PLA1A, FGG, CEACAM5, HYAL2, AHRR, CXCL3, CYP1A1, CYP1B1, CYP1A2, CST6, NTRK2, COMP, ITGA10, CTHRC1, TAL1, FIBIN, BEX5, BEX1, ESM1 and GHRL, or (iv) an antibody against the protein DMBT1, in an in vitro diagnostic method of assessing the susceptibility of a subject to develop progressive COPD involving the appearance of irreversible lung damage.

In a sixth aspect, the invention relates to a drug against COPD for use in treating COPD in a subject that has been identified in a method according to the second aspect of the invention as being prone to develop progressive COPD involving the appearance of irreversible lung damage.

The invention further relates to the use of a drug against COPD in the preparation of a pharmaceutical composition for treating COPD in a subject that has been identified in a method according to the second aspect of the invention as being prone to develop progressive COPD involving the appearance of irreversible lung damage.

Moreover, in accordance with this sixth aspect, the invention also provides a method of treating COPD, the method comprising administering a drug against COPD to a subject that has been identified in a method according to the second aspect of the invention as being prone to develop progressive COPD involving the appearance of irreversible lung damage.

In a seventh aspect, the invention relates to the use of (i) a pair of primers for a transcript of the gene DMBT1, (ii) a nucleic acid probe to a transcript of the gene DMBT1, (iii) a microarray comprising a nucleic acid probe to the transcript of DMBT1 and optionally comprising nucleic acid probes to the transcripts of one or more further genes selected from KIAA1199, TMSB15A, DPP6, SLC51B, NUDT11, ELF5, AZGP1, PRRX1, AQP3, SFN, GPR110, GDF15, RASGRF2, RND1, PLA1A, FGG, CEACAM5, HYAL2, AHRR, CXCL3, CYP1A1, CYP1B1, CYP1A2, CST6, NTRK2, COMP, ITGA10, CTHRC1, TAL1, FIBIN, BEX5, BEX1, ESM1 and GHRL, or (iv) an antibody against the protein DMBT1, in an in vitro method of diagnosing stable COPD in a subject or assessing the susceptibility of a subject to develop stable COPD.

In an eighth aspect, the invention relates to a drug against COPD for use in treating or preventing COPD in a subject that has been identified in a method according to the third aspect of the invention as suffering from stable COPD or as being prone to suffer from stable COPD.

The invention also relates to the use of a drug against COPD in the preparation of a pharmaceutical composition for treating or preventing COPD in a subject that has been identified in a method according to the third aspect of the invention as suffering from stable COPD or as being prone to suffer from stable COPD.

In this aspect, the invention likewise relates to a method of treating or preventing COPD, the method comprising administering a drug against COPD to a subject that has been identified in a method according to the third aspect of the invention as suffering from stable COPD or as being prone to suffer from stable COPD.

In a ninth aspect, the invention relates to the use of (i) a pair of primers for a transcript of the gene DMBT1, (ii) a nucleic acid probe to a transcript of the gene DMBT1, (iii) a microarray comprising a nucleic acid probe to the transcript of DMBT1 and optionally comprising nucleic acid probes to the transcripts of one or more further genes selected from KIAA1199, ELF5, AZGP1, PRRX1, AQP3, GPR110, GDF15, RASGRF2, RND1, FGG, CEACAM5, HYAL2, AHRR, CXCL3, CYP1A1, CYP1B1, CYP1A2, CST6, NTRK2, COMP, ITGA10, CTHRC1, TAL1, BEX1 and GHRL, or (iv) an antibody against the protein DMBT1, in an in vitro diagnostic method of assessing the susceptibility of a subject suffering from stable COPD to develop progressive COPD involving the appearance of irreversible lung damage.

In a tenth aspect, the invention relates to a drug against COPD for use in treating COPD in a subject suffering from stable COPD, wherein the subject has been identified in a method according to the fourth aspect of the invention as being prone to develop progressive COPD involving the appearance of irreversible lung damage.

The invention further refers to the use of a drug against COPD in the preparation of a pharmaceutical composition for treating COPD in a subject suffering from stable COPD, wherein the subject has been identified in a method according to the fourth aspect of the invention as being prone to develop progressive COPD involving the appearance of irreversible lung damage.

The invention according to this tenth aspect also relates to a method of treating COPD, the method comprising administering a drug against COPD to a subject suffering from stable COPD, wherein the subject has been identified in a method according to the fourth of the invention as being prone to develop progressive COPD involving the appearance of irreversible lung damage.

In an eleventh aspect, the present invention provides an in vitro method of monitoring the progression of COPD in a subject, the method comprising:
  determining the level of expression of one or more genes selected from NTRK2 and RASGRF2 in a first sample obtained from the subject;
  determining the level of expression of the one or more genes in a second sample obtained from the subject at a later point in time than the first sample;
  comparing the level of expression of the one or more genes in the second sample to the level of expression of the corresponding gene(s) in the first sample; and
  assessing the progression of COPD in the subject, wherein a decrease in the level of expression of NTRK2 and/or RASGRF2 in the second sample as compared to the level of expression of the corresponding gene(s) in the first sample is indicative of an amelioration of COPD in the subject, and
wherein an increase in the level of expression of NTRK2 and/or RASGRF2 in the second sample as compared to the level of expression of the corresponding gene(s) in the first sample is indicative of a worsening of COPD in the subject.

The following description of general and preferred features and embodiments relates to each one of the methods, uses and drugs against COPD provided in the present specification, including in particular those according to the above-described first, second, third, fourth, fifth, sixth, seventh, eighth, ninth, tenth and eleventh aspects of the invention, unless explicitly indicated otherwise.

Chronic obstructive pulmonary disease (COPD) is a lung disease characterized by persistent airflow limitation that is usually progressive and associated with an enhanced chronic inflammatory response in the airways and the lung to noxious particles or gases. COPD is typically classified into four different stages based on the extent of non-reversible pulmonary obstruction to be determined by spirometry, as specified by the Global Initiative for Obstructive Lung Disease (GOLD) (see, e.g., Vestbo et al., 2013; and Pauwels et al., 2001). COPD stage I ("mild COPD") is characterized by an $FEV_1/FVC$ ratio of <70% and an $FEV_1$ of ≥80%. At stage I, the patient may not be aware that his/her lung function is abnormal. COPD stage II ("moderate COPD") is characterized by an $FEV_1/FVC$ ratio of <70% and an $FEV_1$ of ≥50% and <80%. This is the stage at which patients typically seek medical attention because of chronic respiratory symptoms or an exacerbation of their disease. COPD stage III ("severe COPD") is characterized by an $FEV_1/FVC$ ratio of <70% and an $FEV_1$ of ≥30% and <50%. COPD stage IV ("very severe COPD") is characterized by an $FEV_1/FVC$ ratio of <70% and an $FEV_1$ of <30%, or chronic respiratory failure and an $FEV_1$ of <50%. The pathological development of COPD may be preceded by chronic respiratory symptoms (particularly chronic bronchitis) without airways obstruction ($FEV_1/FVC$ ratio of ≥70%), which is also referred to as "stage 0" or "at risk for COPD". The terms "stage I", "stage II", "stage III", "stage IV", and "stage 0" as used in the present specification refer to the corresponding GOLD stages, i.e., the corresponding COPD stages according to the above-described GOLD criteria.

As used herein, the term "stable COPD" (used synonymously with "stable early-stage COPD") refers to the initial stages of COPD that precede the development of irreversible lung damage. In particular, "stable COPD" refers to the initial COPD stages from the earliest signs for the onset of the disease through to mild airflow limitation characterized by an $FEV_1/FVC$ ratio of <70% and an $FEV_1$ of ≥80%. "Stable COPD" thus preferably refers to COPD stage 0 (i.e., the COPD "at risk" stage) and COPD stage I (according to GOLD criteria), and more preferably refers to COPD stage I.

The terms "progressive COPD" and "progressive COPD involving the appearance of irreversible lung damage" are used herein synonymously/interchangeably, and refer to the disease stage of COPD in which irreversible damage to the lungs occurs and progressively worsens. In particular, "progressive COPD" refers to the COPD disease stage characterized by moderate airflow limitation, i.e., an $FEV_1/FVC$ ratio of <70% and an $FEV_1$ of ≥50% and <80%. Accordingly, it is particularly preferred that "progressive COPD" refers to COPD stage II (according to GOLD criteria).

As used herein, the terms "KIAA1199", "DMBT1", "TMSB15A", "DPP6", "SLC51B", "NUDT11", "ITGA10", "CST6", "TAL1", "FIBIN", "BEX5", "BEX1", "ESM1", "GHRL", "NTRK2", "SFN", "GPR110", "FGG", "CEACAM5", "AZGP1", "COMP", "PRRX1", "AHRR", "CYP1A1", "CYP1A2", "CYP1B1", "GDF15", "ELF5", "AQP3", "RASGRF2", "PLA1A", "HYAL2", "CTHRC1", "RND1" and "CXCL3" each refer to the respective human gene, the corresponding mRNA (including all possible transcripts/splice variants), and the corresponding protein (including all possible isoforms). These terms also refer to homologs and/or orthologs of the corresponding human genes that are found in other (non-human) species, particularly other mammalian species, as well as their corresponding mRNAs and their corresponding proteins. It is to be understood that, if the subject to be tested in the methods of the present invention is a non-human animal (particularly a non-human mammal), then the one or more marker genes (the level of expression of which is to be determined) will be the homologs/orthologs of the indicated human genes that are found in the non-human animal to be tested. Preferably, the subject is a human and, accordingly, the above-mentioned terms preferably refer to the respective human genes and the corresponding mRNAs and proteins.

The full names of the human forms of the above-mentioned marker genes, their Entrez Gene ID, and NCBI reference sequences of their mRNAs and proteins are listed in the following Table 1:

TABLE 1

Overview of the marker genes provided herein (human forms), including their full names, their Entrez Gene ID, and NCBI reference sequences of their mRNAs and their proteins (where applicable, different mRNA transcripts/splice variants and the corresponding protein isoforms are indicated; further possible mRNA variants and protein isoforms of the indicated genes may also be used to determine the corresponding levels of marker gene expression in accordance with the invention).

| Marker gene | Full name | Gene ID | mRNA (NCBI ref. seq.) | Protein (NCBI ref. seq.) |
| --- | --- | --- | --- | --- |
| KIAA1199 | KIAA1199 | 57214 | NM_018689.1 (preferably as indicated in SEQ ID NO: 38) | NP_061159.1 |
| DMBT1 | deleted in malignant brain tumors 1 | 1755 | NM_004406.2 (preferably as indicated in SEQ ID NO: 26) NM_007329.2 (preferably as indicated in SEQ ID NO: 32) NM_017579.2 (preferably as indicated in SEQ ID NO: 35) | NP_004397.2 NP_015568.2 NP_060049.2 |
| TMSB15A | thymosin beta 15a | 11013 | NM_021992.2 (preferably as indicated in SEQ ID NO: 41) | NP_068832.1 |
| DPP6 | dipeptidyl-peptidase 6 | 1804 | NM_001039350.1 (preferably as indicated in SEQ ID NO: 45) NM_001936.3 (preferably as indicated in SEQ ID NO: 46) NM_130797.2 (preferably as indicated in SEQ ID NO: 47) | NP_001034439.1 NP_001927.3 NP_570629.2 |
| SLC51B | solute carrier family 51, beta subunit | 123264 | NM_178859.3 (preferably as indicated in SEQ ID NO: 48) | NP_849190.2 |
| NUDT11 | nudix (nucleoside diphosphate linked moiety X)-type motif 11 | 55190 | NM_018159.3 (preferably as indicated in SEQ ID NO: 36) | NP_060629 |
| ITGA10 | integrin, alpha 10 | 8515 | NM_003637.3 (preferably as indicated in SEQ ID NO: 24) | NP_003628.2 |
| CST6 | cystatin E/M | 1474 | NM_001323.3 (preferably as indicated in SEQ ID NO: 21) | NP_001314.1 |
| TAL1 | T-cell acute lymphocytic leukemia 1 | 6886 | NM_003189.2 (preferably as indicated in SEQ ID NO: 49) | NP_003180.1 |

TABLE 1-continued

Overview of the marker genes provided herein (human forms), including their full names, their Entrez Gene ID, and NCBI reference sequences of their mRNAs and their proteins (where applicable, different mRNA transcripts/splice variants and the corresponding protein isoforms are indicated; further possible mRNA variants and protein isoforms of the indicated genes may also be used to determine the corresponding levels of marker gene expression in accordance with the invention).

| Marker gene | Full name | Gene ID | mRNA (NCBI ref. seq.) | Protein (NCBI ref. seq.) |
|---|---|---|---|---|
| FIBIN | fin bud initiation factor homolog (zebrafish) | 387758 | NM_203371.1 (preferably as indicated in SEQ ID NO: 50) | NP_976249.1 |
| BEX5 | brain expressed, X-linked 5 | 340542 | NM_001012978.2 (preferably as indicated in SEQ ID NO: 5) NM_001159560.1 (preferably as indicated in SEQ ID NO: 13) | NP_001012996.1 NP_001153032.1 |
| BEX1 | brain expressed, X-linked 1 | 55859 | NM_018476.3 (preferably as indicated in SEQ ID NO: 37) | NP_060946.3 |
| ESM1 | endothelial cell-specific molecule 1 | 11082 | NM_001135604.1 (preferably as indicated in SEQ ID NO: 12) NM_007036.4 (preferably as indicated in SEQ ID NO: 31) | NP_001129076.1 NP_008967.1 |
| GHRL | ghrelin/obestatin prepropeptide | 51738 | NM_001134941.1 (preferably as indicated in SEQ ID NO: 8) NM_001134944.1 (preferably as indicated in SEQ ID NO: 9) NM_001134945.1 (preferably as indicated in SEQ ID NO: 10) NM_001134946.1 (preferably as indicated in SEQ ID NO: 11) | NP_001128413.1 NP_001128416.1 NP_001128417.1 NP_001128418.1 NP_001128418.1 |
| NTRK2 | neurotrophic tyrosine kinase, receptor, type 2 | 4915 | NM_001007097.1 (preferably as indicated in SEQ ID NO: 51) NM_001018064.1 (preferably as indicated in SEQ ID NO: 52) NM_001018065.2 (preferably as indicated in SEQ ID NO: 6) NM_001018066.2 (preferably as indicated in SEQ ID NO: 7) NM_006180.3 (preferably as indicated in SEQ ID NO: 53) | NP_001007098.1 NP_001018074.1 NP_001018075.1 NP_001018076.1 NP_006171.2 |
| SFN | stratifin | 2810 | NM_006142.3 (preferably as indicated in SEQ ID NO: 29) | NP_006133.1 |
| GPR110 | G protein-coupled receptor 110 | 266977 | NM_025048.2 (preferably as indicated in SEQ ID NO: 42) NM_153840.2 | NP_079324.2 NP_722582.2 |

TABLE 1-continued

Overview of the marker genes provided herein (human forms), including their full names, their Entrez Gene ID, and NCBI reference sequences of their mRNAs and their proteins (where applicable, different mRNA transcripts/splice variants and the corresponding protein isoforms are indicated; further possible mRNA variants and protein isoforms of the indicated genes may also be used to determine the corresponding levels of marker gene expression in accordance with the invention).

| Marker gene | Full name | Gene ID | mRNA (NCBI ref. seq.) | Protein (NCBI ref. seq.) |
|---|---|---|---|---|
| CYP1B1 | cytochrome P450, family 1, subfamily B, polypeptide 1 | 1545 | NM_000104.3 (preferably as indicated in SEQ ID NO: 2) | NP_000095.2 |
| FGG | fibrinogen gamma chain | 2266 | NM_000509.4 (preferably as indicated in SEQ ID NO: 4) NM_021870.2 (preferably as indicated in SEQ ID NO: 40) | NP_000500.2 NP_068656.2 |
| CEACAM5 | carcinoembryonic antigen-related cell adhesion molecule 5 | 1048 | NM_004363.2 (preferably as indicated in SEQ ID NO: 54) | NP_004354.2 |
| AZGP1 | alpha-2-glycoprotein 1, zinc-binding | 563 | NM_001185.3 (preferably as indicated in SEQ ID NO: 14) | NP_001176.1 |
| COMP | cartilage oligomeric matrix protein | 1311 | NM_000095.2 (preferably as indicated in SEQ ID NO: 1) | NP_000086.2 |
| PRRX1 | paired related homeobox 1 | 5396 | NM_006902.3 (preferably as indicated in SEQ ID NO: 56) NM_022716.2 (preferably as indicated in SEQ ID NO: 57) | NP_008833.1 NP_073207.1 |
| AHRR | aryl-hydrocarbon receptor repressor | 57491 | NM_001242412.1 (preferably as indicated in SEQ ID NO: 17) NM_020731.4 (preferably as indicated in SEQ ID NO: 39) | NP_001229341.1 NP_065782.2 |
| GDF15 | growth differentiation factor 15 | 9518 | NM_004864.2 (preferably as indicated in SEQ ID NO: 27) | NP_004855.2 |
| ELF5 | E74-like factor 5 (ets domain transcription factor) | 2001 | NM_001243080.1 (preferably as indicated in SEQ ID NO: 18) NM_001243081.1 (preferably as indicated in SEQ ID NO: 19) NM_001422.3 (preferably as indicated in SEQ ID NO: 22) NM_198381.1 (preferably as indicated in SEQ ID NO: 58) | NP_001230009.1 NP_001230010.1 NP_001413.1 NP_938195.1 |
| AQP3 | aquaporin 3 (Gill blood group) | 360 | NM_004925.4 (preferably as indicated in SEQ ID NO: 28) | NP_004916.1 |

TABLE 1-continued

Overview of the marker genes provided herein (human forms), including their full names, their Entrez Gene ID, and NCBI reference sequences of their mRNAs and their proteins (where applicable, different mRNA transcripts/splice variants and the corresponding protein isoforms are indicated; further possible mRNA variants and protein isoforms of the indicated genes may also be used to determine the corresponding levels of marker gene expression in accordance with the invention).

| Marker gene | Full name | Gene ID | mRNA (NCBI ref. seq.) | Protein (NCBI ref. seq.) |
|---|---|---|---|---|
| RASGRF2 | Ras protein-specific guanine nucleotide-releasing factor 2 | 5924 | NM_006909.2 (preferably as indicated in SEQ ID NO: 30) | NP_008840.1 |
| PLA1A | phospholipase A1 member A | 51365 | NM_001206960.1 (preferably as indicated in SEQ ID NO: 15) NM_001206961.1 (preferably as indicated in SEQ ID NO: 16) NM_015900.3 (preferably as indicated in SEQ ID NO: 34) | NP_001193889.1 NP_001193890.1 NP_056984.1 |
| HYAL2 | hyalurono-glucosaminidase 2 | 8692 | NM_003773.4 (preferably as indicated in SEQ ID NO: 25) NM_033158.4 (preferably as indicated in SEQ ID NO: 43) | NP_003764.3 NP_149348.2 |
| CTHRC1 | collagen triple helix repeat containing 1 | 115908 | NM_001256099.1 (preferably as indicated in SEQ ID NO: 20) NM_138455.3 (preferably as indicated in SEQ ID NO: 44) | NP_001243028.1 NP_612464.1 |
| RND1 | Rho family GTPase 1 | 27289 | NM_014470.3 (preferably as indicated in SEQ ID NO: 33) | NP_055285.1 |
| CXCL3 | chemokine (C-X-C motif) ligand 3 | 2921 | NM_002090.2 (preferably as indicated in SEQ ID NO: 23) | NP_002081.2 |
| CYP1A1 | cytochrome P450, family 1, subfamily A, polypeptide 1 | 1543 | NM_000499.3 (preferably as indicated in SEQ ID NO: 3) | NP_000490.1 |
| CYP1A2 | cytochrome P450, family 1, subfamily A, polypeptide 2 | 1544 | NM_000761.4 (preferably as indicated in SEQ ID NO: 59) | NP_000752.2 |

In the methods according to the present invention, including in particular the methods according to the first, second, third, fourth and eleventh aspect of the invention, the level of expression of one or more genes is determined in a sample obtained from the subject to be tested.

The level of expression can be determined, e.g., by determining the level of transcription or the level of translation of the corresponding marker gene(s). Thus, the amount of mRNA of these gene(s) in the sample can be measured or the amount of the corresponding protein(s) can be measured in order to determine the level of expression of the respective genes. This can be accomplished using methods known in the art, as described, e.g., in Green et al., 2012. The level of transcription of these gene(s) can, for example, be determined using a quantitative (real-time) reverse transcriptase polymerase chain reaction ("qRT-PCR") or using a microarray (see, e.g., Ding et al., 2004). The use of a microarray can be advantageous, e.g., if the level of transcription of a number of different marker genes is to be determined. Using a microarray can also be advantageous if various different diseases/disorders or the susceptibility to various diseases/disorders is to be tested or diagnosed simultaneously. If the level of transcription is to be determined, it may further be advantageous to include one or more RNase inhibitors in the sample from the subject. The level of translation of the corresponding marker gene(s) can, for example, be determined using antibody-based assays, such as an enzyme-linked immunosorbent assay (ELISA) or a radioimmunoassay (RIA), wherein antibodies directed specifically against the protein(s) to be quantified are employed, or mass spectrometry, a gel-based or blot-based assay, or flow cytometry (e.g., FACS). If the level of translation is to be determined, it may be advantageous to include one or more protease inhibitors in the sample from the subject. Since mRNA can be isolated and quantified more easily and in a more cost-effective manner than proteins, it is preferred in the methods of the present invention that the level of expression of the one or more genes is determined by determining the level of transcription of the corresponding gene(s). The level of transcription is preferably determined using qRT-PCR or a microarray.

The subject to be tested in accordance with the present invention may be an animal and is preferably a mammal. The mammal to be tested in accordance with the invention may be, e.g., a rodent (such as, e.g., a guinea pig, a hamster, a rat or a mouse), a murine (such as, e.g., a mouse), a canine (such as, e.g., a dog), a feline (such as, e.g., a cat), a porcine (such as, e.g., a pig), an equine (such as, e.g., a horse), a primate, a simian (such as, e.g., a monkey or an ape), a monkey (such as, e.g., a marmoset or a baboon), an ape (such as, e.g., a gorilla, a chimpanzee, an orang-utan or a gibbon), or a human. It is particularly envisaged that non-human mammals are to be tested, which are economically, agronomically or scientifically important. Scientifically important mammals include, e.g., mice, rats and rabbits. Non-limiting examples of agronomically important mammals are sheep, cattle and pigs. Economically important mammals include, e.g., cats and dogs. Most preferably, the subject to be tested in accordance with the present invention is a human.

In the second and the fourth aspect of the invention, it is furthermore preferred that the subject to be tested is a subject (preferably a human) that has been diagnosed as suffering from stable COPD or is suspected of suffering from stable COPD.

In accordance with the third aspect of the invention, it is preferred that the subject to be tested is a subject (preferably a human) that is suspected to suffer from stable COPD or a subject (preferably a human) suspected to be prone to suffer from stable COPD.

The sample obtained from the subject to be tested can, in principle, be any tissue sample or serum from the subject. Preferably, the sample is a lung tissue sample. More preferably, the sample is a transbronchial lung biopsy sample or a bronchoalveolar lavage (BAL) sample.

In some of the methods provided herein, including in particular the methods according to the second and the third aspect of the invention, the level of expression of one or more specific genes is compared to a control expression level of the corresponding gene(s) in a healthy subject. Such control expression levels can be established as part of the respective methods of the invention, which may thus include a further step of determining the level of expression of the corresponding gene(s) in a sample obtained from a healthy subject (i.e., a subject that does not suffer from COPD and does not have an increased risk of developing COPD) or in a mixture of samples from several healthy subjects (e.g., about 10, about 20, about 50, about 100, or about 500 healthy subjects). It is to be understood that the healthy subject(s) will be of the same species as the subject to be tested and should preferably have the same age, gender and ethnicity as the subject to be tested. Alternatively, these control expression levels can also be derived from the medical literature or from experiments conducted before carrying out the methods of the invention. It will be understood that the conditions under which the control expression levels are or were obtained (regardless of whether they are derived from the literature or earlier experiments or whether they are determined in the course of carrying out the methods of the invention), including also the type/origin of the sample (or mixture of samples) from the healthy subject, should be identical or at least similar/comparable to the conditions used for determining the level of expression of the one or more genes in the sample obtained from the subject to be tested.

In the method according to the fourth aspect, the level of expression of one or more specific genes is compared to a control expression level of the corresponding gene(s) in a subject suffering from stable COPD. Such control expression levels can be established as part of the method according to the fourth aspect of the invention, which may thus include a further step of determining the level of expression of the corresponding gene(s) in a sample obtained from a subject suffering from stable COPD (particularly a subject that has been diagnosed as suffering from stable COPD) or in a mixture of samples from several subjects (e.g., about 10, about 20, about 50, about 100, or about 500 subjects) suffering from stable CORD. It is to be understood that these control subject(s) will be of the same species as the subject to be tested and should preferably have the same age, gender and ethnicity as the subject to be tested. Alternatively, the corresponding control expression levels can also be derived from experiments conducted before carrying out the method of the fourth aspect of the invention. It will be understood that the conditions under which the control expression levels are or were obtained (regardless of whether they are derived from earlier experiments or whether they are determined in the course of carrying out the method of the fourth aspect), including also the type/origin of the sample (or mixture of samples) from the control subject, should be identical or at least similar/comparable to the conditions used for determining the level of expression of the one or more genes in the sample obtained from the subject to be tested. The control subject suffering from stable COPD in accordance with the fourth aspect of the invention is preferably a subject suffering from stage I COPD (particularly a subject that has been diagnosed as suffering from stage I COPD).

In the methods according to the second, third and fourth aspect of the present invention, the level of expression of DMBT1 and optionally of one or more further marker genes is determined. Preferably, the level of expression of DMBT1 and at least one of the corresponding further marker genes is determined, more preferably the level of expression of DMBT1 and at least two of these further marker genes is determined, and even more preferably the level of expression of DMBT1 and at least three of the corresponding further marker genes is determined, whereby the reliability of the diagnosis or assessment can be further improved. In general, the greater the number of marker genes the expression of which is altered (as defined in the corresponding aspect of the invention), and also the more pronounced the upregulation or downregulation of the expression of each of these marker genes, the more likely it will be that the subject tested is prone to develop progressive COPD (in the methods of the second and the fourth aspect) or that the subject tested suffers from stable COPD or is prone to suffer from stable COPD (in the method of the third aspect of the invention).

Thus, both (i) the number of tested marker genes showing an altered expression level as described above and (ii) the extent of alteration of the expression level of each one of the marker genes tested can be taken into consideration when determining whether or not the subject is prone to develop progressive COPD (in accordance with the second or the fourth aspect) or whether or not the subject suffers from stable COPD or is prone to suffer from stable COPD (in accordance with the third aspect of the invention). Further factors, signs and symptoms indicative of COPD, such as, e.g., airflow limitation (as determined, e.g., by spirometry), coughing, expiratory wheezing, further respiratory symptoms, the subject's smoking history, bronchial inflammation and/or further biomarkers (including molecular biomarkers), can additionally be taken into account in order to further improve the accuracy of the determination whether or not the subject is prone to develop progressive COPD (in accordance with the second or the fourth aspect) or whether or not the subject suffers from stable COPD or is prone to suffer from stable COPD (in accordance with the third aspect).

In one embodiment of the method according to the second aspect of the invention, it is preferred that the level of expression of DMBT1 and at least one further gene selected from FGG, CYP1A1, CEACAM5, CTHRC1, NTRK2 and RASGRF2 is determined in the sample obtained from the subject. In this embodiment, it is furthermore preferred that the level of expression of at least two of the aforementioned further genes is determined. For example, the level of expression of DMBT1, FGG and CYP1A1 may be determined, or the level of expression of DMBT1, FGG and CEACAM5 may be determined, or the level of expression of DMBT1, FGG and CTHRC1 may be determined, or the level of expression of DMBT1, FGG and NTRK2 may be determined, or the level of expression of DMBT1, FGG and RASGRF2 may be determined, or the level of expression of DMBT1, CYP1A1 and CEACAM5 may be determined, or the level of expression of DMBT1, CYP1A1 and CTHRC1 may be determined, or the level of expression of DMBT1, CYP1A1 and NTRK2 may be determined, or the level of expression of DMBT1, CYP1A1 and RASGRF2 may be determined, or the level of expression of DMBT1, CEACAM5 and CTHRC1 may be determined, or the level of expression of DMBT1, CEACAM5 and NTRK2 may be determined, or the level of expression of DMBT1, CEACAM5 and RASGRF2 may be determined, or the level of expression of DMBT1, CTHRC1 and NTRK2 may be determined, or the level of expression of DMBT1, CTHRC1 and RASGRF2 may be determined, or the level of expression of DMBT1, NTRK2 and RASGRF2 may be determined. In addition thereto, the level of expression of at least one further gene selected from ELF5, AZGP1, PRRX1, AQP3, SFN, GPR110, GDF15, RASGRF2 and RND1 and/or the level of expression of at least one further gene selected from KIAA1199, TMSB15A, DPP6, SLC51B and NUDT11 (particularly KIAA1199 and/or TMSB15A) may also be determined.

In a further embodiment of the method according to the second aspect of the invention, it is preferred that the level of expression of DMBT1 and at least one further gene selected from ELF5, AZGP1, PRRX1, AQP3, SFN, GPR110, GDF15, RASGRF2 and RND1 is determined in the sample obtained from the subject. In this embodiment, it is furthermore preferred that the level of expression of at least two of the aforementioned further genes is determined. For example, the level of expression of DMBT1, ELF5 and AZGP1 may be determined, or the level of expression of DMBT1, ELF5 and PRRX1 may be determined, or the level of expression of DMBT1, ELF5 and AQP3 may be determined, or the level of expression of DMBT1, ELF5 and SFN may be determined, or the level of expression of DMBT1, ELF5 and GPR110 may be determined, or the level of expression of DMBT1, ELF5 and GDF15 may be determined, or the level of expression of DMBT1, ELF5 and RASGRF2 may be determined, or the level of expression of DMBT1, ELF5 and RND1 may be determined, or the level of expression of DMBT1, AZGP1 and PRRX1 may be determined, or the level of expression of DMBT1, AZGP1 and AQP3 may be determined, or the level of expression of DMBT1, AZGP1 and SFN may be determined, or the level of expression of DMBT1, AZGP1 and GPR110 may be determined, or the level of expression of DMBT1, AZGP1 and GDF15 may be determined, or the level of expression of DMBT1, AZGP1 and RASGRF2 may be determined, or the level of expression of DMBT1, AZGP1 and RND1 may be determined, or the level of expression of DMBT1, PRRX1 and AQP3 may be determined, or the level of expression of DMBT1, PRRX1 and SFN may be determined, or the level of expression of DMBT1, PRRX1 and GPR110 may be determined, or the level of expression of DMBT1, PRRX1 and GDF15 may be determined, or the level of expression of DMBT1, PRRX1 and RASGRF2 may be determined, or the level of expression of DMBT1, PRRX1 and RND1 may be determined, or the level of expression of DMBT1, AQP3 and SFN may be determined, or the level of expression of DMBT1, AQP3 and GPR110 may be determined, or the level of expression of DMBT1, AQP3 and GDF15 may be determined, or the level of expression of DMBT1, AQP3 and RASGRF2 may be determined, or the level of expression of DMBT1, AQP3 and RND1 may be determined, or the level of expression of DMBT1, SFN and GPR110 may be determined, or the level of expression of DMBT1, SFN and GDF15 may be determined, or the level of expression of DMBT1, SFN and RASGRF2 may be determined, or the level of expression of DMBT1, SFN and RND1 may be determined, or the level of expression of DMBT1, GPR110 and GDF15 may be determined, or the level of expression of DMBT1, GPR110 and RASGRF2 may be determined, or the level of expression of DMBT1, GPR110 and RND1 may be determined, or the level of expression of DMBT1, GDF15 and RASGRF2 may be determined, or the level of expression of DMBT1, GDF15 and RND1 may be determined, or the level of expression of DMBT1, RASGRF2 and RND1 may be determined. In addition thereto, the level of expression of at least one further gene selected from FGG, CYP1A1, CEACAM5, CTHRC1, NTRK2 and RASGRF2 and/or the level of expression of at least one further gene selected from KIAA1199, TMSB15A, DPP6, SLC51B and NUDT11 (particularly KIAA1199 and/or TMSB15A) may also be determined.

In a further embodiment of the method according to the second aspect of the invention, it is preferred that the level of expression of DMBT1 and at least one further gene selected from KIAA1199, TMSB15A, DPP6, SLC51B and NUDT11 is determined in the sample obtained from the subject. In this embodiment, it is furthermore preferred that the level of expression of at least two of the aforementioned further genes is determined. For example, the level of expression of KIAA1199, DMBT1 and TMSB15A may be determined, or the level of expression of KIAA1199, DMBT1 and DPP6 may be determined, or the level of expression of KIAA1199, DMBT1 and SLC51B may be determined, or the level of expression of KIAA1199, DMBT1 and NUDT11 may be determined, or the level of expression of DMBT1, TMSB15A and DPP6 may be determined, or the level of expression of DMBT1, TMSB15A and SLC51B may be determined, or the level of expression of DMBT1, TMSB15A and NUDT11 may be determined, or the level of expression of DMBT1, DPP6 and SLC51B may be determined, or the level of expression of DMBT1, DPP6 and NUDT11 may be determined, or the level of expression of DMBT1, SLC51B and NUDT11 may be determined. In addition thereto, the level of expression of at least one further gene selected from FGG, CYP1A1, CEACAM5, CTHRC1, NTRK2 and RASGRF2 and/or the level of expression of at least one further gene selected from ELF5, AZGP1, PRRX1, AQP3, SFN, GPR110, GDF15, RASGRF2 and RND1 may also be determined.

In the method according to the second aspect of the invention, it is particularly preferred that the level of expression of DMBT1 and at least one further gene selected from KIAA1199 and TMSB15A is determined in the sample obtained from the subject. Accordingly, it is preferred that the level of expression of DMBT1 and KIAA1199 is determined, or that the level of expression of DMBT1 and TMSB15A is determined. Most preferably, the level of expression of DMBT1, KIAA1199 and TMSB15A is determined in the sample obtained from the subject. For example, the level of expression of DMBT1, KIAA1199, TMSB15A and at least one further gene selected from FGG, CYP1A1, CEACAM5, CTHRC1, NTRK2, RASGRF2, ELF5, AZGP1, PRRX1, AQP3, SFN, GPR110, GDF15, RASGRF2, RND1, DPP6, SLC51B and NUDT11 may be determined.

In one embodiment of the method according to the third aspect of the invention, it is preferred that the level of expression of DMBT1 and at least one further gene selected from FGG, CYP1A1, CEACAM5, CTHRC1, NTRK2 and RASGRF2 is determined in the sample obtained from the subject. In this embodiment, it is furthermore preferred that the level of expression of at least two of the aforementioned further genes is determined. For example, the level of expression of DMBT1, FGG and CYP1A1 may be determined, or the level of expression of DMBT1, FGG and CEACAM5 may be determined, or the level of expression of DMBT1, FGG and CTHRC1 may be determined, or the level of expression of DMBT1, FGG and NTRK2 may be determined, or the level of expression of DMBT1, FGG and RASGRF2 may be determined, or the level of expression of DMBT1, CYP1A1 and CEACAM5 may be determined, or the level of expression of DMBT1, CYP1A1 and CTHRC1 may be determined, or the level of expression of DMBT1, CYP1A1 and NTRK2 may be determined, or the level of expression of DMBT1, CYP1A1 and RASGRF2 may be determined, or the level of expression of DMBT1, CEACAM5 and CTHRC1 may be determined, or the level of expression of DMBT1, CEACAM5 and NTRK2 may be determined, or the level of expression of DMBT1, CEACAM5 and RASGRF2 may be determined, or the level of expression of DMBT1, CTHRC1 and NTRK2 may be determined, or the level of expression of DMBT1, CTHRC1 and RASGRF2 may be determined, or the level of expression of DMBT1, NTRK2 and RASGRF2 may be determined. In addition thereto, the level of expression of at least one further gene selected from ELF5, AZGP1, PRRX1, AQP3, SFN, GPR110, GDF15, RASGRF2 and RND1 and/or the level of expression of at least one further gene selected from KIAA1199, TMSB15A, DPP6, SLC51B and NUDT11 (particularly KIAA1199 and/or TMSB15A) may also be deter mined.

In a further embodiment of the method according to the third aspect of the invention, it is preferred that the level of expression of DMBT1 and at least one further gene selected from ELF5, AZGP1, PRRX1, AQP3, SFN, GPR110, GDF15, RASGRF2 and RND1 is determined in the sample obtained from the subject. In this embodiment, it is furthermore preferred that the level of expression of at least two of the aforementioned further genes is determined. For example, the level of expression of DMBT1, ELF5 and AZGP1 may be determined, or the level of expression of DMBT1, ELF5 and PRRX1 may be determined, or the level of expression of DMBT1, ELF5 and AQP3 may be determined, or the level of expression of DMBT1, ELF5 and SFN may be determined, or the level of expression of DMBT1, ELF5 and GPR110 may be determined, or the level of expression of DMBT1, ELF5 and GDF15 may be determined, or the level of expression of DMBT1, ELF5 and RASGRF2 may be determined, or the level of expression of DMBT1, ELF5 and RND1 may be determined, or the level of expression of DMBT1, AZGP1 and PRRX1 may be determined, or the level of expression of DMBT1, AZGP1 and AQP3 may be determined, or the level of expression of DMBT1, AZGP1 and SFN may be determined, or the level of expression of DMBT1, AZGP1 and GPR110 may be determined, or the level of expression of DMBT1, AZGP1 and GDF15 may be determined, or the level of expression of DMBT1, AZGP1 and RASGRF2 may be determined, or the level of expression of DMBT1, AZGP1 and RND1 may be determined, or the level of expression of DMBT1, PRRX1 and AQP3 may be determined, or the level of expression of DMBT1, PRRX1 and SFN may be determined, or the level of expression of DMBT1, PRRX1 and GPR110 may be determined, or the level of expression of DMBT1, PRRX1 and GDF15 may be determined, or the level of expression of DMBT1, PRRX1 and RASGRF2 may be determined, or the level of expression of DMBT1, PRRX1 and RND1 may be determined, or the level of expression of DMBT1, AQP3 and SFN may be determined, or the level of expression of DMBT1, AQP3 and GPR110 may be determined, or the level of expression of DMBT1, AQP3 and GDF15 may be determined, or the level of expression of DMBT1, AQP3 and RASGRF2 may be determined, or the level of expression of DMBT1, AQP3 and RND1 may be determined, or the level of expression of DMBT1, SFN and GPR110 may be determined, or the level of expression of DMBT1, SFN and GDF15 may be determined, or the level of expression of DMBT1, SFN and RASGRF2 may be determined, or the level of expression of DMBT1, SFN and RND1 may be determined, or the level of expression of DMBT1, GPR110 and GDF15 may be determined, or the level of expression of DMBT1, GPR110 and RASGRF2 may be determined, or the level of expression of DMBT1, GPR110 and RND1 may be determined, or the level of expression of DMBT1, GDF15 and RASGRF2 may be determined, or the level of expression of DMBT1, GDF15 and RND1 may be determined, or the level of expression of DMBT1, RASGRF2 and RND1 may be determined. In addition thereto, the level of expression of at least one further gene selected from FGG, CYP1A1, CEACAM5, CTHRC1, NTRK2 and RASGRF2 and/or the level of expression of at least one further gene selected from KIAA1199, TMSB15A, DPP6, SLC51B and NUDT11 (particularly KIAA1199 and/or TMSB15A) may also be determined.

In a further embodiment of the method according to the third aspect of the invention, it is preferred that the level of expression of DMBT1 and at least one further gene selected from KIAA1199, TMSB15A, DPP6, SLC51B and NUDT11 is determined in the sample obtained from the subject. In this embodiment, it is furthermore preferred that the level of expression of at least two of the aforementioned further genes is determined. For example, the level of expression of KIAA1199, DMBT1 and TMSB15A may be determined, or the level of expression of KIAA1199, DMBT1 and DPP6 may be determined, or the level of expression of KIAA1199, DMBT1 and SLC51B may be determined, or the level of expression of KIAA1199, DMBT1 and NUDT11 may be determined, or the level of expression of DMBT1, TMSB15A and DPP6 may be determined, or the level of expression of DMBT1, TMSB15A and SLC51B may be determined, or the level of expression of DMBT1, TMSB15A and NUDT11 may be determined, or the level of expression of DMBT1, DPP6 and SLC51B may be determined, or the level of expression of DMBT1, DPP6 and NUDT11 may be determined, or the level of expression of DMBT1, SLC51B and NUDT11 may be determined. In addition thereto, the level of expression of at least one further gene selected from FGG, CYP1A1, CEACAM5, CTHRC1, NTRK2 and RASGRF2 and/or the level of expression of at least one further gene selected from ELF5, AZGP1, PRRX1, AQP3, SFN, GPR110, GDF15, RASGRF2 and RND1 may also be determined.

In the method according to the third aspect of the invention, it is particularly preferred that the level of expression of DMBT1 and at least one further gene selected from KIAA1199 and TMSB15A is determined in the sample obtained from the subject. Accordingly, it is preferred that the level of expression of KIAA1199 and DMBT1 is determined, or that the level of expression of DMBT1 and TMSB15A is determined. Most preferably, the level of expression of KIAA1199, DMBT1 and TMSB15A is determined in the sample obtained from the subject.

In one embodiment of the method according to the fourth aspect of the invention, it is preferred that the level of expression of DMBT1 and at least one further gene selected from FGG, CYP1A1, CEACAM5, CTHRC1, NTRK2 and RASGRF2 is determined in the sample obtained from the subject. In this embodiment, it is furthermore preferred that the level of expression of at least two of the aforementioned further genes is determined. For example, the level of expression of DMBT1, FGG and CYP1A1 may be determined, or the level of expression of DMBT1, FGG and CEACAM5 may be determined, or the level of expression of DMBT1, FGG and CTHRC1 may be determined, or the level of expression of DMBT1, FGG and NTRK2 may be determined, or the level of expression of DMBT1, FGG and RASGRF2 may be determined, or the level of expression of DMBT1, CYP1A1 and CEACAM5 may be determined, or the level of expression of DMBT1, CYP1A1 and CTHRC1 may be determined, or the level of expression of DMBT1, CYP1A1 and NTRK2 may be determined, or the level of expression of DMBT1, CYP1A1 and RASGRF2 may be determined, or the level of expression of DMBT1, CEACAM5 and CTHRC1 may be determined, or the level of expression of DMBT1, CEACAM5 and NTRK2 may be determined, or the level of expression of DMBT1, CEACAM5 and RASGRF2 may be determined, or the level of expression of DMBT1, CTHRC1 and NTRK2 may be determined, or the level of expression of DMBT1, CTHRC1 and RASGRF2 may be determined, or the level of expression of DMBT1, NTRK2 and RASGRF2 may be determined. In addition thereto, the level of expression of at least one further gene selected from ELF5, AZGP1, PRRX1, AQP3, GPR110, GDF15, RASGRF2 and RND1 and/or the level of expression of at least one further gene selected from KIAA1199 and TMSB15A may also be determined.

In a further embodiment of the method according to the fourth aspect of the invention, it is preferred that the level of expression of DMBT1 and at least one further gene selected from ELF5, AZGP1, PRRX1, AQP3, GPR110, GDF15, RASGRF2 and RND1 is determined in the sample obtained from the subject. In this embodiment, it is furthermore preferred that the level of expression of at least two of the aforementioned further genes is determined. For example, the level of expression of DMBT1, ELF5 and AZGP1 may be determined, or the level of expression of DMBT1, ELF5 and PRRX1 may be determined, or the level of expression of DMBT1, ELF5 and AQP3 may be determined, or the level of expression of DMBT1, ELF5 and GPR110 may be determined, or the level of expression of DMBT1, ELF5 and GDF15 may be determined, or the level of expression of DMBT1, ELF5 and RASGRF2 may be determined, or the level of expression of DMBT1, ELF5 and RND1 may be determined, or the level of expression of DMBT1, AZGP1 and PRRX1 may be determined, or the level of expression of DMBT1, AZGP1 and AQP3 may be determined, or the level of expression of DMBT1, AZGP1 and GPR110 may be determined, or the level of expression of DMBT1, AZGP1 and GDF15 may be determined, or the level of expression of DMBT1, AZGP1 and RASGRF2 may be determined, or the level of expression of DMBT1, AZGP1 and RND1 may be determined, or the level of expression of DMBT1, PRRX1 and AQP3 may be determined, or the level of expression of DMBT1, PRRX1 and GPR110 may be determined, or the level of expression of DMBT1, PRRX1 and GDF15 may be determined, or the level of expression of DMBT1, PRRX1 and RASGRF2 may be determined, or the level of expression of DMBT1, PRRX1 and RND1 may be determined, or the level of expression of DMBT1, AQP3 and GPR110 may be determined, or the level of expression of DMBT1, AQP3 and GDF15 may be determined, or the level of expression of DMBT1, AQP3 and RASGRF2 may be determined, or the level of expression of DMBT1, AQP3 and RND1 may be determined, or the level of expression of DMBT1, GPR110 and GDF15 may be determined, or the level of expression of DMBT1, GPR110 and RASGRF2 may be determined, or the level of expression of DMBT1, GPR110 and RND1 may be determined, or the level of expression of DMBT1, GDF15 and RASGRF2 may be determined, or the level of expression of DMBT1, GDF15 and RND1 may be determined, or the level of expression of DMBT1, RASGRF2 and RND1 may be determined. In addition thereto, the level of expression of at least one further gene selected from FGG, CYP1A1, CEACAM5, CTHRC1, NTRK2 and RASGRF2 and/or the level of expression of at least one further gene selected from KIAA1199 and TMSB15A may also be determined.

In the method according to the fourth aspect of the invention, it is particularly preferred that the level of expression of DMBT1 and at least one further gene selected from KIAA1199 and TMSB15A is determined in the sample obtained from the subject. Accordingly, it is preferred that the level of expression of KIAA1199 and DMBT1 is determined, or that the level of expression of DMBT1 and TMSB15A is determined. Most preferably, the level of expression of KIAA1199, DMBT1 and TMSB15A is determined in the sample obtained from the subject.

In the method according to the second aspect of the invention, preferably, it is determined that the subject is prone to develop progressive COPD if the level of expression of a majority of the number of genes tested (i.e., of the number of genes, the expression of which has been tested) is altered in the sense that (i) the level of expression of DMBT1, KIAA1199, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or COMP in the sample from the subject is increased as compared to the control expression level of the corresponding gene(s) and (ii) the level of expression of TMSB15A, DPP6, SLC51B, NUDT11, PLA1A, HYAL2, CST6, ITGA10, CTHRC1, TAL1, FIBIN, BEX5, BEX1, ESM1 and/or GHRL in the sample from the subject is decreased as compared to the control expression level of the corresponding gene(s). If only one marker gene (i.e., DMBT1) is tested, then the alteration of the level of expression of this marker gene is decisive for determining whether or not the subject is prone to develop progressive COPD. If two or more marker genes are tested, then a decrease or increase in the level of expression of a majority of the number of these marker genes is required for determining that the subject is prone to develop progressive COPD. The term "majority" (as in the expression "majority of the number of genes tested") means more than 50% of the number of the marker genes tested.

In accordance with the second aspect, it is furthermore preferred that an alteration in the level of expression of at least 60%, more preferably at least 70%, even more preferably at least 80%, and still more preferably at least 90% of the number of genes tested—i.e., an alteration in the sense that (i) the level of expression of DMBT1, KIAA1199, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or COMP in the sample from the subject is increased as compared to the control expression level of the corresponding gene(s) and (ii) the level of expression of TMSB15A, DPP6, SLC51B, NUDT11, PLA1A, HYAL2, CST6, ITGA10, CTHRC1, TAL1, FIBIN, BEX5, BEX1, ESM1 and/or GHRL in the sample from the subject is decreased as compared to the control expression level of the corresponding gene(s)—is required for determining that the subject is prone to develop progressive COPD.

The decrease or increase in the level of expression of the marker gene(s) tested which is required for determining that the subject is prone to develop progressive COPD in accordance with the second aspect is preferably at least a 1.5-fold decrease or increase, more preferably at least a 2-fold decrease or increase, even more preferably at least a 3-fold decrease or increase, even more preferably at least a 5-fold decrease or increase, and yet even more preferably at least a 10-fold decrease or increase.

In a preferred embodiment of the method according to the second aspect of the invention, it is determined that the subject to be tested is prone to develop progressive COPD if the level of expression of a majority of the number of genes tested is altered in the sense that (i) the level of expression of DMBT1, KIAA1199, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or COMP in the sample from the subject is at least 3-fold (more preferably at least 5-fold, even more preferably at least 10-fold) increased as compared to the control expression level of the corresponding gene(s) and (ii) the level of expression of TMSB15A, DPP6, SLC51B, NUDT11, PLA1A, HYAL2, CST6, ITGA10, CTHRC1, TAL1, FIBIN, BEX5, BEX1, ESM1 and/or GHRL in the sample from the subject is at least 3-fold (more preferably at least 5-fold, even more preferably at least 10-fold) decreased as compared to the control expression level of the corresponding gene(s).

In a further preferred embodiment of the method according to the second aspect of the invention, it is determined that the subject to be tested is prone to develop progressive COPD if the level of expression of at least 70% (more preferably at least 80%, and even more preferably at least 90%) of the number of genes tested is altered in the sense that (i) the level of expression of DMBT1, KIAA1199, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or COMP in the sample from the subject is increased as compared to the control expression level of the corresponding gene(s) and (ii) the level of expression of TMSB15A, DPP6, SLC51B, NUDT11, PLA1A, HYAL2, CST6, ITGA10, CTHRC1, TAL1, FIBIN, BEX5, BEX1, ESM1 and/or GHRL in the sample from the subject is decreased as compared to the control expression level of the corresponding gene(s).

In a further preferred embodiment of the method according to the second aspect of the invention, it is determined that the subject to be tested is prone to develop progressive COPD if the level of expression of at least 70% (more preferably at least 80%, and even more preferably at least 90%) of the number of genes tested is altered in the sense that (i) the level of expression of DMBT1, KIAA1199, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or COMP in the sample from the subject is at least 3-fold (more preferably at least 5-fold, even more preferably at least 10-fold) increased as compared to the control expression level of the corresponding gene(s) and (ii) the level of expression of TMSB15A, DPP6, SLC51B, NUDT11, PLA1A, HYAL2, CST6, ITGA10, CTHRC1, TAL1, FIBIN, BEX5, BEX1, ESM1 and/or GHRL in the sample from the subject is at least 3-fold (more preferably at least 5-fold, even more preferably at least 10-fold) decreased as compared to the control expression level of the corresponding gene(s).

In the method according to the second aspect of the invention, it is particularly preferred to determine the level of expression of DMBT1 and KIAA1199 since the disease stage of COPD is particularly well reflected by the expression patterns of these marker genes. While an initial decrease in the expression of KIAA1199 and a simultaneous increase in the expression of DMBT1 is observed when a subject develops stable COPD, the ratio between the expression levels of KIAA1199 and DMBT1 changes upon entering the progressive stage of COPD, i.e., the expression of KIAA1199 increases while the expression of DMBT1 decreases. Therefore, in a particularly preferred embodiment of the method according to the second aspect, if the difference between the expression levels of DMBT1 and KIAA1199 (i.e., the expression level of DMBT1 minus the expression level of KIAA1199) in the sample from the subject is increased as compared to the difference between the control expression levels of DMBT1 and KIAA1199 (i.e., as compared to the value obtained when subtracting the control expression level of KIAA1199 from the control expression level of DMBT1) by a factor of more than $2^{3.63}$ (i.e., by a factor of more than 12.38; preferably by a factor of more than $2^{3.8}$, i.e., more than 13.93; and more preferably by a factor of more than $2^4$, i.e., more than 16), then it is determined that the subject is prone to develop progressive COPD. This procedure allows to particularly reliably distinguish between progressive COPD and stable COPD (see also FIG. 6E) and, thus, further improves the accurateness of the method of assessing the susceptibility of a subject to develop progressive COPD in accordance with the second aspect of the invention.

In the method according to the third aspect of the invention, preferably, it is determined that the subject suffers from stable COPD or is prone to suffer from stable COPD if the level of expression of a majority (i.e., more than 50%) of the number of genes tested is altered in the sense that (i) the level of expression of DMBT1, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or COMP in the sample from the subject is increased as compared to the control expression level of the corresponding gene(s) and (ii) the level of expression of KIAA1199, TMSB15A, DPP6, SLC51B, NUDT11, PLA1A, HYAL2, CST6, ITGA10, CTHRC1, TAL1, FIBIN, BEX5, BEX1, ESM1 and/or GHRL in the sample from the subject is decreased as compared to the control expression level of the corresponding gene(s).

In accordance with the third aspect, it is furthermore preferred that an alteration in the level of expression of at least 60%, more preferably at least 70%, even more preferably at least 80%, and still more preferably at least 90% of the number of genes tested—i.e., an alteration in the sense that (i) the level of expression of DMBT1, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or COMP in the sample from the subject is increased as compared to the control expression level of the corresponding gene(s) and (ii) the level of expression of KIAA1199, TMSB15A, DPP6, SLC51B, NUDT11, PLA1A, HYAL2, CST6, ITGA10, CTHRC1, TAL1, FIBIN, BEX5, BEX1, ESM1 and/or GHRL in the sample from the subject is decreased as compared to the control expression level of the corresponding gene(s)—is required for determining that the subject suffers from stable COPD or is prone to suffer from stable COPD.

The decrease or increase in the level of expression of the marker gene(s) tested which is required for determining that the subject suffers from stable COPD or is prone to suffer from stable COPD in accordance with the third aspect is preferably at least a 1.5-fold decrease or increase, more preferably at least a 2-fold decrease or increase, even more preferably at least a 3-fold decrease or increase, even more preferably at least a 5-fold decrease or increase, and yet even more preferably at least a 10-fold decrease or increase.

In a preferred embodiment of the method according to the third aspect of the invention, it is determined that the subject to be tested suffers from stable COPD or is prone to suffer from stable COPD if the level of expression of a majority of the number of genes tested is altered in the sense that (i) the level of expression of DMBT1, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or COMP in the sample from the subject is at least 3-fold (more preferably at least 5-fold, even more preferably at least 10-fold) increased as compared to the control expression level of the corresponding gene(s) and (ii) the level of expression of KIAA1199, TMSB15A, DPP6, SLC51B, NUDT11, PLA1A, HYAL2, CST6, ITGA10, CTHRC1, TAL1, FIBIN, BEX5, BEX1, ESM1 and/or GHRL in the sample from the subject is at least 3-fold (more preferably at least 5-fold, even more preferably at least 10-fold) decreased as compared to the control expression level of the corresponding gene(s).

In a further preferred embodiment of the method according to the third aspect of the invention, it is determined that the subject to be tested suffers from stable COPD or is prone to suffer from stable COPD if the level of expression of at least 70% (more preferably at least 80%, and even more preferably at least 90%) of the number of genes tested is altered in the sense that (i) the level of expression of DMBT1, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or COMP in the sample from the subject is increased as compared to the control expression level of the corresponding gene(s) and (ii) the level of expression of KIAA1199, TMSB15A, DPP6, SLC51B, NUDT11, PLA1A, HYAL2, CST6, ITGA10, CTHRC1, TAL1, FIBIN, BEX5, BEX1, ESM1 and/or GHRL in the sample from the subject is decreased as compared to the control expression level of the corresponding gene(s).

In a further preferred embodiment of the method according to the third aspect of the invention, it is determined that the subject to be tested suffers from stable COPD or is prone to suffer from stable COPD if the level of expression of at least 70% (more preferably at least 80%, and even more preferably at least 90%) of the number of genes tested is altered in the sense that (i) the level of expression of DMBT1, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or COMP in the sample from the subject is at least 3-fold (more preferably at least 5-fold, even more preferably at least 10-fold) increased as compared to the control expression level of the corresponding gene(s) and (ii) the level of expression of KIAA1199, TMSB15A, DPP6, SLC51B, NUDT11, PLA1A, HYAL2, CST6, ITGA10, CTHRC1, TAL1, FIBIN, BEX5, BEX1, ESM1 and/or GHRL in the sample from the subject is at least 3-fold (more preferably at least 5-fold, even more preferably at least 10-fold) decreased as compared to the control expression level of the corresponding gene(s).

In the method according to the fourth aspect of the invention, preferably, it is determined that the subject is prone to develop progressive COPD if the level of expression of a majority (i.e., more than 50%) of the number of genes tested is altered in the sense that (i) the level of expression of KIAA1199, GPR110, GDF15, RASGRF2, RND1, FGG, CEACAM5, HYAL2, AHRR, CXCL3, CYP1A1, CYP1B1, CYP1A2, CST6, NTRK2 and/or TAL1 in the sample from the subject is increased as compared to the control expression level of the corresponding gene(s) and (ii) the level of expression of DMBT1, ELF5, AZGP1, PRRX1, AQP3, COMP, ITGA10, CTHRC1, BEX1 and/or GHRL in the sample from the subject is decreased as compared to the control expression level of the corresponding gene(s).

In accordance with the fourth aspect, it is furthermore preferred that an alteration in the level of expression of at least 60%, more preferably at least 70%, even more preferably at least 80%, and still more preferably at least 90% of the number of genes tested—i.e., an alteration in the sense that (i) the level of expression of KIAA1199, GPR110, GDF15, RASGRF2, RND1, FGG, CEACAM5, HYAL2, AHRR, CXCL3, CYP1A1, CYP1B1, CYP1A2, CST6, NTRK2 and/or TAL1 in the sample from the subject is increased as compared to the control expression level of the corresponding gene(s) and (ii) the level of expression of DMBT1, ELF5, AZGP1, PRRX1, AQP3, COMP, ITGA10, CTHRC1, BEX1 and/or GHRL in the sample from the subject is decreased as compared to the control expression level of the corresponding gene(s)—is required for determining that the subject is prone to develop progressive COPD.

The decrease or increase in the level of expression of the marker gene(s) tested which is required for determining that the subject is prone to develop progressive COPD in accordance with the fourth aspect is preferably at least a 1.5-fold decrease or increase, more preferably at least a 2-fold decrease or increase, even more preferably at least a 3-fold decrease or increase, even more preferably at least a 5-fold decrease or increase, and yet even more preferably at least a 10-fold decrease or increase.

In a preferred embodiment of the method according to the fourth aspect of the invention, it is determined that the subject to be tested is prone to develop progressive COPD if the level of expression of a majority of the number of genes tested is altered in the sense that (i) the level of expression of KIAA1199, GPR110, GDF15, RASGRF2, RND1, FGG, CEACAM5, HYAL2, AHRR, CXCL3, CYP1A1, CYP1B1, CYP1A2, CST6, NTRK2 and/or TAL1 in the sample from the subject is at least 3-fold (more preferably at least 5-fold, even more preferably at least 10-fold) increased as compared to the control expression level of the corresponding gene(s) and (ii) the level of expression of DMBT1, ELF5, AZGP1, PRRX1, AQP3, COMP, ITGA10, CTHRC1, BEX1 and/or GHRL in the sample from the subject is at least 3-fold (more preferably at least 5-fold, even more preferably at least 10-fold) decreased as compared to the control expression level of the corresponding gene(s).

In a further preferred embodiment of the method according to the fourth aspect of the invention, it is determined that the subject to be tested is prone to develop progressive COPD if the level of expression of at least 70% (more preferably at least 80%, and even more preferably at least 90%) of the number of genes tested is altered in the sense that (i) the level of expression of KIAA1199, GPR110, GDF15, RASGRF2, RND1, FGG, CEACAM5, HYAL2, AHRR, CXCL3, CYP1A1, CYP1B1, CYP1A2, CST6, NTRK2 and/or TAL1 in the sample from the subject is increased as compared to the control expression level of the corresponding gene(s) and (ii) the level of expression of DMBT1, ELF5, AZGP1, PRRX1, AQP3, COMP, ITGA10, CTHRC1, BEX1 and/or GHRL in the sample from the subject is decreased as compared to the control expression level of the corresponding gene(s).

In a further preferred embodiment of the method according to the fourth aspect of the invention, it is determined that the subject to be tested is prone to develop progressive COPD if the level of expression of at least 70% (more preferably at least 80%, and even more preferably at least 90%) of the number of genes tested is altered in the sense that (i) the level of expression of KIAA1199, GPR110, GDF15, RASGRF2, RND1, FGG, CEACAM5, HYAL2, AHRR, CXCL3, CYP1A1, CYP1B1, CYP1A2, CST6, NTRK2 and/or TAL1 in the sample from the subject is at least 3-fold (more preferably at least 5-fold, even more preferably at least 10-fold) increased as compared to the control expression level of the corresponding gene(s) and (ii) the level of expression of DMBT1, ELF5, AZGP1, PRRX1, AQP3, COMP, ITGA10, CTHRC1, BEX1 and/or GHRL in the sample from the subject is at least 3-fold (more preferably at least 5-fold, even more preferably at least 10-fold) decreased as compared to the control expression level of the corresponding gene(s).

The present invention furthermore relates to the use of the gene DMBT1 as a marker in an in vitro diagnostic method of assessing the susceptibility of a subject to develop progressive COPD. In particular, in accordance with the fifth aspect, the invention relates to the use of a pair of primers for (i.e., binding to) a transcript of the gene DMBT1 in an in vitro diagnostic method of assessing the susceptibility of a subject to develop progressive COPD. Non-limiting examples of such an in vitro method are the methods according to the second aspect of the present invention. The transcript is preferably an mRNA of the gene DMBT1 (e.g., any one of the specific mRNAs of DMBT1 listed in Table 1 above) or a cDNA synthesized from the mRNA of the gene DMBT1 (e.g., a cDNA synthesized from any one of the specific mRNAs of DMBT1 listed in Table 1 above). The primers can be designed using methods known in the art (as also described, e.g., in Green et al., 2012) so as to allow the specific amplification/quantification of the transcript of the gene DMBT1. Furthermore, the primers are preferably DNA primers. The in vitro diagnostic method of assessing the susceptibility of a subject to develop progressive COPD, in which the pair of primers is to be used, preferably comprises a step of determining the expression level of the gene DMBT1 in a sample obtained from the subject. The preferred features/embodiments of the method according to the second aspect of the present invention as described herein, including in particular the preferred embodiments of determining expression levels, the preferred embodiments of the sample, and the preferred embodiments of the subject, also apply to the method in which the pair of primers is to be used.

In accordance with the fifth aspect, the present invention also relates to the use of a nucleic acid probe to (i.e., binding to) a transcript of the gene DMBT1 in an in vitro diagnostic method of assessing the susceptibility of a subject to develop progressive COPD. Non-limiting examples of such an in vitro method are the methods according to the second aspect of the present invention. The transcript is preferably an mRNA of the gene DMBT1 (e.g., any one of the specific mRNAs of DMBT1 listed in Table 1 above) or a cDNA synthesized from the mRNA of the gene DMBT1 (e.g., a cDNA synthesized from any one of the specific mRNAs of DMBT1 listed in Table 1 above). The nucleic acid probe comprises or consists of a nucleic acid capable of hybridizing with the above-mentioned transcript. The nucleic acid probe is preferably a single-stranded DNA probe or a single-stranded RNA probe, more preferably a single-stranded DNA probe. It is furthermore preferred that the nucleic acid probe (which may be, e.g., a single-stranded DNA or a single-stranded RNA, and is preferably a single-stranded DNA) is an oligonucleotide probe having, e.g., 10 to 80 nucleotides, preferably 15 to 60 nucleotides, more preferably 20 to 35 nucleotides, and even more preferably about 25 nucleotides. Such nucleic acid probes can be designed using methods known in the art (as also described, e.g., in Green et al., 2012) so as to allow the specific detection and quantification of the transcript of the corresponding gene. The in vitro diagnostic method of assessing the susceptibility of a subject to develop progressive COPD, in which the nucleic acid probe is to be used, preferably comprises a step of determining the expression level of the gene DMBT1 in a sample obtained from the subject. The preferred features/embodiments of the method according to the second aspect of the invention as described herein, including in particular the preferred embodiments of determining expression levels, the preferred embodiments of the sample, and the preferred embodiments of the subject, also apply to the method in which the nucleic acid probe is to be used.

In the fifth aspect, the invention further relates to the use of a microarray comprising a nucleic acid probe to (i.e., binding to) a transcript of the gene DMBT1 and optionally comprising nucleic acid probes to the transcripts of one or more further genes selected from KIAA1199, TMSB15A, DPP6, SLC51B, NUDT11, ELF5, AZGP1, PRRX1, AQP3, SFN, GPR110, GDF15, RASGRF2, RND1, PLA1A, FGG, CEACAM5, HYAL2, AHRR, CXCL3, CYP1A1, CYP1B1, CYP1A2, CST6, NTRK2, COMP, ITGA10, CTHRC1, TAL1, FIBIN, BEX5, BEX1, ESM1 and GHRL in an in vitro diagnostic method of assessing the susceptibility of a subject to develop progressive COPD. The microarray preferably comprises nucleic acid probes to the transcript of DMBT1 and to the transcripts of at least one, more preferably at least two, even more preferably at least three of the above-mentioned further genes. Each of the transcripts is preferably an mRNA of the corresponding gene (including, e.g., any one of the corresponding specific mRNAs listed in Table 1 above) or a cDNA synthesized from the mRNA of the gene (including, e.g., a cDNA synthesized from any one of the corresponding specific mRNAs listed in Table 1 above). Each of the nucleic acid probes is preferably a single-stranded DNA probe or a single-stranded RNA probe, more preferably a single-stranded DNA probe. It is furthermore preferred that the nucleic acid probes (which may be, e.g., single-stranded DNA or single-stranded RNA, preferably single-stranded DNA) are oligonucleotide probes having, e.g., 10 to 80 nucleotides, preferably 15 to 60 nucleotides, more preferably 20 to 35 nucleotides, and even more preferably about 25 nucleotides. The in vitro diagnostic method of assessing the susceptibility of a subject to develop progressive COPD, in which the microarray is to be used, preferably comprises a step of determining the expression level of the gene DMBT1 and optionally of the one or more further genes in a sample obtained from the subject. The preferred features/embodiments of the method according to the second aspect of the invention as described herein, including in particular the preferred embodiments of determining expression levels, the preferred embodiments of the sample, and the preferred embodiments of the subject, also apply to the method in which the microarray is to be used.

In accordance with the fifth aspect, the invention is also directed to the use of an antibody against (i.e., binding to) the protein DMBT1 in an in vitro diagnostic method of assessing the susceptibility of a subject to develop progressive COPD. The antibody binds specifically to the protein DMBT1 and may be, e.g., a polyclonal antibody or a monoclonal antibody. Preferably, the antibody is a monoclonal antibody. The antibody may further be a full/intact immunoglobulin molecule or a fragment/part thereof (such as, e.g., a separated light or heavy chain, an Fab fragment, an Fab/c fragment, an Fe fragment, an Fab' fragment, or an F(ab')$_2$ fragment), provided that the fragment/part substantially retains the binding specificity of the corresponding full immunoglobulin molecule. The antibody may also be a modified and/or altered antibody, such as a chimeric or humanized antibody, a bifunctional or trifunctional antibody, or an antibody construct (such as a single-chain variable fragment (scFv) or an antibody-fusion protein). The antibody can be prepared using methods known in the art, as also described, e.g., in Harlow et al., 1998. For example, monoclonal antibodies can be prepared by methods such as the hybridoma technique (see, e.g., Köhler et al., 1975), the trioma technique, the human B-cell hybridoma technique (see, e.g., Kozbor et al., 1983) or the EBV-hybridoma technique (see, e.g., Cole et al., 1985). The protein DMBT1 may be, e.g., the specific DMBT1 protein listed in Table 1 above. The in vitro diagnostic method of assessing the susceptibility of a subject to develop progressive COPD, in which the antibody is to be used, preferably comprises a step of determining the amount of the protein DMBT1 in a sample obtained from the subject. The preferred features/embodiments of the method according to the second aspect of the invention as described herein, including in particular the preferred embodiments of determining the amount of a specific protein in a sample (as discussed in connection with the determination of translation levels), the preferred embodiments of the sample, and the preferred embodiments of the subject, also apply to the method in which the antibody is to be used.

Moreover, in accordance with the seventh aspect, the present invention relates to the use of a pair of primers for (i.e., binding to) a transcript of the gene DMBT1 in an in vitro method of diagnosing stable COPD in a subject or assessing the susceptibility of a subject to develop stable COPD. Non-limiting examples of such an in vitro method are the methods according to the third aspect of the present invention. The transcript is preferably an mRNA of the gene DMBT1 (e.g., any one of the specific mRNAs of DMBT1 listed in Table 1 above) or a cDNA synthesized from the mRNA of the gene DMBT1 (e.g., a cDNA synthesized from any one of the specific mRNAs of DMBT1 listed in Table 1 above). The primers can be designed using methods known in the art (as also described, e.g., in Green et al., 2012) so as to allow the specific amplification/quantification of the transcript of the gene DMBT1. Furthermore, the primers are preferably DNA primers. The in vitro method of diagnosing stable COPD in a subject or assessing the susceptibility of a subject to develop stable COPD, in which the pair of primers is to be used, preferably comprises a step of determining the expression level of the gene DMBT1 in a sample obtained from the subject. The preferred features/embodiments of the method according to the third aspect of the present invention as described herein, including in particular the preferred embodiments of determining expression levels, the preferred embodiments of the sample, and the preferred embodiments of the subject, also apply to the method in which the pair of primers is to be used.

In accordance with the seventh aspect, the present invention also relates to the use of a nucleic acid probe to (i.e., binding to) a transcript of the gene DMBT1 in an in vitro method of diagnosing stable COPD in a subject or assessing the susceptibility of a subject to develop stable COPD. Non-limiting examples of such an in vitro method are the methods according to the third aspect of the present invention. The transcript is preferably an mRNA of the gene DMBT1 (e.g., any one of the specific mRNAs of DMBT1 listed in Table 1 above) or a cDNA synthesized from the mRNA of the gene DMBT1 (e.g., a cDNA synthesized from any one of the specific mRNAs of DMBT1 listed in Table 1 above). The nucleic acid probe comprises or consists of a nucleic acid capable of hybridizing with the above-mentioned transcript. The nucleic acid probe is preferably a single-stranded DNA probe or a single-stranded RNA probe, more preferably a single-stranded DNA probe. It is furthermore preferred that the nucleic acid probe (which may be, e.g., a single-stranded DNA or a single-stranded RNA, and is preferably a single-stranded DNA) is an oligonucleotide probe having, e.g., 10 to 80 nucleotides, preferably 15 to 60 nucleotides, more preferably 20 to 35 nucleotides, and even more preferably about 25 nucleotides. Such nucleic acid probes can be designed using methods known in the art (as also described, e.g., in Green et al., 2012) so as to allow the specific detection and quantification of the transcript of the corresponding gene. The in vitro method of diagnosing stable COPD in a subject or assessing the susceptibility of a subject to develop stable COPD, in which the nucleic acid probe is to be used, preferably comprises a step of determining the expression level of the gene DMBT1 in a sample obtained from the subject. The preferred features/embodiments of the method according to the third aspect of the invention as described herein, including in particular the preferred embodiments of determining expression levels, the preferred embodiments of the sample, and the preferred embodiments of the subject, also apply to the method in which the nucleic acid probe is to be used.

In the seventh aspect, the invention further relates to the use of a microarray comprising a nucleic acid probe to (i.e., binding to) a transcript of the gene DMBT1 and optionally comprising nucleic acid probes to the transcripts of one or more further genes selected from KIAA1199, TMSB15A, DPP6, SLC51B, NUDT11, ELF5, AZGP1, PRRX1, AQP3, SFN, GPR110, GDF15, RASGRF2, RND1, PLA1A, FGG, CEACAM5, HYAL2, AHRR, CXCL3, CYP1A1, CYP1B1, CYP1A2, CST6, NTRK2, COMP, ITGA10, CTHRC1, TAL1, FIBIN, BEX5, BEX1, ESM1 and GHRL in an in vitro method of diagnosing stable COPD in a subject or assessing the susceptibility of a subject to develop stable COPD. The microarray preferably comprises nucleic acid probes to the transcript of DMBT1 and to the transcripts of at least one, more preferably at least two, even more preferably at least three of the above-mentioned further genes. Each of the transcripts is preferably an mRNA of the corresponding gene (including, e.g., any one of the corresponding specific mRNAs listed in Table 1 above) or a cDNA synthesized from the mRNA of the gene (including, e.g., a cDNA synthesized from any one of the corresponding specific mRNAs listed in Table 1 above). Each of the nucleic acid probes is preferably a single-stranded DNA probe or a single-stranded RNA probe, more preferably a single-stranded DNA probe. It is furthermore preferred that the nucleic acid probes (which may be, e.g., single-stranded DNA or single-stranded RNA, preferably single-stranded DNA) are oligonucleotide probes having, e.g., 10 to 80 nucleotides, preferably 15 to 60 nucleotides, more preferably 20 to 35 nucleotides, and even more preferably about 25 nucleotides. The in vitro method of diagnosing stable COPD in a subject or assessing the susceptibility of a subject to develop stable COPD, in which the microarray is to be used, preferably comprises a step of determining the expression level of the gene DMBT1 and optionally of the one or more further genes in a sample obtained from the subject. The preferred features/embodiments of the method according to the third aspect of the invention as described herein, including in particular the preferred embodiments of determining expression levels, the preferred embodiments of the sample, and the preferred embodiments of the subject, also apply to the method in which the microarray is to be used.

In accordance with the seventh aspect, the invention is also directed to the use of an antibody against (i.e., binding to) the protein DMBT1 in an in vitro method of diagnosing stable COPD in a subject or assessing the susceptibility of a subject to develop stable COPD. The antibody binds specifically to the protein DMBT1 and may be, e.g., a polyclonal antibody or a monoclonal antibody. Preferably, the antibody is a monoclonal antibody. The antibody may further be a full/intact immunoglobulin molecule or a fragment/part thereof (such as, e.g., a separated light or heavy chain, an Fab fragment, an Fab/c fragment, an Fv fragment, an Fab' fragment, or an F(ab')$_2$ fragment), provided that the fragment/part substantially retains the binding specificity of the corresponding full immunoglobulin molecule. The antibody may also be a modified and/or altered antibody, such as a chimeric or humanized antibody, a bifunctional or trifunctional antibody, or an antibody construct (such as a single-chain variable fragment (scFv) or an antibody-fusion protein). The antibody can be prepared using methods known in the art, as also described, e.g., in Harlow et al., 1998. For example, monoclonal antibodies can be prepared by methods such as the hybridoma technique (see, e.g., Köhler et al., 1975), the trioma technique, the human B-cell hybridoma technique (see, e.g., Kozbor et al., 1983) or the EBV-hybridoma technique (see, e.g., Cole et al., 1985). The protein DMBT1 may be, e.g., the specific DMBT1 protein listed in Table 1 above. The in vitro method of diagnosing stable COPD in a subject or assessing the susceptibility of a subject to develop stable COPD, in which the antibody is to be used, preferably comprises a step of determining the amount of the protein DMBT1 in a sample obtained from the subject. The preferred features/embodiments of the method according to the third aspect of the invention as described herein, including in particular the preferred embodiments of determining the amount of a specific protein in a sample (as discussed in connection with the determination of translation levels), the preferred embodiments of the sample, and the preferred embodiments of the subject, also apply to the method in which the antibody is to be used.

Furthermore, in accordance with the ninth aspect, the present invention relates to the use of a pair of primers for (i.e., binding to) a transcript of the gene DMBT1 in an in vitro diagnostic method of assessing the susceptibility of a subject suffering from stable COPD to develop progressive COPD involving the appearance of irreversible lung damage. Non-limiting examples of such an in vitro method are the methods according to the fourth aspect of the present invention. The transcript is preferably an mRNA of the gene DMBT1 (e.g., any one of the specific mRNAs of DMBT1 listed in Table 1 above) or a cDNA synthesized from the mRNA of the gene DMBT1 (e.g., a cDNA synthesized from any one of the specific mRNAs of DMBT1 listed in Table 1 above). The primers can be designed using methods known in the art (as also described, e.g., in Green et al., 2012) so as to allow the specific amplification/quantification of the transcript of the gene DMBT1. Furthermore, the primers are preferably DNA primers. The in vitro diagnostic method of assessing the susceptibility of a subject suffering from stable COPD to develop progressive COPD involving the appearance of irreversible lung damage, in which the pair of primers is to be used, preferably comprises a step of determining the expression level of the gene DMBT1 in a sample obtained from the subject. The preferred features/embodiments of the method according to the fourth aspect of the present invention as described herein, including in particular the preferred embodiments of determining expression levels, the preferred embodiments of the sample, and the preferred embodiments of the subject, also apply to the method in which the pair of primers is to be used.

In accordance with the ninth aspect, the present invention also relates to the use of a nucleic acid probe to (i.e., binding to) a transcript of the gene DMBT1 in an in vitro diagnostic method of assessing the susceptibility of a subject suffering from stable COPD to develop progressive COPD involving the appearance of irreversible lung damage. Non-limiting examples of such an in vitro method are the methods according to the fourth aspect of the present invention. The transcript is preferably an mRNA of the gene DMBT1 (e.g., any one of the specific mRNAs of DMBT1 listed in Table 1 above) or a cDNA synthesized from the mRNA of the gene DMBT1 (e.g., a cDNA synthesized from any one of the specific mRNAs of DMBT1 listed in Table 1 above). The nucleic acid probe comprises or consists of a nucleic acid capable of hybridizing with the above-mentioned transcript. The nucleic acid probe is preferably a single-stranded DNA probe or a single-stranded RNA probe, more preferably a single-stranded DNA probe. It is furthermore preferred that the nucleic acid probe (which may be, e.g., a single-stranded DNA or a single-stranded RNA, and is preferably a single-stranded DNA) is an oligonucleotide probe having, e.g., 10 to 80 nucleotides, preferably 15 to 60 nucleotides, more preferably 20 to 35 nucleotides, and even more preferably about 25 nucleotides. Such nucleic acid probes can be designed using methods known in the art (as also described, e.g., in Green et al., 2012) so as to allow the specific detection and quantification of the transcript of the corresponding gene. The in vitro diagnostic method of assessing the susceptibility of a subject suffering from stable COPD to develop progressive COPD involving the appearance of irreversible lung damage, in which the nucleic acid probe is to be used, preferably comprises a step of determining the expression level of the gene DMBT1 in a sample obtained from the subject. The preferred features/embodiments of the method according to the fourth aspect of the invention as described herein, including in particular the preferred embodiments of determining expression levels, the preferred embodiments of the sample, and the preferred embodiments of the subject, also apply to the method in which the nucleic acid probe is to be used.

In the ninth aspect, the invention further relates to the use of a microarray comprising a nucleic acid probe to (i.e., binding to) a transcript of the gene DMBT1 and optionally comprising nucleic acid probes to the transcripts of one or more further genes selected from KIAA1199, TMSB15A, DPP6, SLC51B, NUDT11, ELF5, AZGP1, PRRX1, AQP3, SFN, GPR110, GDF15, RASGRF2, RND1, PLA1A, FGG, CEACAM5, HYAL2, AHRR, CXCL3, CYP1A1, CYP1B1, CYP1A2, CST6, NTRK2, COMP, ITGA10, CTHRC1, TAL1, FIBIN, BEX5, BEX1, ESM1 and GHRL in an in vitro diagnostic method of assessing the susceptibility of a subject suffering from stable COPD to develop progressive COPD involving the appearance of irreversible lung damage. The microarray preferably comprises nucleic acid probes to the transcript of DMBT1 and to the transcripts of at least one, more preferably at least two, even more preferably at least three of the above-mentioned further genes. Each of the transcripts is preferably an mRNA of the corresponding gene (including, e.g., any one of the corresponding specific mRNAs listed in Table 1 above) or a cDNA synthesized from the mRNA of the gene (including, e.g., a cDNA synthesized from any one of the corresponding specific mRNAs listed in Table 1 above). Each of the nucleic acid probes is preferably a single-stranded DNA probe or a single-stranded RNA probe, more preferably a single-stranded DNA probe. It is furthermore preferred that the nucleic acid probes (which may be, e.g., single-stranded DNA or single-stranded RNA, preferably single-stranded DNA) are oligonucleotide probes having, e.g., 10 to 80 nucleotides, preferably 15 to 60 nucleotides, more preferably 20 to 35 nucleotides, and even more preferably about 25 nucleotides. The in vitro diagnostic method of assessing the susceptibility of a subject suffering from stable COPD to develop progressive COPD involving the appearance of irreversible lung damage, in which the microarray is to be used, preferably comprises a step of determining the expression level of the gene DMBT1 and optionally of the one or more further genes in a sample obtained from the subject. The preferred features/embodiments of the method according to the fourth aspect of the invention as described herein, including in particular the preferred embodiments of determining expression levels, the preferred embodiments of the sample, and the preferred embodiments of the subject, also apply to the method in which the microarray is to be used.

In accordance with the ninth aspect, the invention is also directed to the use of an antibody against (i.e., binding to) the protein DMBT1 in an in vitro diagnostic method of assessing the susceptibility of a subject suffering from stable COPD to develop progressive COPD involving the appearance of irreversible lung damage. The antibody binds specifically to the protein DMBT1 and may be, e.g., a polyclonal antibody or a monoclonal antibody. Preferably, the antibody is a monoclonal antibody. The antibody may further be a full/intact immunoglobulin molecule or a fragment/part thereof (such as, e.g., a separated light or heavy chain, an Fab fragment, an Fab/c fragment, an Fv fragment, an Fab' fragment, or an F(ab)$_2$ fragment), provided that the fragment/part substantially retains the binding specificity of the corresponding full immunoglobulin molecule. The antibody may also be a modified and/or altered antibody, such as a chimeric or humanized antibody, a bifunctional or trifunctional antibody, or an antibody construct (such as a single-chain variable fragment (scFv) or an antibody-fusion protein). The antibody can be prepared using methods known in the art, as also described, e.g., in Harlow et al., 1998. For example, monoclonal antibodies can be prepared by methods such as the hybridoma technique (see, e.g., Köhler et al., 1975), the trioma technique, the human B-cell hybridoma technique (see, e.g., Kozbor et al., 1983) or the EBV-hybridoma technique (see, e.g., Cole et al., 1985). The protein KIAA1199 may be, e.g., the specific DMBT1 protein listed in Table 1 above. The in vitro diagnostic method of assessing the susceptibility of a subject suffering from stable COPD to develop progressive COPD involving the appearance of irreversible lung damage, in which the antibody is to be used, preferably comprises a step of determining the amount of the protein DMBT1 in a sample obtained from the subject. The preferred features/embodiments of the method according to the fourth aspect of the invention as described herein, including in particular the preferred embodiments of determining the amount of a specific protein in a sample (as discussed in connection with the determination of translation levels), the preferred embodiments of the sample, and the preferred embodiments of the subject, also apply to the method in which the antibody is to be used.

In accordance with the sixth aspect, the present invention provides a method of treating COPD, the method comprising administering a drug against COPD to a subject that has been identified in a method according to the second aspect of the invention as being prone to develop progressive COPD. The invention likewise provides a drug against COPD for use in treating COPD in a subject that has been identified in a method according to the second aspect as being prone to develop progressive COPD. The invention also relates to the use of a drug against COPD in the preparation of a pharmaceutical composition for treating COPD in a subject that has been identified in a method according to the second aspect as being prone to develop progressive COPD. The subject referred to above is as defined in the methods according to the second aspect of the invention and, accordingly, is preferably a human.

Moreover, in accordance with the eighth aspect, the present invention provides a method of treating or preventing COPD, the method comprising administering a drug against COPD to a subject that has been identified in a method according to the third aspect of the invention as suffering from stable COPD or as being prone to suffer from stable COPD. It will be understood that a subject that has been identified as suffering from stable COPD can be treated by administering a drug against COPD, while a subject that has been identified as being prone to suffer from stable COPD can be prevented from developing COPD by administering a drug against COPD. The invention likewise provides a drug against COPD for use in treating or preventing COPD in a subject that has been identified in a method according to the third aspect as suffering from stable COPD or as being prone to suffer from stable COPD. The invention also relates to the use of a drug against COPD in the preparation of a pharmaceutical composition for treating or preventing COPD in a subject that has been identified in a method according to the third aspect as suffering from stable COPD or as being prone to suffer from stable COPD. The subject referred to above is as defined in the methods according to the third aspect of the invention and, accordingly, is preferably a human.

In accordance with the tenth aspect, the present invention provides a method of treating COPD, the method comprising administering a drug against COPD to a subject suffering from stable COPD, wherein the subject has been identified in a method according to the fourth aspect of the invention as being prone to develop progressive COPD. The invention likewise provides a drug against COPD for use in treating COPD in a subject suffering from stable COPD, wherein the subject has been identified in a method according to the fourth aspect as being prone to develop progressive COPD. The invention also relates to the use of a drug against CORD in the preparation of a pharmaceutical composition for treating CORD in a subject suffering from stable COPD, wherein the subject has been identified in a method according to the fourth aspect as being prone to develop progressive COPD. The subject referred to above is as defined in the methods according to the fourth aspect of the invention and, accordingly, is preferably a human.

The drug against COPD to be administered to a subject in accordance with the sixth, eighth or tenth aspect of the invention is not particularly limited and may be, for example, a $\beta_2$-agonist (such as, e.g., bitolterol, carbuterol, fenoterol, pirbuterol, procaterol, reproterol, rimiterol, salbutamol, levosalbutamol, terbutaline, tulobuterol, arformoterol, bambuterol, clenbuterol, formoterol, olodaterol, salmeterol, indacaterol, or a pharmaceutically acceptable salt of any of the aforementioned agents), a glucocorticoid (such as, e.g., beclometasone, betamethasone, budesonide, ciclesonide, flunisolide, fluticasone, mometasone, triamcinolone, or a pharmaceutically acceptable salt of any of the aforementioned agents), an anticholinergic or a muscarinic antagonist (such as, e.g., aclidinium bromide, glycopyrronium bromide, ipratropium bromide, oxitropium bromide, tiotropium bromide, or a pharmaceutically acceptable salt of any of the aforementioned agents), a mast cell stabilizer (such as, e.g., cromoglicate, nedocromil, or a pharmaceutically acceptable salt of any of the aforementioned agents), a xanthine derivative (such as, e.g., acefylline, ambuphylline, bamifylline, doxofylline, enprofylline, etamiphylline, proxyphylline, theobromine, theophylline, aminophylline, choline theophyllinate, or a pharmaceutically acceptable salt of any of the aforementioned agents), a leukotriene antagonist (such as, e.g., montelukast, pranlukast, zafirlukast, or a pharmaceutically acceptable salt of any of the aforementioned agents), a lipoxygenase inhibitor (such as, e.g., zileuton or a pharmaceutically acceptable salt thereof), a thromboxane receptor antagonist (such as, e.g., ramatroban, seratrodast, or a pharmaceutically acceptable salt of any of the aforementioned agents) a non-xanthine PDE4 inhibitor (such as, e.g., ibudilast, roflumilast, or a pharmaceutically acceptable salt of any of the aforementioned agents), or any other drug against COPD (such as, e.g., amlexanox, eprozinol, fenspiride, omalizumab, epinephrine, hexoprenaline, isoprenaline, isoproterenol, orciprenaline, metaproterenol, atropine, or a pharmaceutically acceptable salt of any of the aforementioned agents), or any combination thereof. A particularly preferred drug against COPD is roflumilast.

In the eleventh aspect, the present invention provides an in vitro method of monitoring the progression of COPD in a subject, the method comprising:

determining the level of expression of one or more genes selected from NTRK2 and RASGRF2 in a first sample obtained from the subject;

determining the level of expression of the one or more genes in a second sample obtained from the subject at a later point in time than the first sample;

comparing the level of expression of the one or more genes in the second sample to the level of expression of the corresponding gene(s) in the first sample; and assessing (or determining) the progression of COPD in the subject, wherein a decrease in the level of expression of NTRK2 and/or RASGRF2 in the second sample as compared to the level of expression of the corresponding gene(s) in the first sample is indicative of an amelioration (i.e., an improvement) of COPD in the subject, and wherein an increase in the level of expression of NTRK2 and/or RASGRF2 in the second sample as compared to the level of expression of the corresponding gene(s) in the first sample is indicative of a worsening of COPD in the subject.

As demonstrated in Example 1 and shown in FIGS. 4A and 8A, a decrease in the level of expression of NTRK2 and/or RASGRF2 is indicative of an amelioration/improvement of COPD whereas an increase in the level of expression of these genes is indicative of a worsening of COPD. Monitoring the progression of COPD in a subject suffering from this disease can be useful, e.g., for assessing the prospects of success of a treatment, of a new medication, or of a new dosing regimen.

In the eleventh aspect, it is preferred that the level of expression of the gene NTRK2 and optionally of the gene RASGRF2 is determined. More preferably, the level of expression of the genes NTRK2 and RASGRF2 is determined.

The level of expression of the above-mentioned marker genes in the first sample and in the second sample according the eleventh aspect of the invention can be determined as described in connection with the methods of the second to fourth aspects of the invention. For example, the level of transcription or the level of translation of the marker gene(s) NTRK2 and/or RASGRF2 can be determined. It is preferred that the level of expression of the one or more genes selected from NTRK2 and RASGRF2 in the first sample and in the second sample is determined by determining the level of transcription of the corresponding gene(s). The level of transcription is preferably determined using qRT-PCT or a microarray.

The subject to be tested in the method according to the eleventh aspect of the invention is as defined in connection with the methods of the second to fourth aspects of the invention, and preferably is a human or a non-human mammal, more preferably a human. It is furthermore preferred that the subject to be tested/monitored in accordance with the eleventh aspect is a subject (preferably a human) that has been diagnosed as suffering from COPD (e.g., at the point in time when the first sample was obtained).

While the first sample and the second sample obtained from the subject can, in principle, be any tissue sample or serum from the subject, they should both originate from the same type of tissue of the subject (or should both be serum samples). Preferably, the first sample and the second sample are lung tissue samples. More preferably, the first sample and the second sample are transbronchial lung biopsy samples or they are bronchoalveolar lavage (BAL) samples.

The second sample has been obtained from the subject at a later point in time than the first sample. For instance, the second sample may have been obtained from the subject about 2 months to about 12 months, preferably about 3 months to about 9 months (e.g., about 3 months or about 4 months, or about 5 months, or about 6 months, or about 7 months, or about 8 months, or about 9 months), and more preferably about 3 months to about 6 months after the first sample was obtained from the subject.

As used herein, the term "about" refers to ±10% of the indicated numerical value, and in particular to ±5% of the indicated numerical value. Whenever the term "about" is used, a specific reference to the exact numerical value indicated is also included. If the term "about" is used in connection with a parameter that is quantified in integers, such as the number of nucleotides in a given nucleic acid, the numbers corresponding to ±10% or ±5% of the indicated numerical value are to be rounded to the nearest integer. For example, the expression "about 25 nucleotides" refers to the range of 23 to 28 nucleotides, in particular the range of 24 to 26 nucleotides, and preferably refers to the specific value of 25 nucleotides.

It is to be understood that the present invention specifically relates to each and every combination of features and embodiments described herein, including any combination of general and/or preferred features/embodiments. In particular, the invention specifically relates to all combinations of preferred features (including all degrees of preference) of the methods and uses provided herein.

In this specification, a number of documents including patent applications, scientific literature and manufacturers' manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The invention is also described by the following illustrative figures. The appended figures show:

FIG. 1: Study design of the COPD-AUVA study conducted at the Vienna Medical University (see Example 1).

Figure 2:
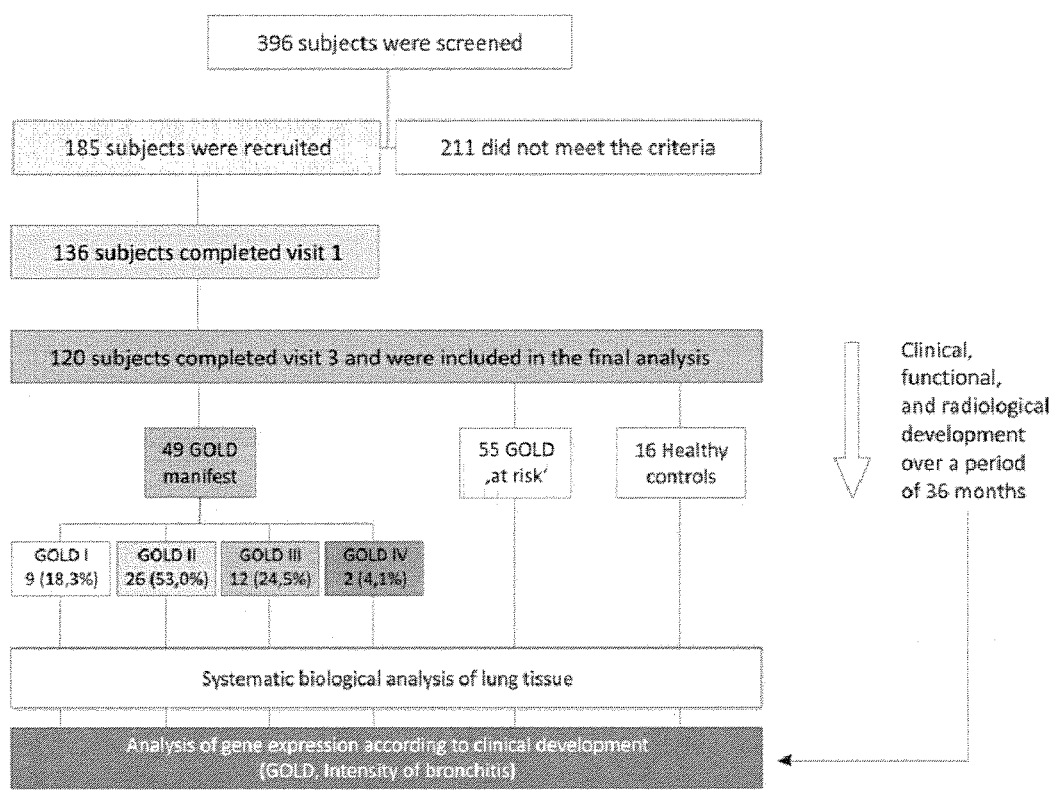

FIG. 2: Overview of the numbers of subjects of different disease states who underwent the COPD-AUVA study.

FIG. 3: Overview of healthy subjects (A) and of subjects with either chronic bronchitis but no signs of pulmonary obstruction (COPD "at risk"; "GOLD 0") at visit 1 (B) or with manifest COPD at visit 1 (C), as well as the development of COPD (severity according to GOLD criteria), bronchitis and smoking habits in these subjects over the period from visit 1 (day 0) to visit 2 (12 months) to visit 3 (36 months). The term "pack years" refers to a person's cigarette consumption calculated as the packs of cigarettes (each pack containing 20 cigarettes) smoked per day, multiplied by the length of cigarette consumption in years. (D) Clinical characteristics of participants in the COPD-AUVA study and changes between baseline and visit 3 (see Example 1).

Figure 4:
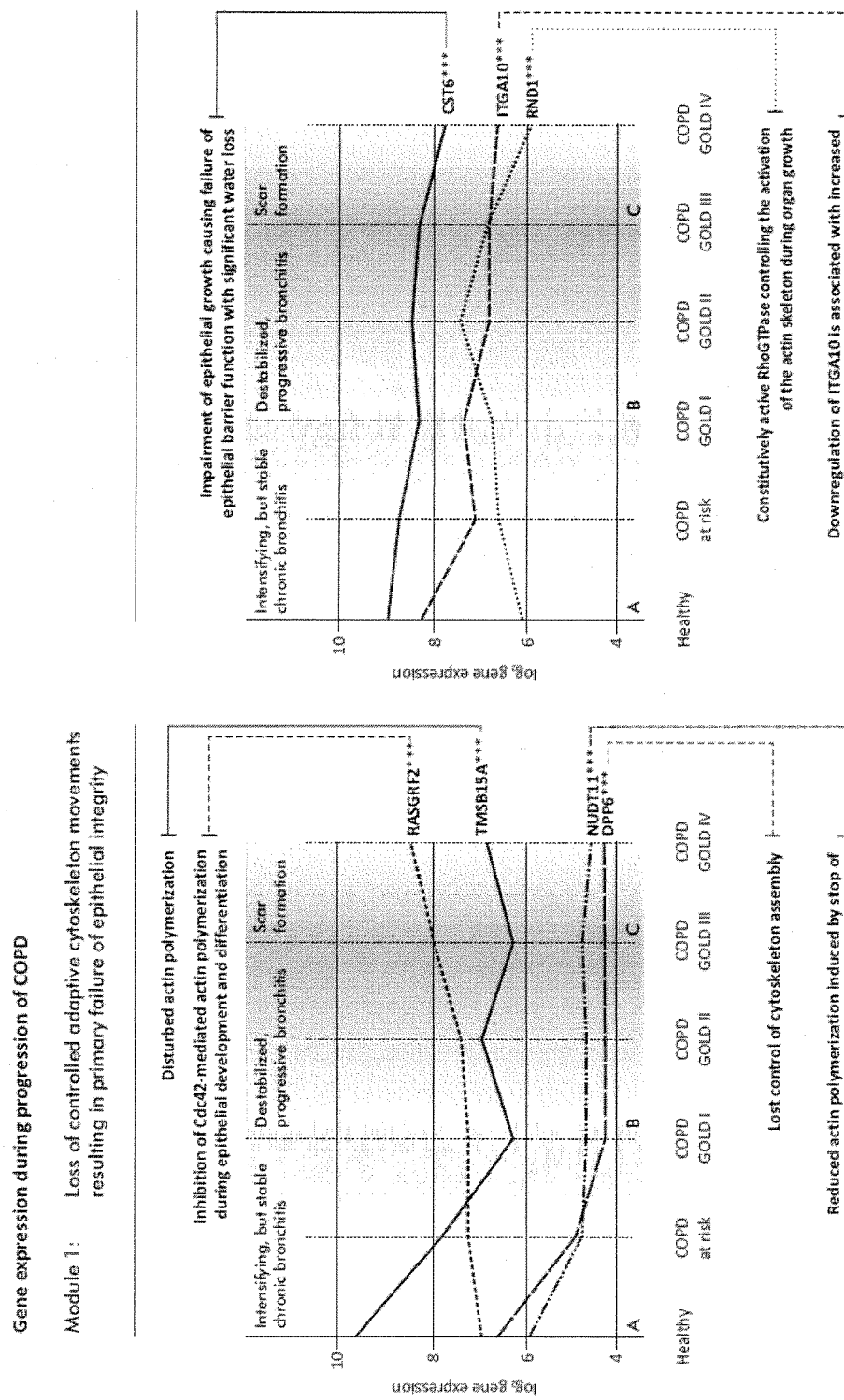
Figure 4:
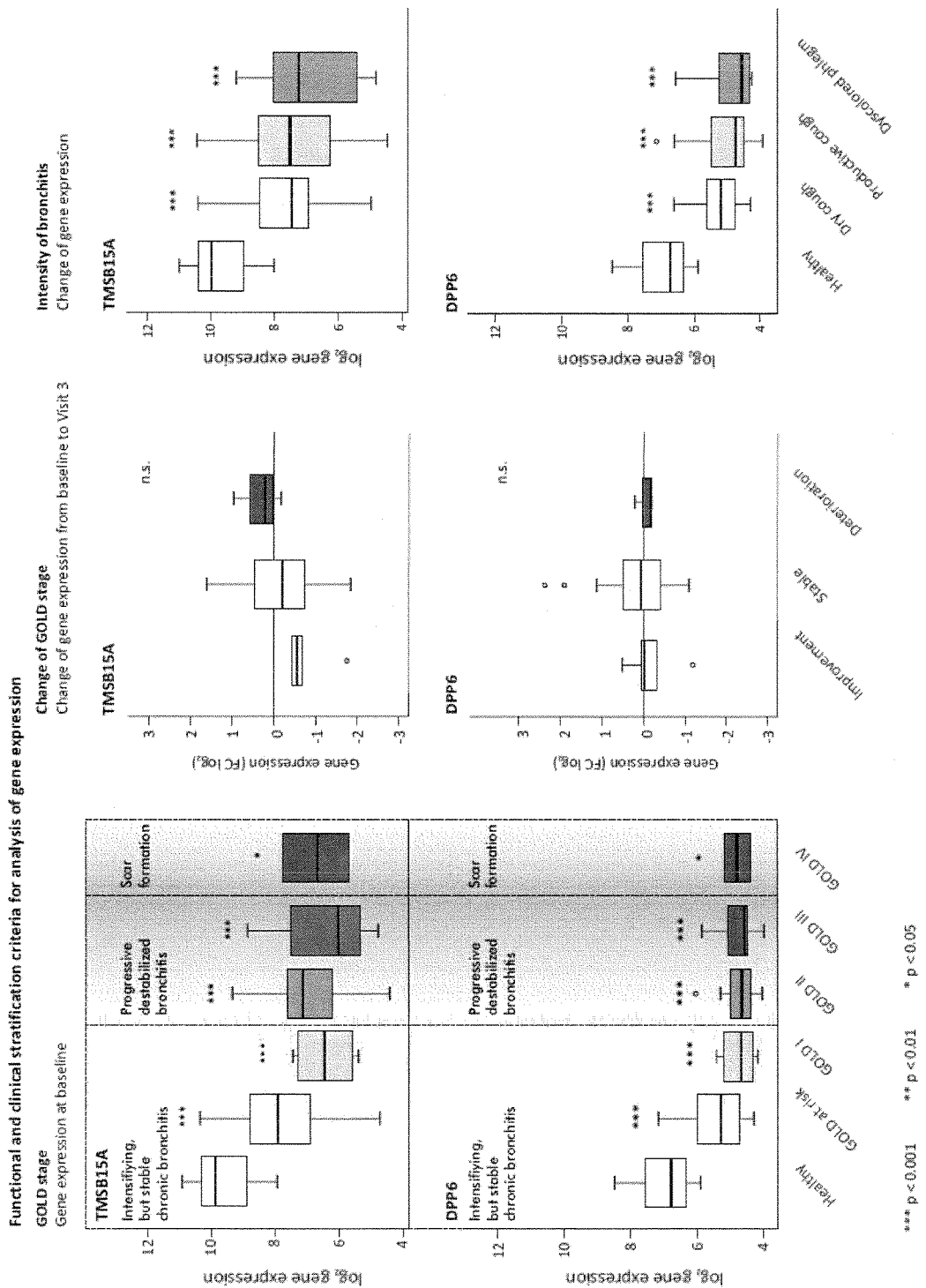
Figure 4:
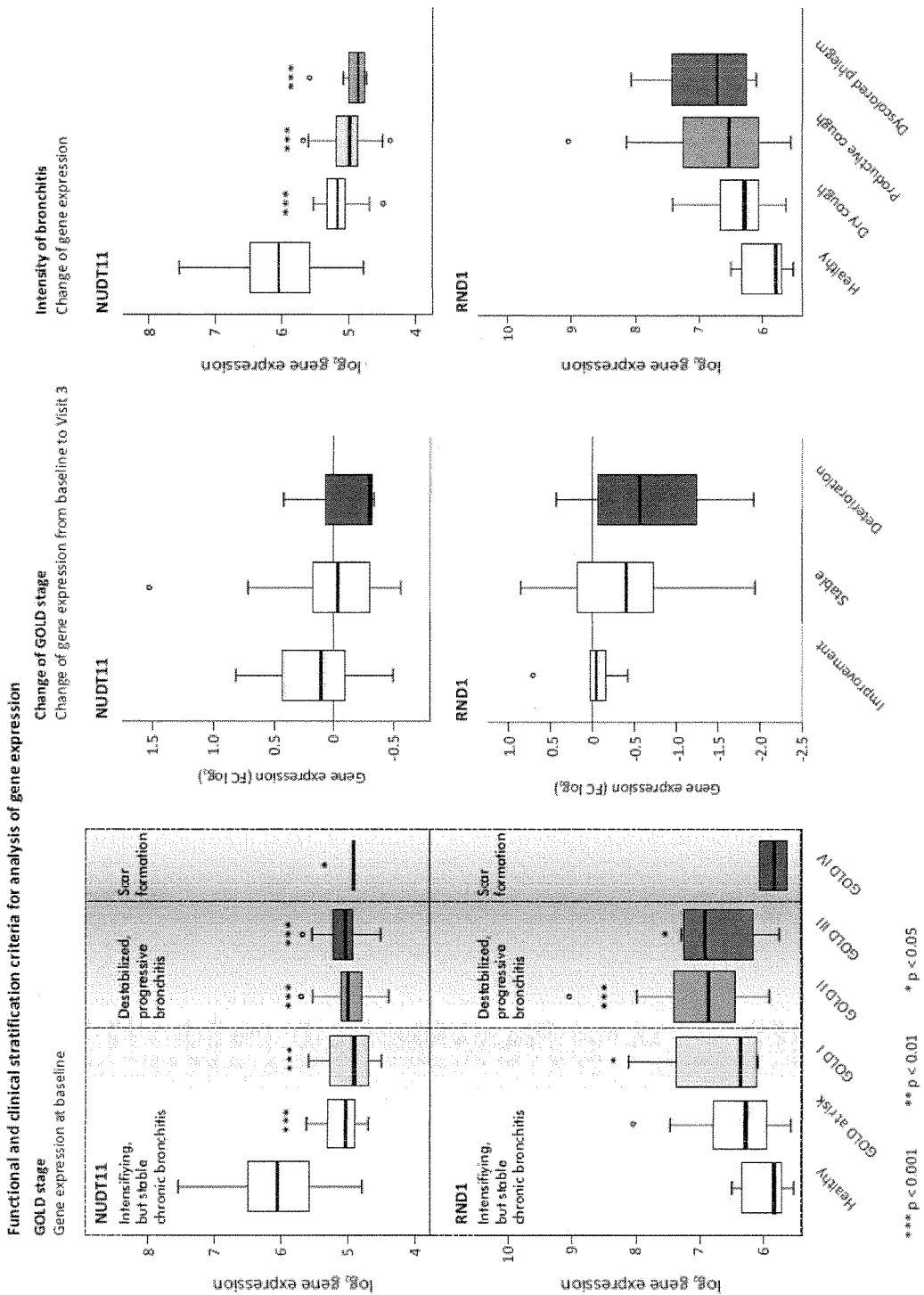
Figure 4:
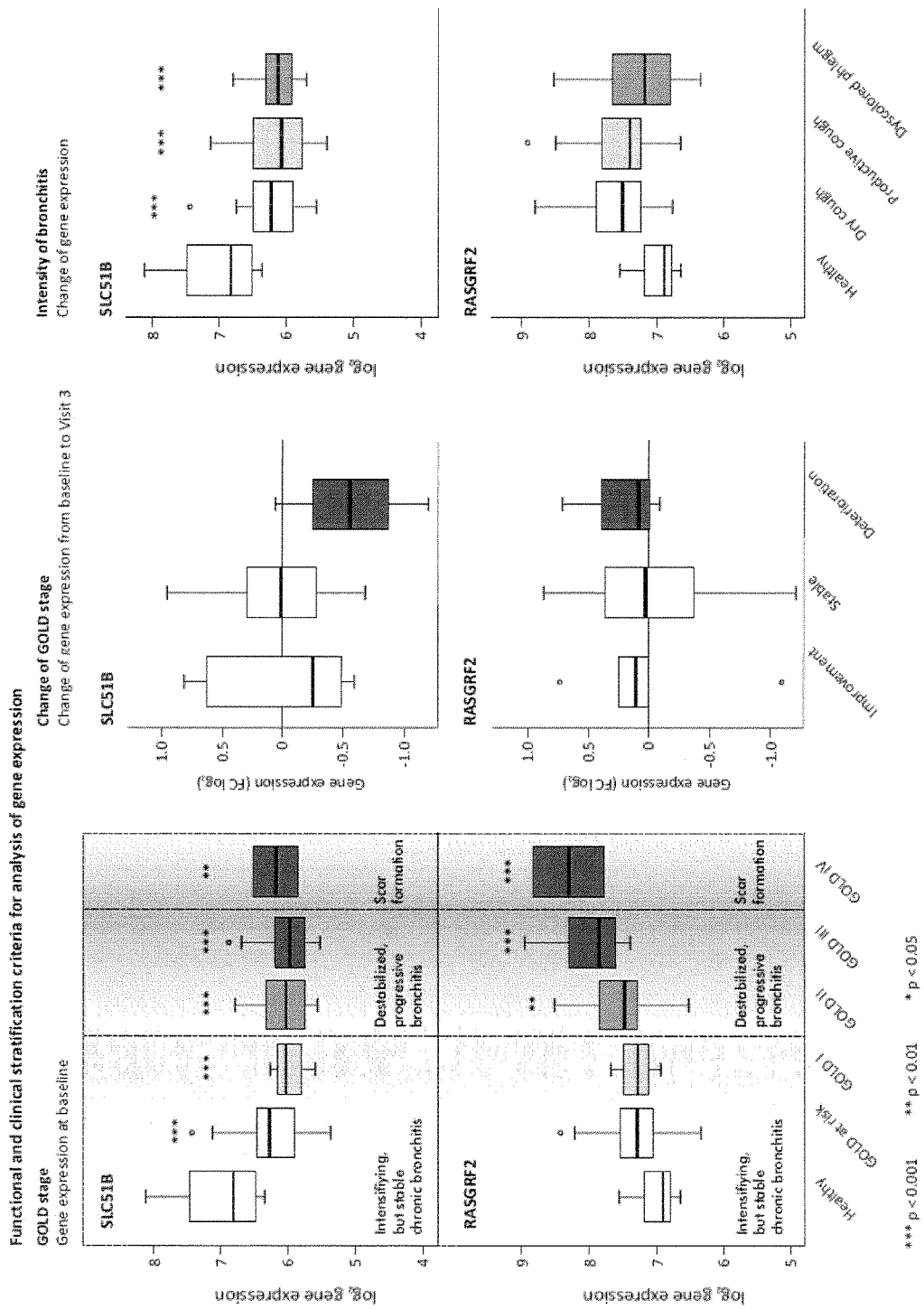

FIG. 4: COPD Pathology module 1: Development of chronic bronchitis: Progressive inhibition of adaptive motility of mucosal cells caused by the inhibition of coordinated actin cytoskeleton movements.

Chronic bronchitis starts with the significant downregulation of genes that control assembly, polymerization, motility, stabilization and energy supply of F actin-mediated cytoskeleton movements (suppression of thymosin beta 15A (TMSB15A), dipeptidyl-peptidase 6 (DPP6), nudix (nucleo-side diphosphate linked moiety X)-type motif 11 (NUDT11), and integrin alpha 10 (ITGA10)). At the same time, expression of the RASGRF2 gene known to inhibit Cdc42-mediated polymerization of actin during cellular movements is progressively increased during advancement of COPD (FIGS. 4A and 4D) indicating that the inhibition of cellular motility is not only a leading mechanism in early stages of COPD development, but also part of the progressive membrane destruction in later stages of COPD.

Of note, reduced expression of these genes is also connected to increasing intensity of bronchial inflammation. This characteristic expression pattern includes the SLC51B gene (FIG. 4D) which is as yet largely known for its capacity to transport steroid-precursor molecules in intestinal cells.

The compensatory activation of the GTPase RND1 (Rho family GTPase 1) best known for its ability to control the organization of the actin cytoskeleton in response to growth factor stimulation is just increased up to COPD GOLD stage II not only indicating a complete failure of actin-dependent cellular cytoskeleton organization in later stages of COPD, but also the loss of the regenerative capacity, as also demonstrated within Module 3 (see FIGS. 6A-6E). This in turn concurs rather well with the progressive downregulation of the cystatin M/E (CST6) gene being annotated with both functional differentiation of epithelial cells and maintenance of surface integrity.

As the coordinated action of these molecules is required for controlled movements of epithelial cells during pivotal processes, such as growth, intercalation and extrusion of cells within a cohesive cell layer system, the loss of these functions causes a profound disturbance of membrane integrity allowing for the development of non-specific bronchial inflammation that basically reflects all constituents of ventilated air including combustion products, such as cigarette smoke or welding fumes.

FIG. 5: COPD Pathology module 2: Bi-phasic activation of mucosal immunity.

Driven by this loss of cellular cohesion, the bronchus develops a diverse mucosal immune response that combines mechanisms of acute inflammation, such as the expression of fibrinogen (FGG) (FIGS. 5A and 5D), the upregulation of carcinoembryonic antigen-related cell adhesion molecule 5 (CEACAM 5) (FIGS. 5A and 5D), and aryl hydrocarbon receptor (AHR) signaling, the latter characterized by increased expression of cytochrome P450, family 1, subfamily A polypeptide 1 (CYP1A1) and cytochrome P450, family 1, subfamily B polypeptide 1 (CYP1B1) (FIGS. 5A and 5E, 5F). Intensity of AHR signaling is significant, in spite of the increased compensatory expression of the aryl hydrocarbon receptor repressor gene (AHRR), most likely reflecting the continuous impact of smoke. As CEACAMs have recently been shown to act as surface receptors for gram-negative bacteria such as *Neisseria meningitidis, Haemophilus influenzae* and *Moraxella catarrhalis* being frequently found in progressive bronchitis, this mechanism is prone to contribute to episodes of intensified bronchial inflammation.

Nonetheless, neither FGG nor CEACAM5 expression causes short-term worsening of non-reversible pulmonary obstruction (FIG. 5D, middle panel), although the activation of both genes significantly contributes to the intensity of bronchial inflammation (FIG. 4D, right panel). This differs from CYP1A2, KIAA1199 and phospholipase A1 member A (PLA1A) expression (FIGS. 4b and e) that all correlate with a significant deterioration of pulmonary function. While CYP1A2 expression as part of a smoke-induced AHR signaling response fits well to the current perception of COPD development, the strong correlation of KIAA1199 and PLA1A expression with deterioration of pulmonary function according to GOLD criteria points towards another direction, the complete failure of the bronchial compartment system.

KIAA1199 has recently been demonstrated to activate matrix hyaluronidases while phospholipase A1 member A (PLA1A) is known to activate T cells in response to non-specific inflammatory stimulation. It has presently been found that the significant upregulation of KIAA1199 is characteristic for the second phase of increased bronchial inflammation in GOLD stages 111 and IV (FIG. 5B) which follows a phase of non-progressive bronchial inflammation characterizing GOLD stage I (FIG. 5A). Notably, during this stabilization phase both the expression of KIAA1199 and of PLA1A is reduced as well (FIG. 5B). Given the strong proinflammatory impact of a degradation of high molecular mass hyaluronan, these observations indicate that the final increase of inflammatory activity in COPD GOLD stage Ill and IV is the combined result of permanently disturbed epithelial integrity and a secondary destruction of the hyaluronan matrix within the bronchial wall by the activation of matrix hyaluronidases. This view is supported by the expression pattern of matrix hyaluronidase 2 (HYAL2) itself which represents the leading hyaluronan-degrading enzyme in humans (FIG. 5C).

Figure 6:
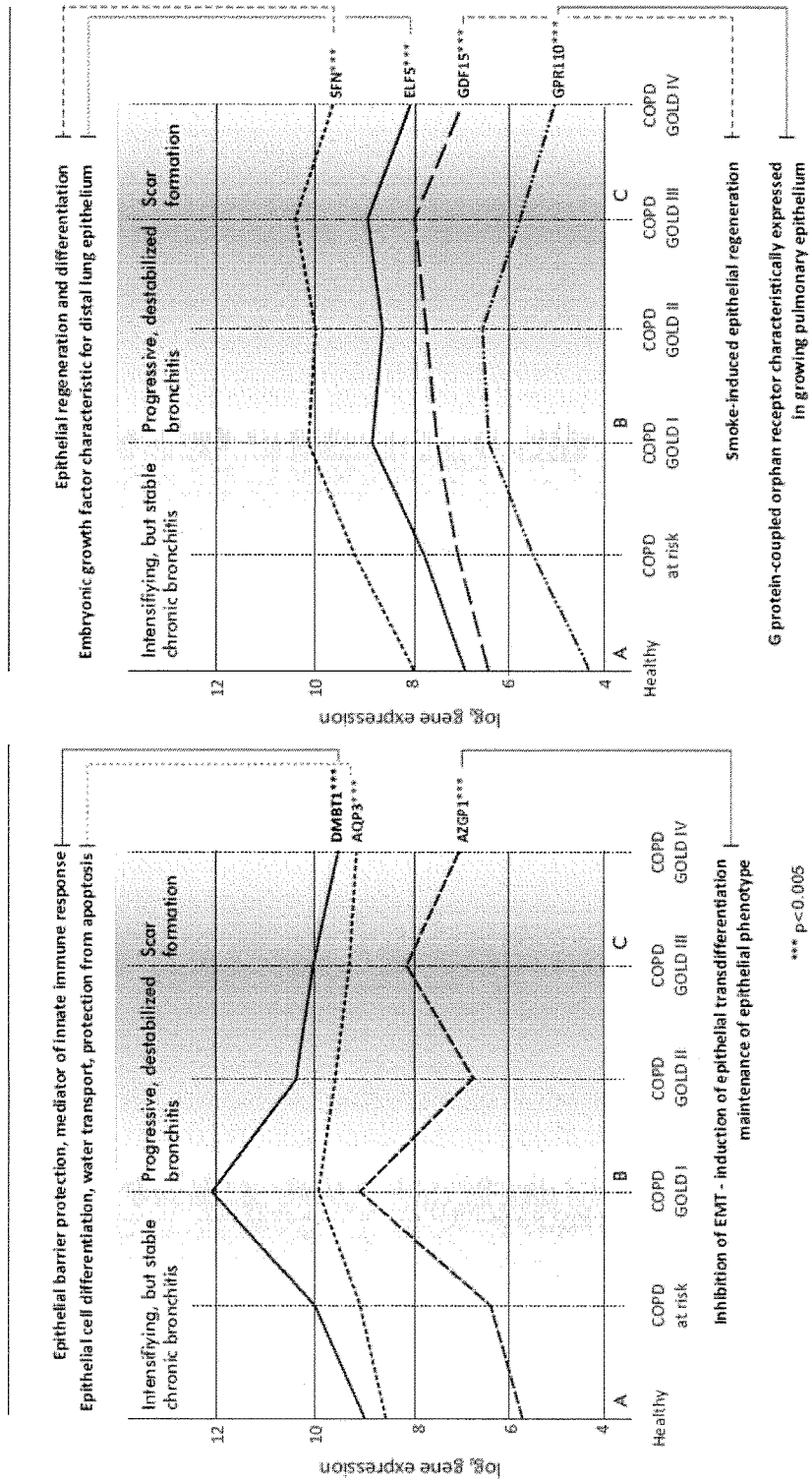
Figure 6:
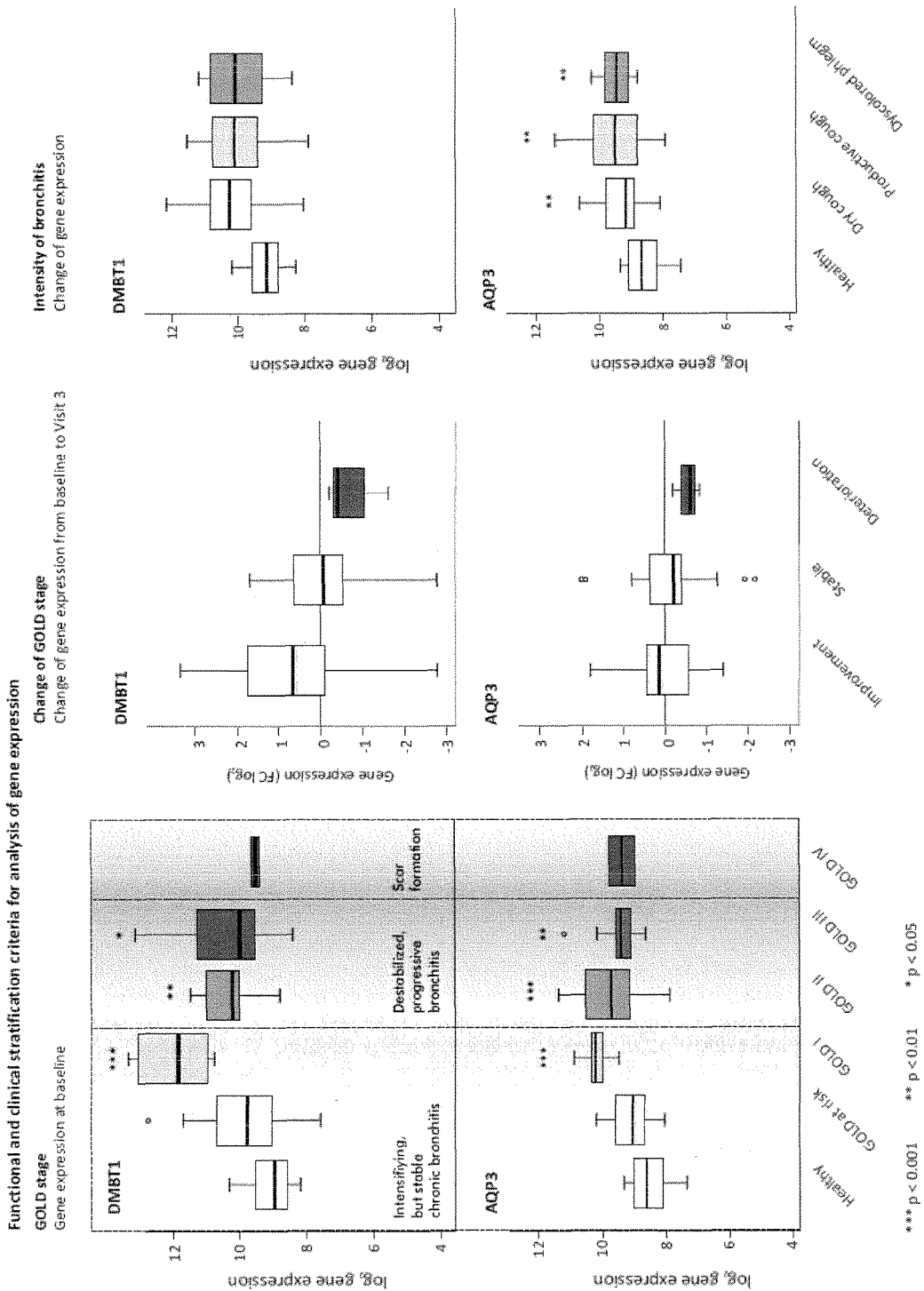
Figure 6:
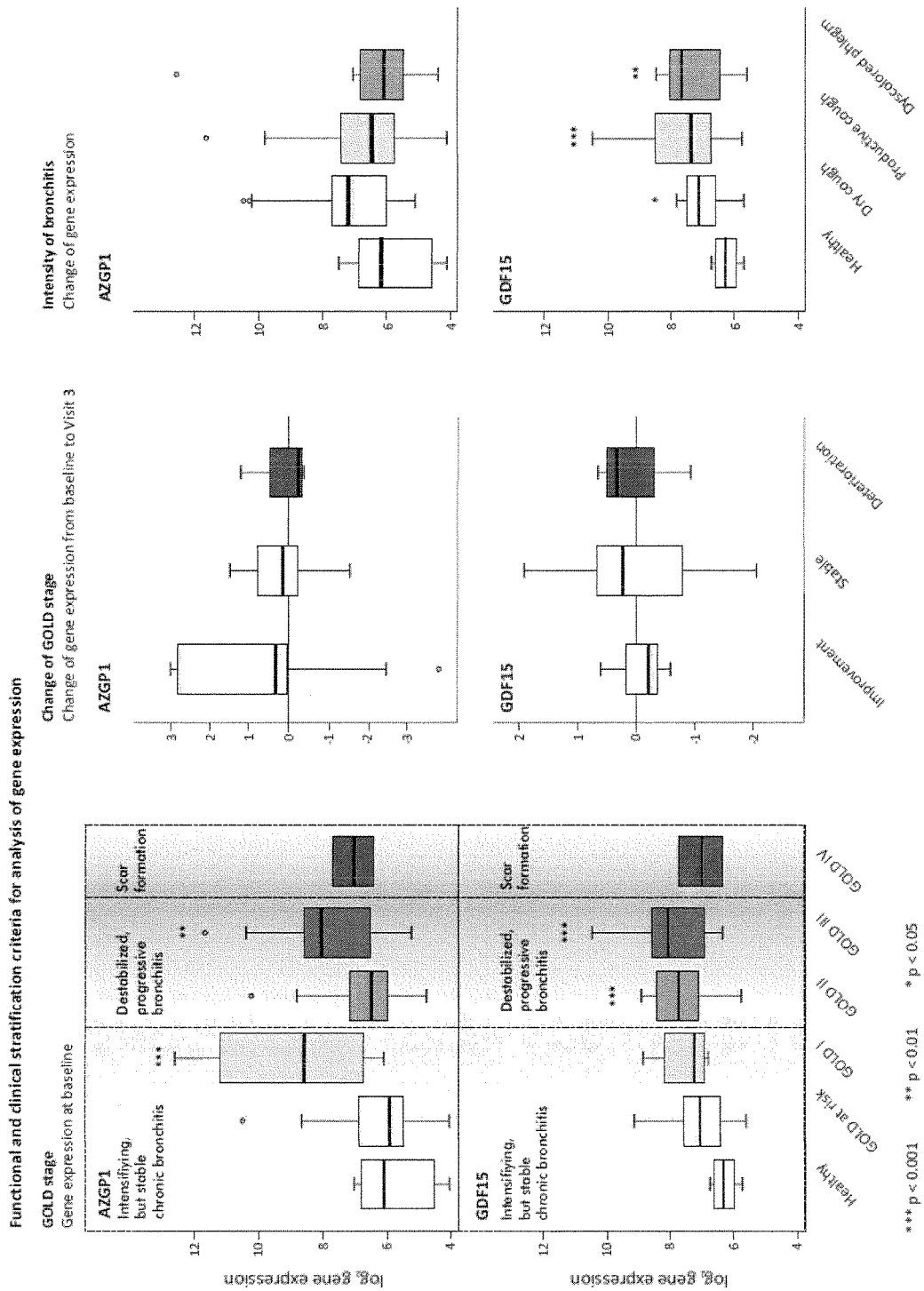
Figure 6:
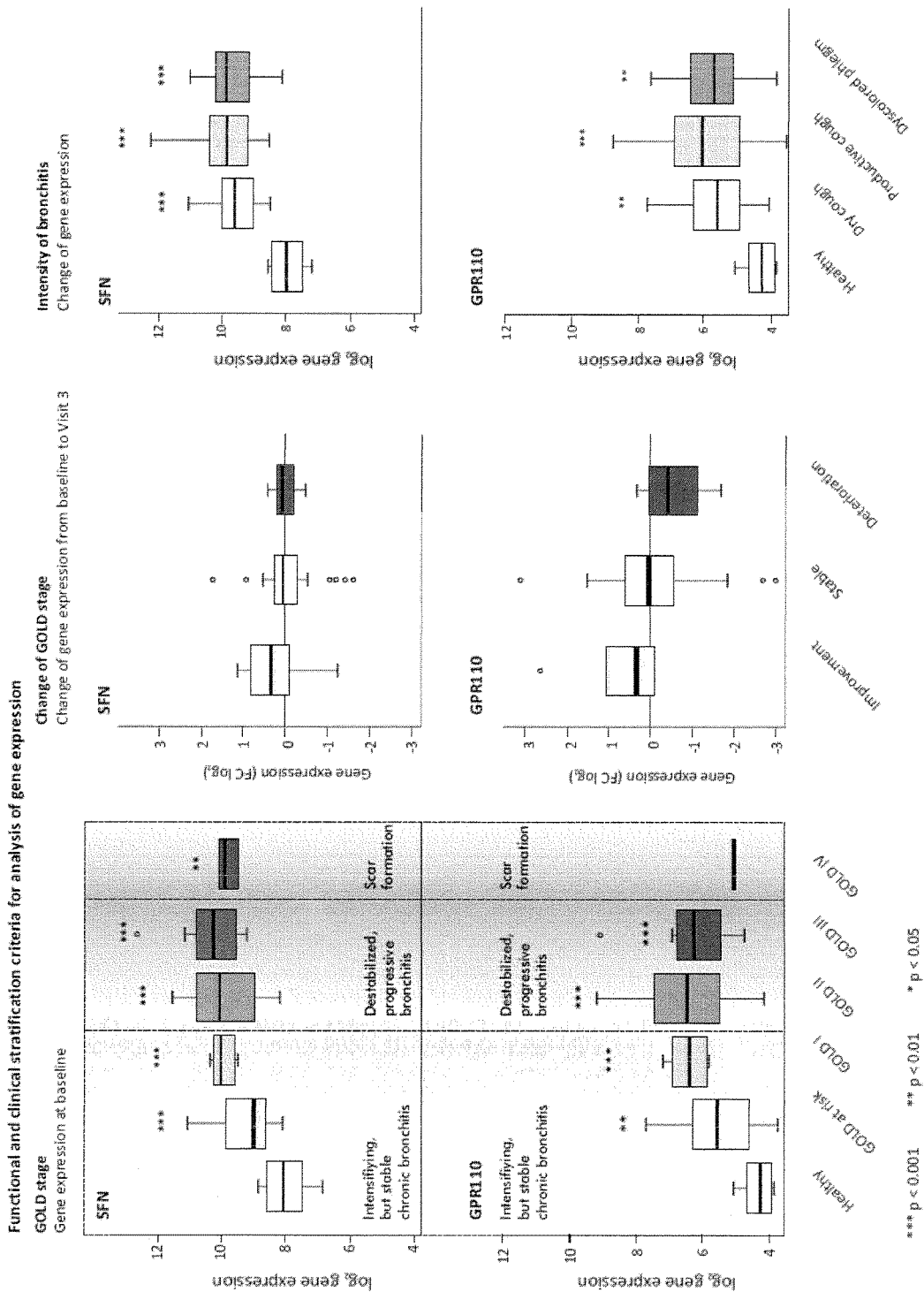
Figure 6:
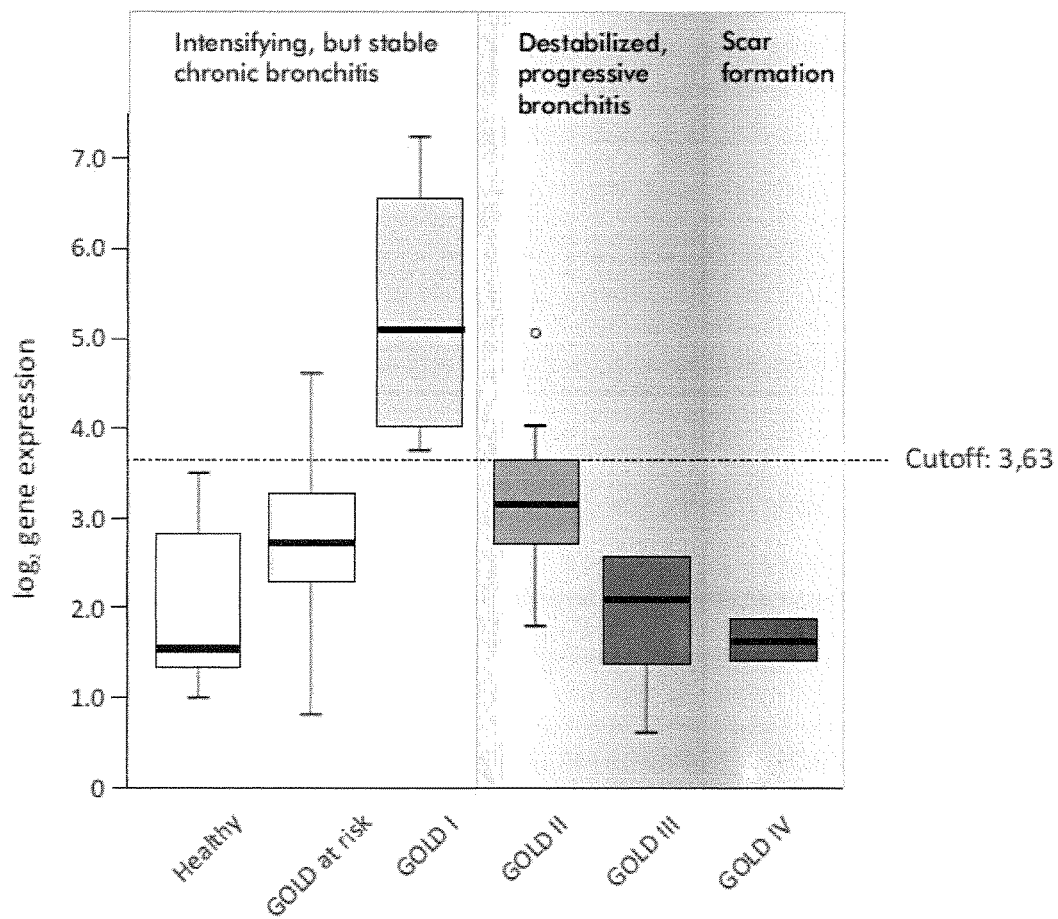

FIG. 6: COPD Pathology module 3: The impact of intensified regenerative repair: temporary suspension of progressive bronchial inflammation.

Maintaining the structural integrity of the mucosa as well as upholding essential components of the bronchial wall is part of effective wound healing and as such an indispensable measure to prevent the intrusion of antigens, allergens and infectious agents into submucosal compartments. It is thus not surprising that various genes guiding functions of epithelial repair are upregulated in response to increased inflammation, as demonstrated in FIG. 6A. However, only a small group of these genes is significantly contributing to the temporary suspension of progressive bronchial inflammation in GOLD stage I, genes known to participate in epithelial regeneration and differentiation, bacterial defense and transepithelial water transport (FIGS. 6A-6C): a) deleted in malignant brain tumors 1 (DMBT1), b) zinc-binding alpha-2-glycoprotein 1 (AZGP1), and c) aquaporin 3 (AQP3). However, this regenerative impulse does not last long as expression of these genes decreases again once progression of inflammation resumes stressing the impact of KIAA1199 expression and matrix degradation on bronchial inflammation. Although further genes closely related to epithelial repair, such as stratifin (SFN), the G protein-coupled orphan receptor 110 (GPR110), the smoke-inducible growth differentiation factor 15 (GDF15), and E74-like factor 5 (ELF5) are expressed throughout a much longer period of COPD development (FIG. 6A), the effectiveness of this wound healing approach is evidently not sufficient to maintain bronchial integrity and to balance bronchial inflammation in the presence of epithelial disintegration and progressive hyaluronan breakdown.

As a result, simultaneous measurement of DMBT1 and KIAA1199 gene expression is capable of discerning stable from progressive COPD (according to GOLD criteria), if the difference between DMBT1 and KIAA1199 expression exceeds a value of 3.63 (FIG. 6E). The importance of intensified KIAA1199 expression for progressive epithelial inflammation is further stressed by the fact that in chronic inflammatory wound healing of diabetic skin, expression of KIAA1199 is significantly upregulated, whereas in normal skin repair, KIAA1199 expression is reduced (see FIG. 8). It should also be noted that KIAA1199 expression in aged skin is in general significantly higher than in the skin from younger individuals (p<0.01).

Figure 7:
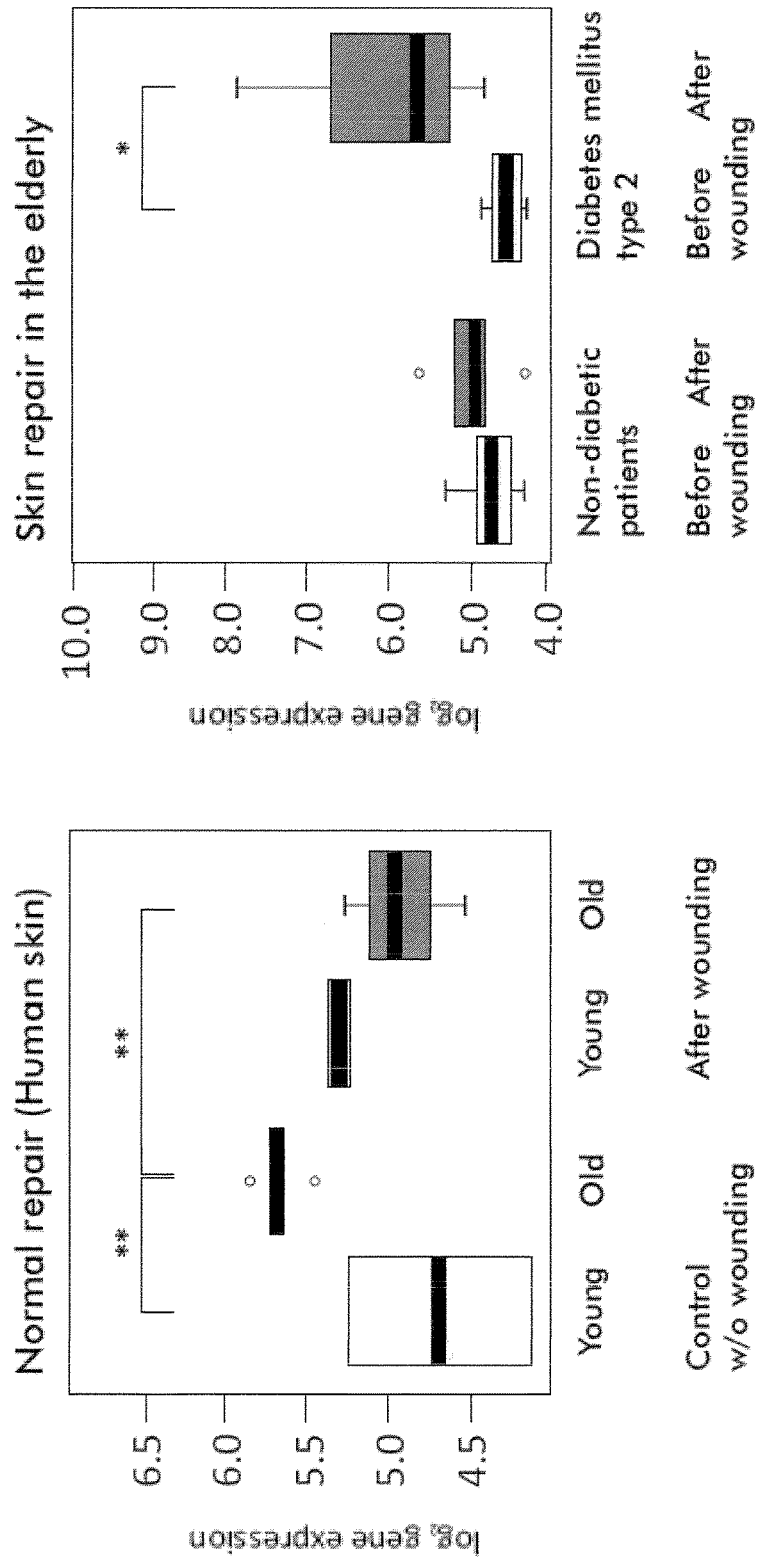

FIG. 7: Expression of KIAA1199 in skin wound healing.

FIG. 8: COPD Pathology module 4: Scar formation by predominant mesenchymal repair as the result of regenerative failure in the presence of a prevailing structural deficit.

As in any situation of prevailing unresolved repair that is not life-threatening, activation of "secondary" mesenchymal repair will serve as the exit strategy to remove the structural deficit and to terminate wound healing. During progression of COPD, coordinated gene activation in this regard can be divided into two categories: a) permanent support of mesenchymal repair (expression of NTRK2 and SOS1 genes) (FIGS. 8A and 8B), b) support of mesenchymal repair during both functional "primary" repair and non-functional "secondary" wound healing (expression of COMP, PRRX1 and CTHRC1 genes) (FIGS. 8A-8C).

As in any form of predominantly mesenchymal repair, expression of genes controlling vascular growth and differentiation is progressively diminished. FIG. 8D provides a synopsis of the expression pattern and relevant annotations for all genes related to vascular outgrowth and repair which are significantly regulated during progression of COPD.

The invention will now be described by reference to the following examples which are merely illustrative and are not to be construed as a limitation of the scope of the present invention.

EXAMPLES

Example 1: Controlled Prospective Pilot Trial Aimed at Identifying Symptom-Based Molecular Metabolic Markers for Progressive COPD (Vienna COPD-AUVA Study)

Introduction

In the context of the present invention, a controlled prospective pilot trial aimed at the identification of symptom-based molecular metabolic markers for progressive COPD was conducted at the Vienna Medical University between 2007 and 2012. The Vienna COPD-AUVA study combined the assessment of validated clinical measures for COPD following in part the overall strategy of the ECLIPSE trial (Vestbo et al., 2011), the largest and most elaborate study addressing progress and variability of COPD.

For stratification of patients, a three-year analysis (day 0, 12 months, and 36 months) of symptom scoring (St. George Respiratory questionnaire, activity and symptom score), assessment of pulmonary function, cardiopulmonary exercise testing, and radiological evaluation by computer-assisted tomography (high-resolution mode) were combined with whole genome transcription analysis plus quantitative RT-PCR assessment and mass spectrometry proteomics. As shown in FIG. 1, the patients were grouped into three strata, two of which presented at the start of the study with regular lung function, either without any sign of a cardiopulmonary disease (healthy volunteers) or with symptoms of chronic bronchitis (COPD "at risk"), and a group of volunteers having symptoms of chronic bronchitis together with deteriorated lung function (COPD at GOLD stages I-IV).

Study visits were performed at base line and after 12 and 36 months, respectively. Each visit was performed on an ambulatory basis and included medical history, physical examination, pulmonary function tests (PFT), cardiopulmonary exercise tests (CPET), radiological assessment by computer-assisted tomography (CAT) scans and a bronchoscopy. On each visit, both personal and occupational history was taken as well as smoking history which comprised onset and duration of symptoms related to COPD, production of phlegm (frequency, quantity, and color), intensity of symptoms measured by the St. George Respiratory Questionnaire (SGRQ; activity and symptom score index) and assessment of life quality using the SF-36 questionnaire. The rate of exacerbations (frequency, number of hospitalizations, use of antibiotics, corticosteroids or combined treatment) and the individual medication were also recorded.

Pulmonary function tests (PFT) were taken at each visit and included blood drawings, body plethysmography, spirometry and quantitative measurement of pulmonary gas exchange at rest and during symptom-limited cardiopulmonary exercise testing (CPET). PFT was performed with an Autobox DL 6200 (Sensor Medics, Vienna, Austria), and CPET on a treadmill using the Sensormedics 2900 Metabolic Measurement Cart. Formulas for calculation of reference values were taken from Harnoncourt et al., 1982. Predicted values were derived from the reference values of the Austrian Society of Pneumology following the recommendations of the European Respiratory Society (Rabe et al., 2007).

Serum samples were analyzed for complete cellular blood count, electrolytes, glucose, C-reactive protein, fibrinogen, and coagulation parameters.

Prior to bronchoscopy, CAT scans encompassing high resolution-computed tomography (HRCT) were performed. Following additional informed consent on each visit, bronchoscopy was performed. During bronchoscopy, both bronchoalveolar lavage (BAL) samples and transbronchial biopsy samples (five per segment in each middle lobe) were taken.

Biological analysis was performed in transbronchial lung biopsies taken during bronchoscopy from two pulmonary localizations (5 each) of the middle-lobe after radiological assessment by computer-assisted tomography (CAT) scans including high-resolution scanning. CAT scans were used for the assessment of emphysema formation as well as for the exclusion of tumor development and infection. During the controlled observational period, combined assessment of clinical and molecular development was finally possible in 120 volunteers. Biomarkers were identified in each case by means of the individual changes of pulmonary function and clinical symptoms characteristic for the progression of COPD. As a result, this approach makes use of the well-known variability of clinical phenotypes in COPD and their variable course of progression while at the same time identifying the very set of biomolecules responsible for this type of disease progression.

Clinical Analysis

The study protocol was approved by the ethical committee of the Medical University of Vienna (ClinicalTrials.gov Identifier: NCT00618137). Following informed consent during screening, individuals were stratified at visit 1 (day 0) if they fulfilled the following criteria:

TABLE 2

Stratification of subjects at visit 1 (day 0).

| | Inclusion criteria | Occupational history |
|---|---|---|
| Healthy Controls | Age 18-70 years No history or clinical findings suggestive of any disease | No occupation with increased exposure towards combustion products, |

TABLE 2-continued

Stratification of subjects at visit 1 (day 0).

| | Inclusion criteria | Occupational history |
|---|---|---|
| | Never Smoker Normal pulmonary function test at study entry | particularly no welding or professional car driving |
| COPD, at risk' | Age 18-70 years Chronic bronchitis according to WHO with repeated episodes of phlegm production No history or clinical findings suggestive of bronchial asthma Normal PFT according to GOLD criteria at study entry Smoking history of at least 10 years No history or clinical findings suggestive of cardiovascular or malign disease | Professional car driver or welder with increased occupational exposure towards combustion products of at least 10 years |
| COPD manifest | Age 18-70 years Chronic bronchitis according to WHO with repeated episodes of phlegm production No history or clinical findings suggestive of bronchial asthma Pathological PFT according to GOLD criteria at study entry Smoking history of at least 10 years No history or clinical findings suggestive of cardiovascular or malign disease | Professional car driver or welder with increased occupational exposure towards combustion products of at least 10 years |

396 individuals were screened, 185 of whom met the study criteria. 136 participants finished visit 2 after 12 months, and 120 completed the final visit after 36 months of controlled observation. Throughout the study, all participants were residing and occupied in the greater Vienna area in order to ensure comparable environmental conditions. The control group consisted of 16 healthy volunteers who had never smoked (7 females and 9 males; mean age 36±12.2 years), as also shown in Table 2 above. None of the healthy participants developed any symptom of pulmonary disease during the study period. At the start of the study, 104 participants presented with clinical symptoms of chronic bronchitis according to WHO definition, 55 of whom did not have signs of non-reversible bronchial obstruction (GOLD "at risk"), while the other 49 participants showed bronchial obstruction ranging from GOLD stage I to IV as determined by PFT (see FIG. 3D). All participants in the COPD and COPD "at risk" groups were active cigarette smokers with a smoking history of more than 10 pack years, except for one welder who in addition to a daily expectoration of phlegm reported about frequent episodes of bronchial infection (>2 per year) without radiological signs of bronchiectasis. 64 participants were working as taxi or bus drivers (53%) and 40 active welders (33%) with a previous exposure to welding fumes of more than 10 years.

At visit 1, the majority of participants with manifest COPD had bronchial obstruction GOLD stage II and III (n=38), while the remaining subjects were in COPD GOLD stage I (n=9) and IV (n=2) (see FIG. 3D). Mean age in GOLD stages I and II was 50±9.5 and 56±10.4 yrs. respectively, compared to 52±9.0 yrs. in GOLD stage III and 63±11 yrs. in GOLD stage IV. 29% of the participants in the GOLD "at risk" group were already presenting with a continuous daily expectoration of sputum, and sputum was frequently discolored (yellow, green, brown) in 27%.

During controlled observation (36 months), 14 participants (12%) had a progression of disease according to GOLD, 7 (13%) in the GOLD "at risk" group, 1 (11%) in GOLD I, 3 (12%) in GOLD II, and 3 (25%) in GOLD III. Improvement of bronchial obstruction according to GOLD was observed in 13 individuals (5 participants in both GOLD stage I and II, and 3 cases in GOLD stage III and IV), mostly connected to a cessation of cigarette smoking.

As part of the observational design of the study, participants were not specifically encouraged to stop smoking. Accordingly, smoking habits changed only slightly: only 5 participants of the "COPD at risk" group (9%) and 2 participants in the "manifest COPD" group (4%) stopped smoking during the observational period, while 31% reduced cigarette smoking (data not shown). These changes did not significantly alter both occurrence and intensity of chronic bronchitis symptoms, as 27 participants (23%) demonstrated improvement and deterioration of cough and sputum production.

Biological/Molecular Analysis (Gene Transcription in Pulmonary Tissue)

RNAlater (Ambion, lifetechnologies) was used for tissue asservation. The lung biopsy material was disrupted using Lysing Matrix D ceramic balls in a Fastprep 24 system (MP Biomedical, Eschwege). A chaotropic lysis buffer (RLT, RNeasy Kit, Qiagen, Hilden) was used, followed by a phenol/chloroform extraction and subsequent clean up using the spin column approach of the RNeasy Mini Kit (Qiagen, Hilden) according to the manufacturer's manual, including a DNase I digestion on the chromatography matrix. RNA quantification was done spectrophotometrically using a NanoDrop 1000 device (Thermo Scientific) and quality control was performed on the Agilent 2100 Bioanalyzer. A cut off for the amount of 1 microgram and a RNA integrity number of 7.0 was chosen.

Total RNA samples were hybridized to Human Genome U133plus 2.0 array (Affymetrix, St. Clara, Calif.), interrogating 47,000 transcripts with more than 54,000 probe sets.

Array hybridization was performed according to the supplier's instructions using the "GeneChip® Expression 3' Amplification One-Cycle Target Labeling and Control reagents" (Affymetrix, St. Clara, Calif.). Hybridization was carried out overnight (16 h) at 45° C. in the GeneChip® Hybridization Oven 640 (Affymetrix, St. Clara, Calif.). Subsequent washing and staining protocols were performed with the Affymetrix Fluidics Station 450. For signal enhancement, antibody amplification was carried out using a biotinylated anti-streptavidin antibody (Vector Laboratories, U.K.), which was cross-linked by a goat IgG (Sigma, Germany) followed by a second staining with streptavidin-phycoerythrin conjugate (Molecular Probes, Invitrogen). The scanning of the microarray was done with the GeneChip® Scanner 3000 (Affymetrix, St. Clara, Calif.) at 1.56 micron resolution.

The data analysis was performed with the MAS 5.0 (Microarray Suite statistical algorithm, Affymetrix) probe level analysis using GeneChip Operating Software (GCOS 1.4) and the final data extraction was done with the DataMining Tool 3.1 (Affymetrix, St. Clara, Calif.).

CEL files were imported and processed in R/Bioconductor (Gentleman et al., 2004). Briefly, data was preprocessed using quantile normalization (Gentleman et al., 2004) and combat (Johnson et al., 2007), linear models were calculated using limma (Smyth G K, 2005) and genes with a p-value of the f-statistics <5e-3 were called significant. Those genes were grouped into 20 clusters of co-regulated genes. The procedure of modeling and clustering was repeated for GOLD and phlegm as covariates.

For subsequent Gene Ontology (GO)-analysis it was necessary to separate the effects of GOLD and phlegm on gene expression. To this end, the GOLD classifications were grouped into "no COPD" (healthy and GOLD 0) and "COPD" (GOLD grades I-IV). Similarly, phlegm was reclassified into a "phlegm" group (productive or severe) and a "no phlegm" group (health or no/dry). Based on these reclassifications, gene expression was modeled using a 2×2 factorial design, resulting in five different lists of genes: (1) genes which are regulated with phlegm in the presence of COPD, (2) genes which are regulated with phlegm in the absence of COPD, (3) genes which are regulated with COPD in the presence of COPD, (4) genes which are regulated with COPD in the absence of COPD and finally (5) genes which are regulated differently with COPD, depending on whether there is phlegm or not.

These lists were annotated with respect to their biological functions as catalogued in the Gene Ontology (GO) database using the ClueGO plugin for the Cytoscape framework.

Results of Combined Clinical and Molecular Analysis

Activation of Epithelial Repair Mechanisms

Systematic analysis of the significant changes of gene expression during COPD development reveals a differentiated picture: As shown in FIGS. 6A to 6D, mechanisms of regeneration and repair commence as soon as the chronic inflammatory process in the peripheral bronchial tree is established. This is already the case in persistent or repeatedly manifesting bronchitis (COPD "at risk"). The functions associated with this kind of aberration from the normal equilibrium, in ontological terms still only potential COPD, include mediators involved in the regulation of embryonic epidermal and pulmonary growth, such as ELF5 (E74-like factor 5; ETS domain transcription factor) which confers spatially controlled outgrowth of epithelial structures (Metzger et al., 2008; Yaniw et al., 2005) as well as mucosal immunity of the lung (Lei et al., 2007). Not surprisingly, the expression of ELF5 is accompanied by a significant upregulation of stratifin (SFN) conferring increased epidermal regeneration and differentiation (Medina et al., 2007), yet also reduced deposition of matrix proteins including collagen I (Chavez-Muñoz et al., 2012) and reduced functions of non-specific surface immunity (Butt et al., 2012). This regenerative phase of repair involves not only the G protein-coupled orphan receptor GPR110 and the smoke-inducible growth differentiation factor 15 (GDF15) (Wu et al., 2012), a member of the bone morphogenic protein-transforming growth factor-beta superfamily, but also mediators directing differentiated epithelial repair, such as the zinc-binding alpha-2-glycoprotein 1 (AZGP1), and the DMBT1 gene (deleted in malignant brain tumors 1) which is strongly upregulated during acute but resolving bacterial inflammation in enteral epithelia during appendicitis (Kaemmerer et al., 2012), suggesting a functional relevance for mucosal defense (Diegelmann et al., 2012). The almost identical expression profile of DMBT1 and AZGP1, a mediator capable of inducing a strong epithelial transdifferentiation in tumor cells (Kong et al., 2010), suggests an as yet undefined combinatory effect of both mediators on cellular differentiation during epithelial regeneration. Notably, the expression of these genes is strongly increased in individuals with COPD GOLD I and decreases significantly with progression of COPD, as also shown in FIG. 6A. In line with this observation, all mediators conveying epithelial regeneration and differentiation were found to be significantly downregulated during the transition from COPD stage III to COPD stage IV.

Activation of mediators of regenerative repair was also found in individuals demonstrating significant symptoms of bronchial inflammation, as demonstrated by a uniform increase of gene expression of SFN, GPR110 (see also FIG. 6D), and aquaporin 3 (AQP3) (see FIG. 6A) being an additional mediator known to guide proliferation and differentiation of epithelial cells (Nakahigashi et al., 2011; Kim et al., 2010). However, expression of these factors did not further increase with an increase of severity of bronchial inflammation, much in contrast to mediators capable of intensifying inflammation on epithelial surfaces, such as the carcinoembryonic antigen-related cell adhesion molecule 5 (CEACAM5) (see FIGS. 5A and 5D), or factors being part of the preferentially mesenchymal wound healing response during inflammatory repair (Agarwal et al., 2012; Agarwal et al., 2013), such as the cartilage oligomeric matrix protein (COMP) (see FIGS. 8A and 8C). The study design allowed as well for the measurement of changes of gene expression occurring throughout the study period of 3 years, possibly indicating significant changes of repair during short-term progression of COPD. Here, a significant downregulation of GPR110 and DMBT1 genes correlating with deteriorated lung function according to GOLD was found, as also shown in FIGS. 6B and 6D. This decrease of regenerative gene activity started already in GOLD stage II, where it was accompanied by a striking increase of repair functions related to mesenchymal wound healing (see also FIG. 8).

Progressive Activation of Mesenchymal Repair

During later stages of COPD, expression of mediators favoring mesenchymal repair became increasingly prominent. This did not only relate to the increased expression of the COMP gene (see FIGS. 8A and 8C), but also to the expression of potent activators of mesenchymal stem cells, such as the son of sevenless homolog 1 (SOS1) gene, a guanine nucleotide exchange factor for RAS proteins acting as the cognate receptor for hepatocyte growth factor, and to the paired related homeobox 1 gene (PRRX1), a transcriptional co-activator of RAS transcription factors belonging to the HOX family of early differentiation factors able to induce mesenchymal outgrowth in liver cirrhosis (Jiang et al., 2008) as well as epithelial-to-mesenchymal transition (EMT) during cancer development (Ocana et al., 2012). While their pattern of expression indicates that both COMP and PRRX1 genes take also part in the regenerative phase of wound healing characterizing GOLD stage I and II, their later increase during transition from GOLD stage III to IV suggests an additional involvement in the progressive scarring of the airways. Increased expression of pro-fibrotic factors is further demonstrated by the striking increase of expression of neurotrophic tyrosine kinase receptor type 2 (or tropomyosin receptor kinase B receptor; TrkB) (NTRK2). NTRK2/TrkB, thus far known to act as high affinity receptor for various neurotrophic growth factors during nerve development, is also capable of promoting resistance of mesenchymal cells towards apoptosis and anoikis (Frisch et al., 2013). The combined increase of profibrotic mediators includes as well the expression of the collagen triple helix repeat containing 1 gene (CTHRC1) capable of conferring fibrotic organ dystrophy (Spector et al., 2013). Notably, while the increased expression of CTHRC1 starts only at GOLD stage II, cumulative activation of NTRK2/TrkB is a hallmark throughout progression of COPD in general, suggesting a permanent contribution of NTRK2/TrkB signaling to the aberrant repair response in the peripheral airways during COPD development. This view is further supported by the observation that a disturbed TrkB axis may contribute to experimental pulmonary fibrosis (Avcuoglu et al., 2011).

With the exception of COMP expression, where clinical deterioration correlates with worsening of bronchial obstruction according to GOLD (see also FIG. 8C), neither increased long-term expression of NTRK2 (see also FIG. 8B), nor of PRRX1 (see also FIG. 8B) or CTHRC1 genes (see also FIG. 8C) demonstrate a comparable short-term impact on bronchial obstruction during the controlled 3-year observational study period. Corresponding results were obtained when assessing the correlation of gene expression with progressive bronchial inflammation: while the expression of all genes favoring mesenchymal repair is increased as a result of intensified bronchitis, significant changes were only found for the PRRX1 and CTHRC1 genes (see also FIGS. 8B and 8C).

Loss of Structural Integrity of Epithelial Surfaces

Unexpectedly, the present analysis revealed a very significant downregulation of expression of a group of genes which guide movement, distribution and activation of the cellular cytoskeleton and which, as a result, are likely to profoundly influence structural integrity and barrier function of the mucosal surface. The downregulation of these genes takes place already during establishment of chronic bronchitis, well before the establishment of bronchial obstruction according to GOLD, as also shown in FIG. 4A. The genes closely connected to this development are thymosin beta 15 A (TMSB15A), dipeptidyl-peptidase 6 (DPP6), nudix (nucleoside diphosphate linked moiety X)-type motif 11 (NUDT11), integrin alpha 10 (ITGA10), cystatin E/M (CST6), and PRICKLE2 (data not shown). Notably, the two genes most significantly decreased during progression of COPD, TMSB15A and DPP6, are also significantly downregulated in correlation with symptoms of increased bronchial inflammation (see also FIG. 4B). Beta thymosins are controllers of both composition and sequestration of the actin cytoskeleton (Hannappel, 2007; Huff et al., 2001; Malinda et al., 1999), by that influencing membrane structure, surface stability and cellular phenotype (Husson et al., 2010). One of the outcomes of elevated levels of beta thymosins during wound healing seems to be a protection from fibrotic aberrations of repair (De Santis et al., 2011), in part by preventing the expression of α-smooth muscle stress fibers preventing them from a transdifferentiation into myofibroblasts most characteristic for fibrotic tissue development. Currently, little is known about the function of DPP6 in regenerative wound healing. However, DPP6, a member of the S9B family of membrane-bound serine proteases which is lacking any detectable protease activity, has recently been demonstrated to confer membrane stability and controlled outgrowth of cells during nerve development including close control of cell attachment and motility (Lin et al., 2013). Moreover, given its proven association with and control of membrane-bound ion channel expression and activation (Jerng et al., 2012), in particular of voltage-gated potassium channels, expression of DPP6 is also capable of controlling the resting membrane potential (Nadin et al., 2013), thereby controlling both activity and intracellular distribution of the actin cytoskeleton (Mazzochi et al., 2006; Chifflet et al., 2003).

Combined with the striking reduction of TMSB15A gene expression, the significant decrease of DPP6 expression suggests a severe disturbance of regular movement and distribution of the cellular actin skeleton, reducing physicochemical integrity of the epithelial lipid bilayers. As this occurs already very early in COPD development, this finding could indicate an initiating and possibly predisposing mechanism leading to non-specific surface inflammation.

Cystatin M/E (CST6), on the other side, is an epithelium-specific protease inhibitor belonging to the cystatin family of secreted cysteine protease inhibitors indispensable for the physiological regulation of protease activity during growth and differentiation of epithelial structures. CST6 is expressed both in dermal and bronchial epithelia where it characterizes the status of functional differentiation (Zeeuwen et al., 2009). Significant downregulation of CST6 has already been shown to cause a marked disturbance of both surface integrity and differentiation status in the dermis of mice (Zeeuwen et al., 2010). Progressive downregulation of CST6 as observed during advancement of COPD is thus likely to destabilize the intricate balance between proteases and protease inhibitors, by that contributing to a loss of surface stability as well as cellular adhesion and differentiation in the regenerating bronchial epithelium. Within this context, significant downregulation of two other genes intricately involved in the regulation of cell adhesion and motility has also been observed, namely of integrin α10 (ITGA10) being part of differentiated mesenchymal structures, and the nudix (nucleoside diphosphate linked moiety X)-type motif hydrolase 11 (NUDT11), capable of hydrolyzing diphosphoinositol polyphosphates derived from cellular lipid bilayer structures, and diadenosine polyphosphates, mostly based on adenosine triphosphate (ATP).

The consequence of these changes in gene expression is expected to be a disintegration of the epithelial barrier function, probably starting on the cellular level (continuous shear stress within the cellular lipid bilayer due to uncoordinated accumulation and movements of the actin cytoskeleton attached to it), and aggravated by disintegration of the extracellular matrix composition itself. This is supported by the significant increase of gene expression of the KIAA1199 gene during progression of COPD from GOLD stage I to GOLD stage IV (see FIG. 5B). Increased expression of KIAA1199, in addition to mediating cellular attachment and contact inhibition (Tian et al., 2013), has just recently been demonstrated to cause the leakage of endoplasmatic reticulum (ER) contents into the cytosol of cancer cells (Evensen et al., 2013). Moreover, increased expression of KIAA1199 is capable of activating hyaluronidases (HAase), enzymes capable of degrading high-molecular mass hyaluronic acid (HMM-HA), one of the major constituents of the extracellular matrix (Toole, 2004). Biological responses triggered by hyaluronic acid (HA) depend on the HA polymer length. HMM-HA has strong anti-inflammatory properties (Kothapaili et al., 2007), whereas low-molecular-mass HA promotes inflammation and concomitant cellular proliferation (Pure et al., 2009). In support of this view, degradation of HA has been shown to trigger skin inflammation by generation of low molecular weight fragments of HA (Yoshida et al., 2013).

In line with this, expression of HA synthases (HAS1-3) is not changed during progression of COPD (see FIG. 5G), while the hyaluronidase 2 (HYAL2) gene is upregulated between GOLD stages I and III (see also FIG. 5C). Indeed, the pattern of expression of both HYAL1 And HYAL2 follows the expression pattern of KIAA1199, showing a downregulation during the most intense regenerative phase of repair in COPD progression (chronic bronchitis and COPD GOLD I). Upregulation of KIAA1199 in turn is synchronous to that of the PLA1A gene (see FIG. 5B) which is a phosphatidylserine-specific phospholipase expressed in macrophages stimulated by typical mechanisms of surface immunity, such as toll-like receptor 4 (TLR4) signaling (Wakahara et al., 2007). Both intensified KIAA1199 and PLA1A expression were found to be connected to short-term worsening of pulmonary function according to GOLD criteria (see also FIG. 5B).

Decrease of Pro-Angiogenic Mediators During Progression of COPD

Effective organ repair involves mechanisms concomitantly directing spatially controlled epithelial, mesenchymal and endothelial outgrowth. However, in contrast to gene functions contributing to epithelial and mesenchymal repair, gene expression promoting angiogenesis and vascular differentiation was found to decrease as soon as chronic bronchitis was present. During development of COPD (GOLD stage I and II), this pattern of gene expression proceeded significantly, as also shown in FIG. 8D. Even the increase of Bex1 and Ghrelin (GHRL) gene expression occurring at GOLD stage I is rather small and insignificant compared to gene functions aimed at the regeneration of epithelial outgrowth, such as DMBT1 and AZGP1. Some of the functions, such as FIBIN (fin bud initiation factor homolog), ESM1 (endothelial cell-specific molecule 1) and ghrelin (GHRL) are known to act, in part, as mediators in the early phases of organ development. For instance, FIBIN takes part in mesodermal lateral plate development (Wakahara et al., 2007) which is crucial for early vasculogenesis (Paffett-Lugassy et al., 2013), ESM1 mediates VEGF-A-dependent signaling (Zhang et al., 2012) and is typically expressed in growing vascular tissue which includes tumor angiogenesis (Zhang et al., 2012; Roudnicky et al., 2013; Chen et al., 2010) and regenerative wound healing (Béchard et al., 2001).

Ghrelin, on the other hand, is a typical marker of microvascular development (Li et al., 2007; Wang et al., 2012; Rezaeian et al., 2012) being vital for continuous epithelial oxygen and energy supply preventing excessive apoptosis characteristic for emphysema development (Mimae et al., 2013). BEX1 and BEX5 (Brain Expressed, X-Linked 1 and 5) are genes encoding adapter molecules interfering with p75NTR signaling events. p75NTR is one of the two receptors central to nerve growth factor (NGF) signaling. While BEX1 is known to induce sustained cell proliferation under conditions of growth arrest in response to NGF, much less is known about its possible involvement in angiogenesis and vessel formation, although NGF signaling itself is well-known to promote angiogenesis (Cantarella et al., 2002). One possible interaction could be that reduced BEX1 gene expression would increase p75NTR signaling efficacy causing increased endothelial apoptosis, as the blockade of p75NTR signaling significantly decreases endothelial apoptosis (Han et al., 2008; Caporali et al., 2008). The BEX5 promoter, in turn, contains regulatory binding sites for TAL1 (T-cell acute lymphocytic leukemia 1), a direct transcriptional activator of angiopoietin 2, which is significantly upregulated during angiogenesis (Deleuze et al., 2012). TAL1, however, is downregulated as well during progression of COPD, as also shown in FIG. 8D.

Stage-Dependent Activation of the Immune Response

Based on the significant changes of gene expression measured during progression of COPD, four sequential phases of gene expression were distinguished: Phase 1 is characterized by a rapid increase of genes involved in the acute immune response, such as fibrinogen (FGG) (Duvoix et al., 2013; Cockayne et al., 2012), and products of aryl hydrocarbon receptor (AHR) signaling, such as CYP1A1 (cytochrome P450, family 1, subfamily A, polypeptide 1) and CYP1B1 (cytochrome P450, family 1, subfamily B, polypeptide 1) expression, as also shown in FIGS. 5A to 5E.

This includes as well an increased expression of carcinoembryonic antigen (CEA)-related cell adhesion molecules (CEACAMs), particularly of the CEACAM5 gene (see FIGS. 5A and 5D). At this early stage, still representing chronic bronchitis without significant changes of pulmonary function (COPD "at risk"), expression of genes mediating functions of primarily adaptive immunity, such as RAS-GRF2 (Ras protein-specific guanine nucleotide-releasing factor 2), KIAA1199 or CXCL3 was not significantly changed (see also FIGS. 5H and 5F). At phase 2 (representing GOLD stage I), expression of these genes remained stable or even decreased to some extent (see FIGS. 4A and 5A), probably reflecting the stabilizing outcome of regenerative repair efforts which was most intense at GOLD stage I (see also FIG. 6A). However, phase 3 which includes GOLD stages II and Ill was characterized by a significant increase of expression of all genes related to immunity including genes indicating increased AHR signaling, such as CYP1A1, CYP1A2 and CYP1B1 (see also FIGS. 5A, 5E and 5F). The latter ones most likely reflect the impact of cigarette smoking, all the more as three quarters of the participants were still actives smokers at this stage (see FIG. 3C). Increased gene expression reflecting intensified AHR signaling could be demonstrated in spite of elevated levels of the aryl hydrocarbon receptor repressor (AHRR) gene known to inhibit AHR signaling events, particularly during GOLD stages II and III.

Nonetheless, short-term analysis of gene expression addressing a development of COPD over a period of 3 years (see also FIGS. 5A and 5D; middle) indicates that the overall impact of AHR signaling on the deterioration of pulmonary function is more important than the additional expression of CEACAM5 which, comparable to FGG expression (see also FIG. 5D), seems to reflect the intensity of bronchitis much better. Phase 4 representing GOLD stage IV shows a striking downregulation of the majority of immune-related functions upregulated during earlier phases of COPD development, comparable to the regulation of genes controlling cellular regeneration and differentiation. Interestingly, however, this does not apply to the expression of KIAA1199 and RAS-GRF2 genes which are both upregulated even at GOLD stage IV, the latter one being again capable of influencing cellular movements by inhibition of the actin cytoskeleton (Calvo et al., 2011): RASGRF2 belongs to a group of activators of the GTPase RAS involved as well in the activation of T cells and required for the induction of NF-AT, IL-2 and TNF-α (Ruiz et al., 2007).

Within this context, the slow yet constant and highly significant upregulation of the guanine-nucleotide exchange factor (GEF) son of sevenless homolog 1 (5051) (see FIG. 8A), capable of continually activating RAS, could significantly contribute to the chronic inflammatory process facilitating the bronchial wall scarring characteristic for late stage COPD.

Members of the carcinoembryonic antigen-related cell adhesion molecule (CEACAM) family serve as cellular receptors for typical gram-negative bacteria frequently colonizing the surface of the human airways, such as *Neisseria meningitidis, Haemophilus influenzae* and *Moraxella catarrhalis* expressing opacity (Opa) proteins (Muenzner et al., 2010; Bookwalter et al., 2008; Muenzner et al., 2005). It was recently suggested that non-typable *Haemophilus influenzae* and *Moraxella catarrhalis* are able to increase the expression of their respective receptors on host cells (Klaile et al., 2013). However, no correlation between the expression of members of the CEACAM family and COPD was found under the conditions employed in that study. In the present study, only the expression of the CEACAM5 gene was significantly increased up to GOLD stage III, in that following the inflammatory reaction in general, while significantly decreasing afterwards in GOLD stage IV. This does not, however, exclude the aggravation of mucosal inflammation as a result of a persistent upregulation of CEACAM5, all the more as the expression of CEACAM5 was found to be increased in combination with a growing intensity of bronchial inflammation (see FIG. 5D).

CONCLUSIONS

Between 2007 and 2012, a controlled prospective pilot trial was conducted in finally 120 volunteers in order to identify metabolic markers indicative of the progression of COPD. By adopting parts of the design of the ECLIPSE trial (Vestbo et al., 2011), the largest and most elaborate study performed thus far to identify clinical markers describing both progress and variability of COPD, the Vienna COPD study combined controlled assessment of validated clinical measures with unsupervised assessment of genome-wide gene transcription in pulmonary tissue representing the focus of COPD pathology (Hogg J C, 2004 (b)). The correlation of gene expression with clinical development was based a) on the extent of non-reversible pulmonary obstruction at visit 1 (according to the Global Initiative for Obstructive Lung Disease; GOLD), b) on the worsening of non-reversible obstruction according to GOLD between visit 1 and 3 (covering a period of three years), and c) on symptoms indicative of an increasing intensity of bronchitis being recorded during structured clinical history at visits 1 and 3.

This analysis revealed changes of gene expression indicative of six major deviations from regular maintenance of pulmonary structure and defense: (1) Progressive loss of functions guiding epithelial and (2) vascular regeneration combined with (3) persistent and increasing activation of mechanism of fibroproliferative repair, together indicating a transition from regenerative to fibrotic repair during progression of COPD; (4) intensifying bronchial inflammation being antagonized at GOLD stage I when regenerative repair activity is highest, and culminating afterwards at GOLD stages II and III; (5) a complete loss of structural maintenance at GOLD stage IV connected to a finally failing immunity, both suggestive of the formation of scar tissue; and lastly, a rapid and persistent downregulation of functions controlling the intracellular distribution, aggregation and sequestration of actin polymers which form the cytoskeleton (6). The latter finding is of particular interest as the changes in the transcription of the corresponding genes, in particular the downregulation of TMSB15A, DPP6, NUDT11 and PRICKLE2, were already observed at GOLD stage 0 (COPD "at risk"), well before any change of pulmonary function was measurable. This striking loss occurs together with a significant increase of functions determining bronchial inflammation suggesting that these changes might be the first to predispose the bronchi to persistent inflammation. The outcome of such an early and simultaneous downregulation of the TMSB15A, DPP6, NUDT11 and PRICKLE2 genes will be discussed in the following.

Thymosin beta 15A (TMSB15A) belongs to the group of WH2 (WASP-homologue 2) domain binding proteins which are necessary for the depolymerization of actin filaments during cellular movements (Husson et al., 2010; Hertzog et al., 2004). Formation and rapid movement of actin filaments in turn are indispensable for processes such as cell division, intercalation and cellular extrusion. This applies as well to the regulation of apicobasal cell polarity (Nishimura et al., 2012), and even more important, to the formation and maintenance of tight and adherens junctions (Shen et al., 2005; Calautti et al., 2002). These complex membrane dynamics are not only an answer to external and internal stress, but also part of regular tissue growth and as such energy-dependent. The assembly of the actin skeleton is highly dynamic and creates a layer of epidermal cells acting as an impenetrable fluid-like shield composed of the constantly moving lipid border of the cells (Guillot et al., 2013). Thus, a persistent downregulation of TMSB15A is likely to prevent any fast adaptive arrangement of the surface lipid layers during cellular movements causing repeated perturbations of the epithelial barrier function.

DPP6, on the other hand, is known to stabilize the membrane potential by acting on membrane-bound potassium channels, and has also a profound impact on the organization of the actin cytoskeleton (Chifflet et al., 2003), supporting the perception of a failing barrier function. The same applies to the downregulation of NUDT11 gene expression. The nucleoside diphosphate linked moiety X (nudix)-type motif 11 (NUDT11) gene encodes a type 3 diphosphoinositol polyphosphate phosphohydrolase which generates energy-rich phosphates essential for vesicle trafficking, maintenance of cell-wall integrity in Saccharomyces and for the mediation of cellular responses to environmental salt stress (Dubois et al., 2002). As the adaptive assembly of F and G actin fibers within the cytoskeleton occurs in seconds, it is easily conceivable that energy-rich diphosphoinositol polyphosphates being integral constituents of any cell membrane will be utilized as rapidly accessible source of energy.

These findings point towards a synchronized dysregulation of genes necessary for upholding the epithelial barrier. Moreover, the downregulation of the PRICKLE2 gene was also shown to be vital for the formation of polarized epithelial layers during mouse embryogenesis (Tao et al., 2012). Decreased expression of all four genes (i.e., TMSB15A, DPP6, NUDT11 and PRICKLE2), however, was associated with significantly increased bronchial inflammation, suggesting a functional correlation between the downregulation of genes that guide functionally interrelated features of cytoskeleton assembly with the activation of bronchitis. This sheds a new light on the progression of bronchial inflammation as it indicates a direct connection between the loss of a protective epithelial shield and the aggravation of chronic bronchitis. Based on the physicochemical nature of such an effect, penetration of the epithelial membranes by any potential antigen or allergen is likely to be enhanced, particularly during intensified repair due to repeated smoke-induced damage or following viral infections. This could not only explain the remarkable heterogeneity of inflammatory conditions characteristic for COPD, but also the observation that the capacity to achieve intense cellular regeneration in spite of ongoing inflammation might be helpful in suppressing pro-inflammatory gene expression.

This view is further supported by the significant downregulation of the protease inhibitor cystatin WE (CST6) during progression of COPD (see also FIG. 4A). CST6 is known to control the homeostasis of the stratum corneum, its deficiency in mice causing severe ichthyosis and neonatal lethality (Zeeuwen et al., 2009). The progressive loss of a protease inhibitor in later phases of COPD known to preserve the integrity of epithelial structures will most likely contribute to a failure of the protective barrier function, not only by a disintegration of the epithelial layer but also by facilitating the breakdown of the matrix itself.

In this context, the strong upregulation of the KIAA1199 gene which has been demonstrated to significantly increase the activity of matrix hyaluronidases, is probably equally important, as this upregulation is directly associated with a significant worsening of lung function, even within the relatively short observational period of the present study (see also FIG. 5B). It has recently been shown that matrix structures containing large amounts of high molecular mass hyaluronan as well as the inhibition of hyaluronidase activity protect against both inflammation and cancer progression (Tian et al., 2013). In summary, these findings provide the first conclusive evidence for a progressive breakdown of bronchial surface integrity during the course of COPD development causing growing non-specific bronchial inflammation that varies with frequency and intensity of the physicochemical assaults attacking the bronchial surfaces.

According to results described herein, the response to these assaults is a slow progressive scarring process in the peripheral bronchi, whereby the combined upregulation of CTHRC1, SOS1 and NTRK2 genes (see also FIG. 8A) is likely to indicate mechanisms of preferentially mesenchymal wound healing while the stage dependent expression of the PRRX1 and COMP genes suggests their participation in regular organ repair as well demonstrating the ambiguity between regular matrix support during regenerative repair and scar formation as a result of a progressive failure of the organ's regenerative repair capacity.

This fits well to the progressive downregulation of genes mainly controlling functions of regenerative growth of the vascular tree as demonstrated by the concomitant decrease of the expression of FIBIN, TAL1, BEX1/5, and Ghrelin (GHRL) genes (see also FIG. 8D). Here again, the increasing capacity of the peripheral lung to employ mechanisms of preferentially regenerative repair during GOLD stage I becomes evident as BEX1 and GHRL increase at this stage while progressively decreasing during further progression of COPD.

Thus, in the COPD AUVA study, the clinical progression of COPD has been successfully correlated with the biological analysis of gene expression in pulmonary tissue. In particular, it has been demonstrated that the expression of the genes KIAA1199, DMBT1, ELF5, AZGP1, PRRX1, AQP3, SFN, GPR110, GDF15, RASGRF2, RND1, FGG, CEACAM5, AHRR CXCL3, CYP1A1, CYP1B1, CYP1A2, NTRK2 and COMP is increased in pulmonary tissue samples from subjects prone to develop progressive COPD, while the expression of the genes TMSB15A, DPP6, SLC51B, NUDT11, PLA1A, HYAL2, CST6, ITGA10, CTHRC1, TAL1, FIBIN, BEX5, BEX1, ESM1 and GHRL is decreased in pulmonary tissue samples from subjects prone to develop progressive COPD, as compared to the expression of the corresponding genes in pulmonary tissue samples from healthy subjects. These molecular biomarkers can thus be used for assessing the susceptibility/proneness of a subject to develop progressive COPD in accordance with the present invention, particularly in the method of the second aspect of the invention. Moreover, it has also been demonstrated that the expression of the genes DMBT1, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and COMP is increased in pulmonary tissue samples from subjects suffering from or prone to suffer from stable COPD, while the expression of the genes KIAA1199, TMSB15A, DPP6, SLC51B, NUDT11, PLA1A, HYAL2, CST6, ITGA10, CTHRC1, TAL1, FIBIN, BEX5, BEX1, ESM1 and GHRL is decreased in pulmonary tissue samples from subjects suffering from or prone to suffer from stable COPD, as compared to the expression of the corresponding genes in pulmonary tissue samples from healthy subjects, indicating that these biomarkers are suitable for diagnosing stable COPD or assessing the susceptibility of a subject to develop stable COPD in accordance with the invention, particularly in the method of the third aspect of the invention.

REFERENCES

Agarwal P, et al. *J Biol Chem.* 2012; 287(27):22549-59. doi:10.1074/jbc.M111.335935.
Agarwal P, et al. *Matrix Biol.* 2013; 32(6):325-31. doi: 10.1016/j.matbio.2013.02.010.
Avcuoglu S, et al. *Am J Respir Cell Mol Biol.* 2011; 45(4):768-80. doi:10.1165/rcmb.2010-019500.
Béchard D, et al. *J Biol Chem.* 2001; 276(51):48341-9.
Bookwalter J E, et al. *Infect Immun.* 2008; 76(1):48-55.
Butt A Q, et al. *J Biol Chem.* 2012; 287(46):38665-79. doi:10.1074/jbc.M112.367490.
Calautti E, et al. *J Cell Biol.* 2002; 156:137-48.
Calvo F, et al. *Nat Cell Biol.* 2011; 13(7):819-26. doi: 10.1038/ncb2271.
Cantarelia G, et al. *FASEB J.* 2002; 16(10):1307-9.
Caporali A, et al. *Circ Res.* 2008; 103(2):e15-26. doi: 10.1161/CIRCRESAHA.108.177386.
Chavez-Muñoz C, et al. *J Cell Biochem.* 2012; 113(8):2622-32. doi:10.1002/jcb.24137.
Chen L Y, et al. *J Int Med Res.* 2010; 38(2):498-510.
Chifflet S, et al. *Exp Cell Res.* 2003; 282(1):1-13.
Cockayne D A, et al. *PLoS One.* 2012; 7(6):e38629. doi: 10.1371/journal.pone.0038629.
Cole S P C, et al. *Monoclonal Antibodies and Cancer Therapy.* 1985; 27:77-96.
De Santis M, et al. *Respir Res.* 2011; 12:22. doi:10.1186/1465-9921-12-22.
Deleuze V, et al. *PLoS One.* 2012; 7(7):e40484. doi:10.1371/journal.pone.0040484.
Diegelmann J, et al. *J Biol Chem.* 2012; 287(1):286-98. doi:10.1074/jbc.M111.294355.
Ding C, et al. *J Biochem Mol Biol.* 2004; 37(1):1-10.
Dubois E, et al. *J Biol Chem.* 2002; 277:23755-63.
Duvoix A, et al. *Thorax.* 2013; 68(7):670-6. doi:10.1136/thoraxjnl-2012-201871.
Evensen N A, et al. *J Natl Cancer Inst.* 2013; 105(18):1402-16. doi:10.1093/jnci/djt224.
Frisch S M, et al. *J Cell Sci.* 2013; 126(Pt1):21-9. doi: 10.1242/jcs.120907.
Gentleman R, et al. *Genome Biology.* 2004; 5:R80.
Green, M R et al. Molecular Cloning: A Laboratory Manual. Cold Spring Harbor Laboratory Press. Fourth Edition. 2012. ISBN: 978-1936113422.
Guillot C, et al. *Science.* 2013; 340:1185-9.
Halbert R J, et al. *Eur Respir J.* 2006; 28:523-32.
Han Y, et al. *Biochem Biophys Res Commun.* 2008; 366(3): 685-91.
Han M K, et al. *Am J Respir Crit Care Med.* 2010; 182:598-604.
Hannappel E. *Ann NY Acad Sci.* 2007; 1112:21-37. doi: 10.1196/annals.1415.018.
Harlow E, et al. Using Antibodies: A Laboratory Manual. Cold Spring Harbor Laboratory Press. 1998. ISBN: 978-0879695446.
Harnoncourt K, et al. *Osterreich Arzteztg.* 1982; 37:1640-2.
Hertzog M, et al. *Cell.* 2004; 117:611-623.
Hogg J C, et al. *N Engl J Med.* 2004; 350:2645-2653. (a)
Hogg J C. *Lancet.* 2004; 364:709-721. (b)
Huff T, et al. *Int J Biochem Cell Biol.* 2001; 33:205-220. doi:10.1016/S1357-2725(00)00087-X.
Hurst J R, et al. *N Engl J Med.* 2010; 363:1128-1138.
Husson C, et al. *Ann NY Acad Sci.* 2010; 1194:44-52. doi:10.1111/j.1749-6632.2010.05473.x.
Jerng H H, et al. *PLoS One.* 2012; 7(6):e38205. doi:10.1371/journal.pone.0038205.
Jiang F, et al. *Exp Biol Med* (Maywood). 2008; 233(3):286-96. doi:10.3181/0707-RM-177.
Johnson W E, et al. *Biostatistics.* 2007; 8(1):118-127.
Kaemmerer E, et al. *Histopathology.* 2012; 60(4):561-9.doi: 10.1111/j.1365-2559.2011.04159.x.
Kim N H, et al. *J Invest Dermatol.* 2010; 130(9):2231-9. doi:10.1038/jid.2010.99.
Klaile E, et al. *Respir Res.* 2013; 14:85. doi:10.1186/1465-9921-14-85.
Köhler G, et al. *Nature.* 1975; 256(5517):495-7.
Kong B, et al. *Oncogene.* 2010; 29(37):5146-58. doi: 10.1038/onc.2010.258.
Kothapalli D, et al. *J Cell Biol.* 2007; 176:535-44.
Kozbor D, et al. *Immunol Today.* 1983; 4(3):72-9.
Lei W, et al. *Am J Physiol Lung Cell Mol Physiol.* 2007; 293(5):L1359-68.
Li A, et al. *Biochem Biophys Res Commun.* 2007; 353(2): 238-43.
Lin L, et al. *Nat Commun.* 2013; 4:2270. doi:10.1038/ncomms3270.
Melinda K M, et al. *J Invest Dermatol.* 1999; 113(3):364-8. doi:10.1046/j.1523-1747.1999.00708.x.
Mazzochi C, et al. *Am J Physiol Renal Physiol.* 2006; 291(6):F1113-22.
Medina A., et al. *Mol Cell Biochem.* 2007; 305:255-64.
Metzger D E, et al. *Dev Biol.* 2008; 320(1):149-60. doi: 10.1016/j.ydbio.2008.04.038.
Mimae T, et al. *Thorax.* 2013. doi:10.1136/thoraxjnl-2013-203867.
Muenzner P, et al. *J Cell Biol.* 2005; 170(5):825-36. doi: 10.1083/jcb.200412151
Muenzner P, et al. *Science.* 2010; 329(5996):1197-201. doi:10.1126/science.1190892.
Murray C J L, et al. *Lancet.* 1997; 349:1498-504.
Nadin B M, et al. *PLoS One.* 2013; 8(4):e60831. doi: 10.1371/journal.pone.0060831.
Nakahigashi K, et al. *J Invest Dermatol.* 2011; 131(4):865-73. doi:10.1038/jid.2010.395.
Nishimura T, et al. *Cell.* 2012; 149(5):1084-97. doi:10.1016/j.cell.2012.04.021.
Ocana O H, et al. *Cancer Cell.* 2012; 22(6):709-24. doi: 10.1016/j.ccr.2012.10.012.
Paffett-Lugassy N, et al. *Nat Cell Biol.* 2013; 15(11):1362-9. doi:10.1038/ncb2862.
Pauwels, R A et al. *Am J Respir Crit Care Med.* 2001; 163(5):1256-76.
Price D, et al. *Prim Care Respir J.* 2011; 20(1):15-22. doi:10.4104/perj.2010.00060.
Puré E, et al. *Cell Signal.* 2009; 21(5):651-5. doi:10.1016/j.cellsig.2009.01.024.
Rabe K F, et al. *Am J Respir Crit Care Med.* 2007; 176(6):532-55.
Rezaeian F, et al. *Am J Physiol Heart Circ Physiol.* 2012; 302(3):H603-10. doi:10.1152/ajpheart.00390.2010.
Roudnicky F, et al. *Cancer Res.* 2013; 73(3):1097-106. doi:10.1158/0008-5472.CAN-12-1855.
Ruiz S, et al. *Mol Cell Biol.* 2007; 27(23):8127-42.
Shen L, et al. *Mol Bio Cell.* 2005; 16:3919-36.
Smyth G K. limma: linear models for microarray data. In: Gentleman R, et al. Bioinformatics and Computational Biology Solutions using R and Bioconductor. 2005. Springer, New York, pages 397-420.

Spector I, et al. *Am J Pathol.* 2013; 182(3):905-16. doi:10.1016/j.ajpath.2012.11.004.

Tao H, et al. *Dev Biol.* 2012; 364(2):138-48. doi:10.1016/j.ydbio.2012.01.025.

Tian X, et al. *Nature.* 2013; 499(7458):346-9. doi:10.1038/nature12234.

Toole B P. *Nat Rev Cancer.* 2004; 4(7):528-39.

US Burden of Disease Collaborators. *JAMA.* 2013; 310(6):591-608.

Vestbo J, et al. *N Engl J Med.* 2011; 365(13):1184-92.

Vestbo J, et al. *Am J Respir Crit Care Med.* 2013; 187(4):347-65. doi:10.1164/rccm.201204-0596FP.

Wang L, et al. *Peptides.* 2012; 33(1):92-100. doi:10.1016/j.peptides.2011.11.001.

Wakahara T, et al. *Dev Biol.* 2007; 303(2):527-35.

Wedzicha J A. *Thorax.* 2000; 55:631-632.

Wu Q, et al. *Innate Immun.* 2012; 18(4):617-26. doi:10.1177/1753425911429837.

Yaniw D, et al. *Cell Res.* 2005; 15(6):423-9.

Yoshida H, et al. *Proc Natl Acad Sci USA.* 2013; 110(14):5612-7. doi:10.1073/pnas.1215432110.

Zeeuwen P L J M, et al. *J Invest Dermatol.* 2009; 129:1327-38. doi:10.1038/jid.2009.40.

Zeeuwen P L J M, et al. *FASEB J.* 2010; 24:3744-55. doi:10.1096/fj.10-155879.

Zhang S M, et al. *Biotech Histochem.* 2012; 87(3):172-8. doi:10.3109/10520295.2011.577754.

The invention claimed is:

1. A method of diagnosing and treating a human subject that is prone to develop progressive COPD, the method comprising the steps of:
   a) obtaining a lung biopsy sample obtained from the human subject;
   b) assaying the level of transcription of DMBT1, KIAA1199 and TMSB15A in the lung biopsy sample obtained from the human subject;
   c) diagnosing the human subject as prone to progressive COPD based on increased levels of transcription of DMBT1 and KIAA1199, and a decreased level of transcription of TMSB15A, in the lung biopsy as compared to the level of transcription of DMBT1, KIAA1199 and TMSB15A in a lung biopsy from a healthy human subject; and
   d) administering a drug that is effective to treat COPD to the human subject diagnosed as prone to progressive COPD.

2. The method of diagnosis and treatment of claim 1, wherein the method further comprises:
   i) in step b) assaying the level of transcription of one or more further genes selected from the group consisting of DPP6, SLC51B, NUDT11, ELF5, AZGP1, PRRX1, AQP3, SFN, GPR110, GDF15, RASGRF2, RND1, PLA1A, FGG, CEACAM5, HYAL2, AHRR, CXCL3, CYP1A1, CYP1B1, CYP1A2, CST6, NTRK2, COMP, ITGA10, CTHRC1, TAL1, FIBIN, BEX5, BEX1, ESM1 and GHRL in the lung biopsy sample obtained from the human subject;
   ii) in step c), diagnosing the human subject as prone to progressive COPD based on increased levels of transcription of DMBT1, KIAA1199, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and COMP, and decreased levels of transcription of TMSB15A, DPP6, SLC51B, NUDT11, PLA1A, HYAL2, CST6, ITGA10, CTHRC1, TAL1, FIBIN, BEX5, BEX1, ESM1 and GHRL, in the lung biopsy sample obtained from the human subject as compared to the level of transcription of DMBT1, KIAA1199, TMSB15A, DPP6, SLC51B, NUDT11, ELF5, AZGP1, PRRX1, AQP3, SFN, GPR110, GDF15, RASGRF2, RND1, PLA1A, FGG, CEACAM5, HYAL2, AHRR, CXCL3, CYP1A1, CYP1B1, CYP1A2, CST6, NTRK2, COMP, ITGA10, CTHRC1, TAL1, FIBIN, BEX5, BEX1, ESM1 and GHRL in a lung biopsy from a healthy human subject.

3. The method of claim 2, wherein in step b) the level of transcription of at least one further gene selected from the group consisting of FGG, CYP1A1, CEACAM5, CTHRC1, NTRK2, RASGRF2, ELF5, AZGP1, PRRX1, AQP3, SFN, GPR110, GDF15, RASGRF2, RND1, DPP6, SLC51B and NUDT11 is assayed in the lung biopsy sample obtained from the human subject.

4. The method of claim 1, wherein the level of transcription is determined using a quantitative reverse transcriptase polymerase chain reaction or a microarray.

5. The method of claim 1, wherein the drug is bitolterol, carbuterol, fenoterol, pirbuterol, procaterol, reproterol, rimiterol, salbutamol, levosalbutamol, terbutaline, tulobuterol, arformoterol, bambuterol, clenbuterol, formoterol, olodaterol, salmeterol, indacaterol, beclometasone, betamethasone, budesonide, ciclesonide, flunisolide, fluticasone, mometasone, triamcinolone, aclidinium bromide, glycopyrronium bromide, ipratropium bromide, oxitropium bromide, tiotropium bromide, cromoglicate, nedocromil, acefylline, ambuphylline, bamifylline, doxofylline, enprofylline, etamiphylline, proxyphylline, theobromine, theophylline, aminophylline, choline theophyllinate, montelukast, pranlukast, zafirlukast, zileuton, ramatroban, seratrodast, ibudilast, roflumilast, amlexanox, eprozinol, fenspiride, omalizumab, epinephrine, hexoprenaline, isoprenaline, isoproterenol, orciprenaline, metaproterenol, atropine, or a pharmaceutically acceptable salt of any of the aforementioned agents, or any combination thereof.

6. The method of claim 1, wherein the drug is roflumilast.

* * * * *